(12) United States Patent
Miura et al.

(10) Patent No.: US 9,062,032 B2
(45) Date of Patent: Jun. 23, 2015

(54) AMINOALKYL-SUBSTITUTED N-THIENYLBENZAMIDE DERIVATIVE

(71) Applicant: ASTELLAS PHARMA INC., Tokyo (JP)

(72) Inventors: Masanori Miura, Tokyo (JP); Daisuke Kaga, Tokyo (JP); Susumu Watanuki, Tokyo (JP); Shunichiro Hachiya, Tokyo (JP); Takao Okuda, Tokyo (JP); Ippei Sato, Tokyo (JP); Mai Isomura, Tokyo (JP); Kazuhiro Terai, Tokyo (JP); Yoh Terada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/354,086

(22) PCT Filed: Oct. 25, 2012

(86) PCT No.: PCT/JP2012/077660
§ 371 (c)(1),
(2) Date: Apr. 24, 2014

(87) PCT Pub. No.: WO2013/062065
PCT Pub. Date: May 2, 2013

(65) Prior Publication Data
US 2015/0031727 A1    Jan. 29, 2015

(30) Foreign Application Priority Data

Oct. 27, 2011 (JP) .................................. 2011-236533

(51) Int. Cl.
*A61K 31/4412* (2006.01)
*C07D 409/12* (2006.01)
*C07D 333/68* (2006.01)

(52) U.S. Cl.
CPC ............ *C07D 409/12* (2013.01); *C07D 333/68* (2013.01)

(58) Field of Classification Search
CPC .................................................... C07D 409/12
USPC ...................................... 514/333; 546/281.1
See application file for complete search history.

(56) References Cited

U.S. PATENT DOCUMENTS

| | | |
|---|---|---|
| 2006/0217426 A1 | 9/2006 | Eto et al. |
| 2012/0115851 A1 | 5/2012 | Eto et al. |
| 2013/0029973 A1 | 1/2013 | Hachiya et al. |
| 2013/0053369 A1 | 2/2013 | Hachiya et al. |
| 2013/0336918 A1 | 12/2013 | Lewis et al. |
| 2013/0336919 A1 | 12/2013 | Lewis et al. |
| 2013/0336920 A1 | 12/2013 | Lewis et al. |
| 2013/0336921 A1 | 12/2013 | Lewis et al. |
| 2014/0023611 A1 | 1/2014 | Lewis et al. |

FOREIGN PATENT DOCUMENTS

| | | |
|---|---|---|
| JP | 2007 131532 | 5/2007 |
| WO | 02 28353 | 4/2002 |
| WO | 03 048134 | 6/2003 |
| WO | 2004 085382 | 10/2004 |
| WO | 2006 026619 | 3/2006 |
| WO | 2006 044826 | 4/2006 |
| WO | 2006 093518 | 9/2006 |
| WO | 2011 136269 | 11/2011 |
| WO | 2012 006473 | 1/2012 |
| WO | 2012 006474 | 1/2012 |
| WO | 2012 006475 | 1/2012 |
| WO | 2012 006477 | 1/2012 |
| WO | 2012 054110 | 4/2012 |

OTHER PUBLICATIONS

"Kdigo Clinical Practice Guideline for the diagnosis, Evaluation, Prevention, and Treatment of Chronic Kidney Disease-Mineral and Bone Disorder (CKD-MBD)", Kidney International, vol. 76, Supplement 113, (Aug. 2009).
Sabbagh, et al. "Intestinal Npt2b Plays a Major Role in Phosphate Absorption and Homeostasis", Journal of American Society of Nephrology, vol. 20, pp. 2348-2358, (2009).
International Search Report Issued Jan. 22, 2013 in PCT/JP12/077660 Filed Oct. 25, 2012.
Extended European Search Report issued on Dec. 22, 2014 in European Patent Application No. 12844048.4.
Office Action dated Dec. 3, 2014 issued in corresponding Chinese patent application No. 201280053147.6 with English translation.

*Primary Examiner* — Taofiq A Solola
(74) *Attorney, Agent, or Firm* — Oblon, McClelland, Maier & Neustadt, L.L.P.

(57) ABSTRACT

[Problem] To provide a compound that has an intestinal phosphate transporter (NPT-IIb) inhibitory action and is useful as an active ingredient of an agent for treating and/or preventing hyperphosphatemia.
[Means for Solution] The present inventors conducted their studies on a compound that has an NPT-IIb inhibitory action and is useful as an active ingredient of an agent for treating and/or preventing hyperphosphatemia. As a result, they created an aminoalkyl-substituted N-thienylbenzamide derivative which has NPT-IIb inhibitory action, thereby completing the present invention. The aminoalkyl-substituted N-thienylbenzamide derivative of the present invention has an NPT-IIb inhibitory action and can be used as an agent for preventing and/or treating hyperphosphatemia.

14 Claims, No Drawings

AMINOALKYL-SUBSTITUTED N-THIENYLBENZAMIDE DERIVATIVE

TECHNICAL FIELD

The present invention relates to an aminoalkyl-substituted N-thienylbenzamide derivative useful as an active ingredient of a pharmaceutical composition, for example, a pharmaceutical composition for treating hyperphosphatemia.

BACKGROUND ART

Phosphorus is an essential element in the maintenance of life and plays very important roles in various physiological functions. Phosphorus is taken up in the form of phosphate through the gastrointestinal tract from food, and most of the phosphorus is excreted by incorporation into urine, whereby its total amount in a living is maintained and regulated. It is known that in the process of formation of urine, substantially most of phosphate is filtered at the glomerulus and only a necessary amount thereof is reabsorbed in the tubules. Accordingly, if the filtration ability of the glomerulus decreases as renal failure progresses, excretion of phosphorus becomes insufficient, and abnormal increase in the serum phosphorus level, that is, hyperphosphatemia is caused. Thus, hyperphosphatemia that induces various complications of renal failure is considered to be a factor for reducing the QOL of a patient with renal failure through fractures and bone pain, or a factor of death of a patient with renal failure through cardiovascular diseases resulting from cardiovascular calcification. Consequently, hyperphosphatemia is a very major issue in clinical practice ("KDIGO Clinical Guideline for the Diagnosis, Evaluation, Prevention, and Treatment of Chronic Kidney Disease-Mineral and Bone Disorder (CKD-MBD))", Kidney International, 76, Supplement 113 (2009)).

Currently, for the treatment of hyperphosphatemia, phosphate binders are used, for example, various calcium salt preparations represented by precipitated calcium carbonate, polymers represented by sevelamer hydrochloride, or metal salt preparations such as lanthanum carbonate, aluminum hydroxide, and iron preparations. However, these drugs have various problems, such as poor dose adherence due to the requirement for several grams per day, gastrointestinal symptoms such as constipation and diarrhea, increase in serum calcium levels, and accumulation of various metals. Therefore, development of a novel agent for treating hyperphosphatemia that improves the above factors is required (ibid).

Phosphate transporters present in the brush-border membrane of the gastrointestinal tract and renal tubules are considered to be involved in the absorption and excretion of phosphorus. So far, a large number of phosphate transporters have been reported. Among these, NPT-IIb plays a main role in phosphate absorption in the gastrointestinal tract, and NPT-IIa plays a main role in phosphate reabsorption in the kidneys. In addition, these molecules have been reported to be cotransporters of sodium and phosphate. In this respect, it has been pointed out that if the function of the NPT-IIb is inhibited, phosphorus absorption from the gastrointestinal tract can be suppressed (Journal of the American Society of Nephrology, 20: p 2348-2358 (2009)).

A drug for treating hyperphosphatemia based on this mechanism of action is being studied, and for example, a compound represented by the following general formula has been reported to be a compound having NPT-IIb inhibitory action (Patent Document 1).

[Chem. 1]

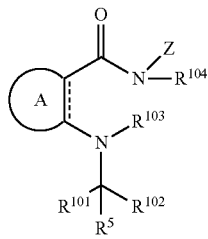

(In the formula, A represents a 5- to 9-membered unsaturated carbocycle portion or unsaturated heterocycle portion; when the carbocycle portion or the heterocycle portion represented by A is substituted with two $C_{1-6}$alkyl groups or $C_{2-6}$alkenyl groups, these alkyl groups or alkenyl groups may form a 5- to 7-membered unsaturated carbocycle in combination with the carbon atoms to which these groups bind; $R^5$ represents an aryl group or the like which may be substituted; $R^{101}$ and $R^{102}$ in combination represent =O, $R^{103}$ and $R^{104}$ represent a hydrogen atom or the like; and Z represents the following Formula (A), (B), or (C) in which $R^6$ and $R^7$ may be the same as or different from each other and represent a hydrogen atom, an aryl group, or the like, and $R^{17}$ represents a hydrogen atom. Regarding other symbols in the formula, see the corresponding gazette.)

[Chem. 2]

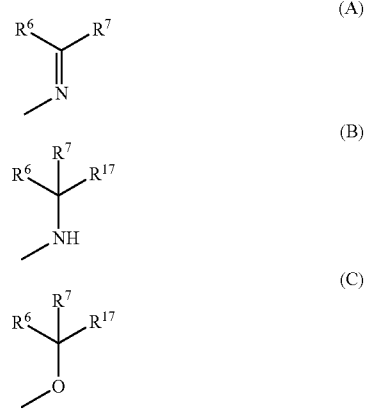

In addition, as compounds that have the NPT-IIb inhibitory action and are used for preventing or treating hyperphosphatemia, a triazole compound (Patent Document 2) and a quinazolone compound (Patent Document 3) have been disclosed.

Moreover, a tetrahydrobenzothiophene derivative that has a carbonylamino group at a 2-position and a carbamoyl group at a 3-position has been reported. For example, a tetrahydrobenzothiophene compound represented by the following general formula is reported to have an antiviral action (Patent Document 4).

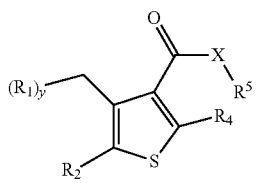

(In the formula, X represents N(R') or an oxygen atom, $R_1$ and $R_2$ form a ring in combination with atoms bonded thereto, y represents 0 to 3, $R_3$ represents a substituted carbocycle or heterocycle, or the like, $R_4$ represents —N(R')—C(O)—$R_7$ or the like, $R_7$ represents a substituted carbocycle or heterocycle, or the like, and R' represents a hydrogen atom or lower alkyl. Regarding other symbols in the formula, see the corresponding gazette.)

A tetrahydrobenzothiophene compound represented by the following general formula is reported to have an antiviral action (Patent Document 5).

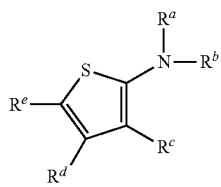

(In the formula, $R^a$ represents a hydrogen atom, an alkyl group, or the like which may be substituted, $R^b$ represents —C(O)—$R^{b1}$ or the like which may be substituted, $R^{b1}$ represents amino, aminoalkyl, a carbocycle, a heterocycle, or the like which may be substituted, $R^c$ represents —C(O)—$R^{b1}$ or the like which may be substituted, and $R^d$ and $R^e$ represent a carbocycle, a heterocycle, formed in combination with atoms bonded thereto or the like which may be substituted. Regarding other symbols in the formula, see the corresponding gazette.)

A tetrahydrobenzothiophene compound represented by the following general formula is reported to have an antitumor action (Patent Document 6).

[Chem. 5]

(In the formula, W represents a carbon atom or a nitrogen atom, A represents 5- to 14-membered cycloalkyl, heteroaryl, or the like which may be substituted, Y represents —$NR^1R^2$ or the like, X represents —C(O)$NR^5R^6$ or the like, $R^1$ represents a hydrogen atom or lower alkyl, $R^2$ represents —C(O) $R^{10}$ or the like, $R^{10}$ represents aryl, heteroaryl, or the like which may be substituted, $R^5$ represents aryl, heteroaryl, or the like which may be substituted, and $R^6$ represents a hydrogen atom or the like. Regarding other symbols in the formula, see the corresponding gazette.)

However, none of Patent Documents 4 to 6 disclose or suggest that these compounds have an NPT-IIb inhibitory action or can be used for preventing or treating hyperphosphatemia.

RELATED ART

Patent Document

[Patent Document 1] Pamphlet of International Publication WO2004/085382
[Patent Document 2] Pamphlet of International Publication WO2003/048134
[Patent Document 3] JP-A-2007-131532
[Patent Document 4] Pamphlet of International Publication WO2006/026619
[Patent Document 5] Pamphlet of International Publication WO2006/093518
[Patent Document 6] Pamphlet of International Publication WO2006/044826

DISCLOSURE OF INVENTION

Problems to be Solved by the Invention

The present invention provides an aminoalkyl-substituted N-thienylbenzamide derivative useful as an active ingredient of a pharmaceutical composition, for example, a pharmaceutical composition for treating hyperphosphatemia.

Means for Solving the Problems

The present inventors conducted thorough research aiming at creating a compound having an NPT-IIb inhibitory action. As a result, they found that an N-thienylbenzamide compound having a characteristic substituent on an aromatic ring of benzamide has an NPT-IIb inhibitory action and an action of inhibiting phosphorus absorption from the intestinal tract, thereby completing the present invention.

That is, the present invention relates to a compound of Formula (I) or a salt thereof and to a pharmaceutical composition containing the compound of Formula (I) or a salt thereof and an excipient.

[Chem. 6]

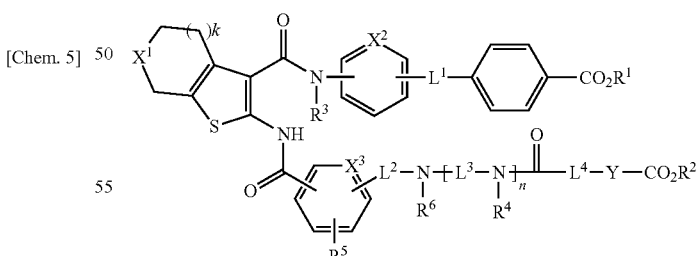

(1)

(In formula,
$X^1$ represents $CH_2$ or O,
k represents 1, 2, or 3,
$R^3$ represents H or lower alkyl,
$X^2$ represents CH or N,
$L^1$ represents lower alkylene,
$R^1$ represents H or lower alkyl,
$X^3$ represents CH or N, $L^2$ represents lower alkylene, $R^5$ represents H or lower alkyl, $R^6$ represents H, lower alkyl, lower alkyl substituted with one to two of $—OR^0$, —C(O)-lower alkyl, $—S(O)_m$-lower alkyl, -lower alkylene-N(lower alkyl)$_2$, $—R^{00}$-heterocycle, $—R^{00}$-phenyl, or $—R^{00}$-cycloalkyl, wherein the heterocycle, phenyl, and cycloalkyl may be substituted with one to two lower alkyl or C(O)-lower alkyl, and $—R^{00}$ may be substituted with one $—OR^0$, $R^{00}$ represents a bond or lower alkylene, $R^0$ represents H or lower alkyl, m represents 0, 1, or 2, $L^3$ represents lower alkylene, n represents 0 or 1, $R^4$ represents H, lower alkyl, -lower alkylene-COO—$R^0$, -lower alkylene-$OR^0$, -lower alkylene-$NHR^0$, -lower alkylene-N(lower alkyl)$_2$, or cycloalkyl, $L^4$ represents a bond, O, or $—NR^0$—, Y represents $—R^{00}$-monocyclic heterocycle-$R^{00}$—, $—R^{00}$-phenyl-$R^{00}$—, -lower alkylene-$NR^0$-lower alkylene-, lower alkylene-O-lower alkylene-, or lower alkylene which may be substituted with a hydroxyl group, and, $R^2$ represents H or lower alkyl.)

In addition, unless otherwise specified, when symbols in a certain chemical formula in the present specification are also used in another chemical formula, the same symbol represents the same meaning.

The present invention also relates to a pharmaceutical composition containing the compound of Formula (I) or a salt thereof, particularly, to a pharmaceutical composition for treating or preventing hyperphosphatemia. Moreover, the pharmaceutical composition includes an agent for treating hyperphosphatemia containing the compound of Formula (I) or a salt thereof.

In addition, the present invention relates to use of the compound of Formula (I) or a salt thereof for the manufacture of a pharmaceutical composition for treating or preventing hyperphosphatemia, use of the compound of Formula (I) or a salt thereof for treating or preventing hyperphosphatemia, the compound of Formula (I) or a salt thereof for treating or preventing hyperphosphatemia, and a method of treating hyperphosphatemia including administering an effective amount of the compound of Formula (I) or a salt thereof to a subject. In addition, the "subject" refers to a human being or other animals that require the treatment or prevention of hyperphosphatemia, and as a certain embodiment, the "subject" refers to a human being that requires the prevention or treatment of hyperphosphatemia.

Effects of the Invention

The compound of Formula (I) or a salt thereof has an NPT-IIb inhibitory action and can be used as an agent for preventing and/or treating hyperphosphatemia, renal insufficiency, or abnormality in bone metabolism caused by renal insufficiency.

EMBODIMENTS FOR CARRYING OUT THE INVENTION

Hereinafter, the present invention will be described in detail.

In the present specification, "lower alkyl" refers to linear or branched alkyl having 1 to 6 carbon atoms (herebelow, abbreviated to $C_{1-6}$), for example, methyl, ethyl, n-propyl, isopropyl, n-butyl, isobutyl, sec-butyl, tert-butyl, n-pentyl, 1-ethylpropyl, n-hexyl, or the like. As another embodiment, the alkyl is methyl, ethyl, n-propyl, isopropyl, tert-butyl, or 1-ethylpropyl, and as still another embodiment, the alkyl is methyl or 1-ethylpropyl.

"Lower alkylene" refers to linear or branched $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene, or the like. As another embodiment, the lower alkylene is methylene, ethylene, trimethylene, tetramethylene, or pentamethylene, and as still another embodiment, the lower alkylene is methylene, ethylene, or trimethylene.

"Cycloalkyl" refers to a saturated $C_{3-10}$ hydrocarbon ring group which may have bridge(s), for example, cyclopropyl, cyclobutyl, cyclopentyl, cyclohexyl, cycloheptyl, cyclooctyl, adamantyl, or the like. As another embodiment, the cycloalkyl is cyclopropyl, cyclobutyl, cyclopentyl, or cyclohexyl.

A "heterocyclic" group refers to a 3- to 15-membered, or, as another embodiment, 5- to 10-membered mono- to tricyclic heterocyclic group containing 1 to 4 hetero atoms selected from oxygen, sulfur, and nitrogen. The heterocyclic group includes a saturated ring, an aromatic ring, and a partially hydrogenated aromatic ring. Sulfur or nitrogen as a ring atom may be oxidized to form oxide or dioxide. The heterocyclic group is specifically monocyclic heteroaryl such as pyridyl, pyrrolyl, pyrazinyl, pyrimidinyl, pyridazinyl, imidazolyl, triazolyl, triazinyl, tetrazolyl, thiazolyl, pyrazolyl, isothiazolyl, oxazolyl, isoxazolyl, thiadiazolyl, oxadiazolyl, thienyl, or furyl; bicyclic heteroaryl such as indolyl, isoindolyl, benzimidazolyl, indazolyl, quinolyl, isoquinolyl, quinazolinyl, quinoxalinyl, phthalazinyl, benzothiazolyl, benzisothiazolyl, benzothiadiazolyl, benzoxazolyl, benzisoxazolyl, benzofuranyl, or benzothienyl; tricyclic heteroaryl such as carbazolyl, dibenzo[b,d]furanyl, or dibenzo[b,d]thienyl; a non-aromatic monocyclic heterocycle such as azetidinyl, pyrrolidinyl, piperidyl, piperazinyl, azepanyl, diazepanyl, morpholinyl, thiomorpholinyl, tetrahydropyridinyl, oxetanyl, tetrahydrofuranyl, tetrahydropyranyl, dioxolanyl, dioxanyl, or tetrahydrothiopyranyl; a non-aromatic bicyclic heterocycle such as indolinyl, tetrahydroquinolyl, tetrahydroisoquinolyl, dihydrobenzimidazolyl, tetrahydrobenzimidazolyl, tetrahydroquinoxalinyl, dihydroquinoxalinyl, dihydrobenzoxazolyl, dihydrobenzoxazinyl, dihydrobenzofuryl, chromanyl, chromenyl, methylenedioxyphenyl, or ethylenedioxyphenyl; or a bridged heterocycle such as quinuclidinyl. As another embodiment, the heterocyclic group is pyridyl, thiazolyl, pyrazinyl, pyrimidinyl, pyrazolyl, oxadiazolyl, thiadiazolyl, furyl, thienyl, tetrahydropyranyl, tetrahydrofuranyl, pyrrolidinyl, piperidyl, piperazinyl, morpholinyl, or quinuclidinyl. As still another embodiment, the heterocyclic group is pyridyl, tetrahydrofuranyl, tetrahydropyranyl, or piperazinyl.

In the present specification, for convenience, a divalent or multivalent cyclic group, that is the group which has a plurality of substituents, is also expressed as a monovalent group such as aryl, cycloalkyl, or a heterocycle.

Some embodiments of the present invention contain the compounds of Formula (I) described below or a salt thereof:

(1) A compound of Formula (I) in which $X^1$ represents $CH_2$, as another embodiment, a compound in which $X^1$ represents O, (2) A compound of Formula (I) in which k represents 1, and as another embodiment, k represents 2 or 3, (3) A compound of Formula (I) in which $R^3$ represents H, (4) A compound of Formula (I) in which $X^2$ represents CH, (5) A compound of Formula (I) in which $L^1$ represents ethylene or trimethylene, and as another embodiment, $L^1$ represents ethylene, (6) A compound of Formula (I) in which $R^1$ represents H, (7) A compound of in Formula (I) in which $X^3$ represents CH, (8) A compound of Formula (I) in which $R^5$ represents H, (9) A compound of Formula (I) in which $L^2$ represents methylene,

(10) A compound of Formula (I) in which $R^6$ represents H, lower alkyl, lower alkyl substituted with one to two of —$OR^0$, —N(lower alkyl)$_2$, —C(O)-lower alkyl, —S(O)$_2$-lower alkyl, -lower alkylene-N(lower alkyl)$_2$, —$R^{00}$-heterocycle, —$R^{00}$-phenyl, or —$R^{00}$-cycloalkyl, wherein the heterocycle, phenyl, and cycloalkyl may be substituted with one to two lower alkyl or C(O)-lower alkyl; as another embodiment, a compound in which $R^6$ represents lower alkyl or cycloalkyl; as still another embodiment, a compound in which $R^6$ represents 1-ethylpropyl or cyclopropyl; an embodiment of the above heterocycle consists of morpholinyl, tetrahydrofuranyl, tetrahydropyranyl, quinuclidinyl, pyridyl, piperidyl, or piperazinyl,

(11) A compound of Formula (I) in which $L^3$ represents ethylene or trimethylene,

(12) A compound of Formula (I) in which $R^4$ represents H, lower alkyl, -lower alkylene-$OR^0$, or -lower alkylene-COO—R; as another embodiment, a compound in which $R^4$ represents H, lower alkyl or lower alkylene-$OR^0$,

(13) A compound of Formula (I) in which n represents 0; as another embodiment, a compound in which n represents 1,

(14) A compound of Formula (I) in which $L^4$ represents a bond or O,

(15) A compound of Formula (I) in which Y represents —$R^{00}$-phenyl-$R^{00}$—; as another embodiment, a compound in which Y represents lower alkylene which may be substituted with a hydroxyl group, —$R^{00}$-monocyclic heterocycle-$R^{00}$—, -lower alkylene-$NR^0$-lower alkylene-, or lower alkylene-O-lower alkylene-; as still another embodiment, a compound in which Y represents lower alkylene which may be substituted with a hydroxyl group, or -lower alkylene-$NR^0$-lower alkylene-; as another embodiment, a compound in which Y represents lower alkylene which may be substituted with a hydroxyl group; an embodiment of the above monocyclic heterocycle consists of piperazinyl, pyridyl or piperidyl,

(16) A compound of in Formula (I) in which $R^2$ represents H,

(17) A compound which has one of the groups according to the above embodiments (1) to (16) or is a combination of two or more of the groups.

In regard to the above embodiment (17), some embodiments of the present invention relating to Formula (I) are exemplified below:

(18) A compound of Formula (I) in which $R^6$ represents lower alkyl or cycloalkyl,

(19) The compound according to embodiment (18), in which n represents 1, and $R^4$ represents H, lower alkyl or lower alkylene-$OR^0$,

(20) The compound according to embodiment (19), in which Y represents lower alkylene which may be substituted with a hydroxyl group,

(21) The compound according to embodiment (20), in which $X^1$ represents $CH_2$ and k represents 1,

(22) The compound according to embodiment (21) in which both the $X^2$ and $X^3$ are CH,

(23) The compound according to embodiment (18), in which n represents 0.

Specific examples of the compounds included in the present invention are exemplified below.

4-(2-{4-[({2-[(3-{[{2-[(3-carboxypropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid, 4-(2-{4-[({2-[(3-{[(2-{[(carboxymethoxy)carbonyl](methyl)amino}ethyl) (pentan-3-yl)amino]methyl}benzoyl)amino]-4,5,6,7-tetrahydro-1-benzothiophen-3-yl}carbonyl)amino]phenyl}ethyl)benzoic acid, 4-(2-{4-[({2-[(3-{[{2-[(4-carboxy-4-methylpentanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid, 4-(2-{4-[({2-[(3-{[{3-[(3-carboxypropanoyl)(methyl)amino]propyl}(pentan-3-yl)amino]methyl}benzoyl)amino]-4,5,6,7-tetrahydro-1-benzothiophen-3-yl}carbonyl)amino]phenyl}ethyl)benzoic acid, 4-(2-{4-[({2-[(3-{[{2-[(3-carboxypropanoyl)(2-methoxyethyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid, 4-(2-{4-[({2-[(3-{[(4-carboxy-4-methylpentanoyl)(pentan-3-yl)amino]methyl}benzoyl)amino]-4,5,6,7-tetrahydro-1-benzothiophen-3-yl}carbonyl)amino]phenyl}ethyl) benzoic acid, 4-(2-{4-[({2-[(3-{[(4-carboxy-3,3-dimethylbutanoyl)(pentan-3-yl)amino]methyl}benzoyl)amino]-4,5,6,7-tetrahydro-1-benzothiophen-3-yl}carbonyl)amino]phenyl}ethyl) benzoic acid, or a salt thereof.

The compound of Formula (I) has a tautomer or a regio isomer depending on the type of substituents. In the present specification, when a compound of the Formula (I) is described in only one form of its isomers, the present invention includes other isomers, separated form of these isomers, or a mixture thereof.

In addition, the compound of Formula (I) has asymmetric carbon atoms or axis chirality in some cases, and there may be optical isomers based on these chiralities. The present invention includes separated optical isomers of the compound of Formula (I) or a mixture thereof.

Moreover, the present invention includes pharmaceutically acceptable prodrugs of the compound represented by Formula (I). The pharmaceutically acceptable prodrugs refer to compounds having a group that can be converted into an amino group, a hydroxyl group, a carboxyl group, or the like by solvolysis or under physiological conditions. Examples of the groups that form the prodrugs include the groups disclosed in Prog. Med., 5, 2157-2161 (1985) or in "Pharmaceutical Research and Development", (Hirokawa Publishing Company, 1990), Vol. 7, Drug Design 163-198.

The salt of the compound of Formula (I) refers to a pharmaceutically acceptable salt of the compound of Formula (I), and an acid addition salt or a salt with a base is formed depending on the type of substituents. Specific examples of the salt include acid addition salts with an inorganic acid such as hydrochloric acid, hydrobromic acid, hydriodic acid, sulfuric acid, nitric acid or phosphoric acid, or with an organic acid such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid or glutamic acid, inorganic salts with a metal such as lithium, sodium, potassium, magnesium, calcium or aluminum, or with an organic base such as methylamine, ethylamine, ethanolamine, lysine, arginine, histidine, meglumine, tromethamine, or ornithine, salts with various amino acids and amino acid derivatives such as acetylleucine, ammonium salts, and the like.

The present invention also includes various hydrates or solvates and polymorphic substances of the compound of Formula (I) and a salt thereof. In addition, the present invention includes compounds labeled with various radioisotopes or non-radioactive isotopes.

(Preparation Process)

The compound of Formula (I) or a salt thereof can be prepared by applying various known synthesis processes, by using characteristics based on the basic structure thereof or the type of substituents. At this time, depending on the type of functional groups, it is in some cases effective to change the functional group to advance with an appropriate protective group (group that can be easily converted into said functional group) at some stage between a starting material and a final intermediate. Examples of the protective group include those disclosed in Wuts (P. G. M. Wuts) and Greene (T. W. Greene), "Greene's Protective Groups in Organic Synthesis (4$^{th}$ edition, 2006)", and the like. The protective group may be appropriately selected and used according to the reaction conditions of the target reaction. After the protective group is introduced as described above, the reaction is performed, and then the protective group is appropriately removed, whereby a desired compound can be obtained.

In addition, a prodrug of the compound of Formula (I) can be prepared by introducing a specific group at some stage between a starting material and an intermediate in a similar manner as described in the above protective group, or by introducing such group to the obtained compound of Formula (I). The reaction can be performed by applying methods known to a person skilled in the art, such as esterification, amidation, and dehydration.

Hereinafter, a typical preparation process of the compound of Formula (I) will be described. Each preparation process can be performed with reference to the literatures cited in the corresponding description. Moreover, the preparation process of the present invention is not limited to the following examples.

Preparation Process 1

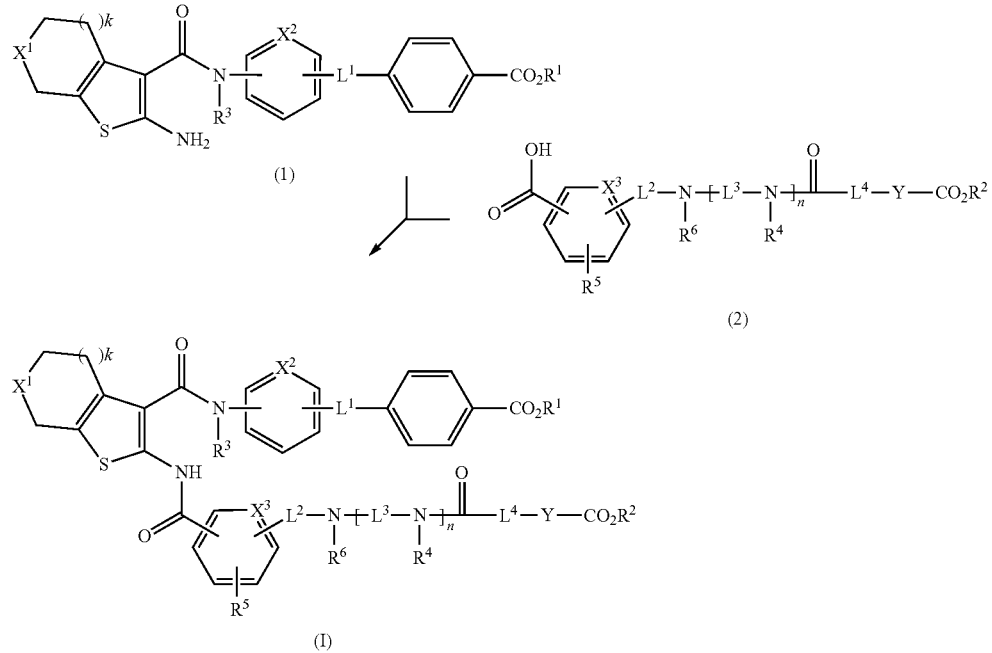

In the following reaction scheme, a compound (I) is simply described as (I).

The compound (I) of the present invention can be obtained from a reaction between a compound (1) and a compound (2).

In this reaction, both the compounds (1) and (2) are used in an equal amount, or one of the compounds is used in an excessive amount than the other. A mixture of these compounds is stirred generally for 0.1 hours to 5 days under cooling to heating preferably at −20° C. to 60° C. in a solvent inactive to the reaction in the presence of a condensing agent. Though not particularly limited, examples of the solvent used herein include aromatic hydrocarbons such as benzene, toluene, and xylene, halogenated hydrocarbons such as dichloromethane, 1,2-dichloroethane, and chloroform, ethers such as diethylether, tetrahydrofuran (THF), dioxane, and dimethoxyethane, N,N-dimethylformamide, dimethylsulfoxide, ethyl acetate, acetonitrile, water, and a mixture of these. Examples of the condensing agent include 1-(3-dimethylaminopropyl)-3-ethylcarbodiimide (WSC), dicyclohexylcarbodiimide, 1,1'-carbonyldiimidazole, diphenylphosphoryl azide and phosphorus oxychloride, but the present invention is not limited thereto. It is preferable to use an additive (for example, 1-hydroxybenzotriazole (HOBt)) in some cases for the reaction. It is advantageous to perform the reaction in the presence of an organic base such as triethylamine, N,N-diisopropylethylamine, or N-methylmorpholine, or an inorganic base such as potassium carbonate, sodium carbonate, or potassium hydroxide, in terms of causing the reaction to proceed smoothly.

In addition, it is also possible to use a method of converting carboxylic acid (2) into a reactive derivative and then reacting this with amine (1). Examples of the reactive derivative of carboxylic acid include acid halides obtained when the carboxylic acid reacts with a halogenating agent such as phosphorus oxychloride or thionyl chloride, mixed acid anhydrides obtained when the carboxylic acid reacts with isobutyl chloroformate or the like, and active esters obtained when the carboxylic acid is condensed with 1-hydroxybenzotriazole or the like. The reaction between these reactive derivatives and the compound (1) can be performed in a solvent inactive to the reaction, such as halogenated hydrocarbons, aromatic hydrocarbons, or ethers, under cooling to heating preferably at −20° C. to 60° C.

[Document]

S. R. Sandler and W. Karo, "Organic Functional Group Preparations", 2nd edition, Vol. 1, Academic Press Inc. 1991

The Chemical Society of Japan., "Jikken Kagaku Koza (Courses in Experimental Chemistry) (5th edition)", Vol. 16, (2005) (MARUZEN Co., Ltd.)

In Formula (I), the compound having a bond at $L^4$ can be prepared by a similar amidation reaction by using a corresponding carboxylic acid and an amine compounds as starting materials.

Preparation Process 2

In this reaction, both the compounds (3) and (4) are used in an equal amount, or one of the compounds used in an excessive amount than the other. A mixture of these is stirred generally for 0.1 hours to 5 days under cooling to heating under reflux preferably at 0° C. to 80° C. in a solvent inactive to the reaction or without using a solvent. Though not particularly limited, examples of the solvent used herein include aromatic hydrocarbons, ethers, halogenated hydrocarbons, N,N-dimethylformamide, dimethylsulfoxide, ethyl acetate, acetonitrile, and a mixture of these. It is advantageous to perform the reaction in the presence of an organic base such as triethylamine, N,N-diisopropylethylamine, or N-methylmorpholine, or an inorganic base such as potassium carbonate, sodium carbonate, or potassium hydroxide, in terms of causing the reaction to proceed smoothly.

[Document]

S. R. Sandler and W. Karo, "Organic Functional Group Preparations", 2nd edition, Vol. 1, Academic Press Inc. 1991

[Chem. 8]

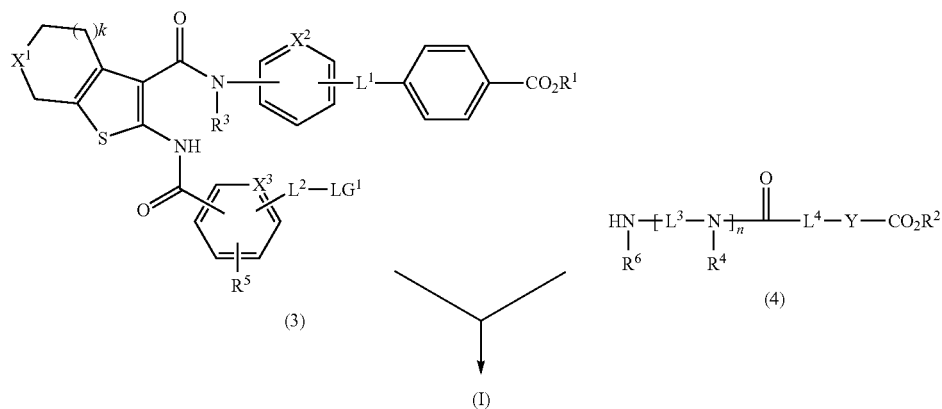

(In the formula, $LG^1$ represents an leaving group.)

The compound (I) of the present invention can be obtained from a reaction between a compound (3) and a compound (4). Herein, examples of the leaving group include halogen, methanesulfonyloxy, p-toluenesulfonyloxy groups and the like.

The Chemical Society of Japan., "Jikken Kagaku Koza (Courses in Experimental Chemistry) (5th edition)", Vol. 14, (2005) (MARUZEN Co., Ltd.)

Preparation Process 3

[Chem. 9]

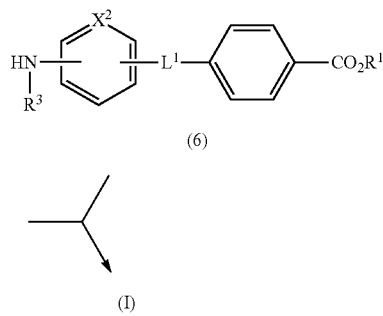

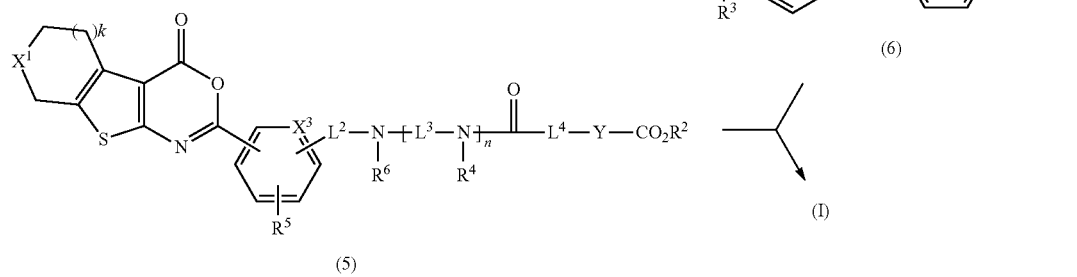

The compound (I) of the present invention can be obtained from a reaction between a compound (5) and a compound (6).

In this reaction, both the compounds (5) and (6) are used in an equal amount, or one of the compounds used in an excessive amount than the other. A mixture of these is stirred generally for 0.1 hours to 5 days under cooling to heating under reflux preferably at −78° C. to 60° C. in a solvent inactive to the reaction or without using a solvent in the presence of a base. Though not particularly limited, examples of the solvent used herein include aromatic hydrocarbons, ethers, and a mixture of these. As the base, butyllithium, lithium diisopropylamide, lithium hexamethyldisilazide, potassium hexamethyldisilazide, sodium hexamethyldisilazide, diisobutylaluminium hydride or pyridine can be used.

Preparation Process 4 agent. Though not particularly limited, examples of the solvent used herein include alcohols, ethers, halogenated hydrocarbons, and a mixture of these. Examples of the reducing agent include sodium cyanoborohydride, sodium triacetoxyborohydride, sodium borohydride, and the like. It is preferable to perform the reaction in the presence of a dehydrating agent such as molecular sieves or an acid such as acetic acid, hydrochloric acid, or a titanium(IV) isopropoxide complex in some cases. Depending on the reaction, an imine generates by the condensation of the compounds (7) and (8) and can be isolated as a stable intermediate in some cases. In this case, the compound (Ia) can be obtained by a reduction reaction of the imine intermediate. In addition, instead of treating the compounds with the reducing agent, it is possible to perform the reaction in a solvent such as methanol, ethanol, or ethyl

[Chem. 10]

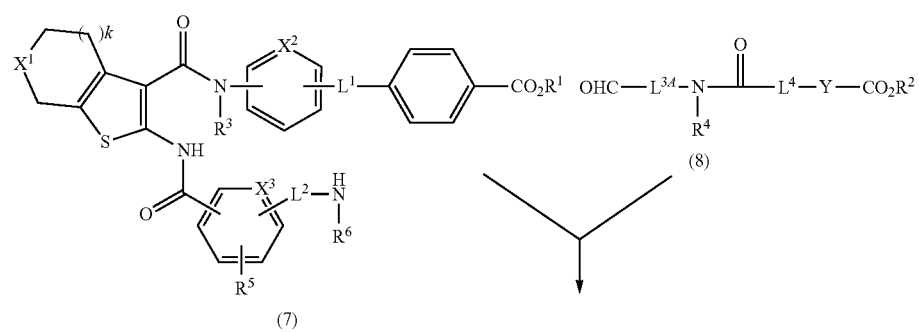

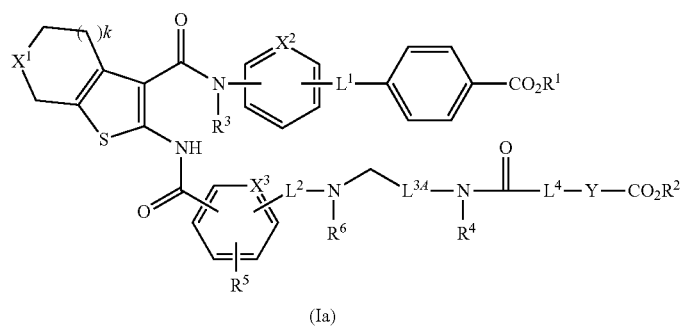

(In the formula, $L^{3A}$ represents lower alkylene that is a group forming $L^3$ of Formula (I) together with an adjacent methylene group in Formula (Ia).)

A compound (Ia) in which n represents 1 and $L^3$ represents —$CH_2$-$L^{3A}$ in the compound (I) of the present invention can be obtained from a reaction between a compound (7) and a compound (8).

In this reaction, both the compounds (7) and (8) are used in an equal amount, or one of the compounds used in an excessive amount than the other. A mixture of these is stirred generally for 0.1 hours to 5 days from −45° C. to heating under reflux preferably at 0° C. to room temperature in a solvent inactive to the reaction in the presence of a reducing acetate in the presence or absence of an acid such as acetic acid or hydrochloric acid by using a reduction catalyst (for example, palladium carbon or Raney nickel). In this case, it is preferable to perform the reaction in a hydrogen atmosphere under normal pressure to 50 atm, under cooling to heating.

[Document]

A. R. Katritzky and R. J. K. Taylor, "Comprehensive Organic Functional Group Transformations II", Vol. 2, Elsevier Pergamon, 2005

The Chemical Society of Japan., "Jikken Kagaku Koza (Courses in Experimental Chemistry) (5th edition)", Vol. 14, (2005) (MARUZEN Co., Ltd.)

Preparation Process 5

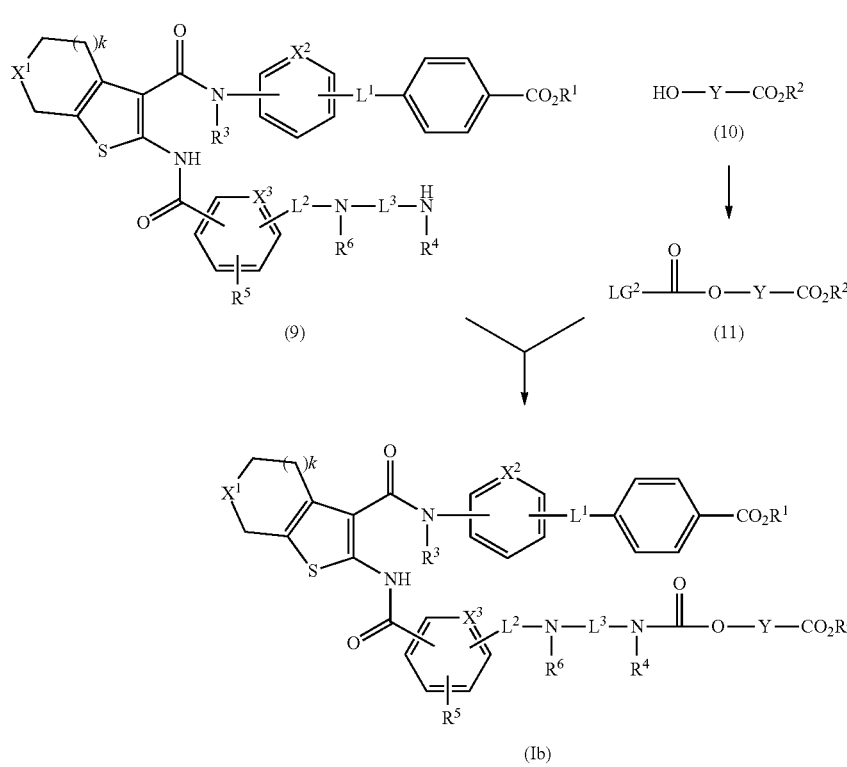

(In the formula, $LG^2$ represents an leaving group.)

A compound (Ib) in which n represents 1 and $L^4$ represents O in the compound (I) of the present invention can be obtained by converting a compound (10) into a carbonate ester derivative (11) and then reacting it with an amine compound (9). Examples of the leaving group include Cl, imidazolyl, phenoxy, and 4-nitrophenoxy groups.

The first step is performed by reacting the compound (10) with a carbonylating reagent in an equal amount or with a carbonylating reagent that is used in an excessive amount than the compound (10) generally for about 0.1 hours to 1 day under cooling to heating preferably at −20° C. to 80° C. in a solvent inactive to the reaction in the presence of a base. In the next step, without quenching the first step reaction, equimolar amount or excess amount of the amine compound (9) is added to the reaction mixture, and this mixture is stirred for about 0.1 hours to 1 day under cooling to heating preferably from −20° C. to 80° C. Though not particularly limited, examples of the solvent used herein include halogenated hydrocarbons, aromatic hydrocarbons, ethers, N,N-dimethylformamide, dimethyl sulfoxide, ethyl acetate, acetonitrile, and a mixture of these. Examples of the carbonylating reagent include diphosgene, triphosgene, 1,1'-carbonyldiimidazole, 4-nitrophenyl chloroformate, and phenyl chloroformate. In case a phenylcarbonate intermediate is stable, this may be isolated first, and then the next reaction may be performed.

[Document]

S. R. Sandler and W. Karo, "Organic Functional Group Preparations", $2^{nd}$ edition, Vol. 2, Academic Press Inc. 1991

A compound of Formula (I) in which n represents 1 and $L^4$ represents —$NR^0$— can also be prepared by ureation reaction using the compound (9) and a compound ($HNR^0$—Y—$CO_2R^2$) corresponding to the compound (10) as starting materials under the conditions similar to those described above.

Preparation Process 6

In the compound (I) of the present invention, a compound having a carboxyl group in a molecule can be prepared by preparing a precursor in which the carboxyl was protected in the method described above followed by deprotection of the precursor. This reaction can be performed with reference to Greene and Wuts, "Protective Groups in Organic Synthesis" $3^{rd}$ edition, John Wiley & Sons Inc, 1999.

Preparation Process of Starting Compound

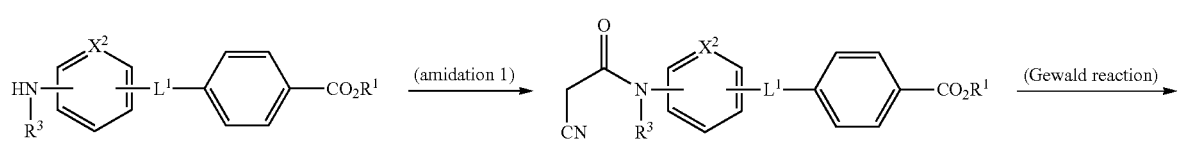

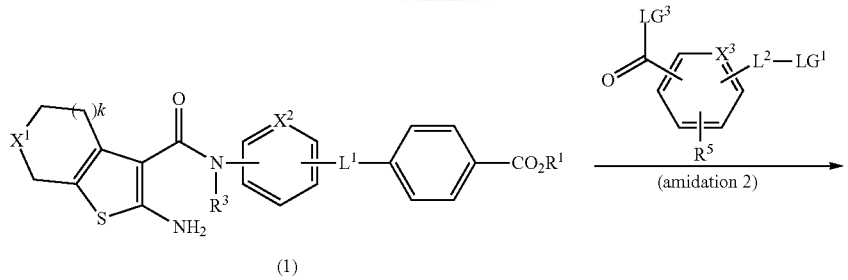

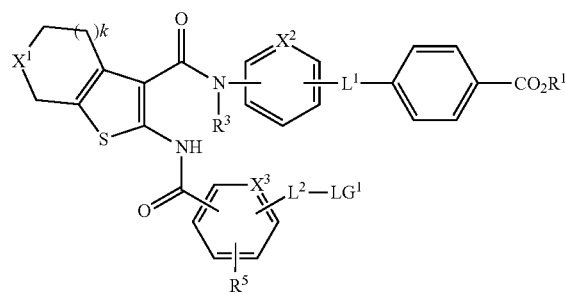

(In the formula, $LG^3$ represents halogen.)

The starting compounds (1) and (3) in the Preparation processes 1 and 2 can be prepared by the reaction described above. In the above description, amidation 1 can be particularly performed by a method using a condensing agent in the conditions of the Preparation process 1. Amidation 2 can be performed by using the conditions similar to a certain case of Preparation process 1 in which a carboxylic acid compound is transformed into a reactive derivative, and then the derivative is reacted with an amine compound. Gewald reaction can be performed with reference to K. Gewald, "Chem. Ber., 98 (1965), 3571".

The starting compounds of the aforementioned Preparation processes 4 to 6 can also be prepared by the above preparation process, otherwise, in some cases, by combining the Preparation processes 1 and 2. For example, the starting compound (7) of the Preparation process 4 can be prepared using the starting material (3) and $R^6NH_2$, under the conditions similar to the Preparation process 2.

[Chem. 13]

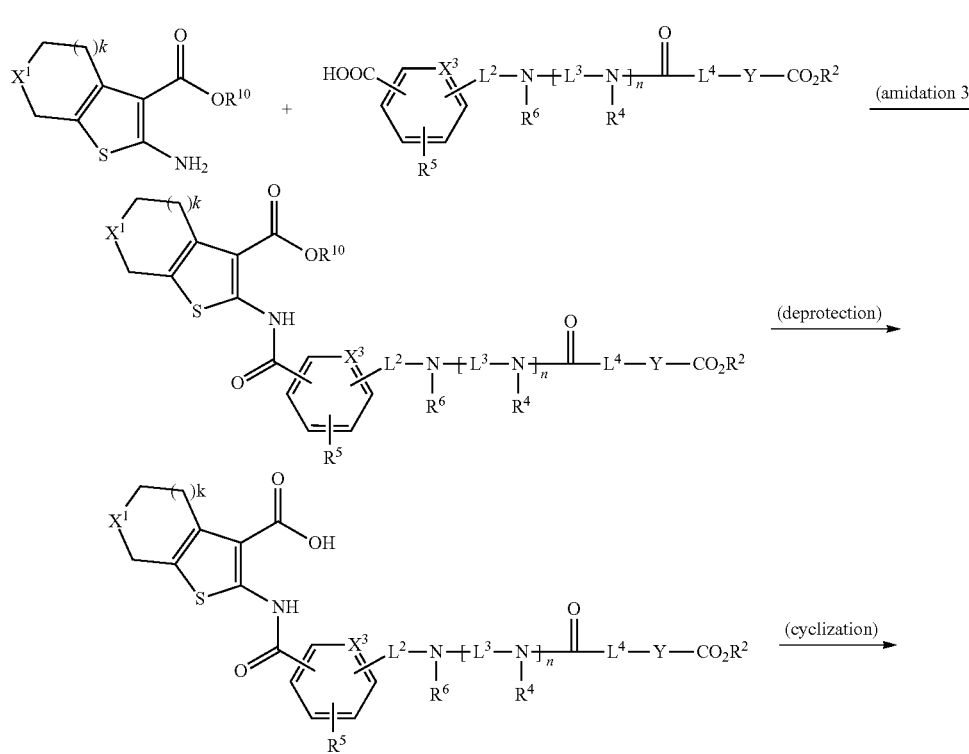

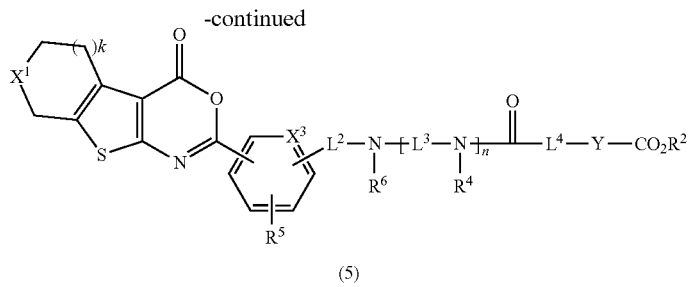

(5)

(In the formula, $R^{10}$ represents a protective group of a carboxyl group.)

The starting compound (5) in the Preparation process 3 can be prepared by the above reaction. In the above formula, amidation 3 can be performed using the conditions of the Preparation process 1. Deprotection can be performed with reference to Greene and Wuts, "Protective Groups in Organic Synthesis", $3^{rd}$ edition, John Wiley & Sons Inc, 1999. Cyclization can be performed with reference to I. A. Kharizomenova, "Chemistry of Heterocyclic Compounds, 1980, vol. 16, 36".

The compound of Formula (I) is isolated and purified as a free compound, a salt thereof, hydrate, solvate, or polymorphic substance. The salt of the compound of Formula (I) can be prepared by a salt preparation reaction using a common method.

Isolation and purification are performed by applying standard chemical operations such as extraction, fractionated crystallization, and various types of fractionation chromatography.

Various isomers can be prepared by selecting appropriate starting compounds, or can be separated using differences in physicochemical characteristics between isomers. For example, an optical isomer is obtained by general optical resolution of a racemate (for example, fractionated crystallization of diastereomeric salt with a chiral base or acid, otherwise chromatography using a chiral column), or can be prepared from an appropriate starting compound that is optically active.

The pharmacological activity of the compound of Formula (I) was confirmed by the following test.

Test Example 1

Inhibitory Action Against $^{33}$P-Phosphate Uptake into Rat NPT-IIb Expression Cell (1) Preparation of Rat NPT-IIb Expression Cell A rat small intestine cDNA library was used as a template, and rat NPT-IIb ORF was cloned into p3×FLAG-CMV-10 by PCR according to the prescribed method. Thereafter, 293 cells were transfected with the cloned rat NPT-IIb expression plasmid, thereby obtaining a rat NPT-IIb stable expression cell line by using G418.

(2) Evaluation System for Inhibition of Phosphate Uptake into Rat NPT-IIb Expression Cell The rat NPT-IIb expression cells were seeded to a 96-well plate, followed by incubation overnight. Thereafter, the culture medium was removed, the plate was washed with buffer A (137 mM N-methyl-D-glucamine, 5.4 mM KCl, 2.8 mM $CaCl_2$, 1.2 mM $MgCl_2$, and 10 mM HEPES (adjusted to pH 7.4 using HCl)), and then buffer B (137 mM NaCl, 5.4 mM KCl, 2.8 mM $CaCl_2$, 1.2 mM $MgCl_2$, 0.1 mM $KH_2PO_4$, and 10 mM HEPES (adjusted to pH 7.4 using KOH)) was added thereto. Subsequently, a compound with a concentration of 10 times the evaluation concentration was prepared by dilution with the buffer B and added thereto. After the resultant was incubated in a $CO_2$ incubator, the buffer B supplemented 50 μCi/mL of $^{33}$P was added thereto, and then the resultant was incubated again in a $CO_2$ incubator. After the reaction, the buffer was removed, the plate was washed with buffer C (137 mM NaCl, 10 mM Tris/HCl, pH 7.2). Thereafter, MicroScint-20 was added thereto, and $^{33}$P uptake was measured using TopCount. An inhibition rate was calculated by the following formula.

Inhibition rate (%)=(1−($^{33}$P uptake of well treated with chemical)/($^{33}$P uptake of DMSO-added well))×100

Table 1 illustrates examples of the inhibition rate (Int. 1) of the $^{33}$P-phosphate uptake into the rat NPT-IIb in some of the compounds of the present invention at a concentration of drug efficacy evaluation of 1 μM. Here, Ex represents the number of example compounds described later (the same shall apply hereinafter).

TABLE 1

| Ex | Int. 1 (%) |
|---|---|
| 2 | 87 |
| 4 | 77 |
| 31 | 87 |
| 37 | 77 |
| 38 | 61 |
| 41 | 73 |
| 43 | 65 |
| 53 | 85 |
| 60 | 86 |
| 66 | 76 |
| 67 | 89 |
| 70 | 60 |
| 79 | 75 |
| 96 | 70 |
| 99 | 71 |
| 109 | 86 |
| 121 | 79 |
| 172 | 48 |

Test Example 2

Action of Inhibiting Increase in Blood Radioactivity in Rat Orally Loaded with $^{32}$P Phosphate (Phosphate Absorption Inhibitory Action)

Male Wistar rats (6- to 7-week old) were fasted for 24 hours and then used as experimental animals. The compound was suspended or dissolved with a solvent, and was used at a concentration of 0.6 mg/mL. The compound was forcibly orally administered at a dose of 3 mg/kg to the animals of a compound-administered group. Control-group animals were administered a solvent containing no compound at a dose of 5 mL/kg. After 5 minutes from administration of the compound or the solvent, a $^{32}$P-containing phosphate solution (8.3 mM $NaH_2PO_4$) was orally administered thereto at a dose of 7.2 mL/kg. After 15 minutes and 30 minutes, the blood was taken from the orbital venous plexus and the serum was collected. Radioactivity in 0.1 mL of the serum was measured by a liquid scintillation counter. $AUC_{0-30\ min}$ in calculated from the measured counts was considered as a phosphate absorption amount. The phosphate absorption inhibitory rate was determined from the $AUC_{0-30\ min}$ value according to the following formula.

Inhibition rate of phosphate absorption (%)=(1−phosphate absorption count of compound-administered group/phosphate absorption count of standard group)×100

Table 2 illustrates examples of the inhibition rate (Int. 2) of phosphate absorption in regard to some of the compounds of Formula (I).

TABLE 2

| Ex | Int. 2 (%) |
|---|---|
| 2 | >60 |
| 4 | 53 |
| 60 | 56 |
| 66 | 59 |

As described above, it was found that the compound of the present invention has an action of inhibiting NPT-IIb-mediated phosphate uptake and exhibits action of inhibiting phosphate absorption from the intestinal tract even in vivo. Consequently, the compound of Formula (I) can be used for the treatment and the like of hyperphosphatemia and the like.

The pharmaceutical composition containing one or two or more kinds of the compound of Formula (I) or a salt thereof as an active ingredient can be prepared using excipients generally used in the related art, that is, using excipients or carriers for medications, by methods generally used.

The composition can be administered in any forms such as oral administration by using a tablet, a pill, a capsule, granules, powder, or liquid, and parenteral administration by using a preparation for injection such as intra-articular injection, intravenous injection, and intramuscular injection, a suppository, an eye drop, an eye ointment, a transdermal liquid, an ointment, a transdermal patch, a transmucosal liquid, a transmucosal patch, or an inhalation.

As a solid composition for oral administration, a tablet, powder, granules, and the like are used. In such a solid composition, one or two or more kinds of active ingredients are mixed with at least one kind of inactive excipient. The composition may contain inactive additives, for example, a lubricant, a disintegrating agent, a stabilizer, and a dissolution adjuvant according to common methods. The tablet or pill may optionally be coated with sugar or with film of a gastric or enteric material.

A liquid composition for oral administration includes a pharmaceutically acceptable emulsion, solution, suspension, syrup, elixir, or the like, and contains a generally used inactive diluent, for example, purified water or ethanol. The liquid composition may contain an auxiliary agent such as a solubilizer, a moisturizer, or a suspension, a sweetener, a flavor, an aromatic, and a preservative, in addition to the inactive diluent.

The injection preparation for parenteral administration contains a sterile aqueous or non-aqueous solution, a suspension, or an emulsion. Examples of the aqueous solution include distilled water for injection and physiological saline. Examples of the non-aqueous solution include alcohols such as ethanol. These compositions may further contain a tonicity agent, a preservative, a moisturizer, an emulsifier, a dispersant, a stabilizer, or a solubilizer. These are sterilized by, for example, filtering in which they are filtered through a bacteria retentive filter, by being mixed with a germicide, or by irradiation. Moreover, these can be used by being prepared as a sterile solid composition and dissolved or suspended in sterile water or a sterile vehicle for injection before use.

Examples of agents for external use include an ointment, a plaster, a cream, a jelly, a cataplasm, a spray, a lotion, eye drops, an eye ointment, and the like. The agent for external use contains generally used substrates of ointments and lotions, an aqueous or non-aqueous liquid formulation, a suspension, an emulsion, and the like.

Transmucosal agents such as an inhalation and a transnasal agent are used in the form of a solid, a liquid or a semisolid, and can be prepared according to methods known in the related art. For example, a known excipient, a pH adjustor, a preservative, a surfactant, a lubricant, a stabilizer, a thickener or the like may be appropriately added thereto. For administration, appropriate devices for inhalation or insufflation can be used. For example, by using a known device such as a metered dose inhaler or an atomizer, the compound can be administered alone or administered as powder of a formulated mixture or as a solution or suspension which is a combination of the compound with a pharmaceutically acceptable carrier. A dry powder inhaler and the like may be for single administration or multiple administration, and dry powder or powder-containing capsules can be used. Alternatively, the compound may be administered in the form of a pressurized aerosol spray using an appropriate ejection agent, for example, a suitable gas such as a chlorofluoroalkane, or carbon dioxide.

Generally, in the case of oral administration, an appropriate daily dose is about 0.001 mg/kg to 100 mg/kg in terms of body weight, preferably 0.1 mg/kg to 30 mg/kg, and more preferably 0.1 mg/kg to 10 mg/kg, which is administered once or two to four times in separate doses. In the case of intravenous administration, an appropriate daily dose is about 0.0001 mg/kg to 10 mg/kg in terms of body weight, which is administered once or plural times in separate doses. In addition, the transmucosal agent is administered once a day or plural times a day in separate doses, in a dose of about 0.001 mg/kg to 100 mg/kg in terms of body weight. The dose is appropriately determined case by case in consideration of the symptoms, age, gender, and the like.

The pharmaceutical composition of the present invention contains one or more kinds of the compound of Formula (I) and a salt thereof as an active ingredient, in an amount of 0.01% by weight to 100% by weight, and 0.01% by weight to 50% by weight as an embodiment, even though the amount varies with the route of administration, dosage forms, site of administration, and the type of excipient or additive.

The compound of Formula (I) can be used concurrently with an agent for treating or preventing various diseases considered to be diseases for which the compound of Formula (I) is effective. In concurrent use, the compound and the agent may be administered simultaneously, administered sequentially one by one, or administered at a desired time interval. The preparation for simultaneous administration may be a combination drug or individual preparations.

Examples

Hereinafter, the preparation process of the compound of Formula (I) will be described in detail based on examples, but the present invention is not limited to the compound described in the following examples. In addition, the preparation process of starting compounds will be shown respectively in preparation examples. The preparation process of the compound of Formula (I) is not limited to the preparation processes of the specific examples shown below. The compound of Formula (I) can be prepared by combining those preparation processes, or by a method that is clearly known to a person skilled in the art.

In addition, in examples, preparation examples, and tables described later, the following abbreviation will be used in some cases.

Pr: preparation example number, Ex: example number, Str: structural formula (In the structural formula, a compound to which "*" is attached is a chiral compound in which the corresponding carbon atom is the chiral center; in the structural formula, if a certain bond of a compound is represented by two cross lines, the bond is a double bond, and the compound is a mixture of an E-isomer and a Z-isomer.), Syn: preparation process (the number means that the corresponding example compound is prepared in a preparation process similar to that of the compound with the example number), PSy: preparation method (the number means that the compound of the corresponding preparation example is prepared in a preparation process similar to that of the compound with the preparation example number; in addition, in case the compounds have more than one preparation example numbers which are separated by ",", this means that the compound is prepared by a successive preparation processes similar to said preparation examples starting from the left), Dat: physicochemical data, ESI+: a value of m/z in mass spectrometry (ionization ESI, (M+H)$^+$ unless otherwise specified)), ESI−: a value of m/z in mass spectrometry (ionization ESI, (M–H)$^-$ unless otherwise specified), EI: a value of m/z in mass spectrometry (ionization EI, (M)$^+$ unless otherwise specified), FAB+: a value of m/z in mass spectrometry (ionization FAB, (M+H)$^+$ unless otherwise specified), FAB−: a value of m/z in mass spectrometry (ionization FAB, (M–H)$^-$ unless otherwise specified), APCI/ESI+: a value of m/z in mass spectrometry (ionization APCI and ESI are performed at the same time, (M+H)$^+$ unless otherwise specified), CI+: a value of m/z in mass spectrometry (ionization CI, (M+H)$^+$ unless otherwise specified), NMR: δ (ppm) of the characteristic peaks of $^1$H NMR spectrum measured in DMSO-d$_6$. $^1$H NMR spectrum of Example 60 was measured at 80° C.

HCl in the structural formula means that the compound is isolated as a hydrochloride.

In addition, a concentration mol/L is represented by M for convenience. For example, a 1M aqueous sodium hydroxide solution means a 1 mol/L aqueous sodium hydroxide solution.

Preparation Example 1

To a mixture of 6.2 mL of 2-(methylamino)ethanol, 6.48 g of sodium hydrogen carbonate, 60 mL of THF, and 30 mL of water was added dropwise 10 mL of ethyl succinyl chloride over 30 minutes under ice cooling, followed by stirring for 3 hours. The reaction mixture was concentrated under reduced pressure, and the residue was purified by silica gel column chromatography (hexane:ethyl acetate=11:4), thereby obtaining 12.0 g of ethyl 4-[(2-hydroxyethyl)(methyl)amino]-4-oxobutanoate.

Preparation Example 2

To a mixture of 11.9 g of ethyl 4-[(2-hydroxyethyl)(methyl)amino]-4-oxobutanoate and 120 mL of methylene chloride was added slowly 26.0 g of Dess-Martin Periodinane under ice cooling, and the mixture was allowed to warm to room temperature over 3 hours. An aqueous sodium hydrogen carbonate solution and an aqueous sodium thiosulfate solution were added to the reaction mixture, followed by stirring for 30 minutes at room temperature. An aqueous layer was extracted with methylene chloride, the organic layers were combined and dried over anhydrous sodium sulfate, and the solvent was removed under reduced pressure. The residue was purified by silica gel column chromatography (hexane:ethyl acetate=1:4), thereby obtaining 4.48 g of ethyl 4-[methyl(2-oxoethyl)amino]-4-oxobutanoate.

Preparation Example 3

By using 2.55 g of 2-(cyclopropylamino)ethanol hydrobromide and 3.54 g of sodium hydrogen carbonate, 0.60 g of ethyl 4-[cyclopropyl(2-hydroxyethyl)amino]-4-oxobutanoate was obtained by the method similar to Preparation Example 1.

Preparation Example 4

To a mixture of 1.0 g of N'-(2,2-dimethoxyethyl)-N,N-diethylethane-1,2-diamine, 0.84 mL of N-ethyl-N-isopropylpropan-2-amine, and 10 ml of methylene chloride was added 0.70 mL of ethyl succinyl chloride under ice cooling, followed by stirring for 1 hour under ice cooling. The reaction mixture was concentrated under reduced pressure, ethyl acetate and water were added thereto, and extracted with ethyl acetate. The organic layer was washed sequentially with water and saturated brine and dried over anhydrous sodium sulfate, followed by concentration under reduced pressure, thereby obtaining 1.2 g as oily product. A mixture of 1.2 g of the obtained oily product, 12 mL of methylene chloride, and 12 mL of trifluoroacetic acid (TFA) was stirred for 4 hours at room temperature. The reaction mixture was concentrated under reduced pressure, an aqueous sodium hydrogen carbonate solution and ethyl acetate were added thereto, and extracted with ethyl acetate. The organic layer was washed sequentially with water and saturated brine and dried over anhydrous sodium sulfate, followed by concentration under reduced pressure, thereby obtaining 0.78 g of ethyl 4-{[2-(diethylamino)ethyl](2-oxoethyl)amino}-4-oxobutanoate.

Preparation Example 5

To a mixture of 50.1 g of methyl 4-[(E)-2-(4-nitrophenyl)vinyl]benzoate, 600 mL of THF, and 200 mL of N,N-dimethylformamide (DMF) was added 10.3 g of 10% palladium carbon (wetted with 55% H$_2$O), followed by stirring for 8 hours at room temperature in a hydrogen atmosphere (1 atm). The inside of the reaction vessel was purged with argon, and then the insoluble material was removed by filtration by using celite. The filtrate was concentrated under reduced pressure, and 1000 mL of water was added to the residue, followed by stirring for 30 minutes at room temperature. The precipitate was collected by filtration, thereby obtaining 44.0 g of methyl 4-[2-(4-aminophenyl)ethyl]benzoate.

Preparation Example 6

To a mixture of 43.9 g of methyl 4-[2-(4-aminophenyl)ethyl]benzoate, 22.3 g of cyanoacetic acid, and 150 mL of DMF was added 49.5 g of WSC.hydrochloride under ice cooling. After the reaction mixture was stirred for 24 hours at room temperature, 450 mL of water was added thereto at room temperature, followed by stirring for 30 minutes at room temperature. Thereafter, the precipitate was collected by filtration, thereby obtaining 54.2 g of methyl 4-(2-{4-[(cyanoacetyl)amino]phenyl}ethyl)benzoate.

Preparation Example 7

To a mixture of 54.0 g of methyl 4-(2-{4-[(cyanoacetyl)amino]phenyl}ethyl)benzoate, 50.0 mL of cyclohexanone, and 300 mL of toluene was added dropwise 15.0 mL of morpholine at room temperature. A Dean-Stark type dehydrating tube was attached to the reactor, and the reaction mixture was stirred for 3 hours with oil bath heated at 120° C. Thereafter, the reaction mixture was heated to reflux and further stirred for 1 hour. The reaction mixture was cooled to room temperature, followed by concentration under reduced pressure. 200 mL of diisopropylether was further added thereto, followed by stirring for 14 hours. The precipitated solid was collected by filtration, thereby obtaining 53.2 g of methyl 4-[2-(4-{[cyano(cyclohexylidene)acetyl]amino}phenyl)ethyl]benzoate. To a mixture of this solid, 4.5 g of sulfur and 80 mL of DMF was added dropwise 12.0 mL of morpholine at room temperature, and the reaction mixture was stirred for 1 hour at 50° C. Saturated brine was added to the reaction mixture, followed by extraction with ethyl acetate, and then the organic layer was washed with water and saturated brine. The organic layer was dried over anhydrous sodium sulfate, followed by filtration, and then the solvent was removed under reduced pressure. Isopropanol was added to the thus obtained residue, and the precipitated solid was collected by filtration, thereby obtaining 43.1 g of methyl 4-[2-(4-{[(2-amino-4,5,6,7-tetrahydro-1-benzothiophen-3-yl)carbonyl]amino}phenyl)ethyl]benzoate.

Preparation Example 8

To a mixture of 6.9 g of methyl 4-[2-(4-{[(2-amino-4,5,6,7-tetrahydro-1-benzothiophen-3-yl)carbonyl]amino}phenyl)ethyl]benzoate, 1.5 mL of pyridine and 69 mL of methylene chloride was added dropwise 3.27 g of 3-(chloromethyl)benzoyl chloride, followed by stirring for 1 hour at room temperature. The reaction mixture was concentrated under reduced pressure, ethanol was added thereto, and the precipitated solid was collected by filtration, thereby obtaining 9.27 g of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate.

Preparation Example 9

A mixture of 8.00 g of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate, 4.8 mL of pentan-3-amine, 3.5 mL of N-ethyl-N-isopropylpropan-2-amine, and 80 mL of DMF was stirred for 13 hours at 80° C. Ethyl acetate and water were added to the reaction mixture, followed by extraction with ethyl acetate. The organic layer was washed sequentially with water and saturated brine and dried over anhydrous sodium sulfate, followed by concentration under reduced pressure. The residue was purified by silica gel column chromatography (2% methanol/chloroform), thereby obtaining 6.57 g of methyl 4-{2-[4-({[2-({3-[(pentan-3-ylamino)methyl]benzoyl}amino)-4,5,6,7-tetrahydro-1-benzothiophen-3-yl]carbonyl}amino)phenyl]ethyl}benzoate.

Preparation Example 10

By using 250 mg of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate and 0.25 mL of N,N'-diisopropylethylenediamine as starting materials, the reaction similar to Preparation Example 9 was performed, thereby obtaining 220 mg of methyl 4-[2-(4-{[(2-{[3-({isopropyl[2-(isopropylamino)ethyl]amino}methyl)benzoyl]amino}-4,5,6,7-tetrahydro-1-benzothiophen-3-yl)carbonyl]amino}phenyl)ethyl]benzoate.

Preparation Example 11

By using 1.0 g of tert-butyl(2-bromoethyl)carbamate, 2.5 mL of pentan-3-amine, and 10 mL of acetonitrile as starting materials, the reaction similar to Preparation Example 9 was performed, thereby obtaining 890 mg of tert-butyl[2-(pentan-3-ylamino)ethyl]carbamate.

Preparation Example 12

To a mixture of 240 mg of methyl 4-(2-{4-[({2-[(3-{[{2-[(tert-butoxycarbonyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate and 5.0 mL of methylene chloride was added 3.0 mL of TFA under ice cooling, followed by stirring for 1 hour at the same temperature and then stirring for 5 hours at room temperature. The reaction mixture was concentrated under reduced pressure, chloroform and a saturated aqueous sodium hydrogen carbonate solution were added thereto, followed by extraction with chloroform. The organic layer was dried over anhydrous sodium sulfate, and the solvent was removed under reduced pressure, thereby obtaining 210 mg of methyl 4-(2-{4-[({2-[(3-{[[(2-aminoethyl)(pentan-3-yl)amino]methyl}benzoyl)amino]-4,5,6,7-tetrahydro-1-benzothiophen-3-yl}carbonyl)amino]phenyl}ethyl)benzoate.

Preparation Example 13

To a mixture of 210 mg of methyl 4-(2-{4-[({2-[(3-{[(2-aminoethyl)(pentan-3-yl)amino]methyl}benzoyl)amino]-4,5,6,7-tetrahydro-1-benzothiophen-3-yl}carbonyl)amino]phenyl}ethyl)benzoate, 0.10 mL of triethylamine, and 10 mL of methylene chloride was added 70 mg of ethyl succinyl chloride under ice cooling, and then the mixture was stirred for 1 hour at the same temperature and then stirred overnight at room temperature. The reaction mixture was concentrated under reduced pressure, chloroform and water were added to the reaction mixture, followed by extraction with chloroform. The organic layer was dried over anhydrous sodium sulfate, and the solvent was removed under reduced pressure. The residue was purified by silica gel column chromatography (10% methanol/chloroform), thereby obtaining 170 mg of methyl 4-(2-{4-[({2-[(3-{[[2-[(4-ethoxy-4-oxobutanoyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate.

Preparation Example 14

To a mixture of 800 mg of methyl 4-{2-[4-({[2-({3-[(pentan-3-ylamino)methyl]benzoyl}amino)-4,5,6,7-tetrahydro-1-benzothiophen-3-yl]carbonyl}amino)phenyl]ethyl}benzoate, 257 mg of tert-butyl methyl(2-oxoethyl)carbamate, 7.5 mg of acetic acid and 16 mL of dichloroethane was added 372 mg of sodium triacetoxyborohydride followed by stirring for 15 hours at room temperature. An aqueous sodium hydrogen carbonate solution was added to the reaction mixture, followed by extraction with ethyl acetate. The organic layer was dried over anhydrous sodium sulfate, followed by concentration under reduced pressure. The residue was purified by silica gel column chromatography (hexane:ethyl acetate=2:1), thereby obtaining 908 mg of methyl 4-(2-{4-[({2-[(3-{[{2-[(tert-butoxycarbonyl)(methyl)amino]ethyl}(pentan-3-yl)amino]methyl}benzoyl)amino]-4,5,6,7-tetrahydro-1-benzothiophen-3-yl)}carbonyl)amino]phenyl}ethyl)benzoate.

Preparation Example 15

To a mixture of 250 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 0.20 mL of N-ethyl-N-isopropylpropan-2-amine and 10 mL of THF under ice cooling was added 70 mg of methyl(S)-(−)-2-isocyanatopropionate, followed by stirring for 1 hour at the same temperature and then for 2 hours at room temperature. Ethyl acetate and an aqueous sodium hydrogen carbonate solution were added to the reaction mixture, followed by extraction with ethyl acetate. The organic layer was washed with saturated brine and dried over anhydrous sodium sulfate, and the solvent was removed under reduced pressure. The residue was purified by silica gel column chromatography (10% methanol/chloroform), thereby obtaining 290 mg methyl 4-{2-[4-({[2-({3-[(4S)-4,7-dimethyl-3,6-dioxo-10-(pentan-3-yl)-2-oxa-5,7,10-triazaundecan-11-yl]benzoyl}amino)-4,5,6,7-tetrahydro-1-benzothiophen-3-yl]carbonyl}amino)phenyl]ethyl}benzoate.

Preparation Example 16

To a mixture of 100 mg of (2R)-4-methoxy-2-methyl-4-oxobutanoic acid and 10 ml of methylene chloride were added 0.10 mL of oxalyl chloride and 0.020 mL of DMF in this order under ice cooling. The reaction mixture was stirred for 1 hour at room temperature and then concentrated under reduced pressure. 5.0 ml of the methylene chloride solution was added to a mixture of 200 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 0.10 mL of triethylamine, and 5.0 ml of methylene chloride under ice cooling, followed by stirring for 1 hour at the same temperature and then for 4 days at room temperature. The reaction mixture was concentrated under reduced pressure, chloroform and water were added thereto, followed by extraction with chloroform. The organic layer was dried over anhydrous sodium sulfate, followed by concentration under reduced pressure. The residue was purified by silica gel column chromatography (10% methanol/chloroform), thereby obtaining 230 mg of methyl 4-(2-{4-[({2-[(3-{[{2-{[(2R)-4-methoxy-2-methyl-4-oxobutanoyl](methyl)amino}ethyl](pentan-3-yl)amino]methyl}benzoyl)amino]-4,5,6,7-tetrahydro-1-benzothiophen-3-yl}carbonyl)amino]phenyl}ethyl)benzoate.

Preparation Example 17

To a mixture of 220 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 0.20 mL of N-ethyl-N-isopropylpropan-2-amine and 5.0 mL of methylene chloride was added 100 mg of 2,2-dimethylglutaric anhydride under ice cooling, followed by stirring for 1 hour at the same temperature and then for a day at room temperature, and the reaction mixture was concentrated under reduced pressure. 200 mg of potassium carbonate and 10 mL of DMF were added to the obtained residue, 150 mg of methyl iodide was further added thereto under ice cooling, and the reaction mixture was stirred for 1 hour under ice cooling and then for a day at room temperature. Ethyl acetate and water were added to the reaction mixture, followed by extraction with ethyl acetate. The organic layer was washed with saturated brine and dried over anhydrous sodium sulfate, followed by concentration under reduced pressure. The residue was purified by silica gel column chromatography (5% methanol/chloroform), thereby obtaining 260 mg of methyl 4-(2-{4-[({2-[(3-{[{2-[(5-methoxy-4,4-dimethyl-5-oxopentanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate.

Preparation Example 18

To a mixture of 1.0 g of 3-(methylamino)propan-1-ol and 10 mL of methanol was added 3.0 g of di-tert-butyl dicarbonate under ice cooling, followed by stirring for 5 days at room temperature. The reaction mixture was concentrated under reduced pressure, and the residue was purified by silica gel column chromatography (hexane:ethyl acetate=3:7), thereby obtaining 2.05 g of tert-butyl(3-hydroxypropyl)methylcarbamate.

Preparation Example 19

To a mixture of 1.5 g of 2-(3-bromophenyl)ethanol, 1.0 g of imidazole and 15 mL of DMF was added 2.8 g of tert-butyl(chloro)diphenylsilane under ice cooling, and the followed by stirring for 1 hour at the same temperature then for a day at room temperature. Diethyl ether and water were added to the reaction mixture, followed by extraction with diethyl ether. The organic layer was washed with saturated brine and dried over anhydrous sodium sulfate, followed by concentration under reduced pressure. The residue was purified by silica gel column chromatography (hexane:ethyl acetate=7:3), thereby obtaining 3.27 g of [2-(3-bromophenyl)ethoxy](tert-butyl)diphenylsilane.

Preparation Example 20

To a mixture of 3.27 g of [2-(3-bromophenyl)ethoxy](tert-butyl)diphenylsilane and 50 mL of THF was slowly added 5.5 mL of butyllithium (1.62 M hexane solution) at −78° C., followed by stirring for 30 minutes at −78° C. In addition, carbon dioxide was blown into the reaction mixture at −78° C., and the temperature thereof was slowly increased to room temperature, followed by stirring for 1 hour at room temperature. Water was added to the reaction mixture, and the mixture was neutralized with 9.0 ml of 1.0 M hydrochloric acid. Ethyl acetate was added thereto to separate the organic layer, the organic layer was washed with saturated brine and dried over anhydrous sodium sulfate, and then the solvent was removed under reduced pressure. The residue was purified by silica gel column chromatography (hexane:ethyl acetate=4:6), thereby obtaining 1.45 g of 3-(2-{[tert-butyl(diphenyl)silyl]oxy}ethyl)benzoic acid.

Preparation Example 21

To a mixture of 480 mg of 3-(2-{[tert-butyl(diphenyl)silyl]oxy}ethyl)benzoic acid and 10 ml of methylene chloride was added 160 mg of 1-chloro-N,N,2-trimethylpropenylamine under ice cooling, followed by stirring for 1 hour at room temperature. 10 ml of a methylene chloride solution containing 450 mg of methyl 4-[2-(4-{[(2-amino-4,5,6,7-tetrahydro-1-benzothiophen-3-yl)carbonyl]amino}phenyl)ethyl]benzoate and 0.20 mL of pyridine was added to the reaction mixture under ice cooling, followed by stirring for 1 hour under ice cooling and then for 4 days at room temperature. The reaction mixture was concentrated under reduced pressure, ethyl acetate and water were added thereto, and the organic layer was separated. The organic layer was washed with a 5% aqueous citric acid solution, a saturated aqueous sodium hydrogen carbonate solution, and saturated brine in this order and dried over anhydrous sodium sulfate, and the solvent was removed under reduced pressure. The residue was purified by silica gel column chromatography (hexane: ethyl acetate=1:1), thereby obtaining 830 mg of methyl 4-[2-(4-{[(2-{[3-(2-{[tert-butyl(diphenyl)silyl]oxy}ethyl)benzoyl]amino}-4,5,6,7-tetrahydro-1-benzothiophen-3-yl)carbonyl]amino}phenyl)ethyl]benzoate.

Preparation Example 22

To a mixture of 830 mg of methyl 4-[2-(4-{[(2-{[3-(2-{[tert-butyl(diphenyl)silyl]oxy}ethyl)benzoyl]amino}-4,5,6,7-tetrahydro-1-benzothiophen-3-yl)carbonyl]amino}phenyl)ethyl]benzoate and 10 mL of THF was added 1.5 mL of tetrabutylammonium fluoride (TBAF) (1.0 M THF solution) under ice cooling, followed by stirring for 4 hours at room temperature and then overnight at 50° C. The reaction mixture was concentrated under reduced pressure, and the residue was purified by silica gel column chromatography (10% methanol/chloroform), thereby obtaining 540 mg of methyl 4-[2-(4-{[(2-{[3-(2-hydroxyethyl)benzoyl]amino}-4,5,6,7-tetrahydro-1-benzothiophen-3-yl)carbonyl]amino}phenyl)ethyl]benzoate.

Preparation Example 23

By using 250 mg of methyl 4-[2-(4-{[(2-{[3-(2-hydroxyethyl)benzoyl]amino}-4,5,6,7-tetrahydro-1-benzothiophen-3-yl)carbonyl]amino}phenyl)ethyl]benzoate and 450 mg of Dess-Martin Periodinane, the reaction similar to Preparation Example 2 was performed, and then the reaction similar to Preparation Example 14 was performed, thereby obtaining 260 mg of methyl 4-{2-[4-({[2-({3-[2-(pentan-3-ylamino)ethyl]benzoyl}amino)-4,5,6,7-tetrahydro-1-benzothiophen-3-yl]carbonyl}amino)phenyl]ethyl}benzoate.

Preparation Example 24

A mixture of 640 mg of methyl glycolate, 0.60 mL of pyridine, and 10 mL of methylene chloride was added to 10 mL of a methylene chloride solution including 1.44 g of 4-nitrophenyl chloroformate at room temperature, followed by stirring for 2 hours at room temperature. The reaction mixture was concentrated under reduced pressure, and diethyl ether and water were added to the residue and an organic layer was separated. The organic layer was sequentially washed with water and saturated brine and dried over anhydrous sodium sulfate, followed by concentration under reduced pressure. The residue was purified by silica gel column chromatography (using chloroform only), thereby obtaining 320 mg of methyl {[(4-nitrophenoxy)carbonyl]oxy}acetate.

Preparation Example 25

To a mixture of 16.5 g of 1-(4-nitrophenyl)ethanone, 16.4 g of methyl 4-formylbenzoate and 100 mL of ethanol was added dropwise 4.0 mL of piperidine at room temperature, followed by heating under reflux for 8 hours. The precipitate was collected by filtration, thereby obtaining 24.6 g of a crude product. The crude product was suspended in 100 mL of ethanol, followed by heating under reflux for 6 hours. The precipitate was collected by filtration, thereby obtaining 24.0 g of methyl 4-[3-(4-nitrophenyl)-3-oxoprop-1-en-1-yl]benzoate.

Preparation Example 26

To a mixture of 5.0 g of methyl 4-[3-(4-nitrophenyl)-3-oxoprop-1-en-1-yl]benzoate and 150 mL of methanol was added dropwise 5.0 mL of concentrated sulfuric acid under ice cooling. In an argon atmosphere, 500 mg of 10% palladium carbon was added to the reaction mixture. After hydrogen (3 atm) purging was performed at room temperature, the mixture was stirred for 24 hours. The insoluble material was removed by filtration by using celite, and then the filtrate was concentrated under reduced pressure. A saturated aqueous sodium hydrogen carbonate solution was added to the residue under ice cooling to neutralize the residue, and then extraction was performed using ethyl acetate. The organic layer was washed with water and saturated brine and then dried over anhydrous sodium sulfate. The solvent was removed under reduced pressure, and the obtained residue was purified by silica gel column chromatography (chloroform), thereby obtaining 2.9 g of methyl 4-[3-(4-aminophenyl)propyl]benzoate.

Preparation Example 27

A mixture of 194 mg of methyl 4-[2-(4-{[(2-{[3-({cyclopropyl[2-(methylamino)ethyl]amino}methyl)benzoyl]amino}-4,5,6,7-tetrahydro-1-benzothiophen-3-yl)carbonyl]amino}phenyl)ethyl]benzoate, 0.050 mL of (2-methoxyethoxy)acetic acid, 84 mg of WSC.hydrochloride, and 5.0 mL of DMF was stirred for 15 hours at room temperature. Water was added to the reaction mixture, followed by extraction with ethyl acetate. The organic layer was washed with saturated brine and then dried over anhydrous sodium sulfate, and the solvent was removed under reduced pressure. The residue was purified by silica gel column chromatography (5% methanol/chloroform), thereby obtaining 200 mg of methyl 4-[2-(4-{[(2-{[3-(11-cyclopropyl-8-methyl-7-oxo-2,5-dioxa-8,11-diazadodecan-12-yl)benzoyl]amino}-4,5,6,7-tetrahydro-1-benzothiophen-3-yl)carbonyl]amino}phenyl)ethyl]benzoate.

Preparation Example 28

By using 1.4 mL of (2-methoxyethoxy)acetic acid and 1.0 g of 3-(methylamino)propan-1-ol as starting materials, the reaction similar to Preparation Example 16 was performed, thereby obtaining 2.19 g of N-(3-hydroxypropyl)-2-(2-methoxyethoxy)-N-methylacetamide.

Preparation Example 29

By using 2.0 g of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate, 1.0 g of tert-butyl [2-(cyclopropylamino)ethyl]carbamate, 0.76 g of potassium carbonate, and 40 mL of DMF, 2.5 g of methyl 4-(2-{4-[({2-[(3-{[{2-[(tert-butoxycarbonyl)amino]ethyl}(cyclopropyl)amino]methyl}benzoyl)amino]-4,5,6,7-tetrahydro-1-benzothiophen-3-yl}carbonyl)amino]phenyl}ethyl)benzoate was obtained by the method similar to Preparation Example 9.

Preparation Example 30

A mixture of 1.0 g of methyl 4-(2-{4-[({2-[(3-{[(2-aminoethyl)(cyclopropyl)amino]methyl}benzoyl)amino]-4,5,6,7-tetrahydro-1-benzothiophen-3-yl}carbonyl)amino] phenyl}ethyl)benzoate, 0.20 mL of ethyl bromoacetate, 212 mg of potassium carbonate, and 20 mL of DMF was stirred overnight at room temperature. Water was added to the reaction mixture, followed by extraction with ethyl acetate. The organic layer was washed with saturated brine and then dried over anhydrous sodium sulfate, and the solvent was removed under reduced pressure. The residue was purified by silica gel column chromatography, thereby obtaining 140 mg of methyl 4-{2-[4-({[2-({3-[(cyclopropyl {2-[(2-ethoxy-2-oxoethyl) amino]ethyl}amino)methyl]benzoyl}amino)-4,5,6,7-tetrahydro-1-benzothiophen-3-yl]carbonyl}amino)phenyl] ethyl}benzoate.

Preparation Example 31

By using 200 mg of tert-butyl(2S)-2-(hydroxymethyl)pyrrolidine-1-carboxylate and 421 mg of Dess-Martin Periodinane, a reaction was performed by the method similar to Preparation Example 2. Thereafter, the reaction product was reacted with 300 mg of methyl 4-{2-[4-({[2-({3-[(pentan-3-ylmino)methyl]benzoyl}amino)-4,5,6,7-tetrahydro-1-benzothiophen-3-yl]carbonyl}amino)phenyl]ethyl}benzoate by the method similar to Preparation Example 14, thereby obtaining 350 mg of tert-butyl(2S)-2-({[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl](pentan-3-yl)amino}methyl)pyrrolidine-1-carboxylate.

Preparation Example 32

To a mixture of 200 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 48 mg of N-ethyl-N-isopropylpropan-2-amine and 4 mL of dioxane was added 44 mg of 3,3-dimethyldihydrofuran-2,5-dione, followed by stirring overnight at 65° C. The reaction mixture was concentrated under reduced pressure, ethyl acetate and water were added to the residue, followed by extraction with ethyl acetate. The organic layer was dried over anhydrous sodium sulfate, and the solvent was removed under reduced pressure. The residue was purified by silica gel column chromatography, thereby obtaining 200 mg of 4-[(2-{[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl](pentan-3-yl)amino}ethyl)(methyl)amino]-2,2-dimethyl-4-oxobutanoic acid.

Preparation Example 33

By using 200 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 60 mg of monoethyl adipate, and 0.10 mL of N-ethyl-N-isopropylpropan-2-amine as starting materials, and using 142 mg of O-(7-azabenzotriazol-1-yl)-N,N,N',N'-tetramethyluronium hexafluorophosphate (HATU) as a condensing agent, the reaction similar to Preparation Example 27 was performed, thereby obtaining 200 mg of methyl 4-(2-{4-[({2-[(3-{[[2-[(6-ethoxy-6-oxohexanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate.

Preparation Example 34

By using 220 mg of methyl 4-(2-{4-[({2-[(3-{[{2-[(chloroacetyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate, 60 mg of sarcosine ethyl ester hydrochloride, and 120 mg of potassium carbonate, 200 mg of methyl 4-{2-[4-({[2-({3-[5,8-dimethyl-6,10-dioxo-2-(pentan-3-yl)-11-oxa-2,5,8-triazamidec-1-yl]benzoyl}amino)-4,5,6,7-tetrahydro-1-benzothiophen-3-yl]carbonyl}amino)phenyl]ethyl}benzoate was obtained by the method similar to Preparation Example 9.

Preparation Example 35

To 4.8 g of tert-butyl ethyl 2,2'-piperazine-1,4-diyldiacetate was added 20 mL of a 4M hydrogen chloride/ethyl acetate solution, followed by stirring for 2 hours at room temperature. The generated insoluble material was collected by filtration, thereby obtaining 4.0 g of [4-(2-ethoxy-2-oxoethyl)piperazin-1-yl]acetic acid dihydrochloride.

Preparation Example 36

By using 200 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate and 79 mg of methyl 3-(bromomethyl)benzoate, the reaction similar to Preparation Example 30 was performed, thereby obtaining 220 mg of methyl 3-{[(2-{[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl](pentan-3-yl)amino}ethyl)(methyl)amino]methyl}benzoate.

Preparation Example 37

To 1.0 g of ethyl 2-(hydroxymethyl)isonicotinate was added 3.0 mL of thionyl chloride, followed by stirring overnight. The reaction mixture was concentrated under reduced pressure, and 4.0 mL of pentan-3-amine and 20 mL of DMF were added to the obtained residue, followed by stirring overnight at 70° C. Water was added to the reaction mixture, followed by extraction with ethyl acetate. The organic layer was dried over anhydrous sodium sulfate, and the solvent was removed under reduced pressure. The residue was purified by silica gel column chromatography, thereby obtaining 1.3 g of ethyl 2-[(pentan-3-ylamino)methyl]isonicotinate.

Preparation Example 38

A mixture of 1.9 g of ethyl 2-{[{2-[(4-tert-butoxy-4-oxobutanoyl)(methyl)amino]ethyl}(pentan-3-yl)amino] methyl}isonicotinate, 8.2 mL of a 1.0 M aqueous sodium hydroxide solution, 8.0 mL of methanol, and 16 mL of THF was stirred overnight at room temperature. The mixture was neutralized using 1.0 M hydrochloric acid, water was added thereto, followed by extraction with chloroform-methanol. The organic layer was washed with saturated brine and dried over anhydrous sodium sulfate, and the solvent was removed under reduced pressure, thereby obtaining 1.5 g of 2-{[{2-[(4-tert-butoxy-4-oxobutanoyl)(methyl)amino]ethyl}(pentan-3-yl)amino]methyl}isonicotinic acid.

Preparation Example 39

To 20 mL of a dioxane solution including 2.0 g of 2-bromo-5-nitropyridine were added 1.58 g of methyl 4-ethynylbenzoate, 4.1 mL of N-isopropylpropan-2-amine and 281 mg of copper (I) iodide, and 504 mg of bis(tri-tert-butylphosphine)palladium(0) was further added thereto in an argon atmosphere, followed by stirring for 1 hour at room temperature. 50 ml of ethyl acetate was added to the reaction mixture, the precipitated insoluble material was collected by filtration, thereby obtaining 2.45 g of methyl 4-[(5-nitropyridin-2-yl)ethynyl]benzoate.

Preparation Example 40

By using 120 mg of 2-({3-[(cyclopropylamino)methyl]benzoyl}amino)-N-[4-(pyridin-4-ylmethyl)phenyl]-4,5,6,7-tetrahydro-1-benzothiophene-3-carboxamide and 120 mg of ethyl 5-chloro-5-oxopentanoate, the reaction similar to Preparation Example 13 was performed, thereby obtaining 105 mg of ethyl 5-(cyclopropyl {3-[(3-{[4-(pyridin-4-ylmethyl)phenyl]carbamoyl}-4,5,6,7-tetrahydro-1-benzothiophen-2-yl)carbamoyl]benzyl}amino)-5-oxopentanoate.

Preparation Example 41

By using 300 mg of methyl 4-{2-[4-({[2-({3-[(cyclopropylamino)methyl]benzoyl}amino)-4,5,6,7-tetrahydro-1-benzothiophen-3-yl]carbonyl}amino)phenyl]ethyl}benzoate, 198 mg of 5-{cyclopropyl[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl]amino}-3,3-dimethyl-5-oxopentanoic acid was obtained by the method similar to Preparation Example 32.

Preparation Example 42

To a mixture of 150 mg of methyl 4-{3-[4-({[2-({3-[(isopropylamino)methyl]benzoyl}amino)-4,5,6,7-tetrahydro-1-benzothiophen-3-yl]carbonyl}amino)phenyl]propyl}benzoate and 3.5 mL of THF was added 0.045 mL of triethylamine and 28 mg of triphosgene under ice cooling, followed by stirring for 3 hours at room temperature. Thereafter, 0.080 mL of ethyl isopipecotate was added to the reaction mixture, followed by stirring for 18 hours at room temperature. An aqueous sodium hydrogen carbonate solution was added to the reaction mixture, followed by stirring for 1 hour at room temperature, and then extraction was performed using chloroform. The organic layer was washed with saturated brine and dried over anhydrous magnesium sulfate, and the solvent was removed under reduced pressure. The residue was purified by basic silica gel column chromatography (NH silica gel manufactured by FUJI SILYSIA CHEMICAL LTD. (amino type silica gel (treated with aminopropyl)), (hexane:ethyl acetate=1:1)), thereby obtaining 178 mg of ethyl 1-{isopropyl[3-({3-[(4-{3-[4-(methoxycarbonyl)phenyl]propyl}phenyl)carbamoyl]-4,5,6,7-tetrahydro-1-benzothiophen-2-yl}carbamoyl)benzyl]carbamoyl}piperidine-4-carboxylate.

Preparation Example 43

By using 116 mg of methyl 4-{3-[4-({[2-({3-[(isopropylamino)methyl]benzoyl}amino)-4,5,6,7-tetrahydro-1-benzothiophen-3-yl]carbonyl}amino)phenyl]propyl}benzoate and 50 mg of 6-(methoxycarbonyl)pyridine-2-carboxylic acid as starting materials, the reaction similar to Preparation Example 33 was performed, thereby obtaining 115 mg of methyl 6-{isopropyl[3-({3-[(4-{3-[4-(methoxycarbonyl)phenyl]propyl}phenyl)carbamoyl]-4,5,6,7-tetrahydro-1-benzothiophen-2-yl}carbamoyl)benzyl]carbamoyl}pyridine-2-carboxylate.

Preparation Example 44

By using 550 mg of methyl 4-{2-[4-({[2-({3-[(isopropylamino)methyl]benzoyl}amino)-4,5,6,7-tetrahydro-1-benzothiophen-3-yl]carbonyl}amino)phenyl]ethyl}benzoate and 200 mg of 4-(diethoxyphosphoryl)butanoic acid as starting materials, the reaction similar to Preparation Example 27 was performed, thereby obtaining 600 mg of methyl 4-[2-(4-{[(2-{[3-({[4-(diethoxyphosphoryl)butanoyl](isopropyl)amino}methyl)benzoyl]amino}-4,5,6,7-tetrahydro-1-benzothiophen-3-yl)carbonyl]amino}phenyl)ethyl]benzoate.

Preparation Example 45

By using 1.0 g of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate and 1.8 mL of 28% aqueous ammonia, 900 mg of methyl 4-[2-(4-{[(2-{[3-(aminomethyl)benzoyl]amino}-4,5,6,7-tetrahydro-1-benzothiophen-3-yl)carbonyl]amino}phenyl)ethyl]benzoate by the method similar to Preparation Example 9.

Preparation Example 46

By using 370 mg of methyl 4-(2-{4-[({2-[(3-{[(chloroacetyl)(pentan-3-yl)amino]methyl}benzoyl)amino]-4,5,6,7-tetrahydro-1-benzothiophen-3-yl}carbonyl)amino]phenyl}ethyl)benzoate and 400 mg of ethyl isopipecotate, the reaction similar to Preparation Example 30 was performed, thereby obtaining 380 mg of ethyl 1-(2-{[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl](pentan-3-yl)amino}-2-oxoethyl)piperidine-4-carboxylate.

Preparation Example 47

To a mixture of 3.0 g of 3-formylbenzoic acid and 30 ml of methylene chloride were added 1.7 mL of oxalyl chloride and 0.020 mL of DMF in this order under ice cooling. The reaction mixture was stirred for 5 hours at room temperature and concentrated under reduced pressure. A mixture of the resultant and 30 ml of methylene chloride was added to a mixture of 2.8 mL of 2-(trimethylsilyl)ethanol, 1.6 mL of pyridine, and 30 ml of methylene chloride, followed by stirring for 2 hours at room temperature. The reaction mixture was concentrated under reduced pressure, water was added thereto, followed by extraction with ethyl acetate. The organic layer was dried over anhydrous sodium sulfate, the solvent was removed under reduced pressure, and the residue was purified by silica gel column chromatography (hexane:ethyl acetate=4:1), thereby obtaining 3.5 g of 2-(trimethylsilyl)ethyl 3-formylbenzoate.

Preparation Example 48

By using 500 mg of 2-(trimethylsilyl)ethyl 3-formylbenzoate and 188 mg of 3-aminopyridine, the reaction similar to Preparation Example 14 was performed, thereby obtaining 505 mg of 2-(trimethylsilyl)ethyl 3-[(pyridin-3-ylamino)methyl]benzoate.

Preparation Example 49

By using 375 mg of 2-(trimethylsilyl)ethyl 3-{[(5-ethoxy-5-oxopentanoyl)(pyridin-3-yl)amino]methyl}benzoate and 1.0 mL of 1.0 M TBAF (THF solution), 160 mg of 3-{[(5-ethoxy-5-oxopentanoyl)(pyridin-3-yl)amino] methyl}benzoic acid was obtained by the method similar to Preparation Example 22.

Preparation Example 50

To a mixture of 8.99 g of tert-butyl 2-({3-[(pentan-3-ylamino)methyl]benzoyl}amino)-4,5,6,7-tetrahydro-1-benzothiophene-3-carboxylate and 100 mL of methylene chloride was added 30 mL of TFA, followed by stirring for 15 hours at room temperature. The reaction mixture was concentrated under reduced pressure, and azeotropy was performed using toluene. 4.3 mL of thionyl chloride and 50 mL of toluene were added to the residue, and 0.10 mL of DMF was added dropwise thereto, followed by stirring for 1 hour at 60° C. The reaction mixture was concentrated under reduced pressure, a saturated aqueous sodium hydrogen carbonate solution was added thereto, followed by extraction with ethyl acetate. The organic layer was washed with saturated brined and dried over anhydrous sodium sulfate, and the solvent was removed under reduced pressure. The residue was purified by silica gel column chromatography (hexane:ethyl acetate=1: 2), thereby obtaining 7.05 g of 2-{3-[(pentan-3-ylamino)methyl]phenyl}-5,6,7,8-tetrahydro-4H-[1]benzothieno[2,3-d] [1,3]oxazin-4-one.

Preparation Example 51

To a mixture of 4.81 g of 2,2-dimethyl-5-oxo-5-{[3-(4-oxo-5,6,7,8-tetrahydro-4H-[1]benzothieno[2,3-d][1,3]oxazin-2-yl)benzyl](pentan-3-yl)amino}pentanoic acid and 50 mL of DMF were added 2.59 g of methyl iodide and 3.16 g of potassium carbonate, followed by stirring for 1 hour at room temperature. Water was added to a reaction mixture, followed by extraction with ethyl acetate. The organic layer was washed with saturated brine and then dried over anhydrous sodium sulfate, and the solvent was removed under reduced pressure. The residue was recrystallized from ethanol, thereby obtaining 3.24 g of methyl 2,2-dimethyl-5-oxo-5-{[3-(4-oxo-5,6,7,8-tetrahydro-4H-[1]benzothieno[2,3-d][1,3]oxazin-2-yl)benzyl](pentan-3-yl)amino}pentanoate as a yellowish white solid.

Preparation Example 52

Lithium hexamethyldisilazide (1.0 M in THF) 1.1 mL was added dropwise to a mixture of 200 mg of methyl 2,2-dimethyl-5-oxo-5-{[3-(4-oxo-5,6,7,8-tetrahydro-4H-[1]benzothieno[2,3-d][1,3]oxazin-2-yl)benzyl](pentan-3-yl) amino}pentanoate, 90 mg of 4-[2-(morpholin-4-yl)ethyl]aniline, and 5.0 mL of THF under ice cooling, followed by stirring for 30 minutes at the same temperature. A saturated aqueous ammonium chloride solution was added to the reaction mixture, followed by extraction with ethyl acetate. The organic layer was washed with saturated brine and dried over anhydrous sodium sulfate, and the solvent was removed under reduced pressure. The residue was purified by silica gel column chromatography (hexane:ethyl acetate=1:1), thereby obtaining 164 mg of methyl 2,2-dimethyl-5-[(3-{[3-({4-[2-(morpholin-4-yl)ethyl]phenyl}carbamoyl)-4,5,6,7-tetrahydro-1-benzothiophen-2-yl]carbamoyl}benzyl)(pentan-3-yl) amino]-5-oxopentanoate.

Preparation Example 53

A borane-THF complex (1.08 M THF solution) 23 mL was added dropwise to a mixture of 3.02 g of tert-butyl 4-[3-(4-nitrophenyl)propanoyl]piperazine-1-carboxylate and THF 40 mL under ice cooling in an argon atmosphere, followed by stirring for 10 minutes at room temperature, and then heating under reflux was performed for 2 hours. The reaction mixture was cooled with ice, and 30 mL of methanol was added dropwise thereto, followed by stirring for 3 hours at 50° C. The reaction mixture was concentrated under reduced pressure, water and ethyl acetate were added to the residue, followed by extraction with ethyl acetate. The organic layer was washed with saturated brine and dried over anhydrous sodium sulfate, and the solvent was removed under reduced pressure. The residue was purified by silica gel column chromatography (5% methanol/chloroform), thereby obtaining 2.78 g of tert-butyl 4-[3-(4-nitrophenyl)propyl]piperazine-1-carboxylate.

Preparation Example 54

By using 180 mg of methyl 2,2-dimethyl-5-oxo-5-[pentan-3-yl(3-{[3-({4-[3-(piperazin-1-yl)propyl] phenyl}carbamoyl)-4,5,6,7-tetrahydro-1-benzothiophen-2-yl]carbamoyl}benzyl)amino]pentanoate and 0.06 mL of a 37% aqueous formalin solution, the reaction similar to Preparation Example 14 was performed, thereby obtaining 152 mg of methyl 2,2-dimethyl-5-[(3-{[3-({4-[3-(4-methylpiperazin-1-yl)propyl]phenyl}carbamoyl)-4,5,6,7-tetrahydro-1-benzothiophen-2-yl]carbamoyl}benzyl)(pentan-3-yl) amino]-5-oxopentanoate.

Preparation Example 55

To a mixture of 680 mg of tert-butyl(5-nitropyridin-2-yl) acetate and 10 mL of DMF was added 373 mg of sodium hydride (55%, dispersion in paraffin liquid) under ice cooling in an argon atmosphere, followed by stirring for 30 minutes at room temperature. In addition, 0.62 mL of methyl iodide was added dropwise thereto under ice cooling, followed by stirring for 5 hours at room temperature. A saturated aqueous ammonium chloride solution was added to the reaction mixture, followed by extraction with ethyl acetate. The organic layer was washed with saturated brine and dried over anhydrous sodium sulfate, and the solvent was removed under reduced pressure. The residue was purified by silica gel column chromatography (hexane:ethyl acetate=1:1), thereby obtaining 582 mg of tert-butyl 2-methyl-2-(5-nitropyridin-2-yl)propanoate.

Preparation Example 56

To a mixture of 200 mg of N-[4-(benzyloxy)phenyl]-2-{[3-(morpholin-4-ylmethyl)benzoyl]amino}-4,5,6,7-tetrahydro-1-benzothiophene-3-carboxamide and 6.0 mL of TFA was added 255 mg of 1,2,3,4,5-pentamethylbenzene, followed by stirring overnight at room temperature. The reaction mixture was concentrated under reduced pressure, and ethyl acetate and a saturated aqueous sodium hydrogen carbonate solution were added thereto, followed by extraction using ethyl acetate. The organic layer was washed with satu-

37 rated brine and dried over anhydrous magnesium sulfate, and the solvent was removed under reduced pressure. The residue was purified by silica gel column chromatography (3% methanol/chloroform), thereby obtaining 169 mg of N-(4-hydroxyphenyl)-2-{[3-(morpholin-4-ylmethyl)benzoyl]amino}-4,5,6,7-tetrahydro-1-benzothiophene-3-carboxamide.

Preparation Example 57

By using 169 mg of N-(4-hydroxyphenyl)-2-{[3-(morpholin-4-ylmethyl)benzoyl]amino}-4,5,6,7-tetrahydro-1-benzothiophene-3-carboxamide and 95 mg of methyl 4-(bromomethyl)benzoate, 193 mg of methyl 4-[(4-{[(2-{[3-(morpholin-4-ylmethyl)benzoyl]amino}-4,5,6,7-tetrahydro-1-benzothiophen-3-yl)carbonyl]amino}phenoxy)methyl]benzoate was obtained by the method similar to Preparation Example 30.

Preparation Example 58

By using 610 mg of methyl 4-(2-{4-[({2-[(3-{[{1-[N-(tert-butoxycarbonyl)-N-methylglycyl]piperidin-4-yl}(cyclopropyl)amino]methyl}benzoyl)amino]-4,5,6,7-tetrahydro-1-benzothiophen-3-yl}carbonyl)amino]phenyl}ethyl)benzoate and 5.0 mL of TFA as starting materials, the deprotection reaction similar to Preparation Example 12 and the amidation reaction similar to Preparation Example 32 were performed sequentially, thereby obtaining 240 mg of 4-{[2-(4-{cyclopropyl[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl]amino}piperidin-1-yl)-2-oxoethyl](methyl)amino}-4-oxobutanoic acid.

Preparation Example 59

By using 250 mg of methyl 4-{2-[4-({[2-({3-[(cyclopropylamino)methyl]benzoyl}amino)-4,5,6,7-tetrahydro-1-benzothiophen-3-yl]carbonyl}amino)phenyl]ethyl}benzoate and 153 mg of ethyl 2-chloropyrimidine-5-carboxylate as starting materials, the reaction similar to Preparation Example 30 was performed, thereby obtaining 307 mg of ethyl 2-{cyclopropyl[3-({3-[(4-{2-[4-(methoxycarbonyl)phenyl]ethyl}phenyl)carbamoyl}-4,5,6,7-tetrahydro-1-benzothiophen-2-yl}carbamoyl)benzyl]amino}pyrimidine-5-carboxylate.

Preparation Example 60

A mixture of 22.2 g of 2-{[3-(morpholin-4-ylmethyl)benzoyl]amino}-4,5,6,7-tetrahydro-1-benzothiophene-3-carboxylic acid and 230 mL of toluene was heated at 60° C., and 20 mL of thionyl chloride was added thereto, followed by stirring for 1 hour at 60° C. The insoluble material was collected by filtration and washed with toluene. A saturated aqueous sodium hydrogen carbonate solution and ethyl acetate were added to the material collected by filtration, followed by extraction with ethyl acetate. The organic layer was washed with a saturated aqueous sodium chloride solution and dried over anhydrous sodium sulfate, and the solvent was removed under reduced pressure. The residue was washed with ethanol, thereby obtaining 18.9 g of 2-[3-(morpholin-4-ylmethyl)phenyl]-5,6,7,8-tetrahydro-4H-[1]benzothieno[2,3-d][1,3]oxazin-4-one.

Preparation Example 61

By using 300 mg of methyl 4-{2-[4-({[2-({3-[(cyclopropylamino)methyl]benzoyl}amino)-4,5,6,7-tetrahydro-1-benzothiophen-3-yl]carbonyl}amino)phenyl]ethyl}benzoate and 289 mg of ethyl 4-bromobutyrate, the reaction similar to Preparation Example 30 was performed, thereby obtaining 201 mg of methyl 4-(2-{4-[({2-[(3-{[cyclopropyl(4-ethoxy-4-oxobutyl)amino]methyl}benzoyl)amino]-4,5,6,7-tetrahydro-1-benzothiophen-3-yl}carbonyl)amino]phenyl}ethyl)benzoate.

Preparation Example 62

To a mixture of 5.27 g of benzyl 5-methylthiophene-2-carboxylate and 100 mL of carbon tetrachloride were added 4.18 g of N-bromosuccinimide (NBS) and 142 mg of azobisisobutyronitrile (AIBN), followed by stirring overnight at 80° C. The reaction mixture was concentrated under reduced pressure, and the residue was purified by silica gel column chromatography (hexane:ethyl acetate=7:3), thereby obtaining 4.44 g of benzyl 5-(bromomethyl)thiophene-2-carboxylate.

Preparation Example 63

To a mixture of 2.18 g of benzyl 5-(bromomethyl)thiophene-2-carboxylate and 26 mL of toluene was added 1.86 g of triphenylphosphine, followed by stirring overnight at 80° C. The insoluble material was collected by filtration, thereby obtaining 2.89 g of ({5-[(benzyloxy)carbonyl]-2-thienyl}methyl)(triphenyl)phosphonium bromide.

Preparation Example 64

A mixture of 3.01 g of methyl 5-(morpholin-4-ylmethyl)thiophene-2-carboxylate and 30 mL of 6.0 M hydrochloric acid was subjected to heating under reflux overnight at 100° C. The reaction mixture was concentrated under reduced pressure, and the residue was washed with acetonitrile, thereby obtaining 3.05 g of 5-(morpholin-4-ylmethyl)thiophene-2-carboxylic acid hydrochloride.

Preparation Example 65

By using 3.42 g of methyl 6-methylpyrazine-2-carboxylate and 4.40 g of NBS, a bromination reaction was performed by the method similar to Preparation Example 62. Thereafter, by using 10 mL of morpholine as amine, the reaction similar to Preparation Example 9 was performed, thereby obtaining 987 mg of methyl 6-(morpholin-4-ylmethyl)pyrazine-2-carboxylate.

Preparation Example 66

By using 1.2 g of tert-butyl 4-(4-ethoxy-4-oxobutanoyl)piperazine-1-carboxylate and 1.0 mL of 4.0 M hydrogen chloride/ethyl acetate solution, the reaction similar to Preparation Example 35 was performed, thereby obtaining 900 mg of ethyl 4-oxo-4-(piperazin-1-yl)butanoate hydrochloride.

Preparation Example 67

To a mixture of 306 mg of N-cyclopropyl-N-[3-({3-[(4-{2-[4-(methoxycarbonyl)phenyl]ethyl}phenyl)carbamoyl}-4,5,6,7-tetrahydro-1-benzothiophen-2-yl}carbamoyl)benzyl]glycine hydrochloride and 5.0 mL of dichloromethane were added 0.182 mL of triethylamine, 91 mg of methyl N-methylglycinate hydrochloride, 125 mg of WSC.hydrochloride and 88 mg of HOBt, followed by stirring for 15 hours at room temperature. Water was added to the reaction mixture, followed by extraction with ethyl acetate. The organic layer was washed with saturated brine and then dried over anhydrous sodium sulfate, and the solvent was removed under reduced pressure. The residue was purified by silica gel column chromatography, thereby obtaining 152 mg of methyl N-cyclopropyl-N-[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl]glycyl-N-methylglycinate.

Preparation Example 68

By a method similar to Preparation Example 37, 197 mg of methyl 4-(2-{4-[({2-[(3-{[(2-hydroxyethyl)(pentan-3-yl)amino]methyl}benzoyl)amino]-4,5,6,7-tetrahydro-1-benzothiophen-3-yl}carbonyl)amino]phenyl}ethyl)benzoate was reacted with 0.10 mL of thionyl chloride, and then the resultant was reacted with 325 mg of ethyl isonipecotate, thereby obtaining 206 mg of ethyl 1-(2-{[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl](pentan-3-yl)amino}ethyl)piperidine-4-carboxylate.

Preparation Example 69

To a mixture of 2.88 g of ({5-[(benzyloxy)carbonyl]-2-thienyl}methyl)(triphenyl)phosphonium bromide, 823 mg of 4-nitrobenzaldehyde and 30 mL of THF was added dropwise 1.0 mL of a 5.0 M sodium methoxide/methanol solution, followed by stirring overnight at room temperature. Water was added to the reaction mixture, followed by extraction with ethyl acetate. The organic layer was washed sequentially with 1.0 M hydrochloric acid, a saturated aqueous sodium hydrogen carbonate solution, and saturated brine and then dried over anhydrous sodium sulfate, and the solvent was removed under reduced pressure. The residue was purified by silica gel column chromatography (hexane:ethyl acetate=4:6). 10 mL of methanol and 10 mL of THF were added to the obtained residue, and 98 mg of 10% palladium carbon was added thereto under an argon flow, followed by stirring overnight at room temperature in a hydrogen atmosphere. The reaction mixture was filtered using celite, and the solvent was removed under reduced pressure. The residue was purified by silica gel column chromatography (hexane:ethyl acetate=1:1), thereby obtaining 765 mg of methyl 5-[2-(4-aminophenyl)ethyl]thiophene-2-carboxylate.

Compounds of Preparation Examples 70 to 315 shown in the following table were prepared in the similar manner as in Preparation Examples 1 to 69. The following table shows the structure, physicochemical data, and preparation process of the compounds of preparation examples.

Example 1

To a mixture of 1.00 g of methyl 4-{2-[4-({[2-({3-[(pentan-3-ylamino)methyl]benzoyl}amino)-4,5,6,7-tetrahydro-1-benzothiophen-3-yl]carbonyl}amino)phenyl]ethyl}benzoate, 1.00 g of sodium triacetoxyborohydride, 0.50 mL of acetic acid and 20 mL of methylene chloride was added 473 mg of ethyl 4-[methyl(2-oxoethyl)amino]-4-oxobutanoate, followed by stirring for 1 hour at room temperature. 498 mg of sodium triacetoxyborohydride and 237 mg of ethyl 4-[methyl(2-oxoethyl)amino]-4-oxobutanoate were further added to the reaction mixture, followed by stirring for 2 hours at room temperature. An aqueous sodium hydrogen carbonate solution was added to the reaction mixture, followed by extraction with methylene chloride. The organic layer was dried over anhydrous sodium sulfate, and the solvent was removed under reduced pressure. The residue was purified by basic silica gel column chromatography (ethyl acetate), thereby obtaining 1.19 g of methyl 4-(2-{4-[({2-[(3-{[{2-[(4-ethoxy-4-oxobutanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate.

Example 2

A mixture of 1.18 g of methyl 4-(2-{4-[({2-[(3-{[{2-[(4-ethoxy-4-oxobutanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate, 5.0 mL of a 1.0 M aqueous sodium hydroxide solution, and 24 mL of ethanol was subjected to heating under reflux for 2 hours. The reaction mixture was concentrated under reduced pressure, and 4 mL of 1.0 M hydrochloric acid was added thereto. Then, 600 mg of lactobionic acid was added thereto to neutralize the mixture, and the solvent was removed under reduced pressure. The residue was purified by silica gel column chromatography (10% methanol/chloroform) to afford 1.10 g of a product. 3.0 mL of acetonitrile and 0.40 mL of 1.0 M hydrochloric acid were added to 300 mg of this product, and the reaction mixture was purified by ODS column chromatography (50% acetonitrile/0.01 M hydrochloric acid), followed by lyophilization, thereby obtaining 253 mg of 4-(2-{4-[({2-[(3-{[{2-[(3-carboxypropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid hydrochloride.

Example 2A

To a mixture of 100 mg of the 4-(2-{4-[({2-[(3-{[{2-[(3-carboxypropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid which was obtained by the chromatographic purification as described in Example 2, 3.0 mL of ethanol, 1.5 mL of water and 0.26 mL of an 1.0 M aqueous sodium hydroxide solution was added dropwise 1.3 mL of a 0.1 M aqueous magnesium chloride solution. The reaction mixture was stirred overnight with heating under reflux, and then the precipitated solid was collected by filtration, thereby obtaining 89 mg of a hydrate of magnesium 4-(2-{4-[({2-[(3-{[{2-[(3-carboxylatopropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate as the crystal. ESI+: 781.

Example 3

A mixture of 100 mg of methyl {[(4-nitrophenoxy)carbonyl]oxy}acetate and 5.0 mL of THF was added to a mixture of 180 mg of methyl 4-[2-(4-{[(2-{[3-({[2-(methylamino)ethyl](pentan-3-yl)amino}methyl)benzoyl]amino}-4,5,6,7-tetrahydro-1-benzothiophen-3-yl)carbonyl]amino}phenyl)ethyl]benzoate, 0.15 mL of N-ethyl-N-isopropylpropan-2-amine, and 5.0 mL of THF under ice cooling, followed by stirring for 3 hours at room temperature. The reaction mixture was concentrated under reduced pressure, and ethyl acetate and a saturated aqueous sodium hydrogen carbonate solution were added to the residue, followed by extraction with ethyl acetate. The organic layer was washed sequentially with a saturated aqueous sodium hydrogen carbonate solution, water, and saturated brine and dried over anhydrous sodium sulfate, and the solvent was removed under reduced pressure. The residue was purified by basic silica gel column chromatography (hexane:chloroform=4:6), thereby obtaining 204 mg of methyl 4-{2-[4-({[2-({3-[7-methyl-3,6-dioxo-10-(pentan-3-yl)-2,5-dioxa-7,10-diazaundecan-11-yl]benzoyl}amino)-4,5,6,7-tetrahydro-1-benzothiophen-3-yl]carbonyl}amino)phenyl]ethyl}benzoate.

Example 4

To a mixture of 203 mg of methyl 4-{2-[4-({[2-({3-[7-methyl-3,6-dioxo-10-(pentan-3-yl)-2,5-dioxa-7,10-diazaundecan-11-yl]benzoyl}amino)-4,5,6,7-tetrahydro-1-benzothiophen-3-yl]carbonyl}amino)phenyl]ethyl}benzoate, 4.0 mL of methanol and 4.0 mL of THF was added 1.5 mL of a 1.0 M aqueous sodium hydroxide solution at room temperature, followed by stirring for 14 hours at 60° C. 1.5 mL of 1.0 M hydrochloric acid was added to the reaction mixture under ice cooling, followed by concentration under reduced pressure. A mixed solvent (methanol/chloroform=15/85) was added to the residue, the insoluble material was filtered, and the filtrate was concentrated under reduced pressure. The residue was purified by silica gel column chromatography (15% methanol/chloroform). A mixed solvent (acetonitrile/water=90/10) was added to the obtained product, 0.5 mL of 1.0 M hydrochloric acid was added thereto under ice cooling, and the solvent was removed under reduced pressure. The residue was subjected to lyophilization, thereby obtaining 186 mg of 4-(2-{4-[({2-[(3-{[(2-{[(carboxymethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoic acid hydrochloride.

Example 4A

To a mixture of 100 mg of the 4-(2-{4-[({2-[(3-{[(2-{[(carboxymethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoic acid which was obtained by the chromatographic purification as described in Example 4 and 0.5 mL of ethanol was added 0.26 mL of a 1.0 M aqueous sodium hydroxide solution at room temperature, followed by stirring for 15 minutes at 80° C. 1.3 mL of a 0.1 M aqueous magnesium chloride solution was added dropwise to the reaction mixture, and the reaction mixture was stirred for 30 minutes with heating under reflux. 0.49 mL of water was added to the reaction mixture, followed by heating under reflux for additional 1 hour. 1.5 mL of ethanol was added to the reaction mixture, followed by stirring for additional 1 hour with heating under reflux, and then the mixture was cooled to room temperature. The precipitated solid was collected by filtration, thereby obtaining 105 mg of a hydrate of magnesium 4-(2-{4-[({2-[(3-{[(2-{[(carboxylatomethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoate as the crystal.
ESI+: 783.

Example 5

A mixture of 195 mg of methyl 4-[2-(4-{[(2-{[3-(11-cyclopropyl-8-methyl-7-oxo-2,5-dioxa-8,11-diazadodecan-12-yl)benzoyl]amino}-4,5,6,7-tetrahydro-1-benzothiophen-3-yl)carbonyl]amino}phenyl)ethyl]benzoate, 1.0 mL of a 1.0 M aqueous sodium hydroxide solution, and 5.0 mL of methanol was stirred for 15 hours at 60° C. The reaction mixture was concentrated under reduced pressure, 1.0 mL of 1.0 M hydrochloric acid was added to the residue, and extraction was performed by using chloroform. The organic layer was dried over anhydrous sodium sulfate, and the solvent was removed under reduced pressure. The residue was purified by silica gel column chromatography (10% methanol/chloroform). The obtained foam-like material was dissolved in 5.0 mL of ethyl acetate, and 0.13 mL of 4.0 M hydrogen chloride/ethyl acetate solution was added thereto under ice cooling, followed by stirring for 2 hours at room temperature. The precipitated solid was collected by filtration and washed with ethyl acetate, followed by drying under reduced pressure, thereby obtaining 108 mg of 4-[2-(4-{[(2-{[3-(11-cyclopropyl-8-methyl-7-oxo-2,5-dioxa-8,11-diazadodecan-12-yl)benzoyl]amino}-4,5,6,7-tetrahydro-1-benzothiophen-3-yl)carbonyl]amino}phenyl)ethyl]benzoic acid hydrochloride.

Example 6

A mixture of 140 mg of methyl 4-{2-[4-({[2-({3-[(cyclopropyl{2-[(2-ethoxy-2-oxoethyl)amino]ethyl}amino)methyl]benzoyl}amino)-4,5,6,7-tetrahydro-1-benzothiophen-3-yl]carbonyl}amino)phenyl]ethyl}benzoate, 1.0 mL of a 1.0M aqueous sodium hydroxide solution, 1.0 mL of methanol, and 2.0 mL of THF was stirred overnight at room temperature. To the reaction mixture was added 1.0 mL of 1.0 M hydrochloric acid. The precipitated solid was collected by filtration, thereby obtaining 113 mg of 4-(2-{4-[({2-[(3-{[{2-[(carboxymethyl)amino]ethyl}(cyclopropyl)amino]methyl}benzoyl)amino]-4,5,6,7-tetrahydro-1-benzothiophen-3-yl}carbonyl)amino]phenyl)}ethyl)benzoic acid.

Example 7

By using 160 mg of methyl 4-[2-(4-{[(2-{[3-({cyclopropyl[2-(methylamino)ethyl]amino})methyl)benzoyl]amino}-4,5,6,7-tetrahydro-1-benzothiophen-3-yl)carbonyl]amino}phenyl)ethyl]benzoate and 70 mg of methyl 3-(bromomethyl)benzoate as starting materials, the similar alkylation as in Preparation Example 30 and the hydrolysis similar to Example 2 were sequentially performed, thereby obtaining 69 mg of 3-{[{2-[(3-{[3-({4-[2-(4-carboxyphenyl)ethyl]phenyl}carbamoyl)-4,5,6,7-tetrahydro-1-benzothiophen-2-yl]carbamoyl}benzyl)(cyclopropyl)amino]ethyl}(methyl)amino]methyl}benzoic acid dihydrochloride.

Example 8

By using 320 mg of methyl 4-(2-{5-[({2-[(2-{[{2-[(4-tert-butoxy-4-oxobutanoyl)(methyl)amino]ethyl}(pentan-3-yl)amino]methyl}isonicotinoyl)amino]-4,5,6,7-tetrahydro-1-benzothiophen-3-yl}carbonyl)amino]pyridin-2-yl}ethyl)benzoate as a starting material, removal of a tert-butyl group with 3.0 mL of TFA under the conditions similar to Example 10 as described later, and the hydrolysis similar to Example 2 were performed, thereby obtaining 279 mg of 4-(2-{5-[({2-[(2-{[{2-[(3-carboxypropanoyl)(methyl)amino]ethyl}(pentan-3-yl)amino]methyl}isonicotinoyl)amino]-4,5,6,7-tetrahydro-1-benzothiophen-3-yl}carbonyl)amino]pyridin-2-yl}ethyl)benzoic acid trihydrochloride.

Example 9

A mixture of 180 mg of 4-[2-(4-{[(2-{[3-({[4-(diethoxyphosphoryl)butanoyl](isopropyl)amino}methyl)benzoyl]

amino}-4,5,6,7-tetrahydro-1-benzothiophen-3-yl)carbonyl] amino}phenyl)ethyl]benzoic acid, 0.040 mL of bromotrimethylsilane, and 3.6 mL of chloroform was stirred overnight at room temperature. Water was added to the reaction mixture, followed by extraction with chloroform. The organic layer was dried over anhydrous sodium sulfate, and the solvent was removed under reduced pressure. The residue was purified by silica gel column chromatography, thereby obtaining 42 mg of 4-(2-{4-[({2-[(3-{[{4-[ethoxy(hydroxy) phosphoryl]butanoyl}(isopropyl)amino]methyl}benzoyl) amino]-4,5,6,7-tetrahydro-1-benzothiophen-3-yl}carbonyl) amino]phenyl}ethyl)benzoic acid.

Example 10

A mixture of 675 mg of methyl 5-[{3-[(3-{[6-(1-tert-butoxy-2-methyl-1-oxopropan-2-yl)pyridin-3-yl]carbamoyl}-4,5,6,7-tetrahydro-1-benzothiophen-2-yl)carbamoyl]benzyl}(pentan-3-yl)amino]-2,2-dimethyl-5-oxopentanoate, 10 mL of methylene chloride, and 1.3 mL of TFA was stirred 15 hours at room temperature. The reaction mixture was concentrated under reduced pressure, and a saturated aqueous sodium hydrogen carbonate solution was added to the residue, followed by extraction by using ethyl acetate. The organic layer was washed with saturated brine and dried over anhydrous sodium sulfate, and the solvent was removed under reduced pressure. The residue was purified by silica gel column chromatography (10% methanol/chloroform), thereby obtaining 550 mg of 2-{5-[({2-[(3-{[(5-methoxy-4,4-dimethyl-5-oxopentanoyl)(pentan-3-yl)amino] methyl}benzoyl)amino]-4,5,6,7-tetrahydro-1-benzothiophen-3-yl}carbonyl)amino]pyridin-2-yl}-2-methylpropanoic acid.

Example 11

To a mixture of 410 mg of 2-{5-[({2-[(3-{[(5-methoxy-4,4-dimethyl-5-oxopentanoyl)(pentan-3-yl)amino] methyl}benzoyl)amino]-4,5,6,7-tetrahydro-1-benzothiophen-3-yl}carbonyl)amino]pyridin-2-yl}-2-methylpropanoic acid, 75 mg of 4-methylmorpholine and 10 mL of THF was added 0.089 mL of isobutyl chloroformate under ice cooling, followed by stirring for 10 minutes at room temperature. The reaction mixture was filtered, and then the filtrate was cooled with ice. 65 mg of sodium borohydride and 1.0 mL of water were added thereto, followed by stirring for 10 minutes at room temperature. A saturated aqueous ammonium chloride solution was added to the reaction mixture, followed by extraction with ethyl acetate. The organic layer was washed with saturated brine and dried over anhydrous sodium sulfate, and the solvent was removed under reduced pressure. The residue was purified by silica gel column chromatography (hexane:ethyl acetate=1:2), thereby obtaining 155 mg of methyl 5-[{3-[(3-{[6-(1-hydroxy-2-methylpropan-2-yl)pyridin-3-yl]carbamoyl}-4,5,6,7-tetrahydro-1-benzothiophen-2-yl)carbamoyl]benzyl}(pentan-3-yl) amino]-2,2-dimethyl-5-oxopentanoate.

Example 12

A mixture of 150 mg of 4-{[(2-{[3-(morpholin-4-ylmethyl)benzoyl]amino}-4,5,6,7-tetrahydro-1-benzothiophen-3-yl)carbonyl]amino}benzoic acid, 57 mg of N,N-diethyl-p-phenylenediamine, 61 mg of WSC.hydrochloride, 42 mg of HOBt, and 1.5 mL of methylene chloride was stirred for 3 hours at room temperature. Water was added to the reaction mixture, followed by extraction with methylene chloride. The organic layer was dried over anhydrous sodium sulfate, and the solvent was removed under reduced pressure. The residue was purified by basic silica gel column chromatography (2% methanol/chloroform), thereby obtaining an oily material. Methanol and 4.0 M hydrogen chloride/ethyl acetate solution were added to this material, and the solution was concentrated under reduced pressure. The residue was treated with ethyl acetate, thereby obtaining 85 mg of N-(4-{[4-(diethylamino) phenyl]carbamoyl}phenyl)-2-{[3-(morpholin-4-ylmethyl) benzoyl]amino}-4,5,6,7-tetrahydro-1-benzothiophene-3-carboxamide dihydrochloride.

Example 13

By using 340 mg of 2-[(3-{[cyclopropyl(piperidin-4-yl) amino]methyl}benzoyl)amino]-N-[4-(diethylamino)phenyl]-4,5,6,7-tetrahydro-1-benzothiophene-3-carboxamide and 99 mg of ethyl bromoacetate, a reaction was performed under the conditions similar to Preparation Example 30, thereby obtaining 310 mg of ethyl[4-(cyclopropyl {3-[(3-{[4-(diethylamino)phenyl]carbamoyl}-4,5,6,7-tetrahydro-1-benzothiophen-2-yl)carbamoyl]benzyl}amino)piperidin-1-yl]acetate.

Example 14

By using 1.71 g of tert-butyl 3-(hydroxymethyl)-4-[3-({3-[(4-{2-[4-(methoxycarbonyl)phenyl]ethyl}phenyl)carbamoyl]-4,5,6,7-tetrahydro-1-benzothiophen-2-yl}carbamoyl) benzyl]piperazine-1-carboxylate and 17 mL of TFA, a reaction was performed under the conditions similar to Preparation Example 12, thereby obtaining 1.38 g of methyl 4-(2-{4-[({2-[(3-{[2-(hydroxymethyl)piperazin-1-yl] methyl}benzoyl)amino]-4,5,6,7-tetrahydro-1-benzothiophen-3-yl}carbonyl)amino]phenyl}ethyl) benzoate.

Example 15

To a mixture of 200 mg of 2-{[3-(chloromethyl)benzoyl] amino}-N-[4-(diethylamino)phenyl]-4,5,6,7-tetrahydro-1-benzothiophene-3-carboxamide and 8 mL of DMF was added 1.0 mL of morpholine, followed by stirring for 3 days at room temperature. The reaction mixture was concentrated under reduced pressure, and the residue was purified by silica gel column chromatography (chloroform:methanol:aqueous ammonia solution=50:1:0.1). The obtained residue was dissolved in a mixed solution of ethyl acetate and ethanol (4:1), and 1.0 mL of 4.0 M hydrogen chloride/ethyl acetate solution was further added thereto. The precipitated solid was collected by filtration, thereby obtaining 183 mg of N-[4-(diethylamino)phenyl]-2-{[3-(morpholin-4-ylmethyl)benzoyl] amino}-4,5,6,7-tetrahydro-1-benzothiophene-3-carboxamide dihydrochloride.

Example 16

By using 400 mg of 2-{[3-(chloromethyl)benzoyl]amino}-N-[4-(pyridin-4-ylmethyl)phenyl]-4,5,6,7-tetrahydro-1-benzothiophene-3-carboxamide and 819 mg of ethyl 4-(cyclopropylamino)cyclohexanecarboxylate, the alkylation similar to Preparation Example 30 was performed, and then hydrolysis was performed under the conditions similar to Example 5, thereby obtaining 261 mg of 4-(cyclopropyl{3-[(3-{[4-(pyridin-4-ylmethyl)phenyl]carbamoyl}-4,5,6,7-tetrahydro-1- benzothiophen-2-yl)carbamoyl]benzyl}amino)cyclohexane carboxylic acid dihydrochloride.

Example 17

To a mixture of 350 mg of 2-[3-(morpholin-4-ylmethyl)phenyl]-5,6,7,8-tetrahydro-4H-[1]benzothieno[2,3-d][1,3]oxazin-4-one, 150 mg of 2-N,2-N-diethylpyrimidine-2,5-diamine and 5.0 mL of THF was added dropwise 1.0 mL of lithium hexamethyldisilazide (1.0 M in THF) under ice cooling, followed by stirring for 1 hour at the same temperature. A saturated aqueous ammonium chloride solution was added to the reaction mixture, followed by extraction with ethyl acetate. The organic layer was washed with saturated brine and dried over anhydrous sodium sulfate, and the solvent was removed under reduced pressure. The residue was purified by silica gel column chromatography (methanol/chloroform). Ethyl acetate and 0.5 mL of 4.0 M hydrogen chloride/ethyl acetate solution were sequentially added to the residue, followed by stirring for 30 minutes at room temperature. The insoluble material was collected by filtration, thereby obtaining 174 mg of N-[2-(diethylamino)pyrimidin-5-yl]-2-{[3-(morpholin-4-ylmethyl)benzoyl]amino}-4,5,6,7-tetrahydro-1-benzothiophene-3-carboxamide dihydrochloride.

Example 18

By using 250 mg of methyl 4-(2-{4-[({2-[(3-{[{cis-4-[(benzyloxy)carbonyl]cyclohexyl}(isopropyl)amino]methyl}benzoyl)amino]-4,5,6,7-tetrahydro-1-benzothiophen-3-yl}) carbonyl)amino]phenyl}ethyl)benzoate and 10 mg of 10% palladium carbon, catalytic hydrogen reduction was performed under the conditions similar to Preparation Example 5, thereby obtaining 88 mg of cis-4-{isopropyl[3-({3-[(4-{2-[4-(methoxycarbonyl)phenyl]ethyl}phenyl)carbamoyl]-4,5,6,7-tetrahydro-1-benzothiophen-2-yl}carbamoyl)benzyl]amino}cyclohexanecarboxylic acid.

Example 19

By using 5.34 g of 2-{[3-(chloromethyl)benzoyl]amino}-N-[4-(diethylamino)phenyl]-4,5,6,7-tetrahydro-1-benzothiophene-3-carboxamide and 13.1 g of 1-[4-(cyclopropylamino)piperidin-1-yl]ethanone as starting materials, a reaction was performed under the conditions similar to Preparation Example 29, thereby obtaining 5.37 g of 2-[(3-{[(1-acetylpiperidin-4-yl)(cyclopropyl)amino]methyl}benzoyl)amino]-N-[4-(diethylamino)phenyl]-4,5,6,7-tetrahydro-1-benzothiophene-3-carboxamide.

Example 20

By using 23 mg of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate and 19 mg of methyl [(1-ethylpropyl)amino]acetate as starting materials, alkylation was performed under the conditions similar to Preparation Example 30, and then hydrolysis was performed under the conditions similar to Example 6, thereby obtaining 6.7 mg of 4-(2-{4-[({2-[(3-{[(carboxymethyl)(pentan-3-yl)amino]methyl}benzoyl)amino]-4,5,6,7-tetrahydro-1-benzothiophen-3-yl}carbonyl)amino]phenyl}ethyl)benzoic acid.

Example 21

By using 250 mg of 2-amino-N-[4-(pyridin-4-ylmethyl)phenyl]-4,5,6,7-tetrahydro-1-benzothiophene-3-carboxamide and 244 mg of 5-(morpholin-4-ylmethyl)-2-furoic acid as starting materials, a condensation reaction was performed under the conditions similar to Preparation Example 16, thereby obtaining 307 mg of 2-{[5-(morpholin-4-ylmethyl)-2-furoyl]amino}-N-[4-(pyridin-4-ylmethyl)phenyl]-4,5,6,7-tetrahydro-1-benzothiophene-3-carboxamide dihydrochloride.

Example 22

A mixture of 0.07 mL of lithium hexamethyldisilazide (1.0M in THF) and 0.2 mL of THF was added to a mixture of 11.5 mg of 2-[3-(morpholin-4-ylmethyl)phenyl]-5,6,7,8-tetrahydro-4H-[1]benzothieno[2,3-d][1,3]oxazin-4-one, 4.9 mg of 5-cyclopropyl-1,3,4-thiadiazol-2-amine, and 0.8 mL of THF, followed by stirring overnight at room temperature. Chloroform and a saturated aqueous ammonium chloride solution were added to the reaction mixture, and the organic layer was separated. After the solvent was removed under reduced pressure, the obtained residue was purified, thereby obtaining 11.4 mg of N-(5-cyclopropyl-1,3,4-thiadiazol-2-yl)-2-{[3-(morpholin-4-ylmethyl)benzoyl]amino}-4,5,6,7-tetrahydro-1-benzothiophene-3-carboxamide.

Example 67A

To a mixture of 90 mg of 4-(2-{4-[({2-[(3-{[{2-[(4-carboxy-4-methylpentanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid hydrochloride and 0.5 mL of ethanol was added 0.32 mL of a 1.0 M aqueous sodium hydroxide solution at room temperature, followed by stirring for 5 minutes at room temperature. 1.1 mL of a 0.1 M aqueous magnesium chloride solution was added dropwise to the reaction mixture at 80° C., and then 0.38 mL of water was added thereto, followed by stirring again for 30 minutes at 80° C. 0.4 mL of EtOH was added to the reaction mixture, followed by stirring again for 14 hours at 80° C. 0.9 mL of water was added to the reaction mixture, followed by stirring for additional 1 hour at 80° C. 1.8 mL of water was further added to the reaction mixture, followed by stirring again for 2 hours at 80° C. After the reaction mixture was cooled to room temperature, the precipitate was collected by filtration, thereby obtaining 86 mg of a hydrate of magnesium 4-(2-{4-[({2-[(3-{[{2-[(4-carboxylato-4-methylpentanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate as the crystal.

ESI+: 823

Example 109A

To a mixture of 80 mg of 4-(2-{4-[({2-[(3-{[(4-carboxy-4-methylpentanoyl)(pentan-3-yl)amino]methyl}benzoyl)amino]-4,5,6,7-tetrahydro-1-benzothiophen-3-yl}carbonyl)amino]phenyl}ethyl)benzoic acid and 0.4 mL of ethanol was added 0.21 mL of a 1.0 M aqueous sodium hydroxide solution at room temperature, followed by stirring for 5 minutes at room temperature. 1.0 mL of a 0.1 M aqueous magnesium chloride solution was added dropwise to the reaction mixture at 80° C., and then 0.39 mL of water was added to the reaction mixture, followed by stirring again for 30 minutes at 80° C. 0.4 mL of ethanol was added to the reaction mixture, followed by stirring again for 30 minutes at 80° C. 0.8 mL of water was added to the reaction mixture, followed by stirring for 14 hours at 80° C., and then 0.8 mL of water was further added thereto, followed by stirring again for 2 hours at 80° C. After the reaction mixture was cooled to room temperature, the precipitate was collected by filtration, thereby obtaining 74 mg of a hydrate of magnesium 4-(2-{4-[({2-[(3-{[(4-carboxylato-4-methylpentanoyl)(pentan-3-yl)amino]methyl}benzoyl)amino]-4,5,6,7-tetrahydro-1-benzothiophen-3-yl}carbonyl)amino]phenyl}ethyl)benzoate as the crystal. ESI-: 764.

Example 121A

To a mixture of 80 mg of 4-(2-{4-[({2-[(3-{[(4-carboxy-3,3-dimethylbutanoyl)(pentan-3-yl)amino]methyl}benzoyl)amino]-4,5,6,7-tetrahydro-1-benzothiophen-3-yl}carbonyl)amino]phenyl}ethyl)benzoic acid and 0.4 mL of ethanol was added 0.21 mL of a 1.0 M aqueous sodium hydroxide solution at room temperature, followed by stirring for 5 minutes at room temperature. 1.0 mL of a 0.1 M aqueous magnesium chloride solution was added dropwise to the reaction mixture at 80° C., and then 0.39 mL of water was added thereto, followed by stirring again for 30 minutes at 80° C. 0.4 mL of ethanol was added to the reaction mixture, followed by stirring again for 30 minutes at 80° C. 0.8 mL of water was added to the reaction mixture, followed by stirring for 14 hours at 80° C., and then 0.8 mL of water was further added thereto, followed by stirring again for 2 hours at 80° C. After the reaction mixture was cooled to room temperature, the precipitate was collected by filtration, thereby obtaining 77 mg of a hydrate of magnesium 4-(2-{4-[({2-[(3-{[(4-carboxylato-3,3-dimethylbutanoyl)(pentan-3-yl)amino]methyl}benzoyl)amino]-4,5,6,7-tetrahydro-1-benzothiophen-3-yl}carbonyl)amino]phenyl}ethyl)benzoate as the crystal. ESI-: 764.

Example 148

By using 29 mg of methyl 4-[2-(4-{[(2-{[3-(chloromethyl)benzoyl]amino}-4,5,6,7-tetrahydro-1-benzothiophen-3-yl)carbonyl]amino}phenyl)ethyl]benzoate and 30 mg of methyl 3-(aminomethyl)benzoate hydrochloride as starting materials, amination was performed under the conditions similar to Preparation Example 30, thereafter alkylation with MP-Triacetoxyborohydride (Biotage) was performed under the conditions similar to Example 1, and then hydrolysis was performed under the conditions similar to Example 6, thereby obtaining 15 mg of 3-{[(3-{[3-({4-[2-(4-carboxyphenyl)ethyl]phenyl}carbamoyl)-4,5,6,7-tetrahydro-1-benzothiophen-2-yl]carbamoyl}benzyl)(isopropyl)amino]methyl}benzoic acid.

Compounds of Examples 23 to 246 shown in the following table were prepared in the similar manner as in Examples 1 to 22. The following table shows the structure, physicochemical data, and preparation process of the example compounds.

TABLE 3

| Pr | Str |
|---|---|
| 1 | ![structure] |
| 2 | ![structure] |
| 3 | ![structure] |
| 4 | ![structure] |
| 5 | ![structure] |
| 6 | ![structure] |
| 7 | ![structure] |

TABLE 3-continued

| Pr | Str |
|---|---|
| 8 | (structure) |
| 9 | (structure) |
| 10 | (structure) |
| 11 | (structure) |

TABLE 4

| Pr | Str |
|---|---|
| 12 | (structure) |
| 13 | (structure) |
| 14 | (structure) |

TABLE 4-continued
| Pr | Str |
|---|---|
| 15 | 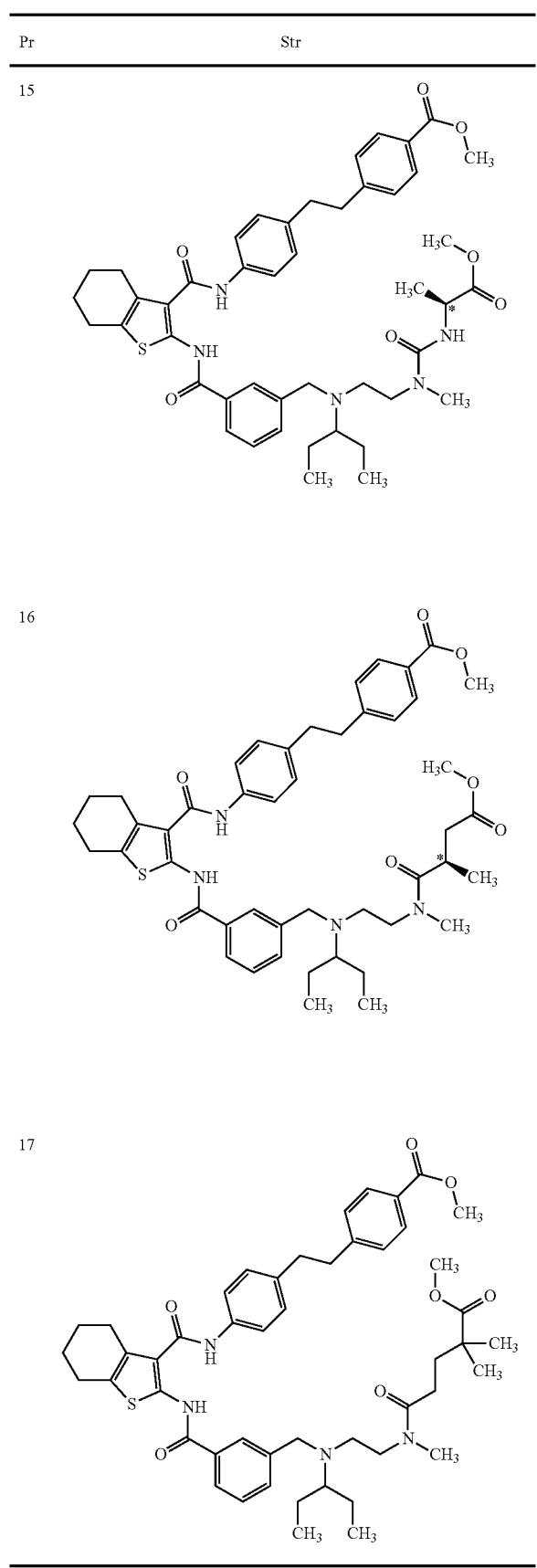 |
| 16 | |
| 17 | |
TABLE 5
| Pr | Str |
|---|---|
| 18 | 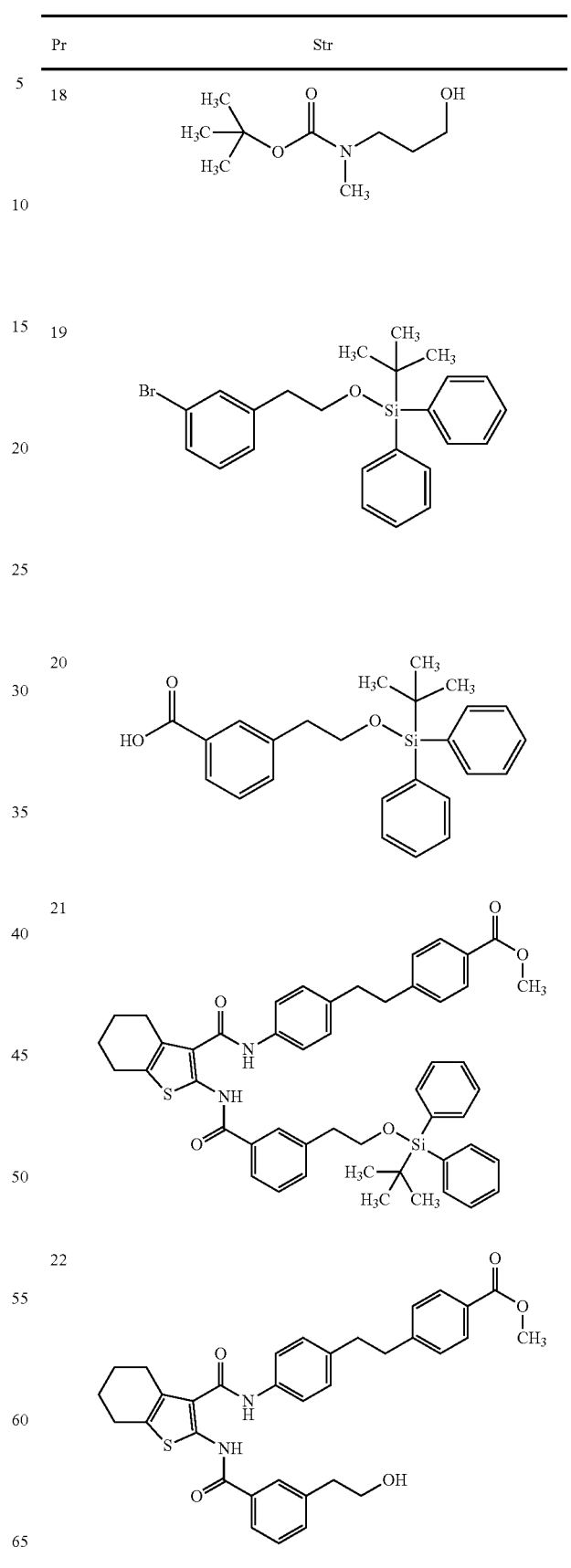 |
| 19 | |
| 20 | |
| 21 | |
| 22 | |

TABLE 5-continued
| Pr | Str |
|---|---|
| 23 | 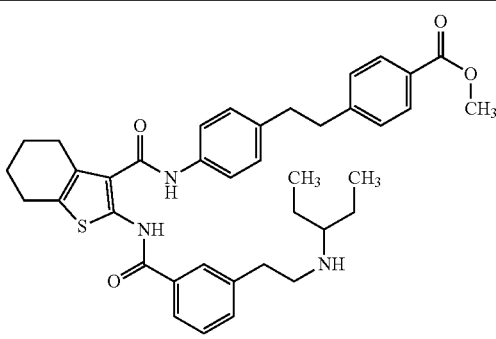 |
| 24 | 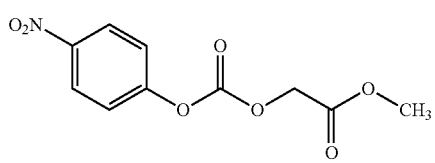 [SMILES: COC(=O)COC(=O)Oc1ccc([N+](=O)[O-])cc1] |
| 25 | 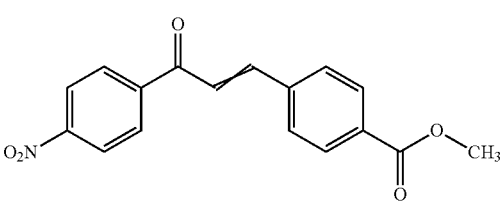 [SMILES: COC(=O)c1ccc(C=CC(=O)c2ccc([N+](=O)[O-])cc2)cc1] |
| 26 | 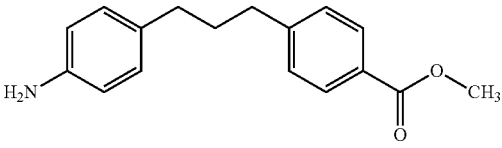 [SMILES: COC(=O)c1ccc(CCCc2ccc(N)cc2)cc1] |
| 27 | 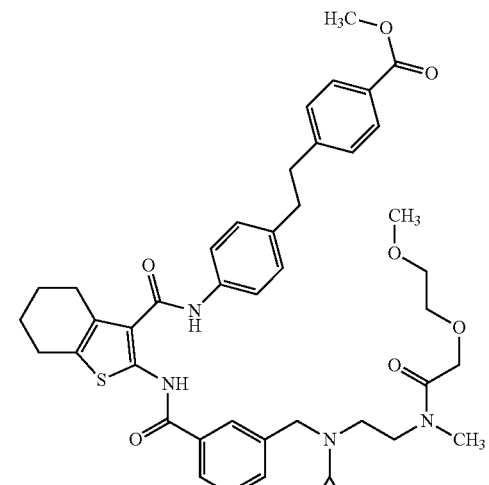 |
TABLE 6
| Pr | Str |
|---|---|
| 28 | 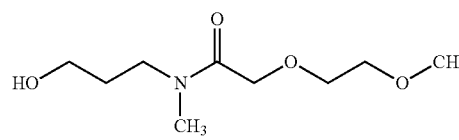 |
| 29 |  |
| 30 | 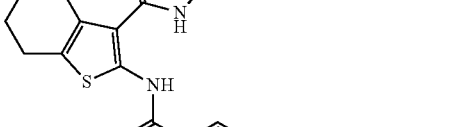 |

TABLE 6-continued
| Pr | Str |
|---|---|
| 31 | 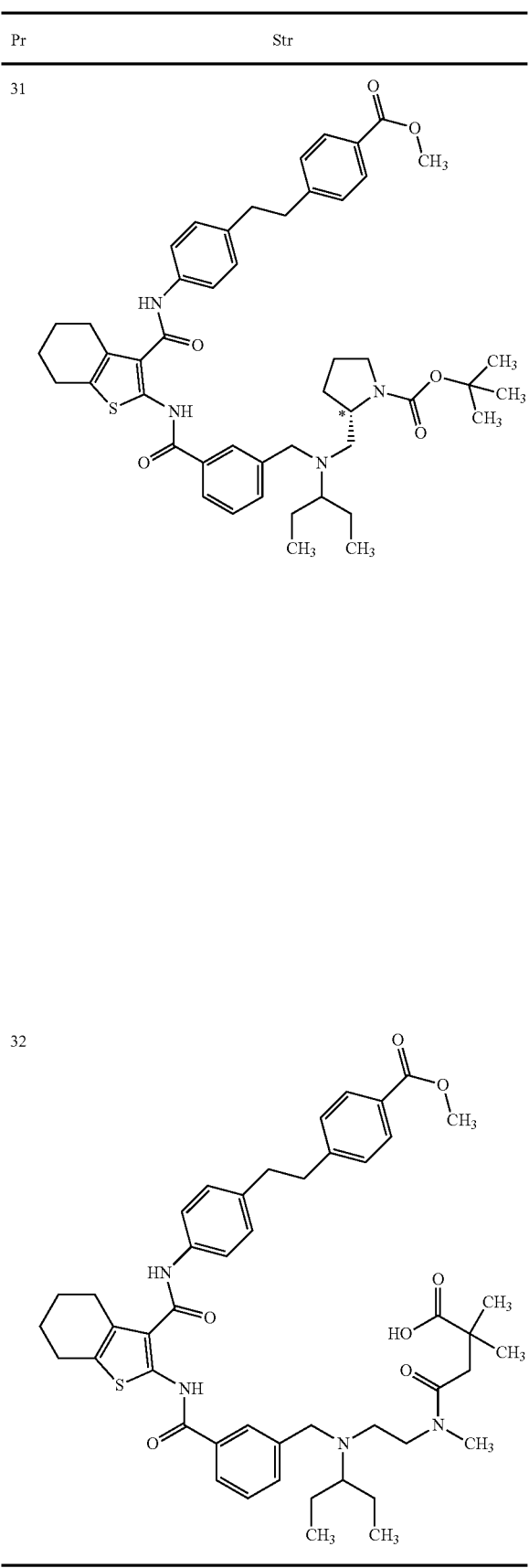 |
| 32 | |
TABLE 7
| Pr | Str |
|---|---|
| 33 | 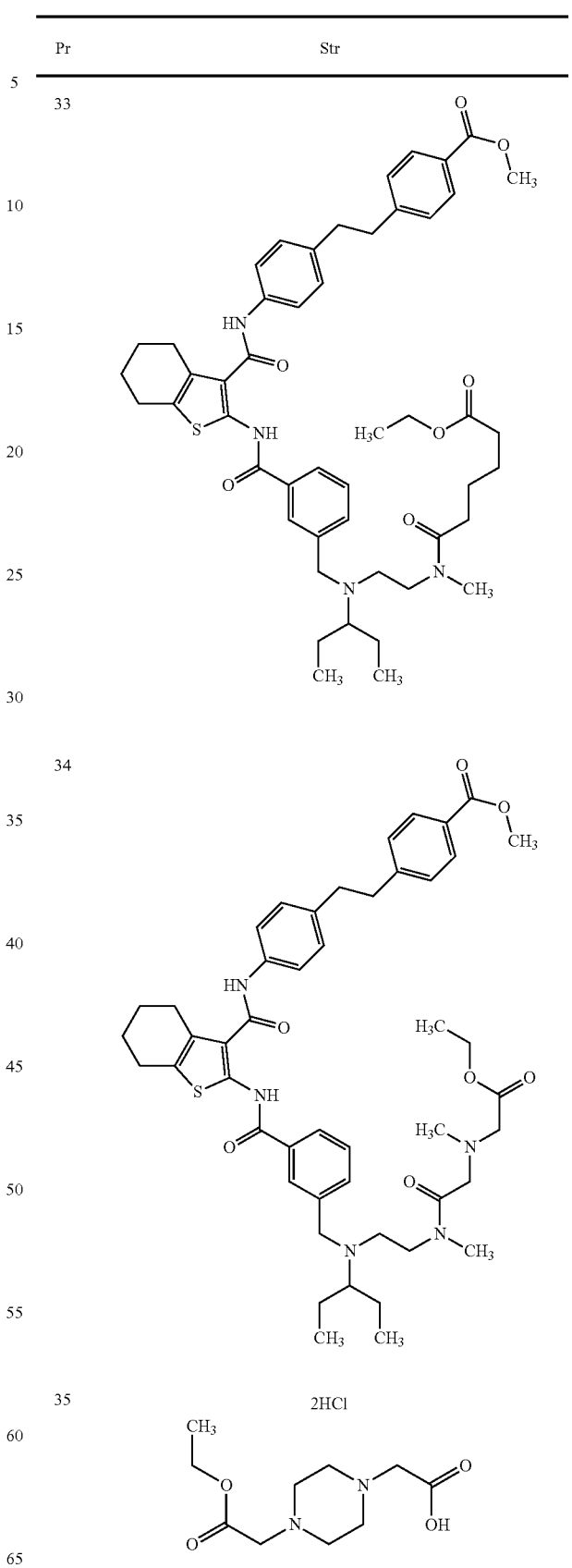 |
| 34 | |

TABLE 7-continued

| Pr | Str |
|---|---|
| 36 | (structure) |
| 37 | (structure) |
| 38 | (structure) |
| 39 | (structure) |

TABLE 8

| Pr | Str |
|---|---|
| 40 | (structure) |
| 41 | (structure) |
| 42 | (structure) |

TABLE 8-continued
| Pr | Str |
|---|---|
| 43 | 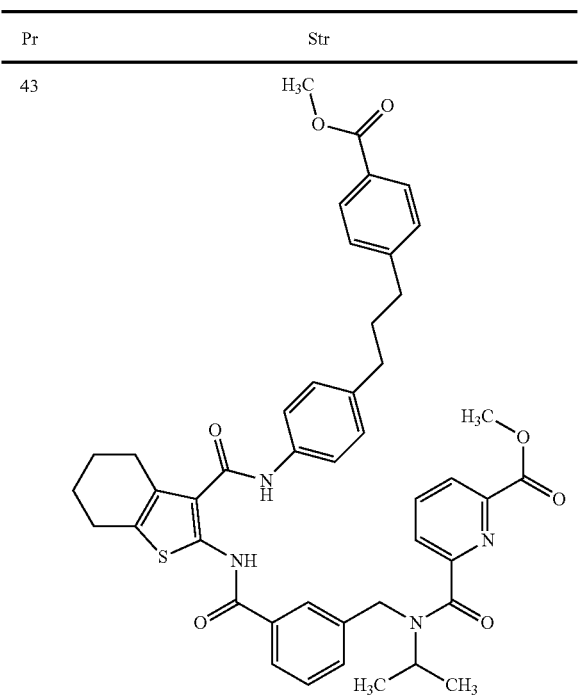 |
| 44 | |
| 45 | |
TABLE 9
| Pr | Str |
|---|---|
| 46 | |
| 47 | |

TABLE 9-continued
| Pr | Str |
|---|---|
| 48 | 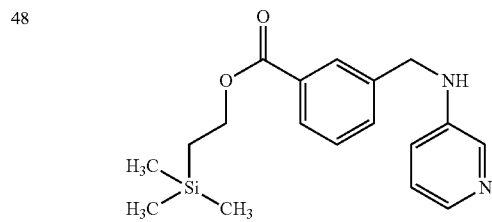 |
| 49 | 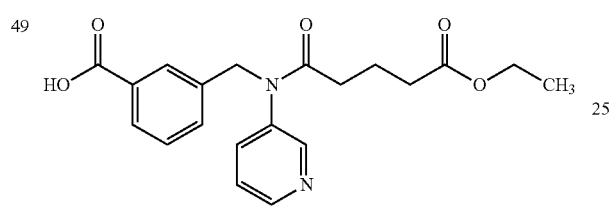 |
| 50 | 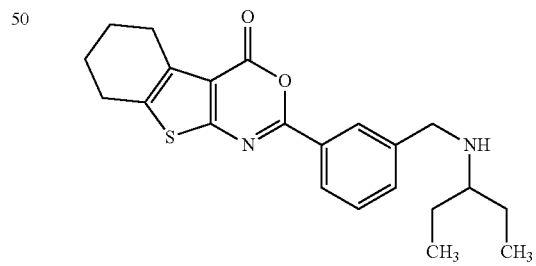 |
| 51 | 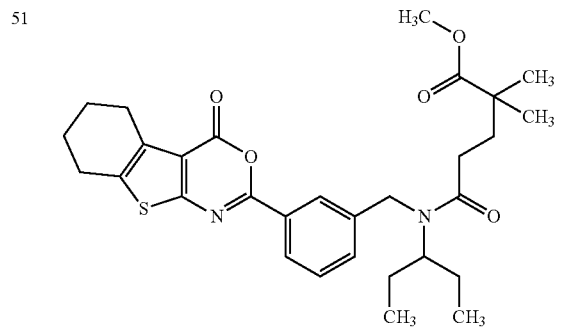 |
TABLE 9-continued
| Pr | Str |
|---|---|
| 52 | 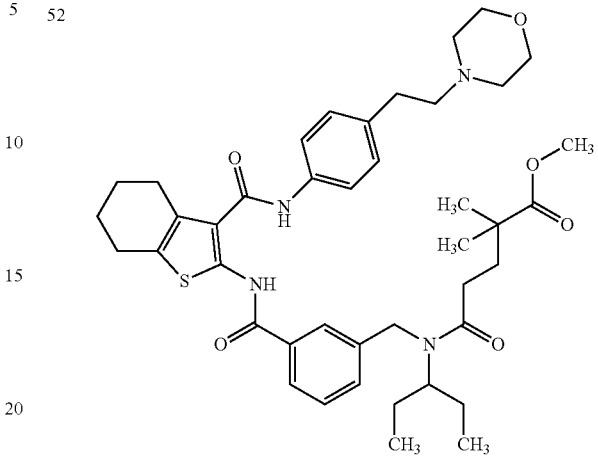 |
| 53 | 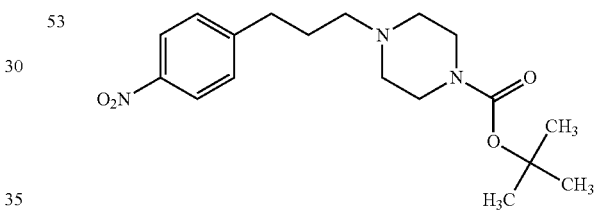 |
TABLE 10
| Pr | Str |
|---|---|
| 54 | 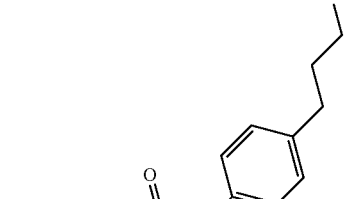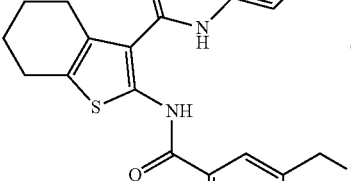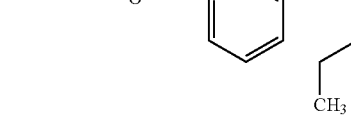 |

TABLE 10-continued

| Pr | Str |
|----|-----|
| 55 | (structure: 5-nitropyridin-2-yl dimethyl acetic acid tert-butyl ester) |
| 56 | (structure: morpholinomethyl benzamide tetrahydrobenzothiophene carboxamide with 4-hydroxyphenyl) |
| 57 | (structure: methyl benzoate phenoxy methyl tetrahydrobenzothiophene with morpholinomethyl benzamide) |
| 58 | (structure: methyl benzoate phenethyl tetrahydrobenzothiophene carboxamide with cyclopropyl piperidinyl N-methyl succinic acid amide) |
| 59 | (structure: methyl benzoate phenethyl tetrahydrobenzothiophene with ethyl pyrimidine-5-carboxylate cyclopropyl benzamide) |
| 60 | (structure: 2-(3-(morpholinomethyl)phenyl)-5,6,7,8-tetrahydro-4H-benzo[4,5]thieno[2,3-d][1,3]oxazin-4-one) |

TABLE 11

| Pr | Str |
|----|-----|
| 61 | (structure: methyl benzoate phenethyl tetrahydrobenzothiophene carboxamide with ethyl butanoate cyclopropyl benzamide) |

TABLE 11-continued
| Pr | Str |
|---|---|
| 62 | 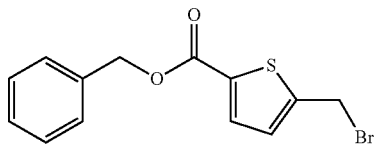 [SMILES: O=C(OCc1ccccc1)c1ccc(CBr)s1] |
| 63 | 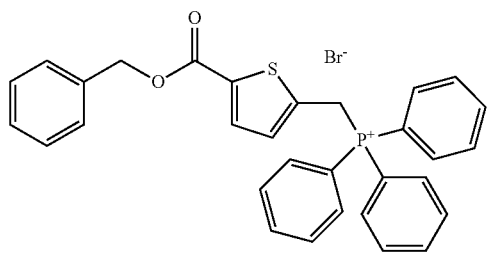 [SMILES: O=C(OCc1ccccc1)c1ccc(C[P+](c2ccccc2)(c2ccccc2)c2ccccc2)s1 ; [Br-]] |
| 64 | 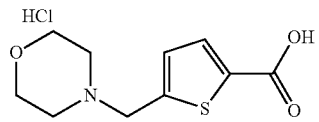 [SMILES: Cl ; O=C(O)c1ccc(CN2CCOCC2)s1] |
| 65 | 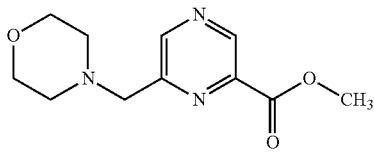 [SMILES: COC(=O)c1cncc(CN2CCOCC2)n1] |
| 66 | 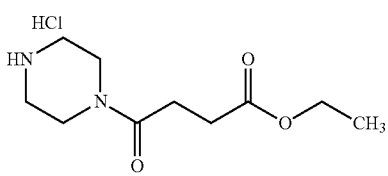 |
| 67 | 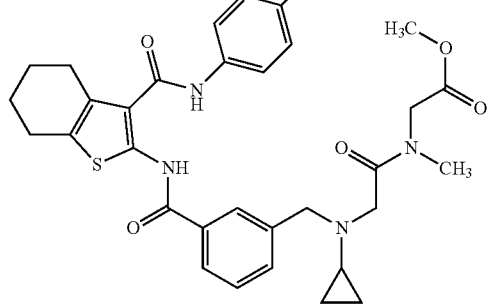 |
| 68 | 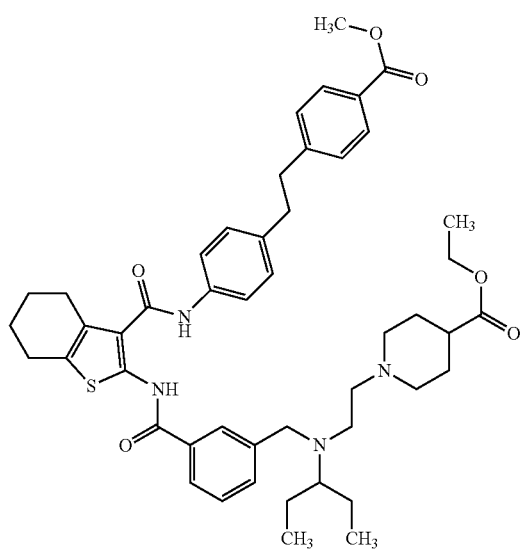 [SMILES: CCOC(=O)C1CCN(CCN(Cc2cccc(C(=O)Nc3sc4c(c3C(=O)Nc3ccc(CCc5ccc(C(=O)OC)cc5)cc3)CCCC4)c2)C(CC)CC)CC1] |
| 69 | 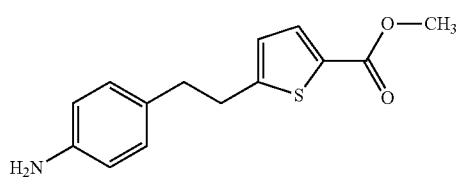 [SMILES: COC(=O)c1ccc(CCc2ccc(N)cc2)s1] |

TABLE 11-continued
| Pr | Str |
|---|---|
| 70 | 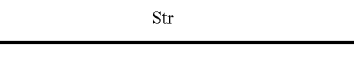 |
TABLE 12
| Pr | Str |
|---|---|
| 71 | |
| 72 | |
| 73 | |
| 74 | |
| 75 | 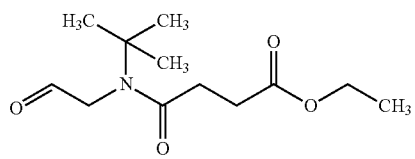 [SMILES: CCOC(=O)CCC(=O)N(CC=O)C(C)(C)C] |
TABLE 12-continued
| Pr | Str |
|---|---|
| 76 | |
| 77 | 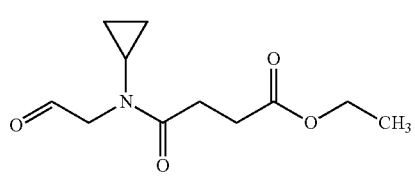 [SMILES: CCOC(=O)CCC(=O)N(CC=O)C1CC1] |
| 78 | |
| 79 | 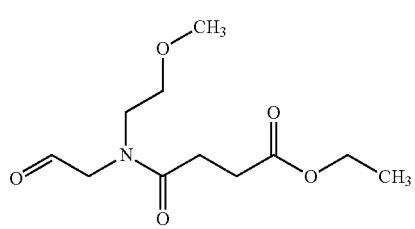 [SMILES: CCOC(=O)CCC(=O)N(CC=O)CCOC] |

TABLE 12-continued
| Pr | Str |
|---|---|
| 80 | 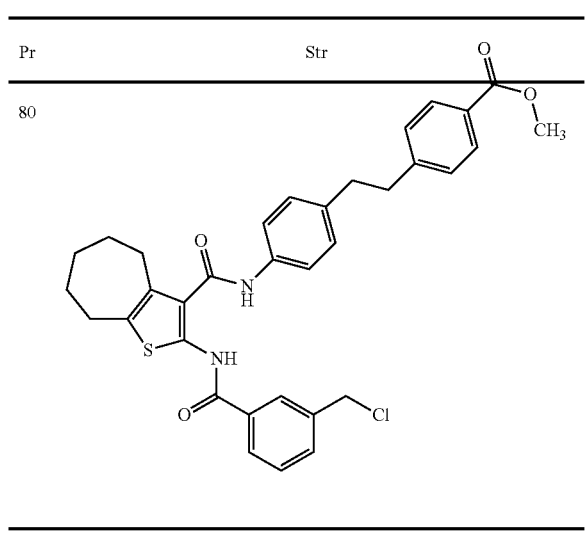 |
TABLE 13
| Pr | Str |
|---|---|
| 81 | 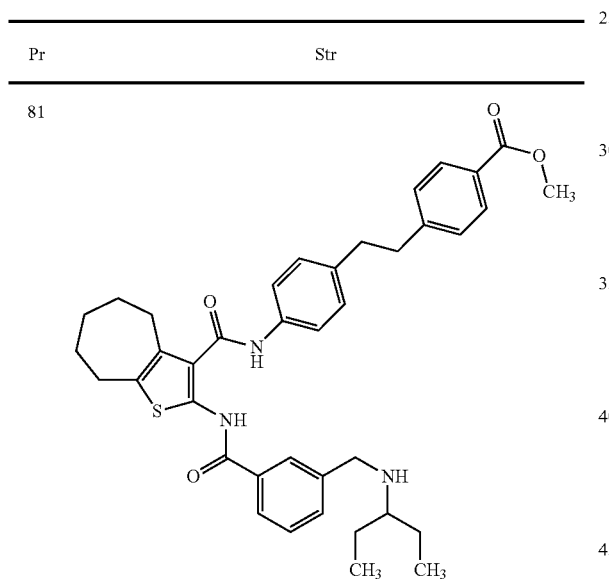 |
| 82 | 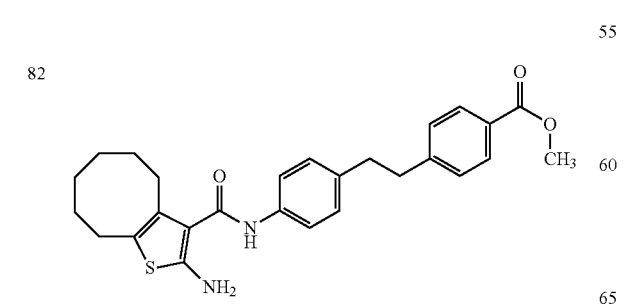 |
TABLE 13-continued
| Pr | Str |
|---|---|
| 83 | 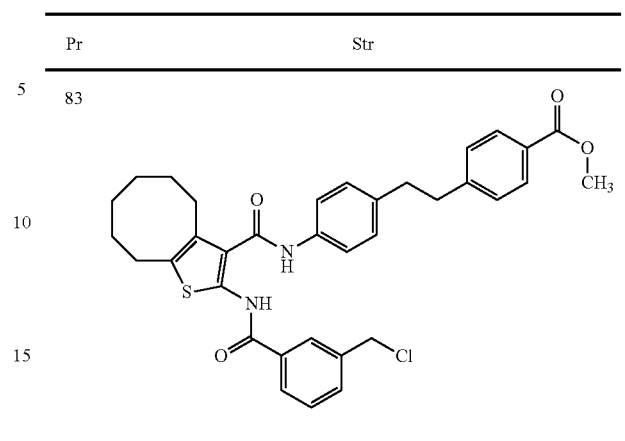 |
| 84 | 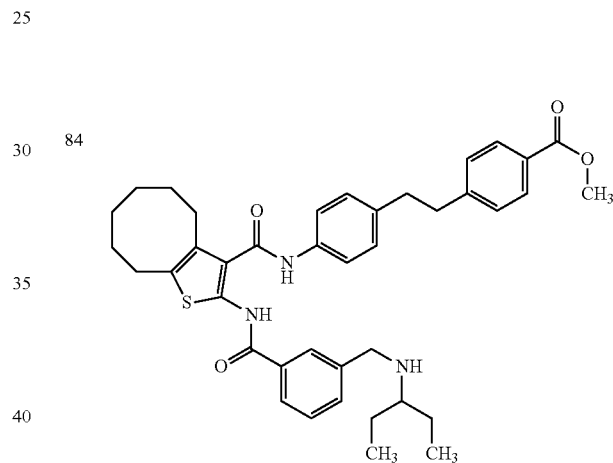 |
| 85 | 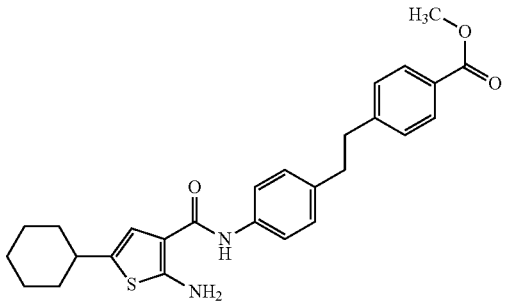 [SMILES: COC(=O)c1ccc(CCc2ccc(NC(=O)c3cc(C4CCCCC4)sc3N)cc2)cc1] |

TABLE 13-continued
| Pr | Str |
|---|---|
| 86 | 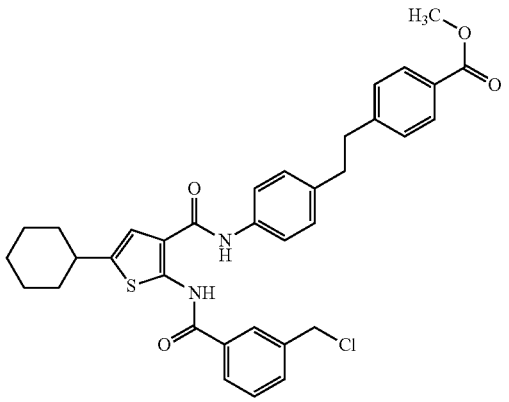 [SMILES: COC(=O)c1ccc(CCc2ccc(NC(=O)c3cc(C4CCCCC4)sc3NC(=O)c3cccc(CCl)c3)cc2)cc1] |
| 87 | 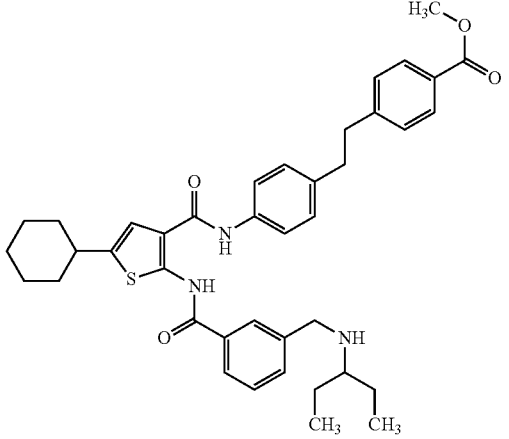 [SMILES: CCC(CC)NCc1cccc(C(=O)Nc2sc(C3CCCCC3)cc2C(=O)Nc2ccc(CCc3ccc(C(=O)OC)cc3)cc2)c1] |
TABLE 14
| Pr | Str |
|---|---|
| 88 | 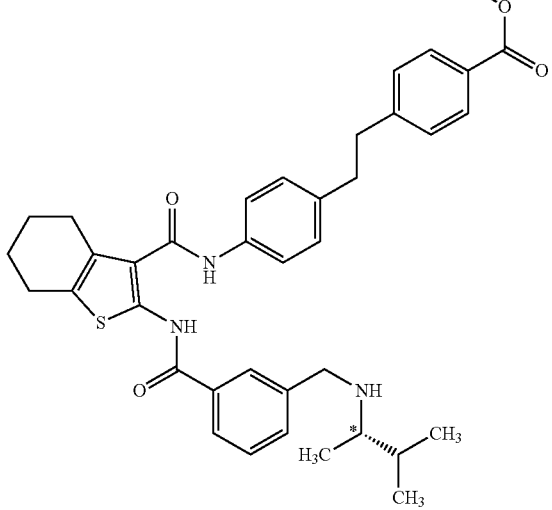 |
| 89 | 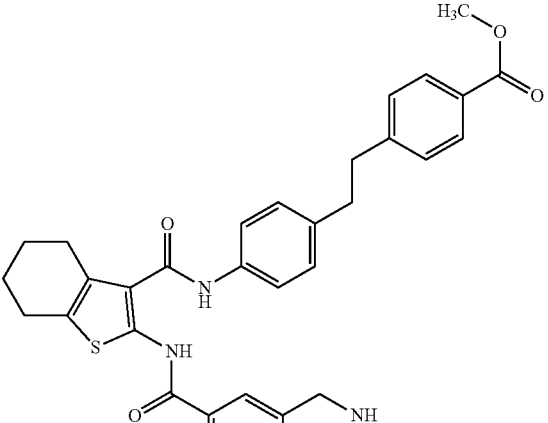 |
| 90 | 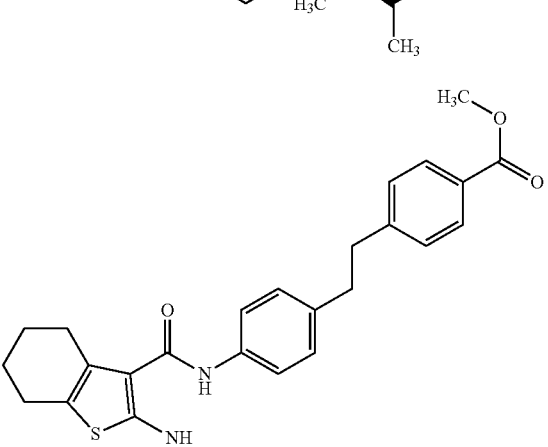 |
| 91 | 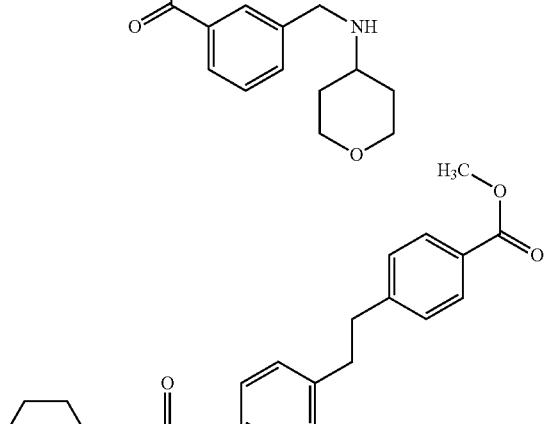 |

TABLE 14-continued
| Pr | Str |
|---|---|
| 92 | 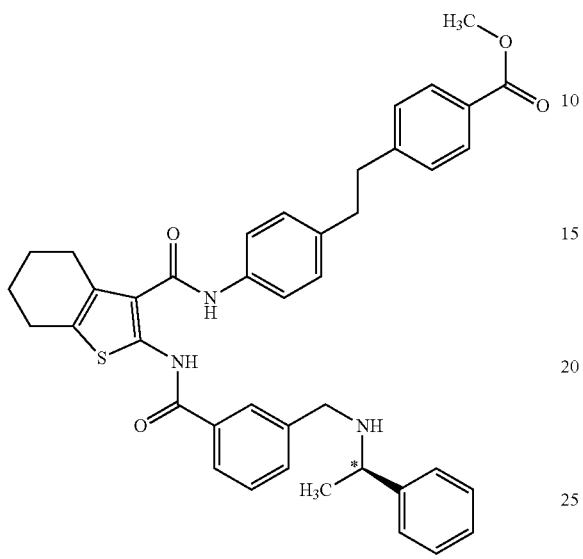 |
TABLE 15
| Pr | Str |
|---|---|
| 93 | 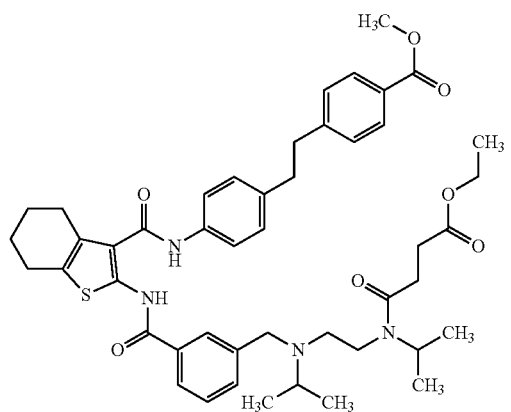 [SMILES: CCOC(=O)CCC(=O)N(CCN(Cc1cccc(C(=O)Nc2sc3c(c2C(=O)Nc2ccc(CCc4ccc(C(=O)OC)cc4)cc2)CCCC3)c1)C(C)C)C(C)C] |
| 94 | 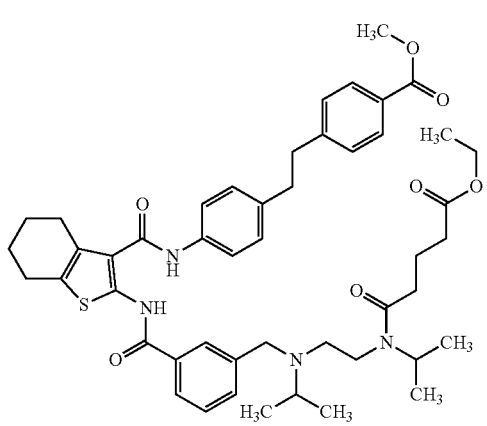 [SMILES: CCOC(=O)CCCC(=O)N(CCN(Cc1cccc(C(=O)Nc2sc3c(c2C(=O)Nc2ccc(CCc4ccc(C(=O)OC)cc4)cc2)CCCC3)c1)C(C)C)C(C)C] |
TABLE 15-continued
| Pr | Str |
|---|---|
| 95 | 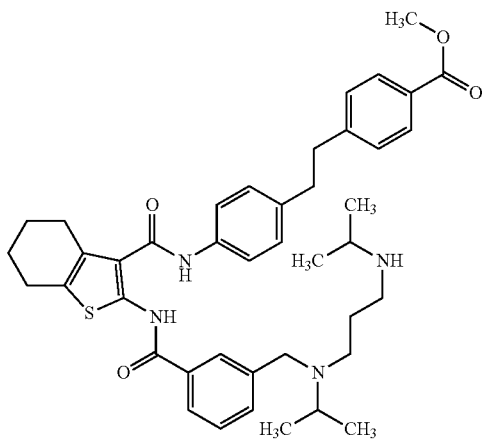 [SMILES: COC(=O)c1ccc(CCc2ccc(NC(=O)c3c(NC(=O)c4cccc(CN(CCCNC(C)C)C(C)C)c4)sc4c3CCCC4)cc2)cc1] |
| 96 | 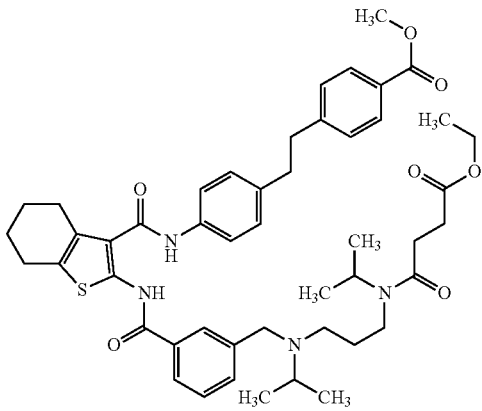 [SMILES: CCOC(=O)CCC(=O)N(CCCN(Cc1cccc(C(=O)Nc2sc3c(c2C(=O)Nc2ccc(CCc4ccc(C(=O)OC)cc4)cc2)CCCC3)c1)C(C)C)C(C)C] |
| 97 | 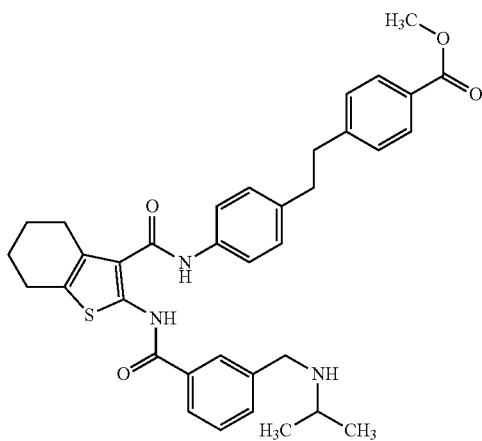 [SMILES: COC(=O)c1ccc(CCc2ccc(NC(=O)c3c(NC(=O)c4cccc(CNC(C)C)c4)sc4c3CCCC4)cc2)cc1] |

TABLE 15-continued
| Pr | Str |
|---|---|
| 98 | 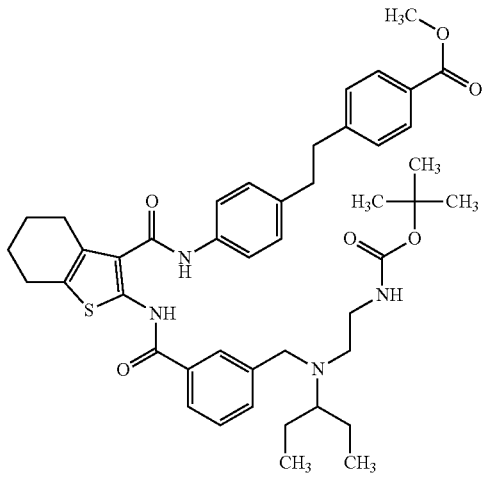 [SMILES: CCC(CC)N(CCNC(=O)OC(C)(C)C)Cc1cccc(C(=O)Nc2sc3c(c2C(=O)Nc2ccc(CCc4ccc(C(=O)OC)cc4)cc2)CCCC3)c1] |
TABLE 16
| Pr | Str |
|---|---|
| 99 | 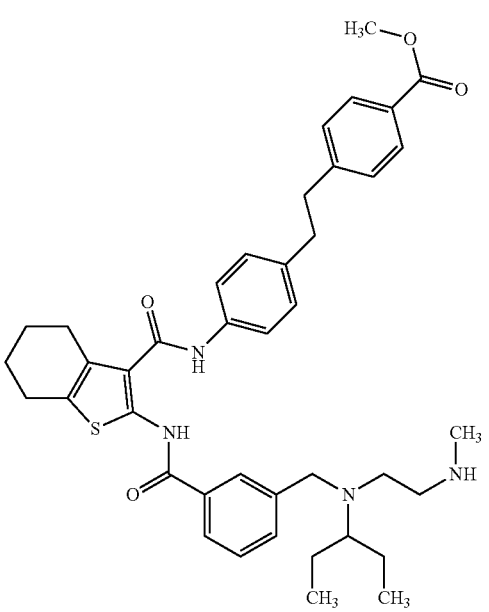 [SMILES: CCC(CC)N(CCNC)Cc1cccc(C(=O)Nc2sc3c(c2C(=O)Nc2ccc(CCc4ccc(C(=O)OC)cc4)cc2)CCCC3)c1] |
TABLE 16-continued
| Pr | Str |
|---|---|
| 100 | |
| 101 | |
| 102 | |

TABLE 16-continued
| Pr | Str | |
|---|---|---|
| 103 | 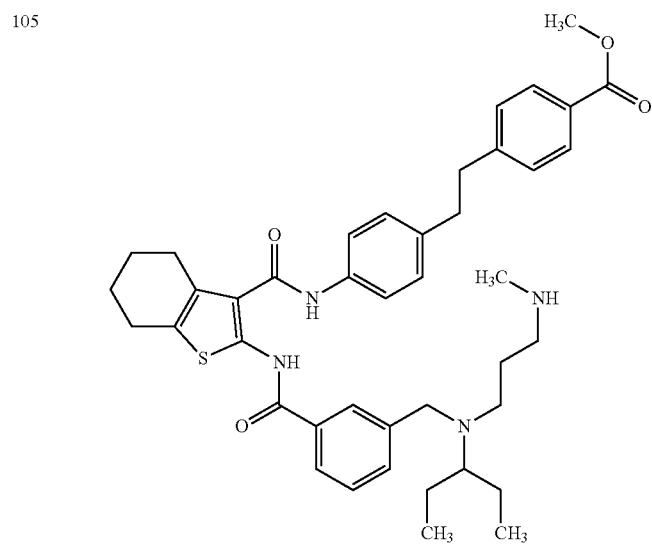 | 5 |
| | | 10 |
TABLE 17
| Pr | Str |
|---|---|
| 104 | |
| 105 | |

TABLE 17-continued

| Pr | Str |
|---|---|
| 106 | (structure) |
| 107 | (structure) |
| 108 | (structure) |

TABLE 18

| Pr | Str |
|---|---|
| 109 | (structure) |
| 110 | (structure) |
| 111 | (structure) |

TABLE 18-continued
| Pr | Str |
|---|---|
| 112 | 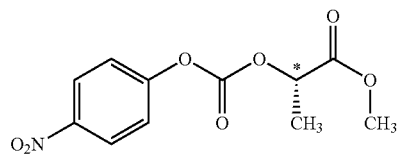 [SMILES: COC(=O)[C@H](C)OC(=O)Oc1ccc([N+](=O)[O-])cc1] |
| 113 | 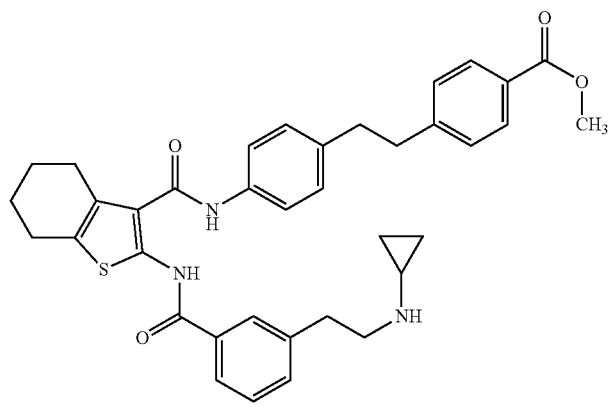 [SMILES: COC(=O)c1ccc(CCc2ccc(NC(=O)c3c(NC(=O)c4cccc(CCNC5CC5)c4)sc4c3CCCC4)cc2)cc1] |
| 114 | 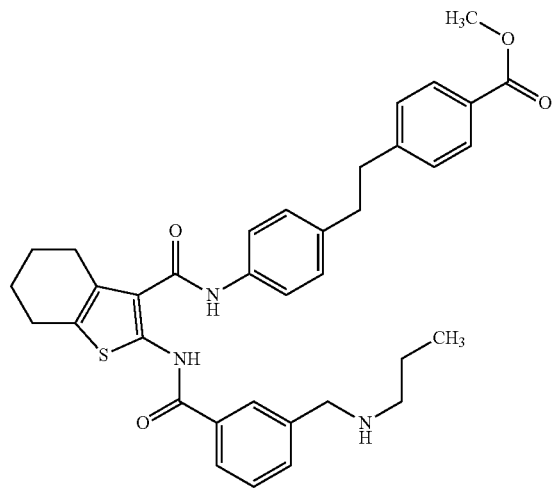 [SMILES: CCCNCc1cccc(C(=O)Nc2sc3c(c2C(=O)Nc2ccc(CCc4ccc(C(=O)OC)cc4)cc2)CCCC3)c1] |

TABLE 19
| Pr | Str |
|---|---|
| 115 | 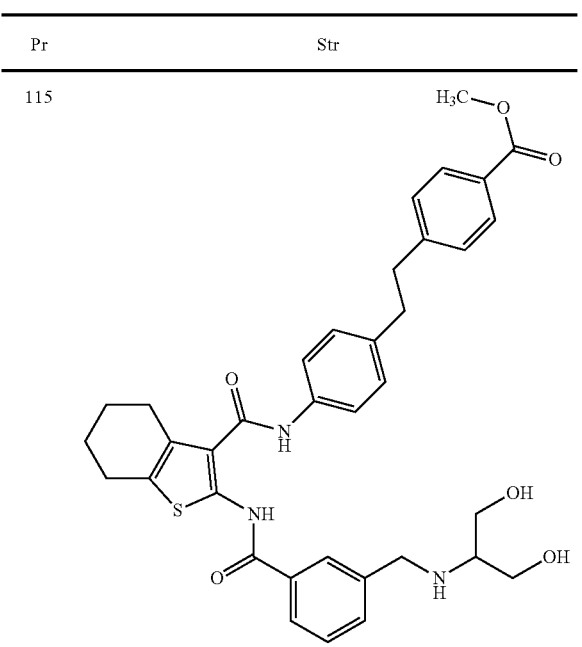 |
| 116 | 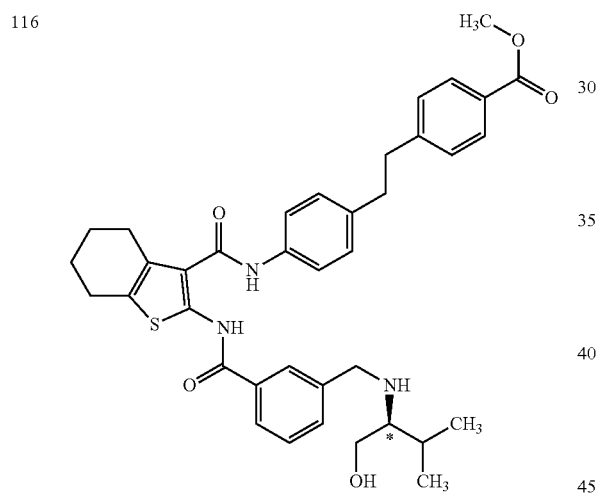 |
| 117 | 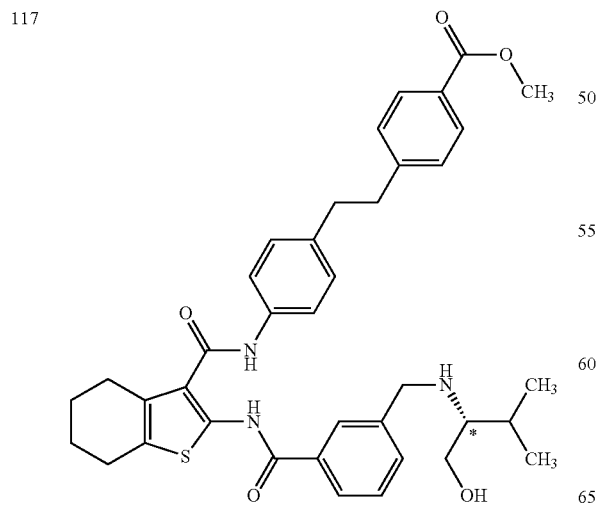 |
| 118 | 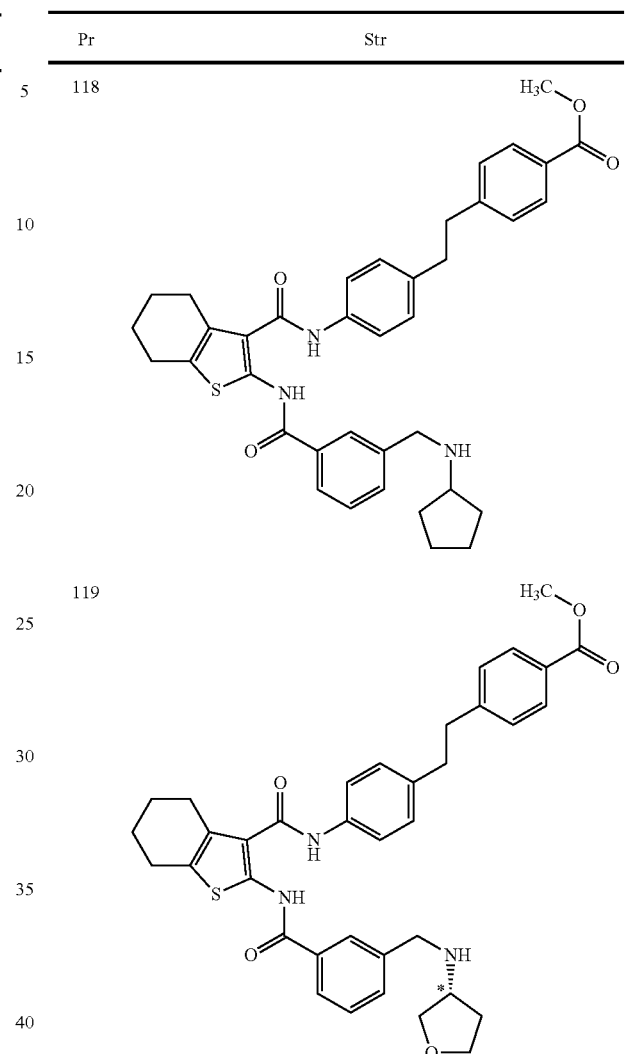 |
| 119 | |
TABLE 20
| Pr | Str |
|---|---|
| 120 | 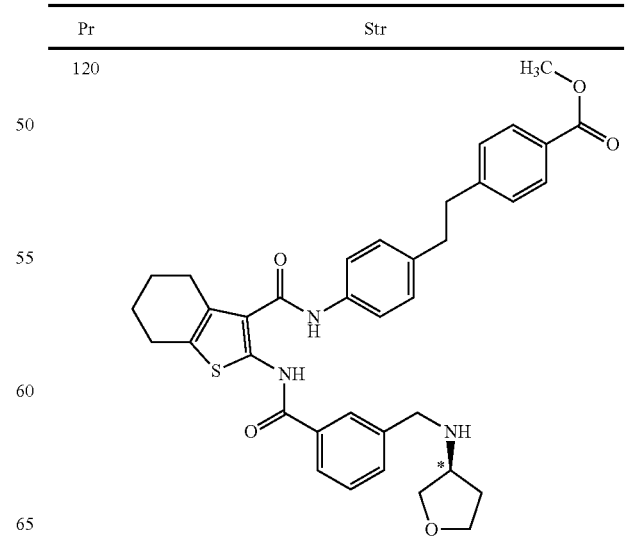 |

TABLE 20-continued
| Pr | Str |
|---|---|
| 121 | 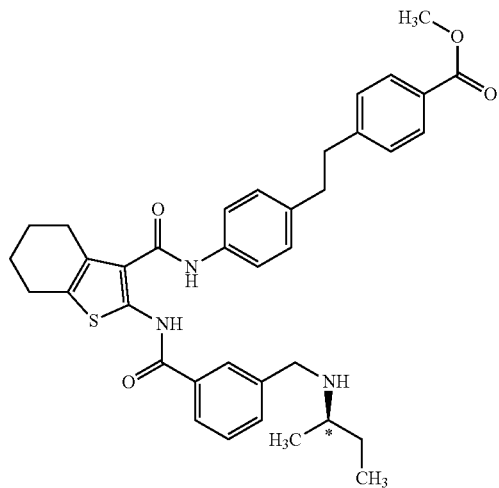 [SMILES: CC[C@@H](C)NCc1cccc(C(=O)Nc2sc3c(c2C(=O)Nc2ccc(CCc4ccc(C(=O)OC)cc4)cc2)CCCC3)c1] |
| 122 | 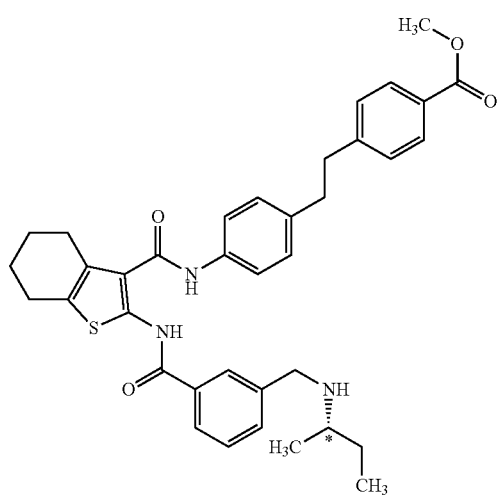 [SMILES: CC[C@H](C)NCc1cccc(C(=O)Nc2sc3c(c2C(=O)Nc2ccc(CCc4ccc(C(=O)OC)cc4)cc2)CCCC3)c1] |
| 123 | 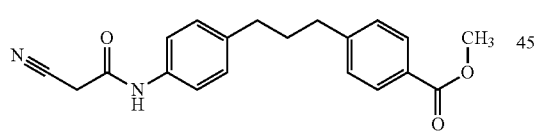 |
| 124 | 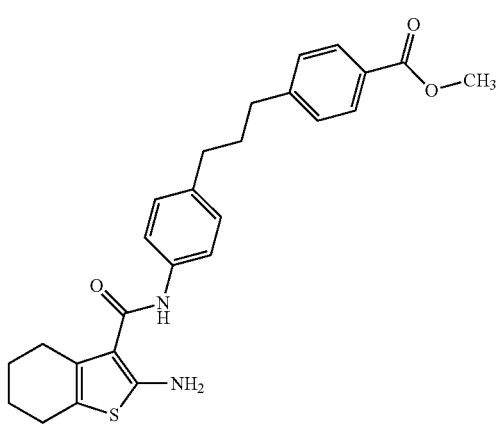 [SMILES: COC(=O)c1ccc(CCCc2ccc(NC(=O)c3c(N)sc4c3CCCC4)cc2)cc1] |
TABLE 20-continued
| Pr | Str |
|---|---|
| 125 | 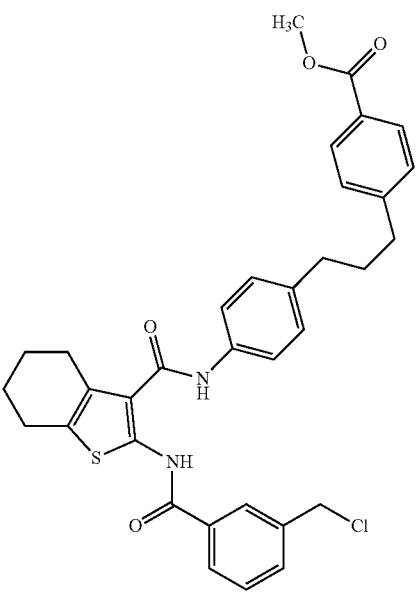 [SMILES: COC(=O)c1ccc(CCCc2ccc(NC(=O)c3c(NC(=O)c4cccc(CCl)c4)sc4c3CCCC4)cc2)cc1] |
TABLE 21
| Pr | Str |
|---|---|
| 126 | 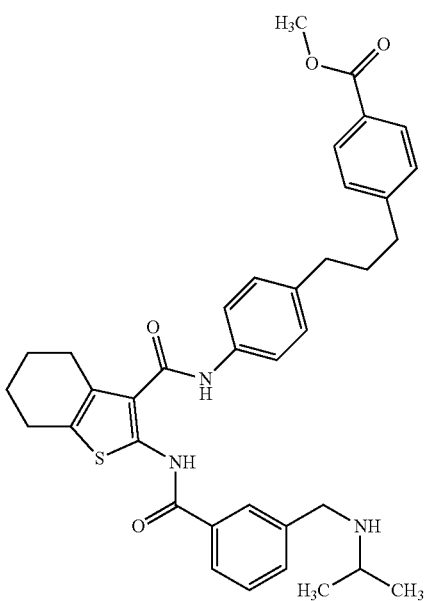 [SMILES: COC(=O)c1ccc(CCCc2ccc(NC(=O)c3c(NC(=O)c4cccc(CNC(C)C)c4)sc4c3CCCC4)cc2)cc1] |

TABLE 21-continued
| Pr | Str |
|----|-----|
| 127 | 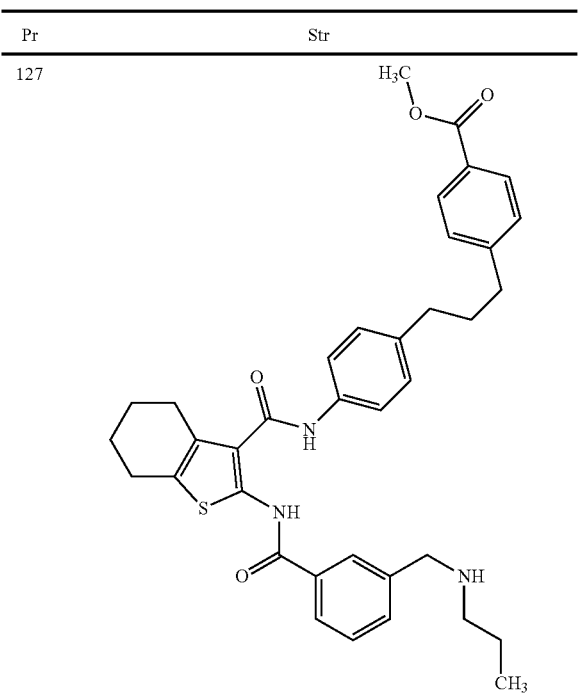 |
| 128 | 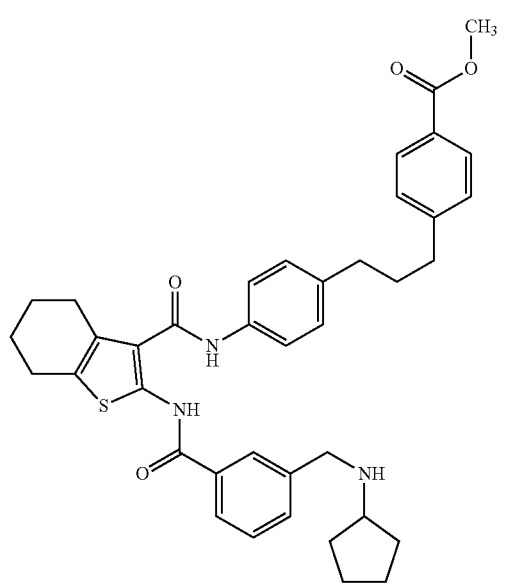 [SMILES: COC(=O)c1ccc(CCCc2ccc(NC(=O)c3c(NC(=O)c4cccc(CNC5CCCC5)c4)sc4c3CCCC4)cc2)cc1] |
| 129 | 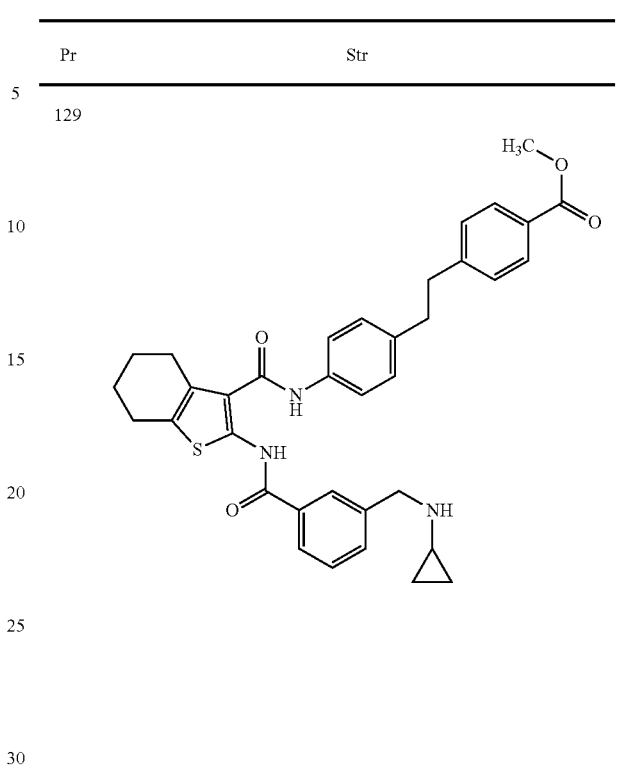 |
| 130 | 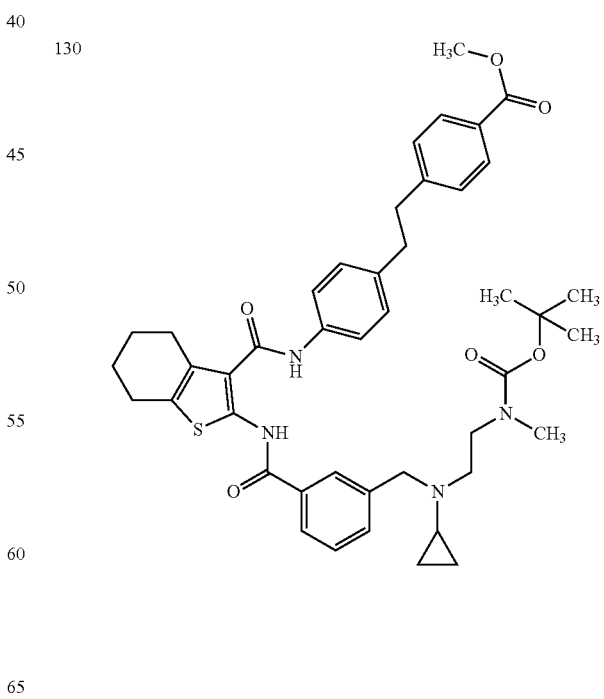 |

TABLE 22
| Pr | Str |
|---|---|
| 131 | 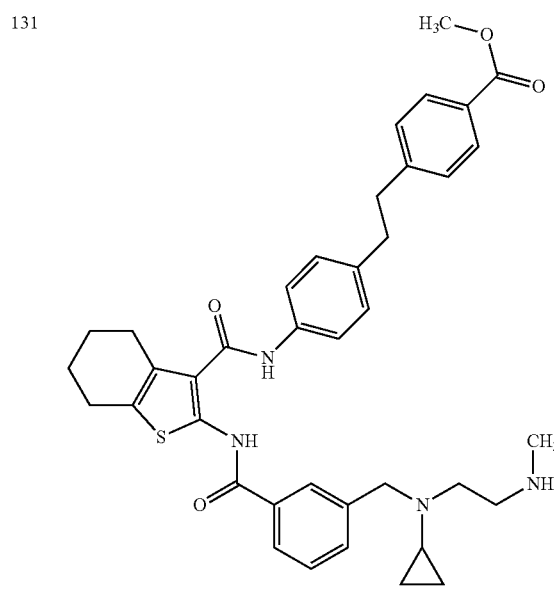 |
| 132 | 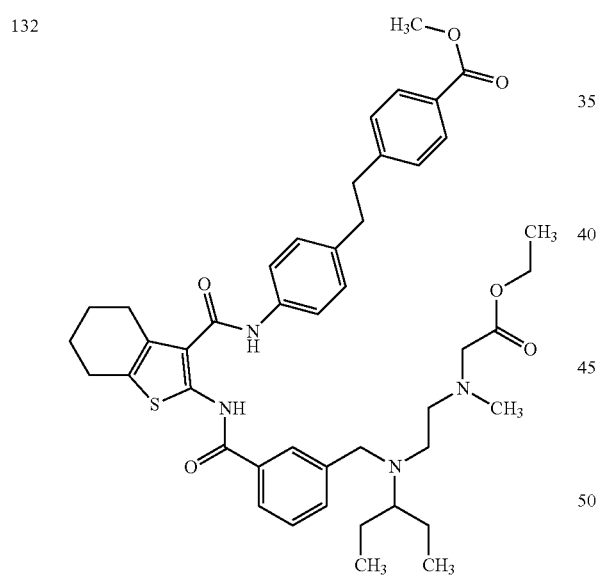 |
| 133 | 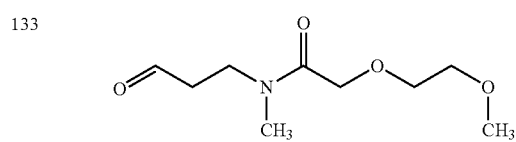 |
TABLE 22-continued
| Pr | Str |
|---|---|
| 134 | 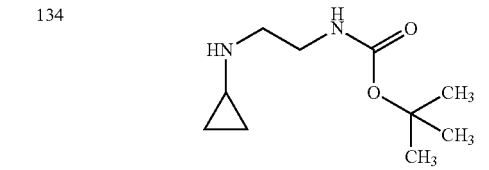 |
| 135 | 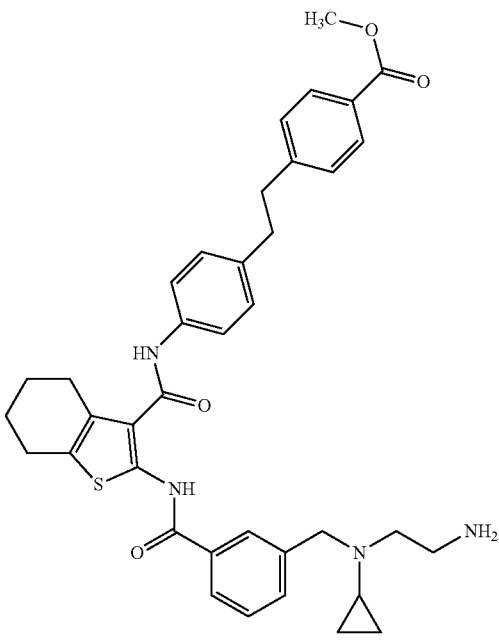 [SMILES: COC(=O)c1ccc(CCc2ccc(NC(=O)c3c(NC(=O)c4cccc(CN(CCN)C5CC5)c4)sc4c3CCCC4)cc2)cc1] |
| 136 | 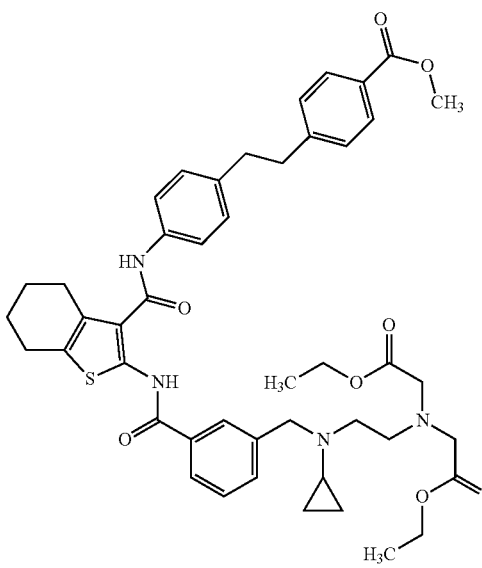 |

TABLE 23
| Pr | Str |
|---|---|
| 137 | 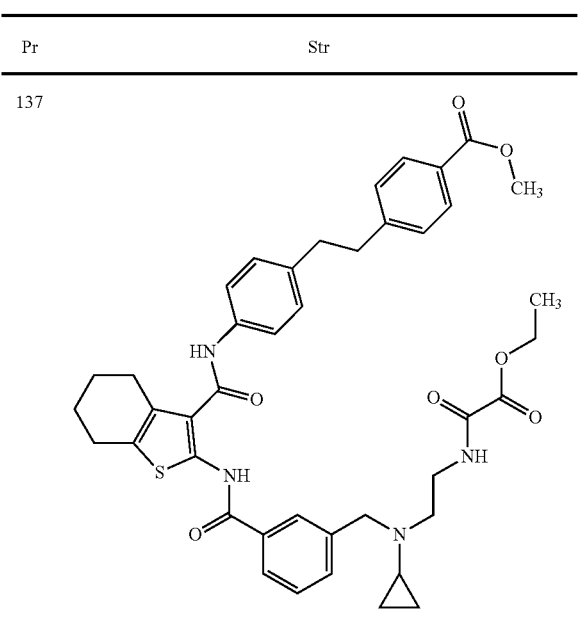 |
| 138 | 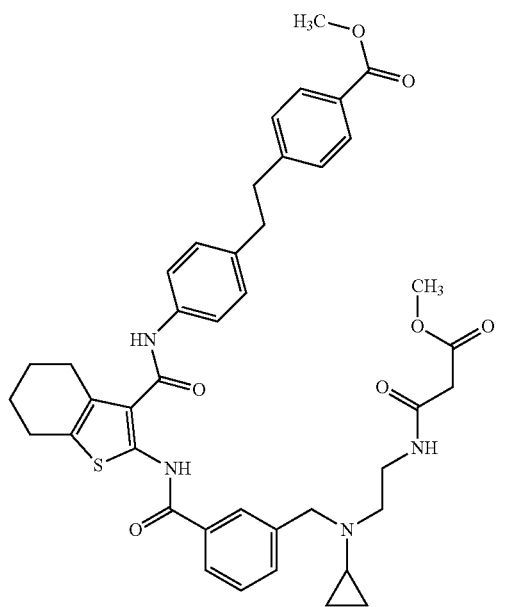 [SMILES: COC(=O)CC(=O)NCCN(Cc1cccc(C(=O)Nc2sc3c(c2C(=O)Nc2ccc(CCc4ccc(C(=O)OC)cc4)cc2)CCCC3)c1)C1CC1] |
TABLE 23-continued
| Pr | Str |
|---|---|
| 139 | 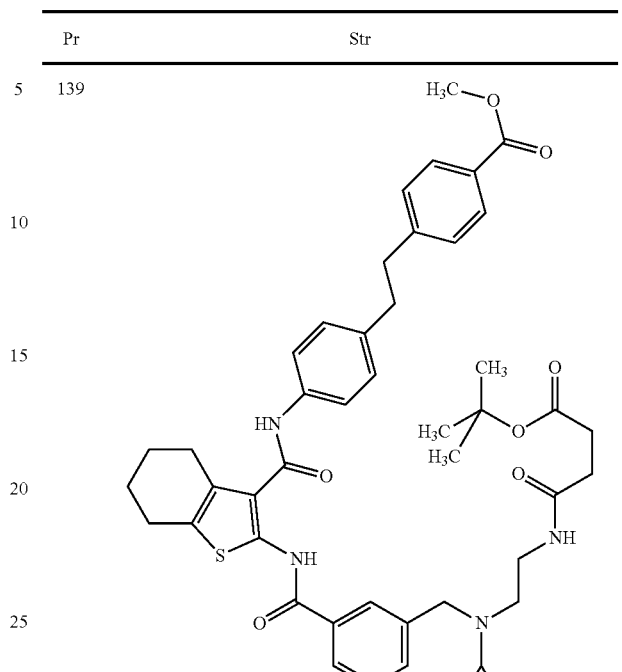 |
| 140 | 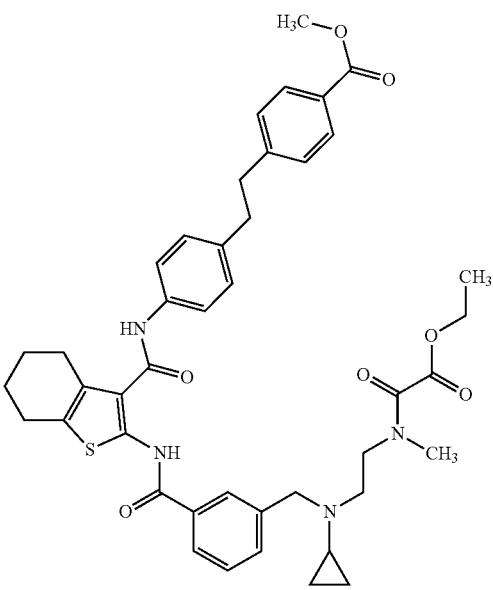 [SMILES: CCOC(=O)C(=O)N(C)CCN(Cc1cccc(C(=O)Nc2sc3c(c2C(=O)Nc2ccc(CCc4ccc(C(=O)OC)cc4)cc2)CCCC3)c1)C1CC1] |

TABLE 24
| Pr | Str |
|---|---|
| 141 | 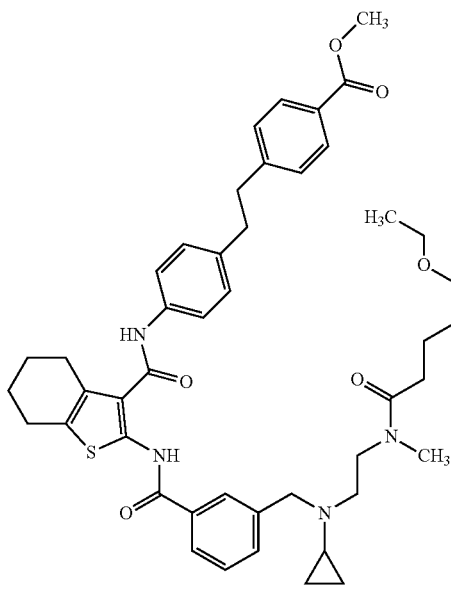 |
| 142 | 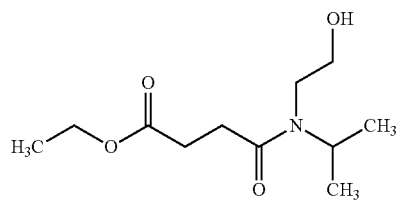 [SMILES: CCOC(=O)CCC(=O)N(CCO)C(C)C] |
| 143 | 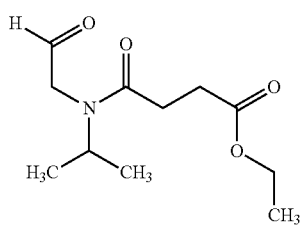 [SMILES: CCOC(=O)CCC(=O)N(CC=O)C(C)C] |
TABLE 24-continued
| Pr | Str |
|---|---|
| 144 | 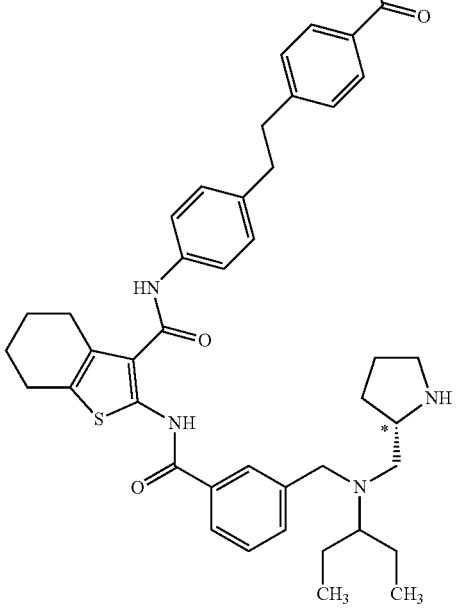 |
| 145 | 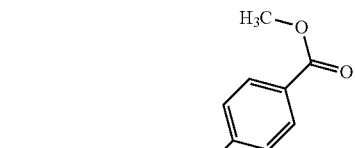 |

TABLE 25
| Pr | Str |
| --- | --- |
| 146 | 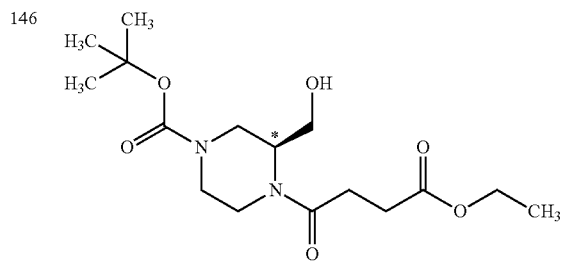 |
| 147 | 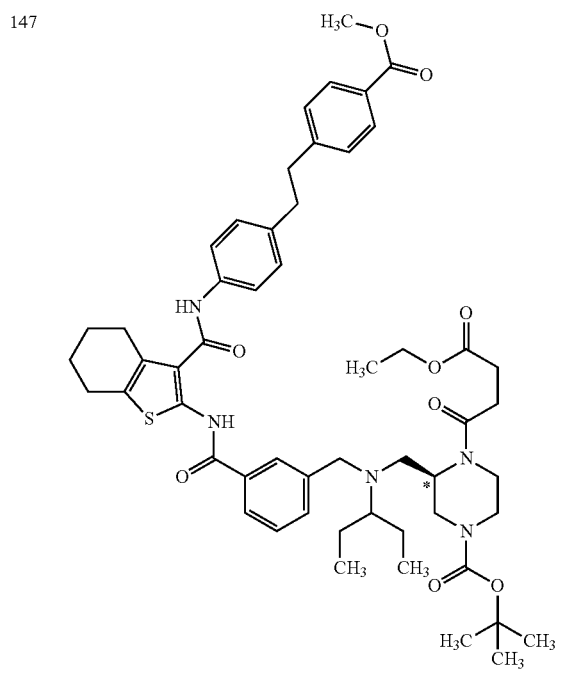 |
| 148 | 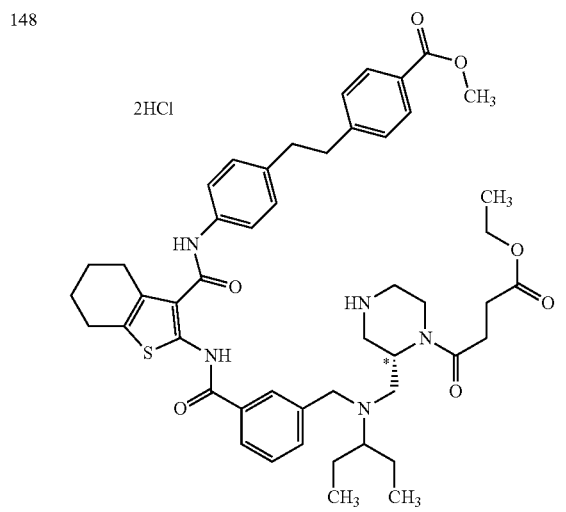 |
TABLE 25-continued
| Pr | Str |
| --- | --- |
| 149 | 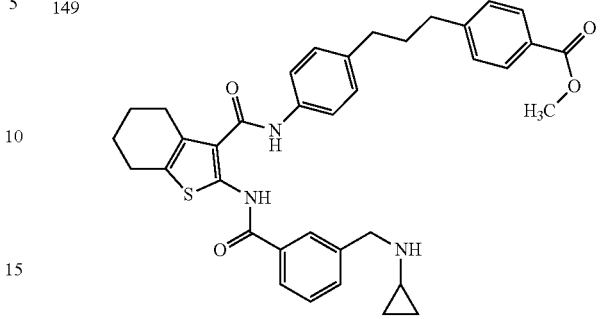 |
| 150 | 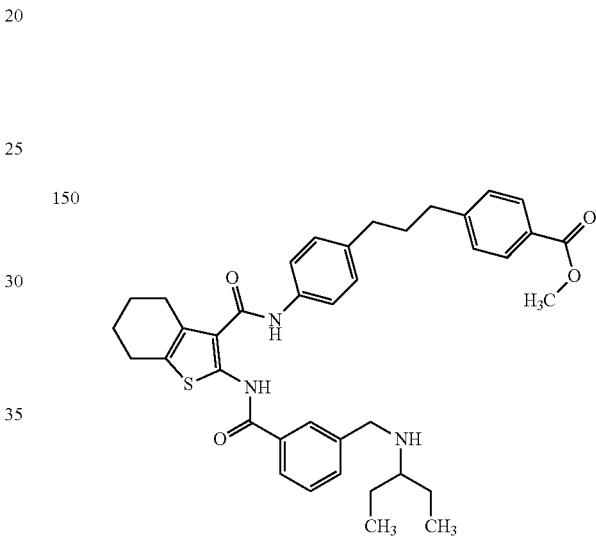 |
| 151 | 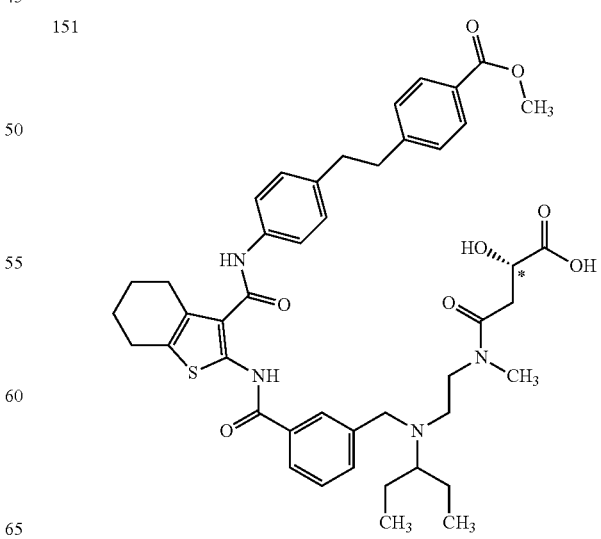 |

TABLE 26
| Pr | Str |
|---|---|
| 152 | 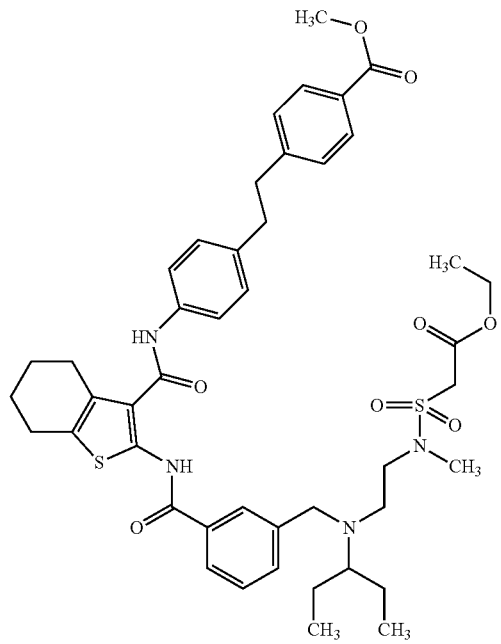 [SMILES: CCOC(=O)CS(=O)(=O)N(C)CCN(Cc1cccc(C(=O)Nc2sc3c(c2C(=O)Nc2ccc(CCc4ccc(C(=O)OC)cc4)cc2)CCCC3)c1)C(CC)CC] |
| 153 | 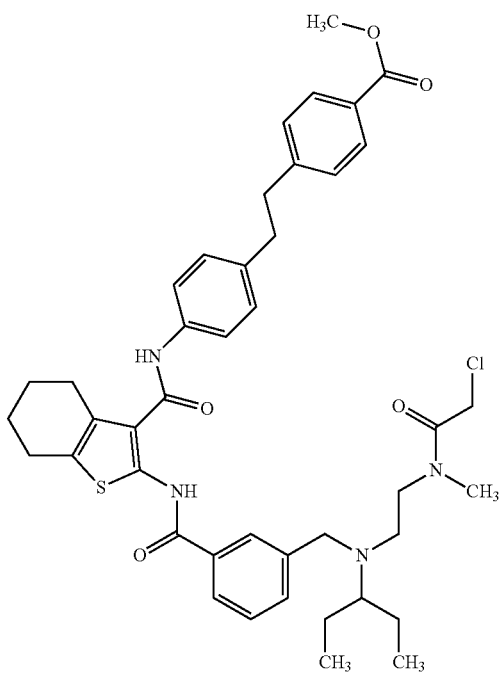 [SMILES: CCC(CC)N(CCN(C)C(=O)CCl)Cc1cccc(C(=O)Nc2sc3c(c2C(=O)Nc2ccc(CCc4ccc(C(=O)OC)cc4)cc2)CCCC3)c1] |
| 154 | 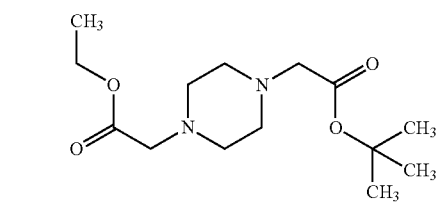 [SMILES: CCOC(=O)CN1CCN(CC(=O)OC(C)(C)C)CC1] |
TABLE 26-continued
| Pr | Str |
|---|---|
| 155 | 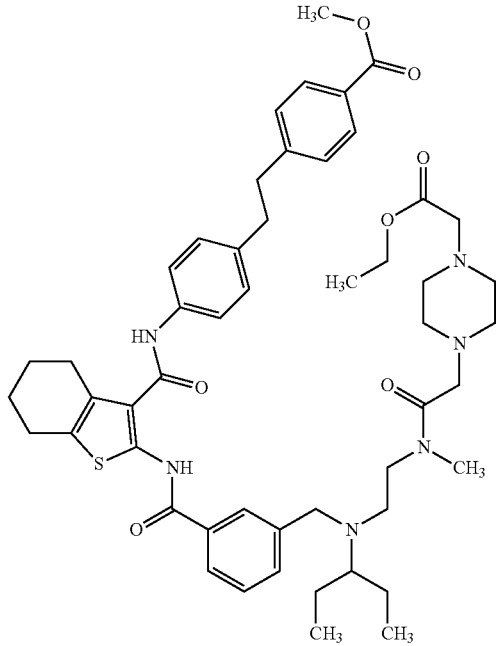 [SMILES: CCOC(=O)CN1CCN(CC(=O)N(C)CCN(Cc2cccc(C(=O)Nc3sc4c(c3C(=O)Nc3ccc(CCc5ccc(C(=O)OC)cc5)cc3)CCCC4)c2)C(CC)CC)CC1] |
| 156 | 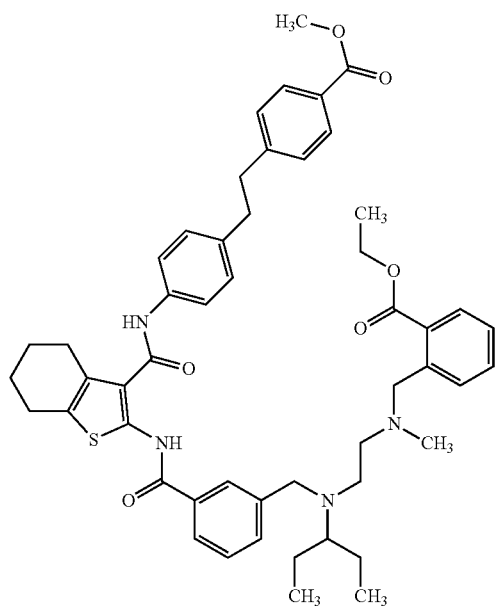 [SMILES: CCOC(=O)c1ccccc1CN(C)CCN(Cc1cccc(C(=O)Nc2sc3c(c2C(=O)Nc2ccc(CCc4ccc(C(=O)OC)cc4)cc2)CCCC3)c1)C(CC)CC] |

TABLE 27
| Pr | Str |
|----|-----|
| 157 | 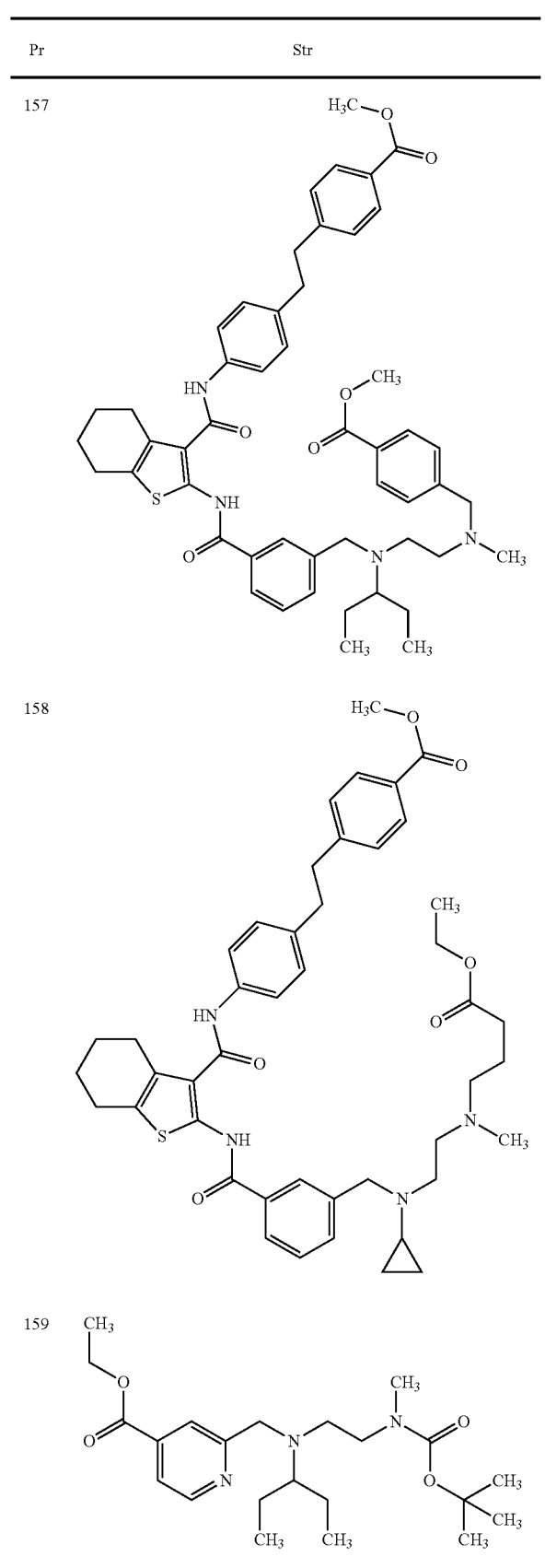 |
| 158 | |
| 159 | |
TABLE 27-continued
| Pr | Str |
|----|-----|
| 160 | 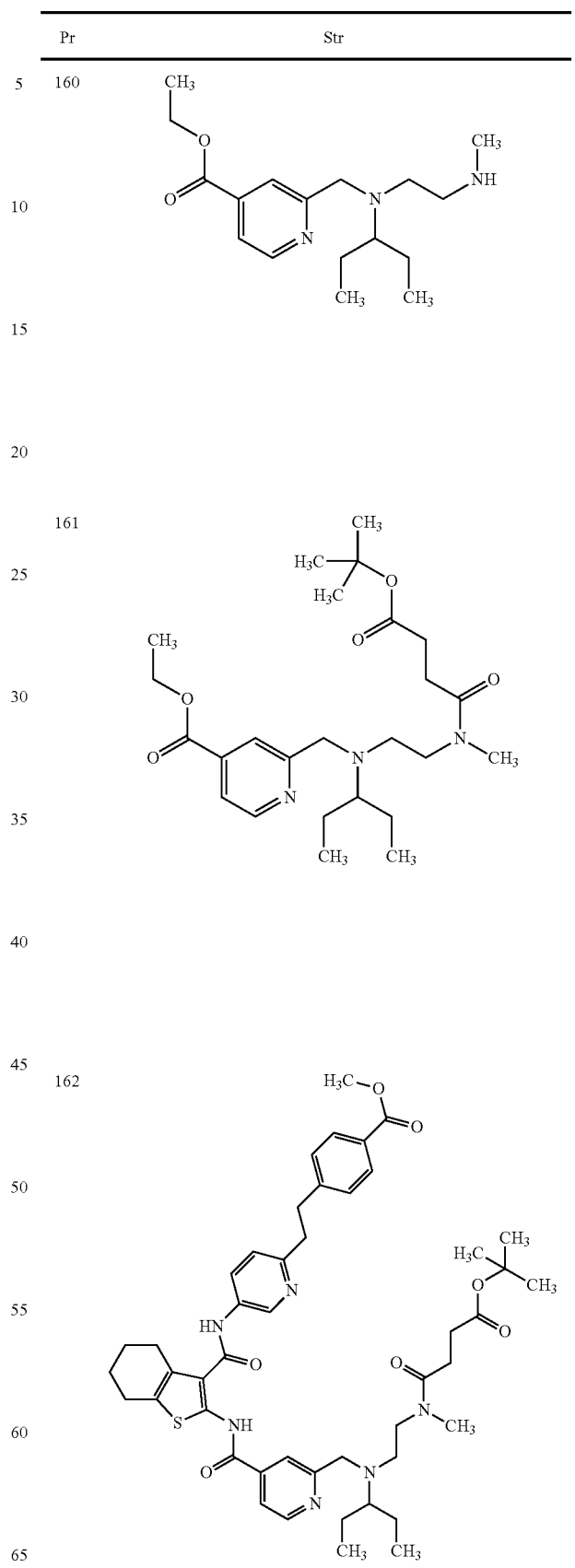 |
| 161 | |
| 162 | |

TABLE 28
| Pr | Str |
|---|---|
| 163 | |
| 164 | |
| 165 | |
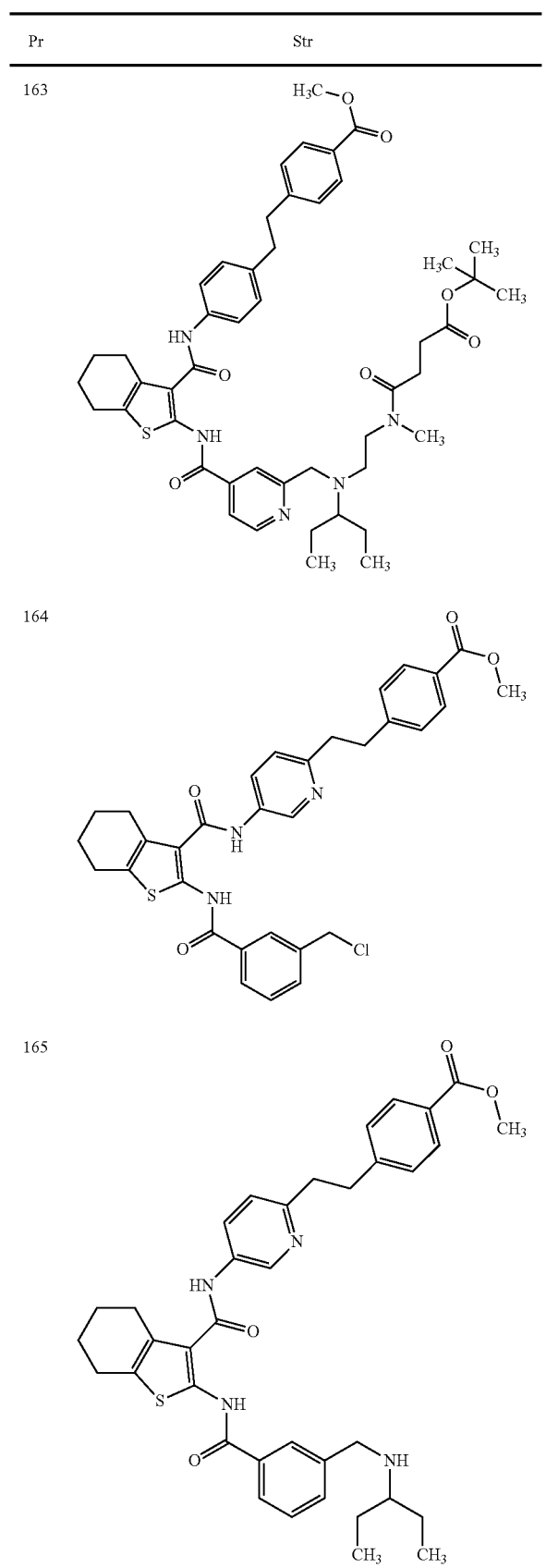
TABLE 28-continued
| Pr | Str |
|---|---|
| 166 | |
| 167 | |
| 168 | |
| 169 | |
| 170 | |
| 171 | |
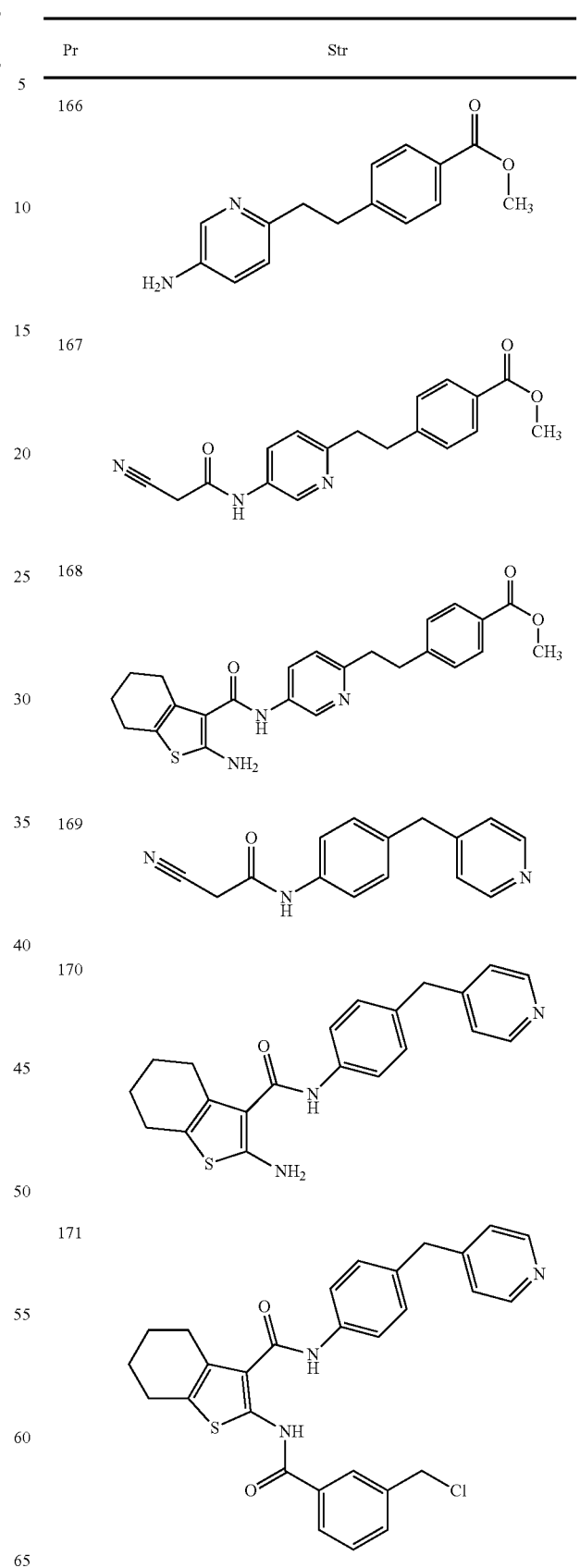

TABLE 29
| Pr | Str |
|---|---|
| 172 | |
| 173 | |
| 174 | |
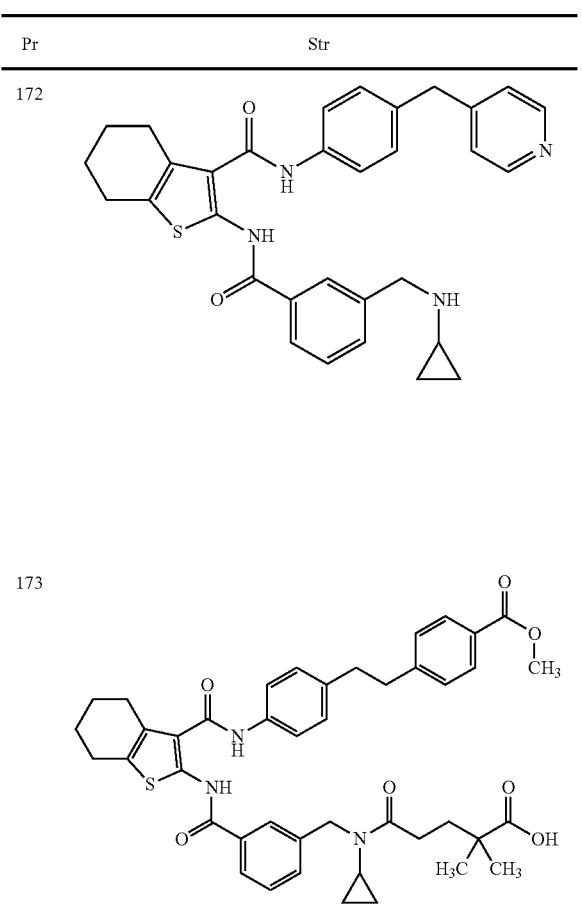
TABLE 29-continued
| Pr | Str |
|---|---|
| 175 | |
| 176 | |
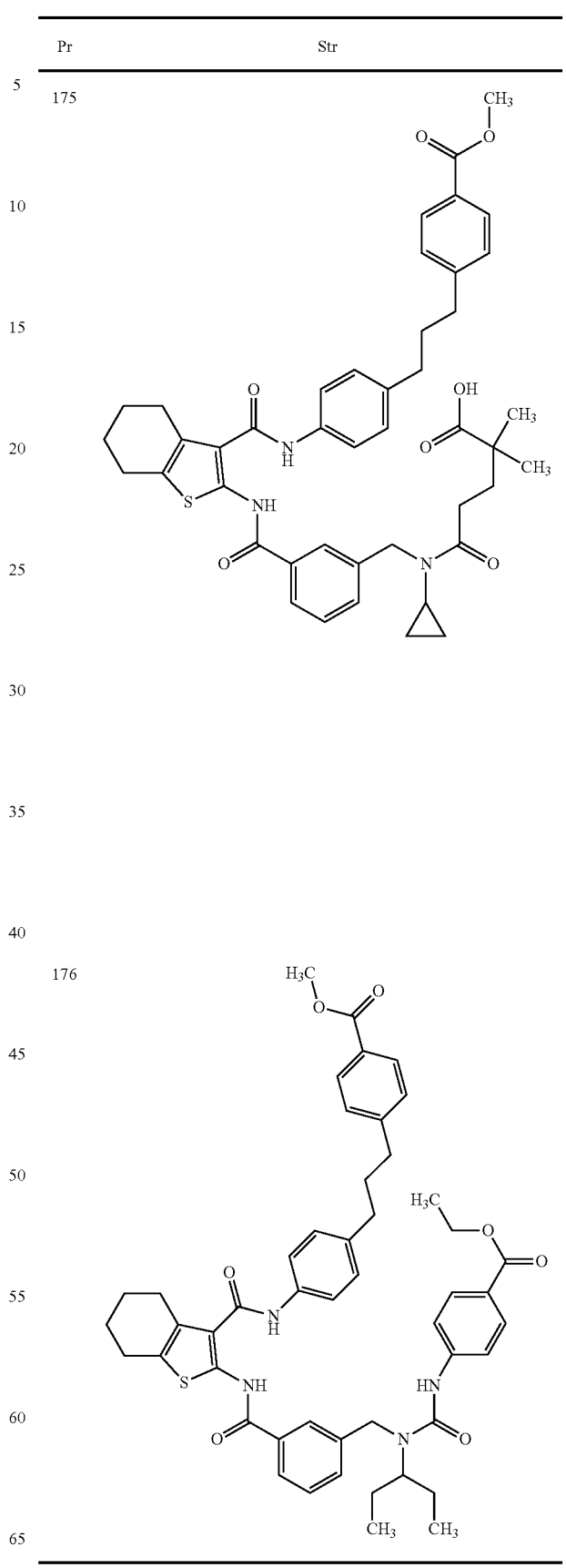

TABLE 30
| Pr | Str |
|---|---|
| 177 | 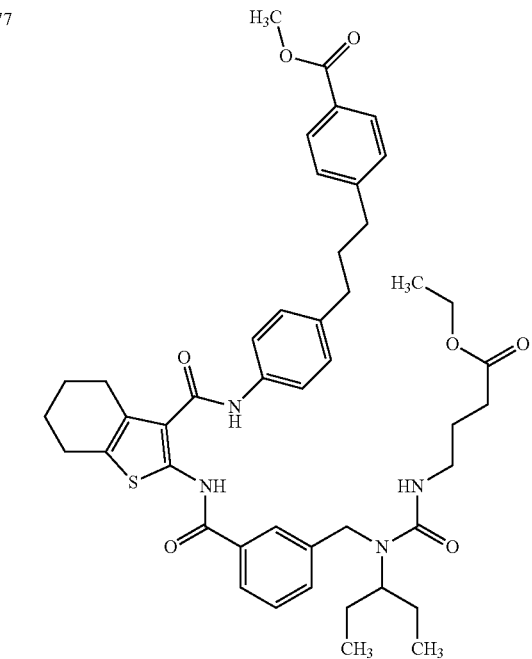 |
| 178 | 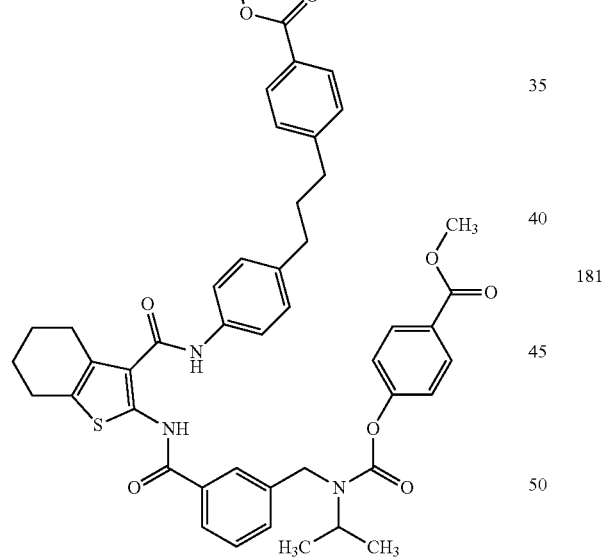 |
| 179 | 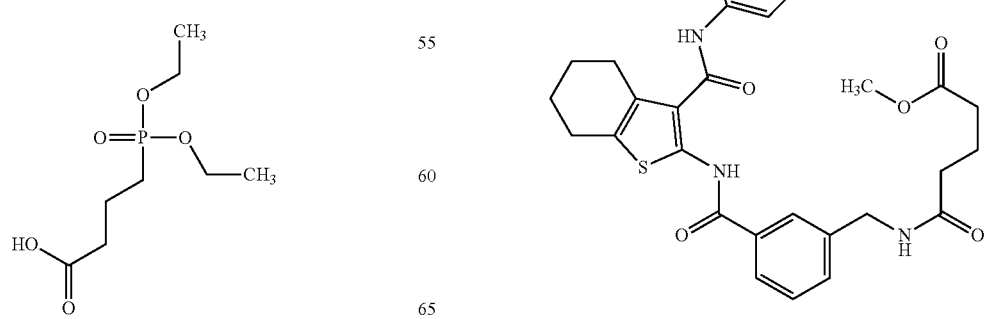 |
TABLE 30-continued
| Pr | Str |
|---|---|
| 180 | 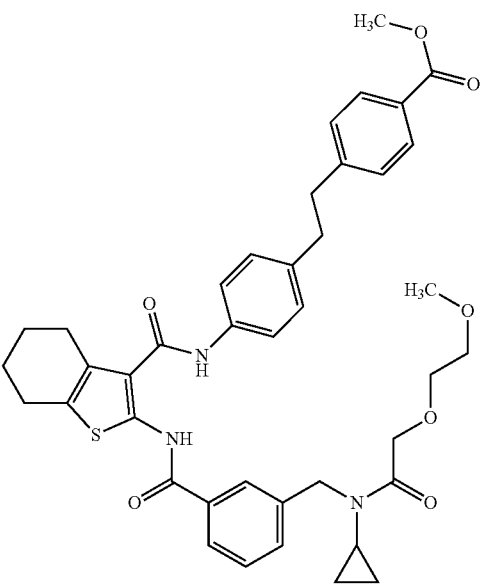 [SMILES: COCCOCC(=O)N(Cc1cccc(C(=O)Nc2sc3c(c2C(=O)Nc2ccc(CCc4ccc(C(=O)OC)cc4)cc2)CCCC3)c1)C1CC1] |
| 181 | 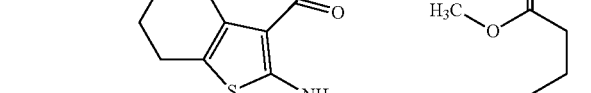 |

TABLE 31
| Pr | Str |
|---|---|
| 182 | 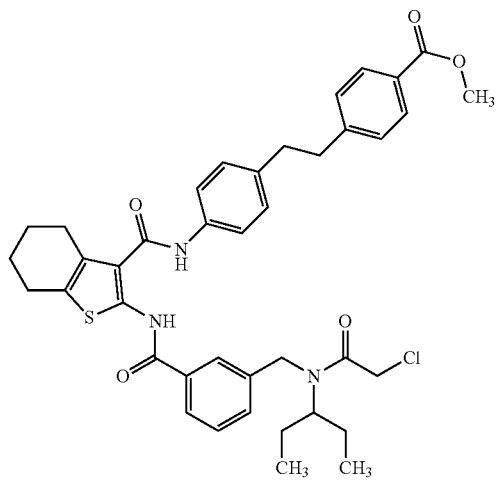 [SMILES: CCC(CC)N(Cc1cccc(C(=O)Nc2sc3c(c2C(=O)Nc2ccc(CCc4ccc(C(=O)OC)cc4)cc2)CCCC3)c1)C(=O)CCl] |
| 183 | 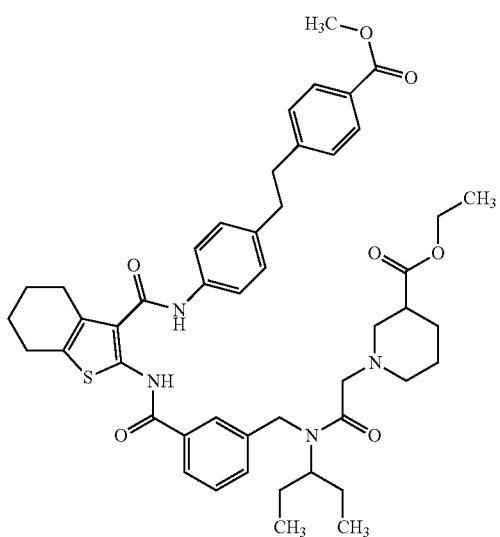 [SMILES: CCOC(=O)C1CCCN(CC(=O)N(Cc2cccc(C(=O)Nc3sc4c(c3C(=O)Nc3ccc(CCc5ccc(C(=O)OC)cc5)cc3)CCCC4)c2)C(CC)CC)C1] |
| 184 | 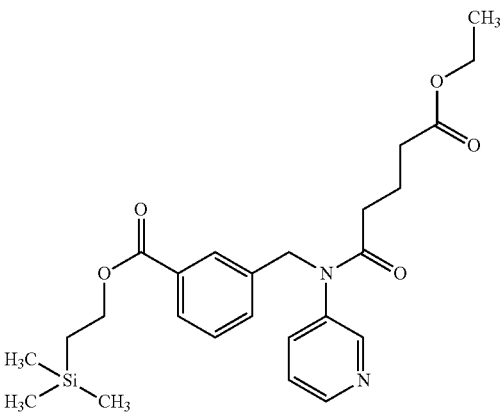 [SMILES: CCOC(=O)CCCC(=O)N(Cc1cccc(C(=O)OCC[Si](C)(C)C)c1)c1cccnc1] |
TABLE 31-continued
| Pr | Str |
|---|---|
| 185 | 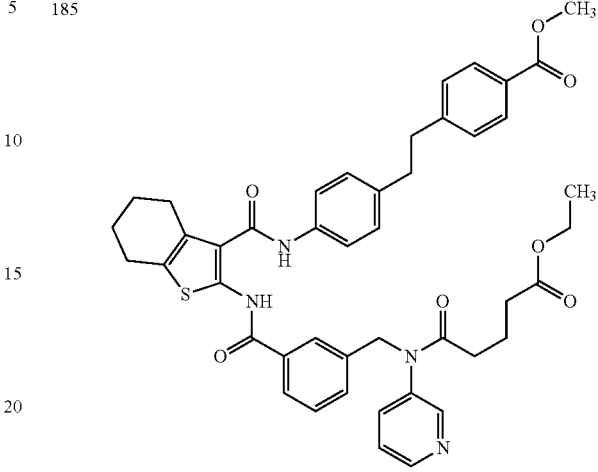 |
| 186 | 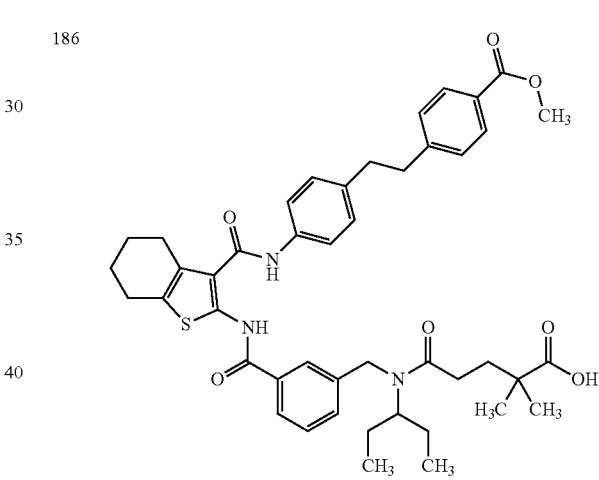 |
| 187 | 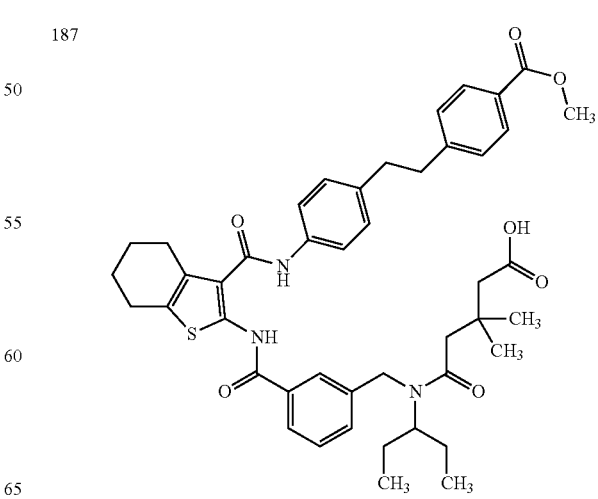 |

TABLE 32
| Pr | Str |
|---|---|
| 188 | 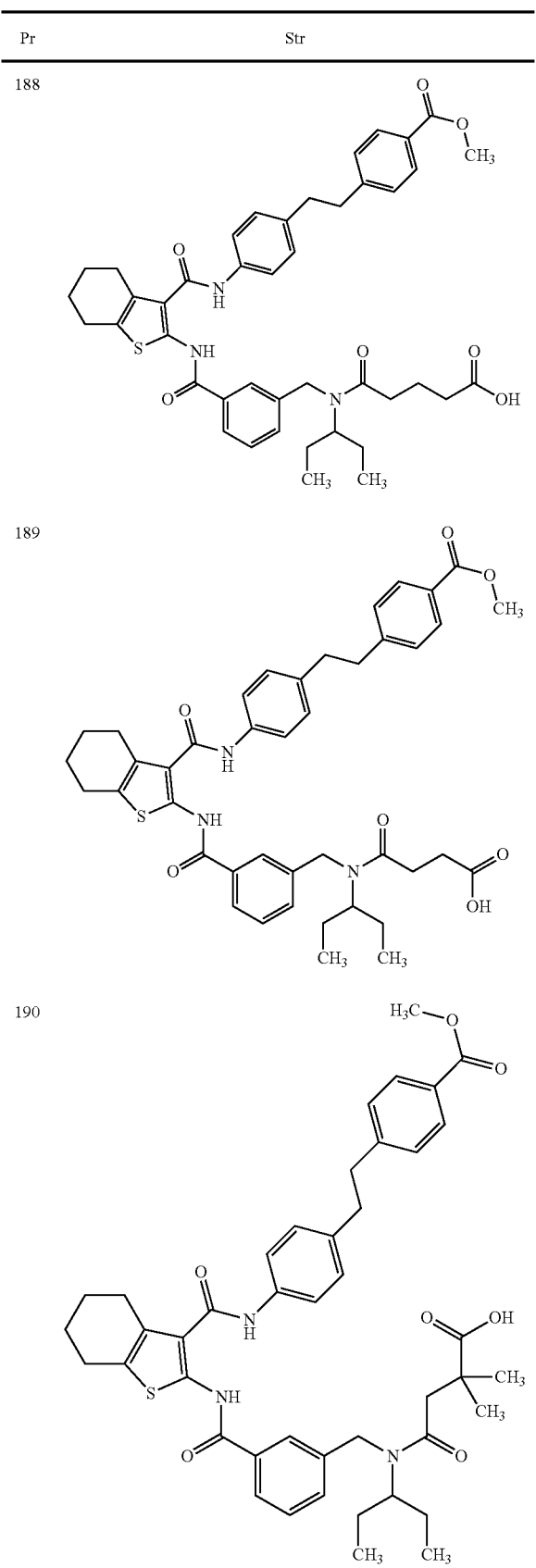 |
| 189 | |
| 190 | |
TABLE 32-continued
| Pr | Str |
|---|---|
| 191 | 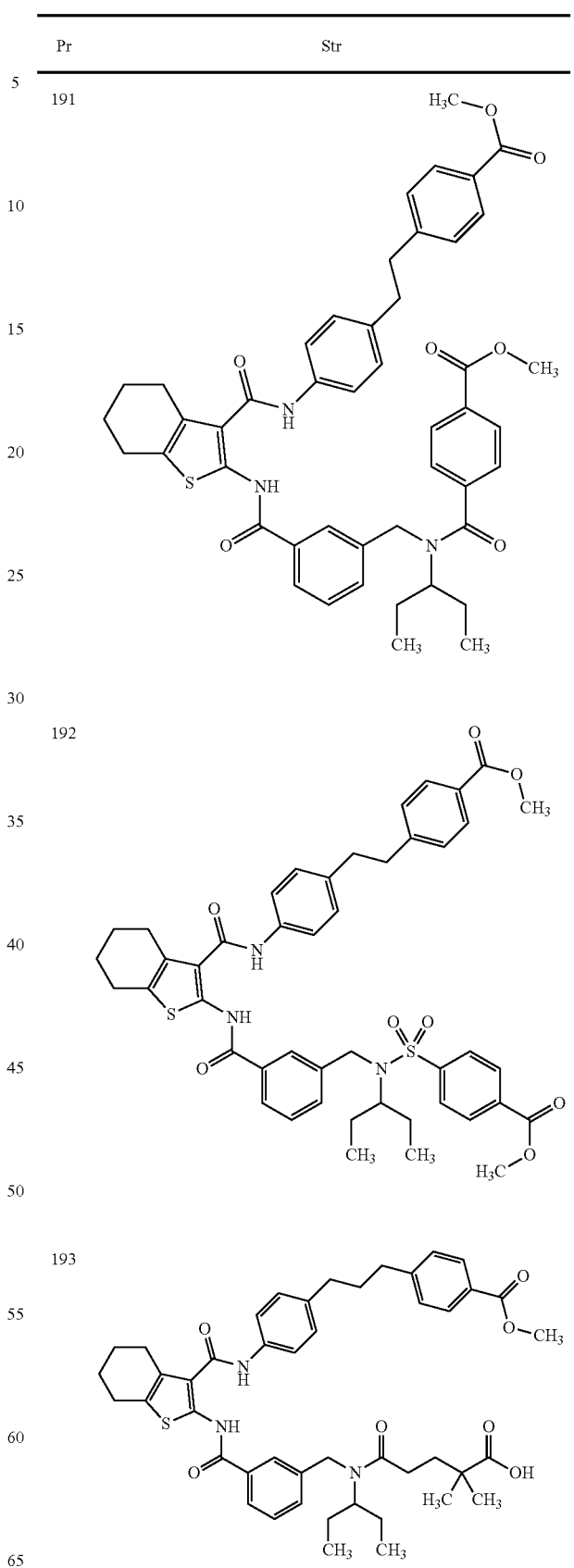 |
| 192 | |
| 193 | |

TABLE 33
| Pr | Str |
|----|-----|
| 194 | 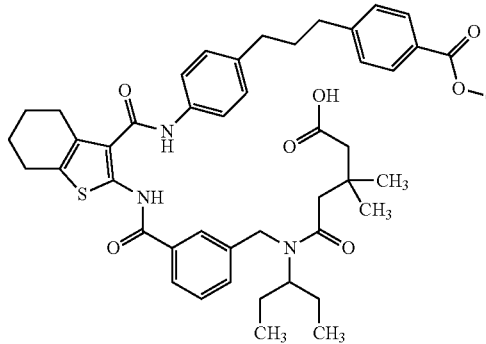 [SMILES: CCC(CC)N(Cc1cccc(C(=O)Nc2sc3c(c2C(=O)Nc2ccc(CCCc4ccc(C(=O)OC)cc4)cc2)CCCC3)c1)C(=O)CC(C)(C)C(=O)O] |
| 195 | 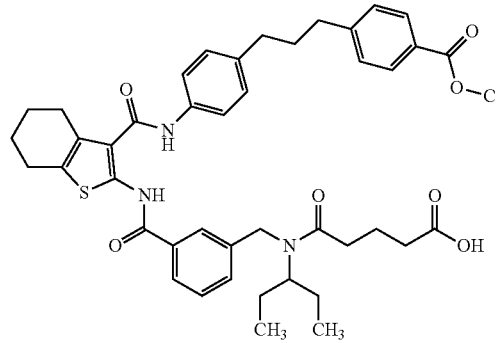 |
| 196 | 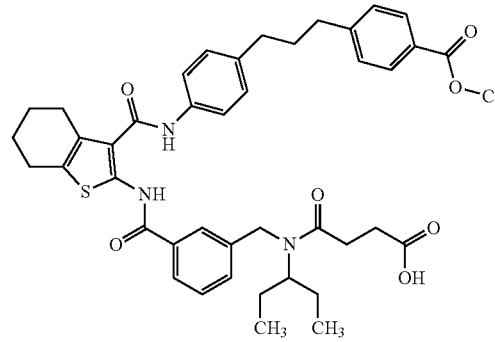 |
| 197 | 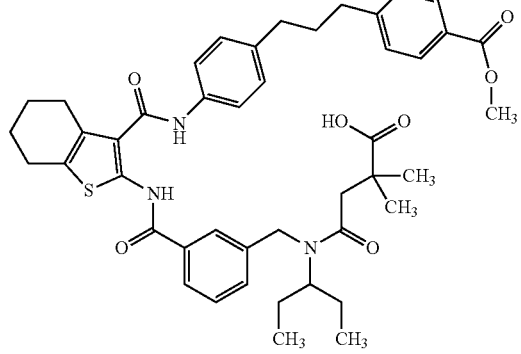 |
TABLE 33-continued
| Pr | Str |
|----|-----|
| 198 | 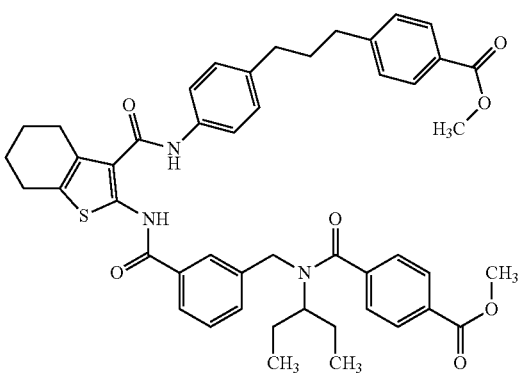 [SMILES: CCC(CC)N(Cc1cccc(C(=O)Nc2sc3c(c2C(=O)Nc2ccc(CCCc4ccc(C(=O)OC)cc4)cc2)CCCC3)c1)C(=O)c1ccc(C(=O)OC)cc1] |
| 199 | 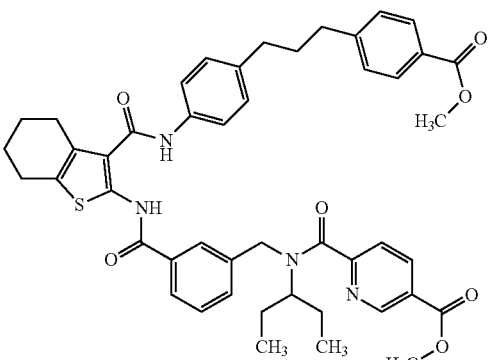 |
| 200 | 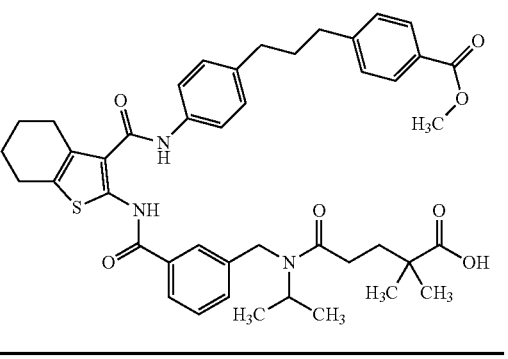 |
TABLE 34
| Pr | Str |
|----|-----|
| 201 | 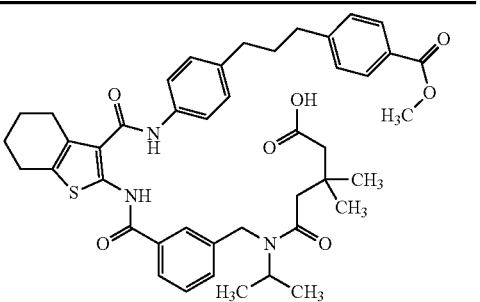 |

TABLE 34-continued
| Pr | Str |
|---|---|
| 202 | 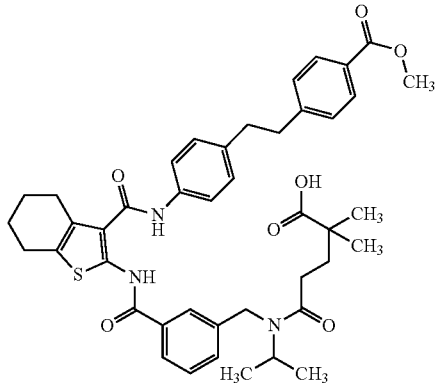 [SMILES: COC(=O)c1ccc(CCc2ccc(NC(=O)c3c(NC(=O)c4cccc(CN(C(=O)CCC(C)(C)C(=O)O)C(C)C)c4)sc4c3CCCC4)cc2)cc1] |
| 203 | |
| 204 | |
TABLE 34-continued
| Pr | Str |
|---|---|
| 205 | 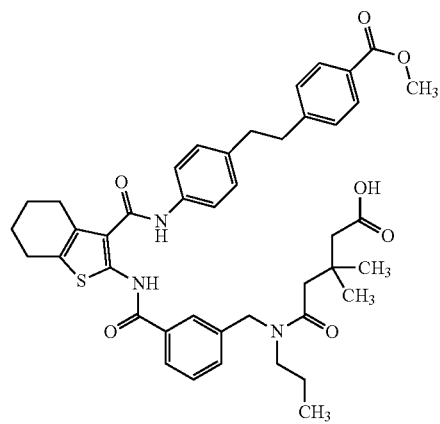 |
| 206 | |
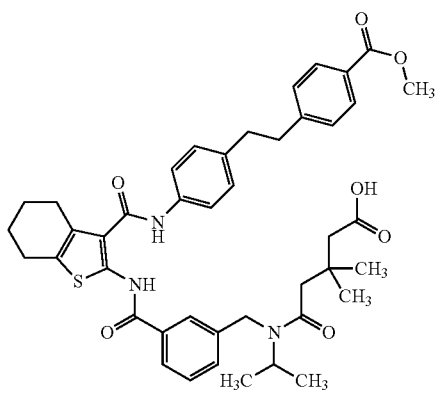 [SMILES: COC(=O)c1ccc(CCc2ccc(NC(=O)c3c(NC(=O)c4cccc(CN(C(=O)CC(C)(C)CC(=O)O)C(C)C)c4)sc4c3CCCC4)cc2)cc1]
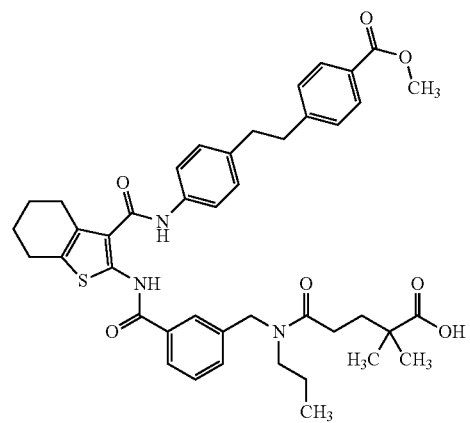 [SMILES: CCCN(Cc1cccc(C(=O)Nc2sc3c(c2C(=O)Nc2ccc(CCc4ccc(C(=O)OC)cc4)cc2)CCCC3)c1)C(=O)CCC(C)(C)C(=O)O]
TABLE 35
| Pr | Str |
|---|---|
| 207 | |

TABLE 35-continued
| Pr | Str |
|---|---|
| 208 | 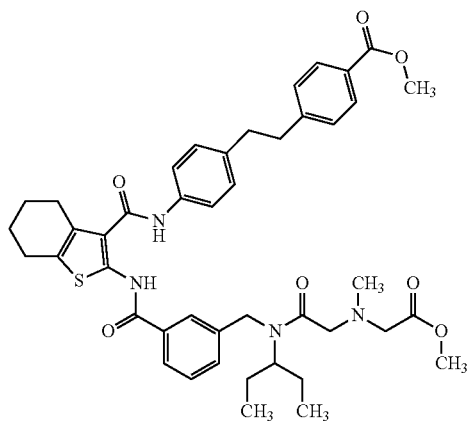 [SMILES: CCC(CC)N(Cc1cccc(C(=O)Nc2sc3c(c2C(=O)Nc2ccc(CCc4ccc(C(=O)OC)cc4)cc2)CCCC3)c1)C(=O)CN(C)CC(=O)OC] |
| 209 | 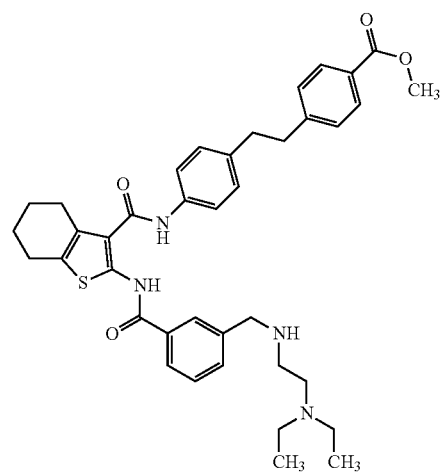 [SMILES: CCN(CC)CCNCc1cccc(C(=O)Nc2sc3c(c2C(=O)Nc2ccc(CCc4ccc(C(=O)OC)cc4)cc2)CCCC3)c1] |
| 210 | 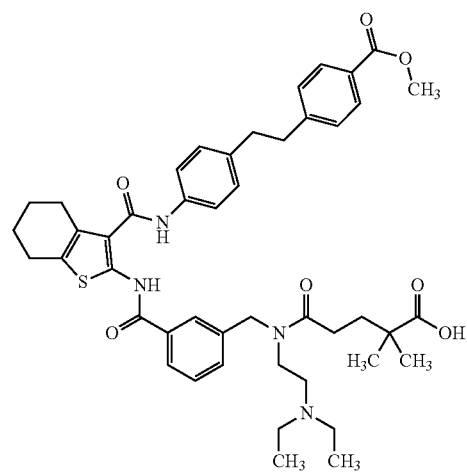 [SMILES: CCN(CC)CCN(Cc1cccc(C(=O)Nc2sc3c(c2C(=O)Nc2ccc(CCc4ccc(C(=O)OC)cc4)cc2)CCCC3)c1)C(=O)CCC(C)(C)C(=O)O] |
| 211 | 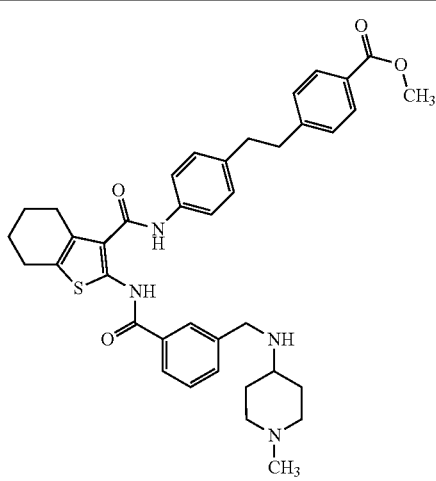 |
| 212 | 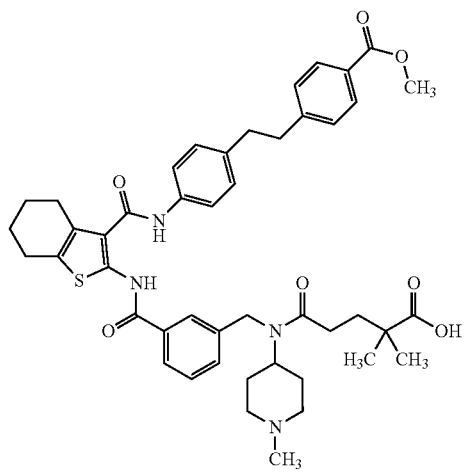 [SMILES: COC(=O)c1ccc(CCc2ccc(NC(=O)c3c(NC(=O)c4cccc(CN(C(=O)CCC(C)(C)C(=O)O)C5CCN(C)CC5)c4)sc4c3CCCC4)cc2)cc1] |
TABLE 36
| Pr | Str |
|---|---|
| 213 | 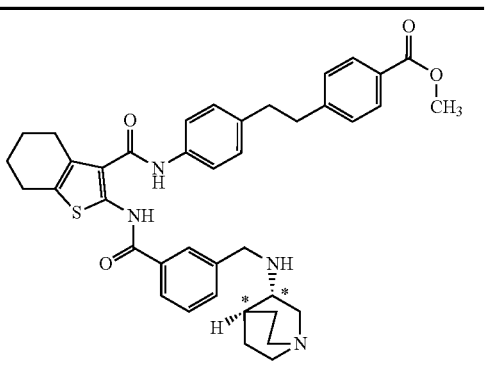 |

TABLE 36-continued
| Pr | Str |
|---|---|
| 214 | 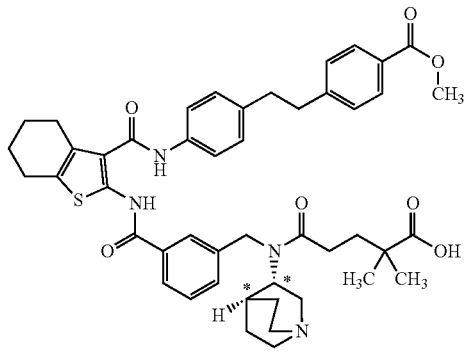 |
| 215 | 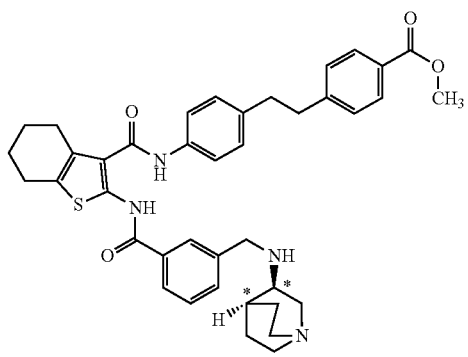 |
| 216 | 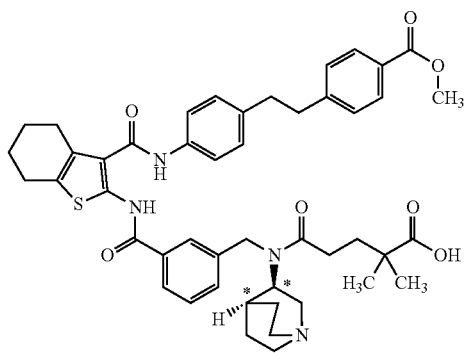 |
| 217 | 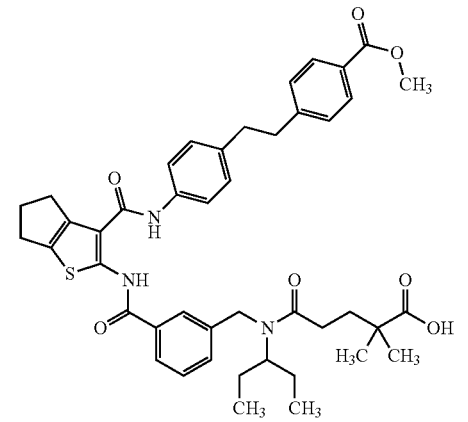 [SMILES: CCC(CC)N(Cc1cccc(C(=O)Nc2sc3c(c2C(=O)Nc2ccc(CCc4ccc(C(=O)OC)cc4)cc2)CCC3)c1)C(=O)CCC(C)(C)C(=O)O] |
TABLE 36-continued
| Pr | Str |
|---|---|
| 218 |  |
TABLE 37
| Pr | Str |
|---|---|
| 219 | 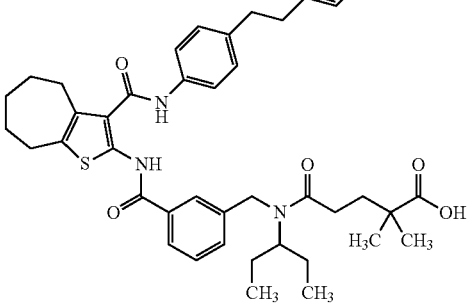 |
| 220 | 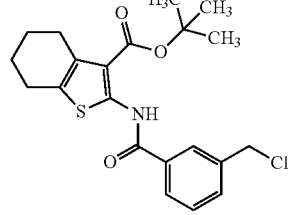 |
| 221 | 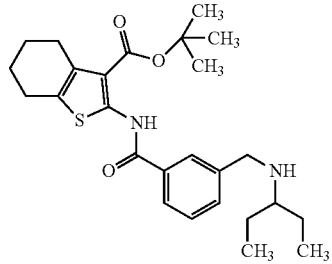 [SMILES: CCC(CC)NCc1cccc(C(=O)Nc2sc3c(c2C(=O)OC(C)(C)C)CCCC3)c1] |
| 222 | 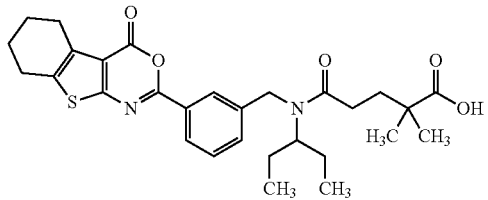 [SMILES: CCC(CC)N(Cc1cccc(-c2nc3sc4c(c3c(=O)o2)CCCC4)c1)C(=O)CCC(C)(C)C(=O)O] |
| 223 | 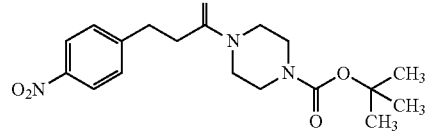 |

TABLE 37-continued
| Pr | Str |
|---|---|
| 224 | 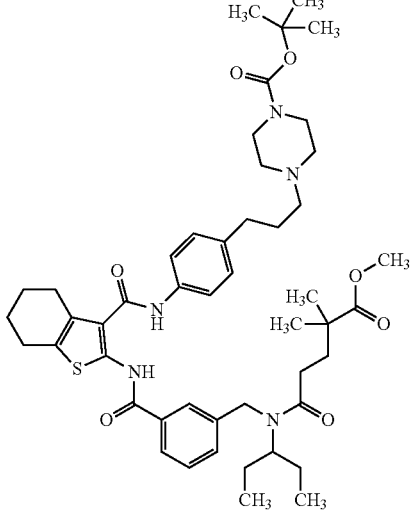 [SMILES: CCC(CC)N(Cc1cccc(C(=O)Nc2sc3c(c2C(=O)Nc2ccc(CCCN4CCN(C(=O)OC(C)(C)C)CC4)cc2)CCCC3)c1)C(=O)CCC(C)(C)C(=O)OC] |
| 225 | 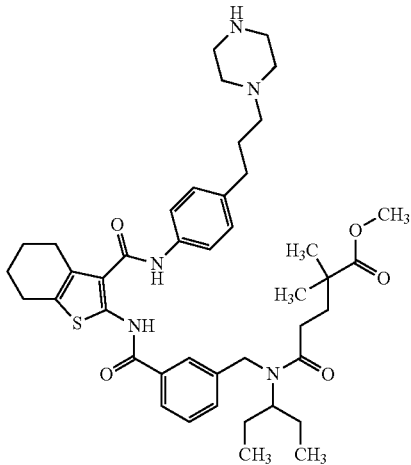 [SMILES: CCC(CC)N(Cc1cccc(C(=O)Nc2sc3c(c2C(=O)Nc2ccc(CCCN4CCNCC4)cc2)CCCC3)c1)C(=O)CCC(C)(C)C(=O)OC] |
| 226 | 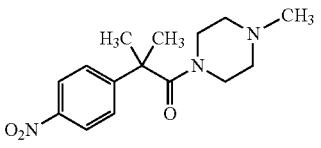 [SMILES: CN1CCN(C(=O)C(C)(C)c2ccc([N+](=O)[O-])cc2)CC1] |
TABLE 38
| Pr | Str |
|---|---|
| 227 | 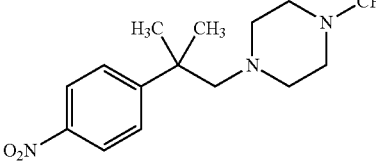 |
TABLE 38-continued
| Pr | Str |
|---|---|
| 228 | 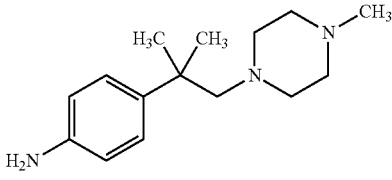 [SMILES: CN1CCN(CC(C)(C)c2ccc([N+](=O)[O-])cc2)CC1] |
| 229 | 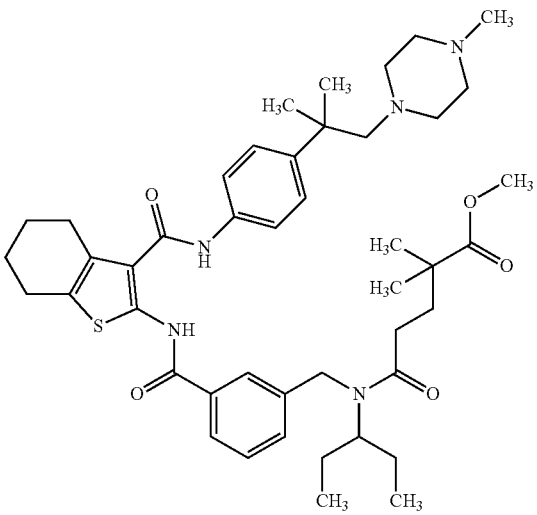 [SMILES: CCC(CC)N(Cc1cccc(C(=O)Nc2sc3c(c2C(=O)Nc2ccc(C(C)(C)CN4CCN(C)CC4)cc2)CCCC3)c1)C(=O)CCC(C)(C)C(=O)OC] |
| 230 | 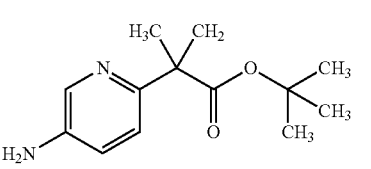 |
| 231 | 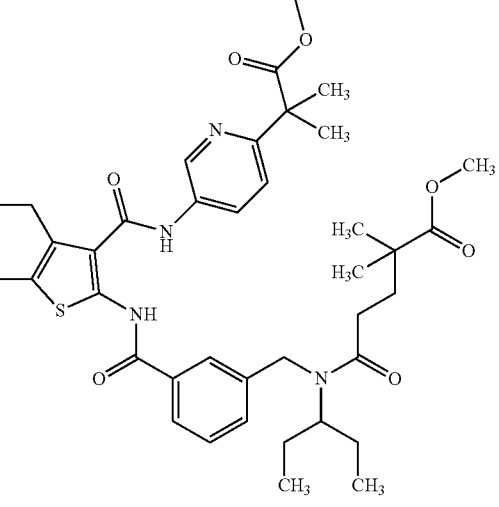 |

TABLE 38-continued
| Pr | Str |
|---|---|
| 232 | 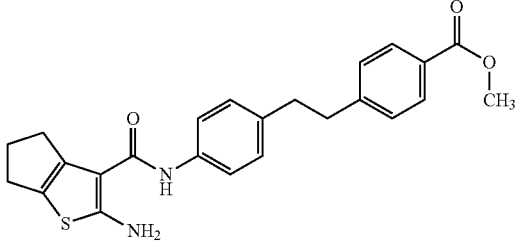 [SMILES: COC(=O)c1ccc(CCc2ccc(NC(=O)c3c(N)sc4c3CCC4)cc2)cc1] |
| 233 | 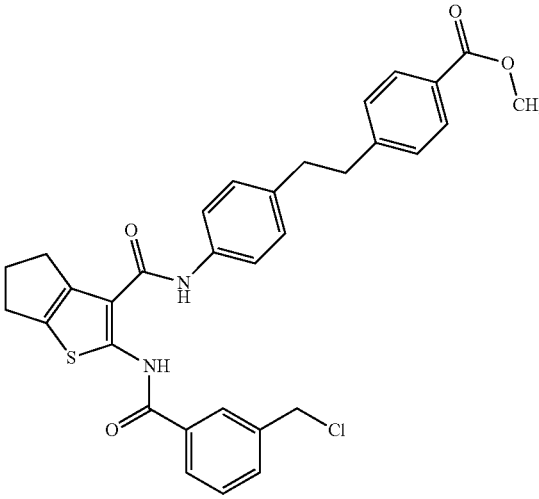 [SMILES: COC(=O)c1ccc(CCc2ccc(NC(=O)c3c(NC(=O)c4cccc(CCl)c4)sc4c3CCC4)cc2)cc1] |
TABLE 39
| Pr | Str |
|---|---|
| 234 | 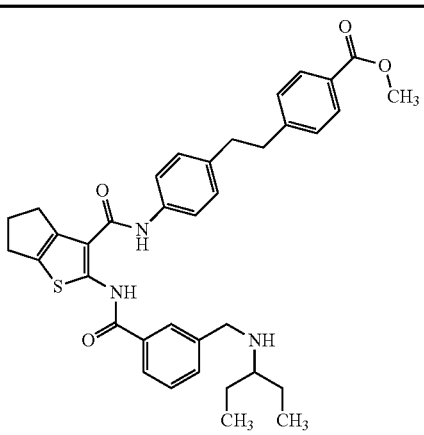 |
| 235 | 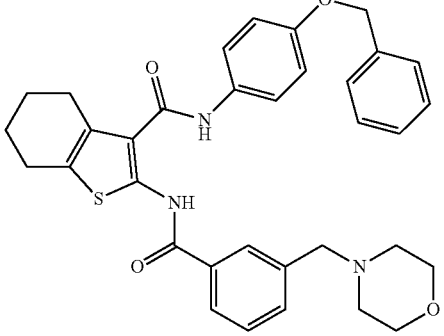 |
| 236 | 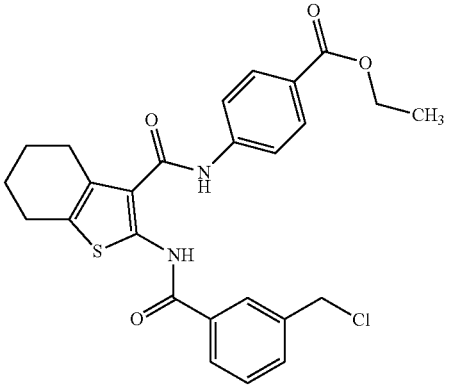 [SMILES: CCOC(=O)c1ccc(NC(=O)c2c(NC(=O)c3cccc(CCl)c3)sc3c2CCCC3)cc1] |
| 237 | 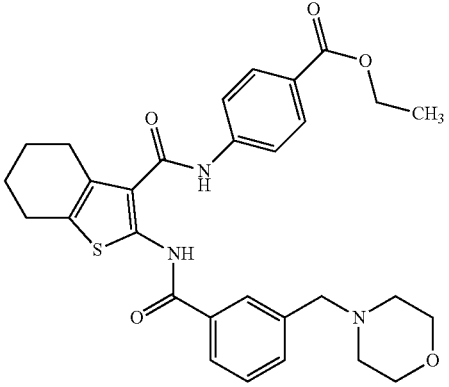 [SMILES: CCOC(=O)c1ccc(NC(=O)c2c(NC(=O)c3cccc(CN4CCOCC4)c3)sc3c2CCCC3)cc1] |
| 238 | 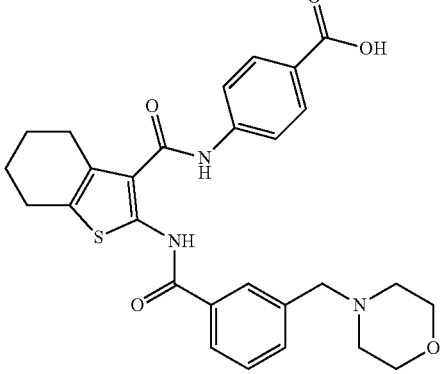 |

TABLE 39-continued

| Pr | Str |
|---|---|
| 239 | |
| 240 | |

TABLE 40

| Pr | Str |
|---|---|
| 241 | |
| 242 | |
| 243 | |
| 244 | |
| 245 | |
| 246 | |
| 247 | |

TABLE 40-continued

| Pr | Str |
|---|---|
| 248 | (structure) |

TABLE 41

| Pr | Str |
|---|---|
| 249 | (structure) |
| 250 | (structure) |
| 251 | (structure) |
| 252 | (structure) |

TABLE 41-continued

| Pr | Str |
|---|---|
| 253 | (structure) |
| 254 | (structure) |
| 255 | (structure) |
| 256 | (structure) |
| 257 | (structure) |
| 258 | (structure) |
| 259 | (structure) |

TABLE 42
| Pr | Str |
|---|---|
| 260 | 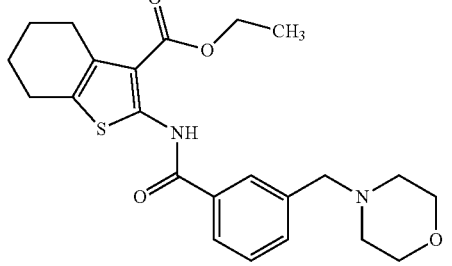 |
| 261 | 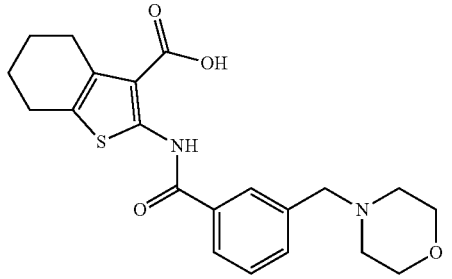 [SMILES: O=C(Nc1sc2c(c1C(=O)O)CCCC2)c1cccc(CN2CCOCC2)c1] |
| 262 | 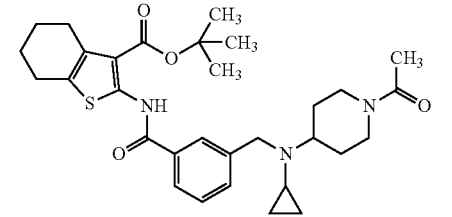 [SMILES: CC(=O)N1CCC(N(Cc2cccc(C(=O)Nc3sc4c(c3C(=O)OC(C)(C)C)CCCC4)c2)C2CC2)CC1] |
| 263 | 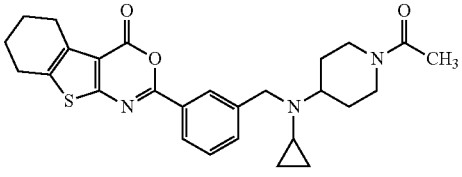 [SMILES: CC(=O)N1CCC(N(Cc2cccc(-c3nc4sc5c(c4c(=O)o3)CCCC5)c2)C2CC2)CC1] |
| 264 | 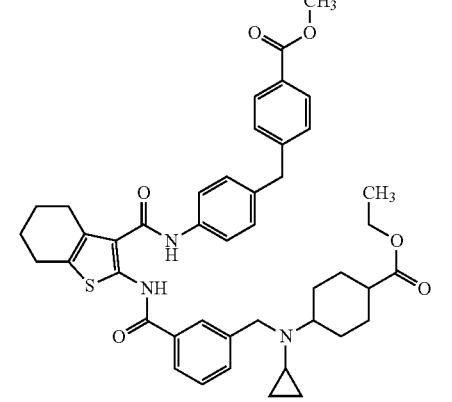 [SMILES: CCOC(=O)C1CCC(N(Cc2cccc(C(=O)Nc3sc4c(c3C(=O)Nc3ccc(Cc5ccc(C(=O)OC)cc5)cc3)CCCC4)c2)C2CC2)CC1] |
TABLE 42-continued
| Pr | Str |
|---|---|
| 265 | 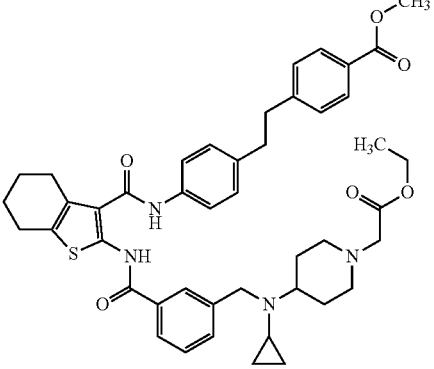 |
| 266 | 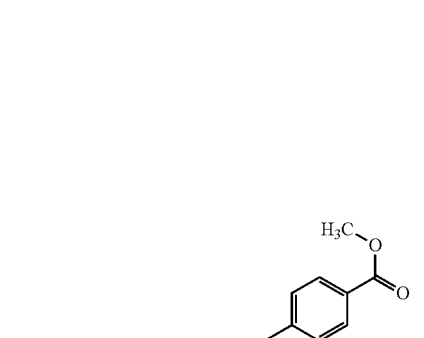 |
| 267 | 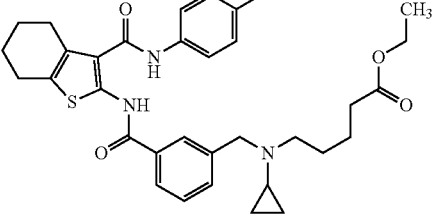 |

TABLE 43

| Pr | Str |
|---|---|
| 268 | (structure) |
| 269 | (structure) |
| 270 | (structure) |
| 271 | (structure) |
| 272 | (structure) |
| 273 | (structure) |
| 274 | (structure) |
| 275 | (structure) |

TABLE 43-continued

| Pr | Str |
|---|---|
| 276 | (structure) |
| 277 | (structure, 2HCl) |

TABLE 44

| Pr | Str |
|---|---|
| 278 | (structure) |
| 279 | (structure) |

TABLE 44-continued

| Pr | Str |
|---|---|
| 280 | (structure) |
| 281 | (structure) |
| 282 | (structure) |
| 283 | (structure) |

TABLE 45

| Pr | Str |
|---|---|
| 284 | (structure) |
| 285 | (structure) |
| 286 | (structure) |
| 287 | (structure) |

TABLE 45-continued
| Pr | Str |
|---|---|
| 288 | 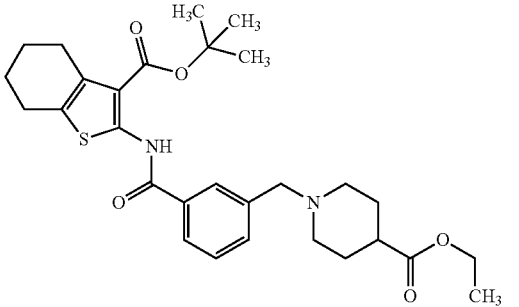 [SMILES: CCOC(=O)C1CCN(Cc2cccc(C(=O)Nc3sc4c(c3C(=O)OC(C)(C)C)CCCC4)c2)CC1] |
| 289 | 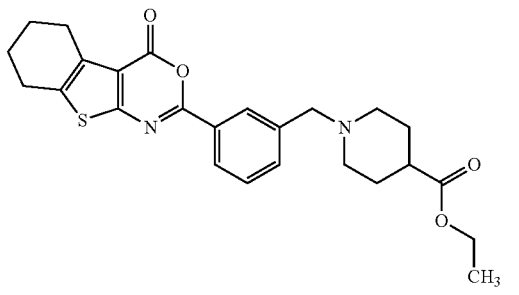 [SMILES: CCOC(=O)C1CCN(Cc2cccc(-c3nc4sc5c(c4c(=O)o3)CCCC5)c2)CC1] |
| 290 | 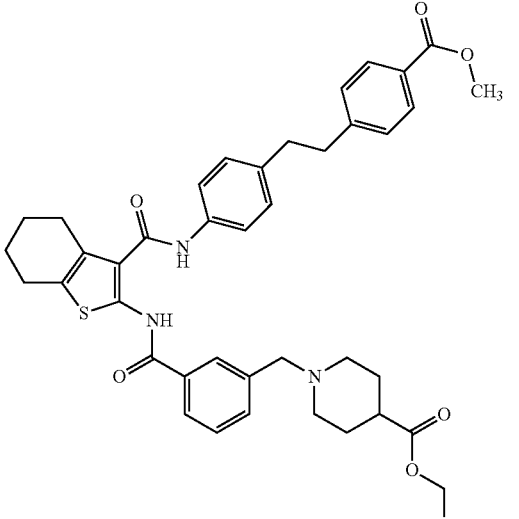 |
| 291 | 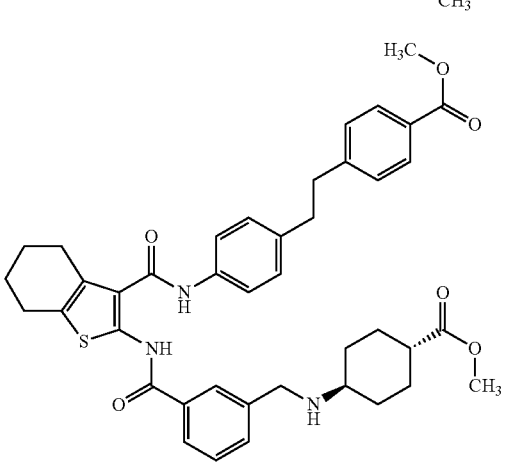 |
TABLE 46
| Pr | Str |
|---|---|
| 292 | 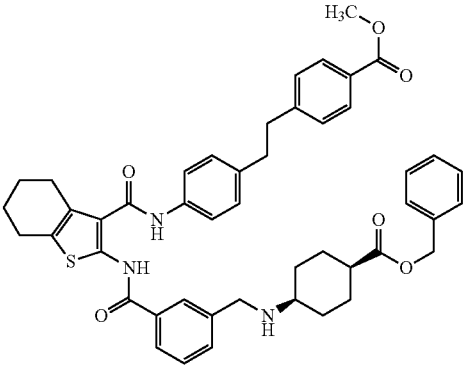 [SMILES: COC(=O)c1ccc(CCc2ccc(NC(=O)c3c(NC(=O)c4cccc(CN[C@H]5CC[C@@H](C(=O)OCc6ccccc6)CC5)c4)sc4c3CCCC4)cc2)cc1] |
| 293 | 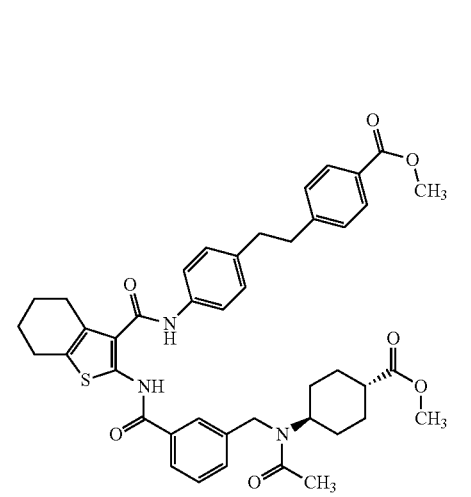 [SMILES: COC(=O)c1ccc(CCc2ccc(NC(=O)c3c(NC(=O)c4cccc(CN(C(C)=O)[C@H]5CC[C@H](C(=O)OC)CC5)c4)sc4c3CCCC4)cc2)cc1] |
| 294 | 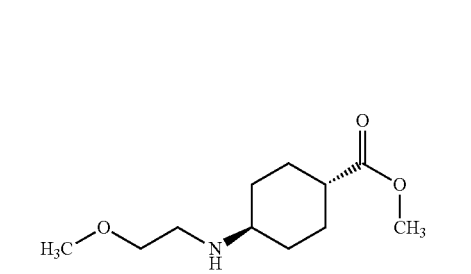 |
| 295 | 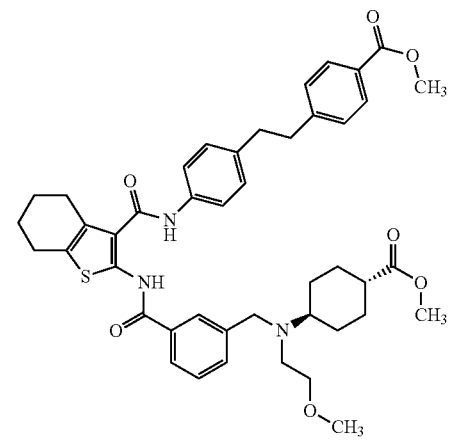 [SMILES: COCCN(Cc1cccc(C(=O)Nc2sc3c(c2C(=O)Nc2ccc(CCc4ccc(C(=O)OC)cc4)cc2)CCCC3)c1)[C@H]1CC[C@H](C(=O)OC)CC1] |

TABLE 46-continued
| Pr | Str |
|---|---|
| 296 | 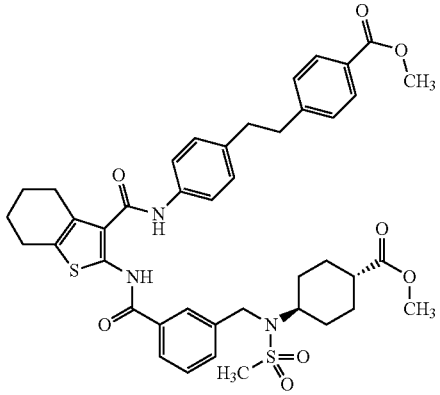 [SMILES: COC(=O)c1ccc(CCc2ccc(NC(=O)c3c(NC(=O)c4cccc(CN([C@H]5CC[C@H](C(=O)OC)CC5)S(C)(=O)=O)c4)sc4c3CCCC4)cc2)cc1] |
| 297 | 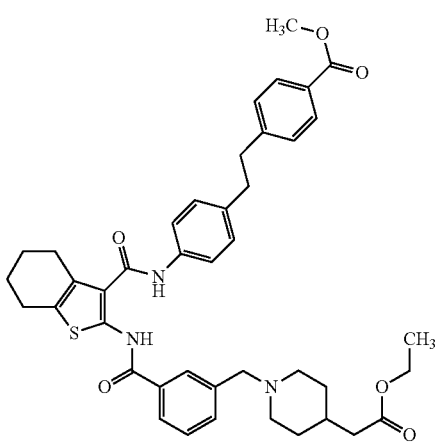 [SMILES: CCOC(=O)CC1CCN(Cc2cccc(C(=O)Nc3sc4c(c3C(=O)Nc3ccc(CCc5ccc(C(=O)OC)cc5)cc3)CCCC4)c2)CC1] |
TABLE 47
| Pr | Str |
|---|---|
| 298 | 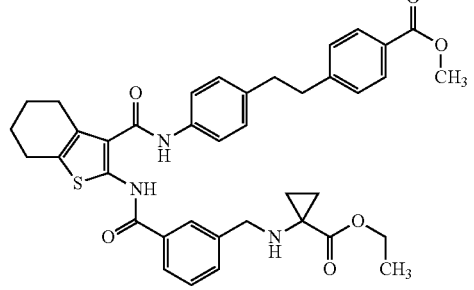 |
| 299 | 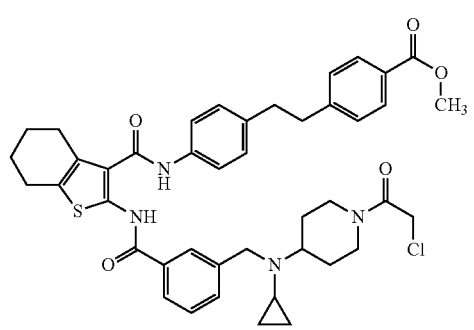 [SMILES: COC(=O)c1ccc(CCc2ccc(NC(=O)c3c(NC(=O)c4cccc(CN(C5CC5)C5CCN(C(=O)CCl)CC5)c4)sc4c3CCCC4)cc2)cc1] |￼
| 300 | 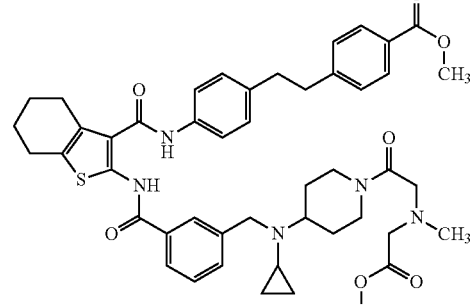 |
| 301 | 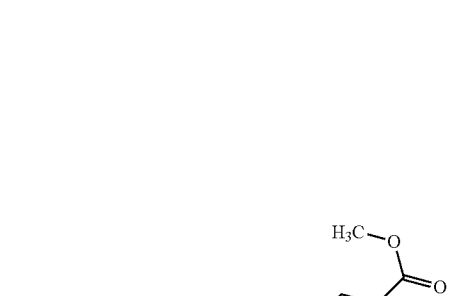 |
| 302 | 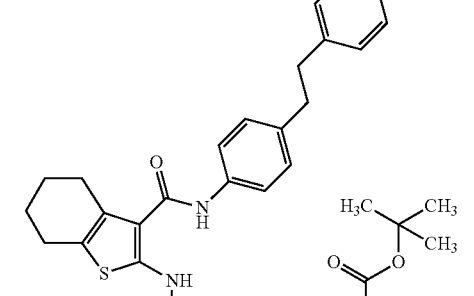 |

TABLE 47-continued
| Pr | Str |
|---|---|
| 303 | 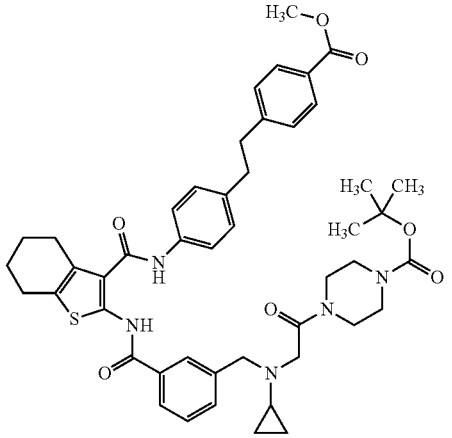 [SMILES: COC(=O)c1ccc(CCc2ccc(NC(=O)c3c(NC(=O)c4cccc(CN(CC(=O)N5CCN(C(=O)OC(C)(C)C)CC5)C5CC5)c4)sc4c3CCCC4)cc2)cc1] |
TABLE 48
| Pr | Str |
|---|---|
| 304 | 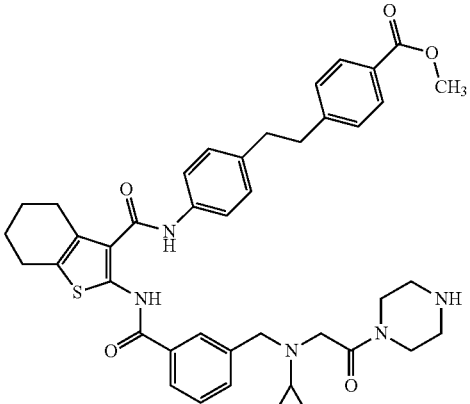 |
| 305 | 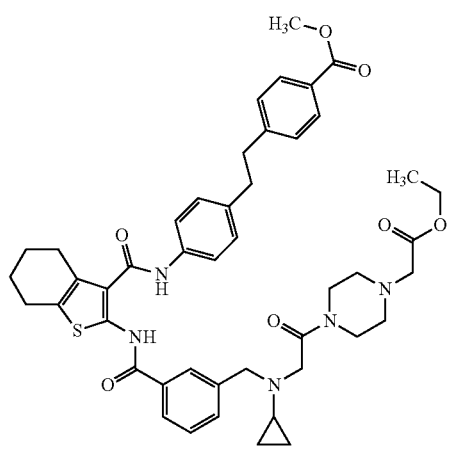 [SMILES: CCOC(=O)CN1CCN(C(=O)CN(Cc2cccc(C(=O)Nc3sc4c(c3C(=O)Nc3ccc(CCc5ccc(C(=O)OC)cc5)cc3)CCCC4)c2)C2CC2)CC1] |
TABLE 48-continued
| Pr | Str |
|---|---|
| 306 | 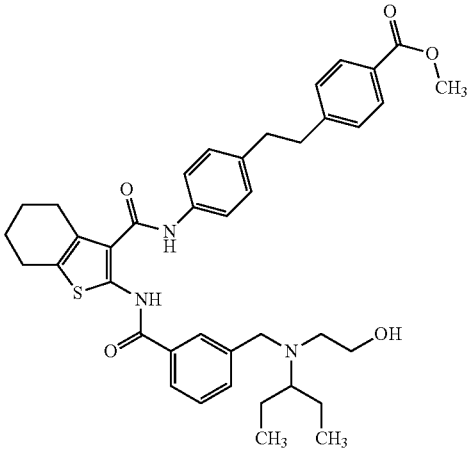 [SMILES: CCC(CC)N(CCO)Cc1cccc(C(=O)Nc2sc3c(c2C(=O)Nc2ccc(CCc4ccc(C(=O)OC)cc4)cc2)CCCC3)c1] |
| 307 | 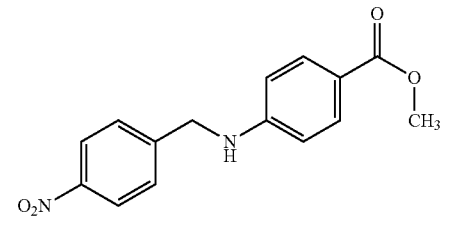 [SMILES: COC(=O)c1ccc(NCc2ccc([N+](=O)[O-])cc2)cc1] |
| 308 | 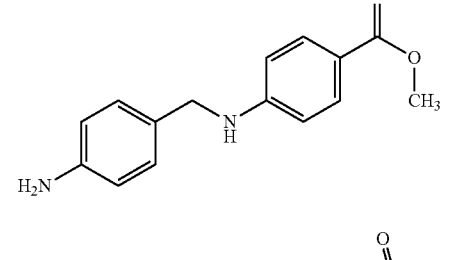 |
| 309 | 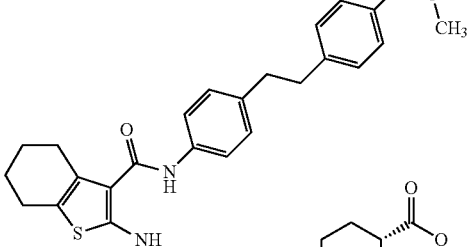 |
| 310 | 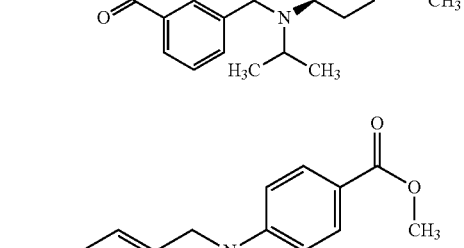 |

TABLE 49
| Pr | Str |
|---|---|
| 311 | 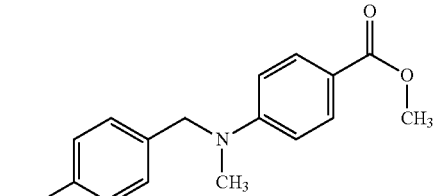 |
| 312 | 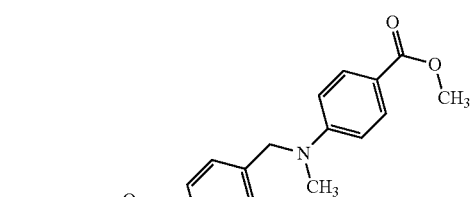 |
| 313 | 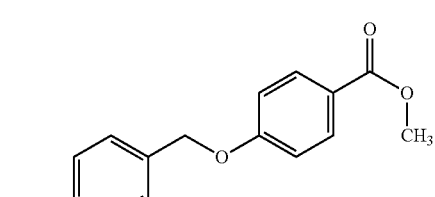 |
| 314 | 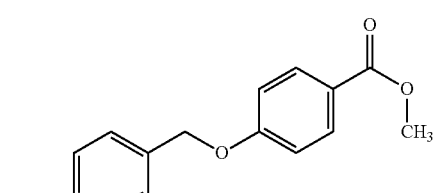 |
| 315 | 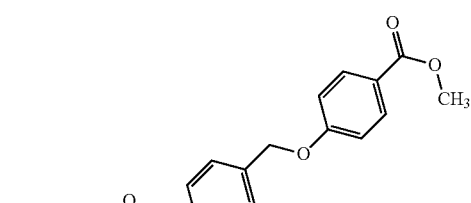 |
TABLE 50
| Ex | Str |
|---|---|
| 1 | 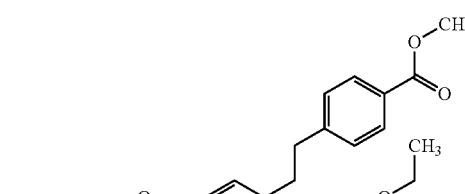 |
| 2 |  HCl |
| 3 | 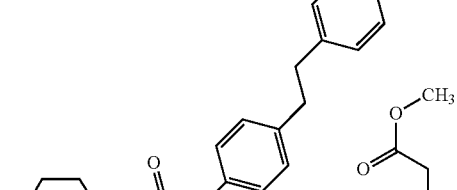 |

TABLE 50-continued
| Ex | Str |
|---|---|
| 4 | 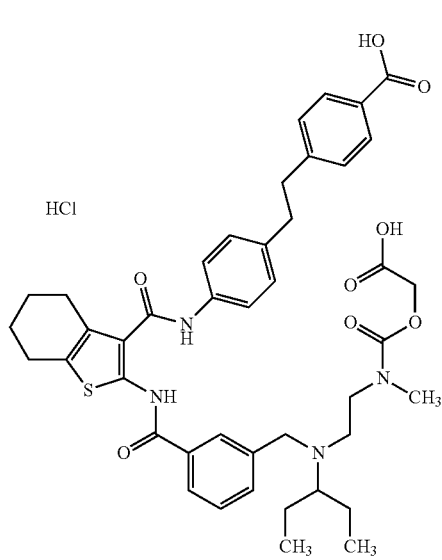 [SMILES: CCC(CC)N(CCN(C)C(=O)OCC(=O)O)Cc1cccc(C(=O)Nc2sc3c(c2C(=O)Nc2ccc(CCc4ccc(C(=O)O)cc4)cc2)CCCC3)c1 ; Cl] |
| 5 | 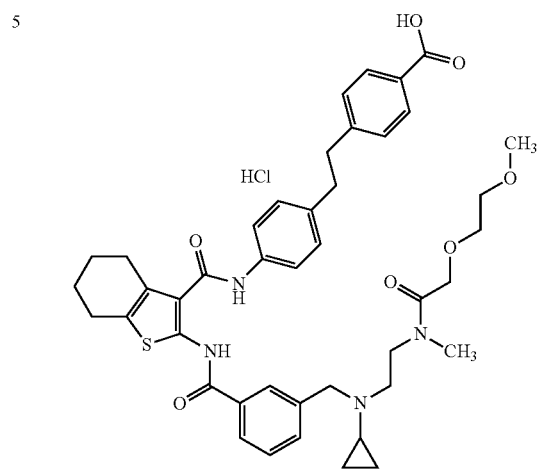 |
TABLE 51
| Ex | Str |
|---|---|
| 6 | 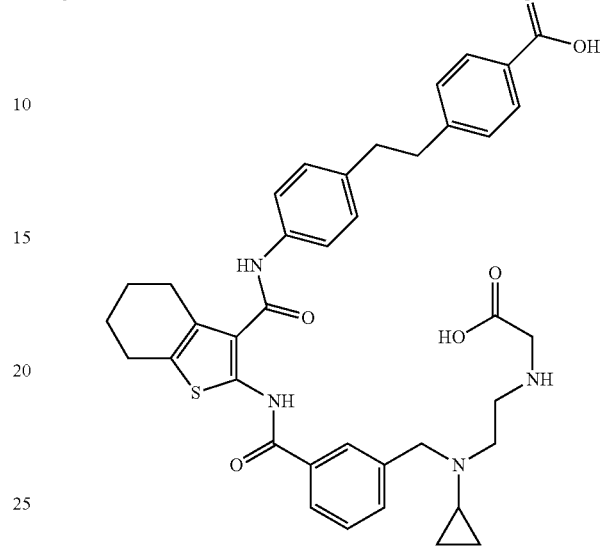 |
| 7 | 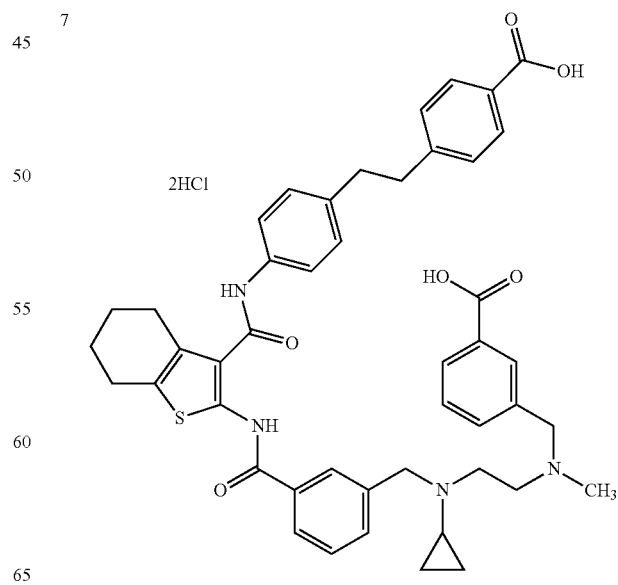 |

TABLE 51-continued
| Ex | Str |
|---|---|
| 8 | 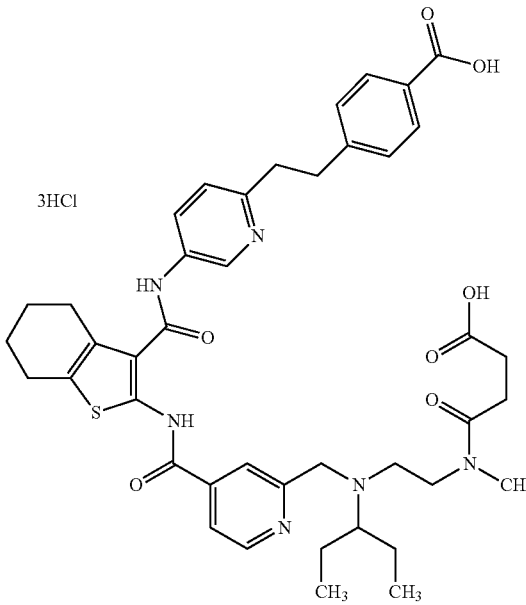 [SMILES: CCC(CC)N(CCN(C)C(=O)CCC(=O)O)Cc1cc(C(=O)Nc2sc3c(c2C(=O)Nc2ccc(CCc4ccc(C(=O)O)cc4)nc2)CCCC3)ccn1] |
| 9 | 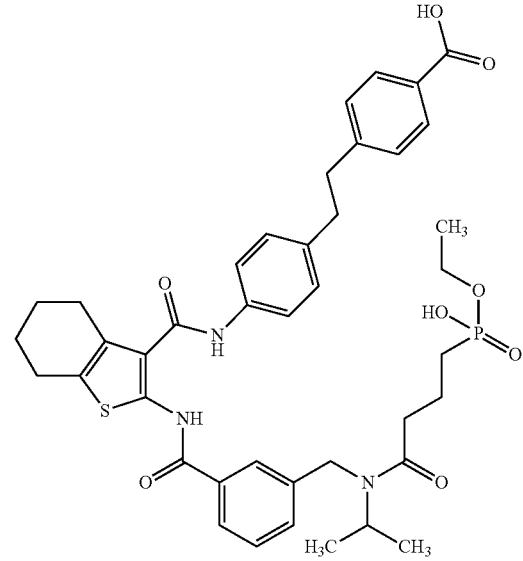 [SMILES: CCOP(=O)(O)CCCC(=O)N(Cc1cccc(C(=O)Nc2sc3c(c2C(=O)Nc2ccc(CCc4ccc(C(=O)O)cc4)cc2)CCCC3)c1)C(C)C] |
| 10 | 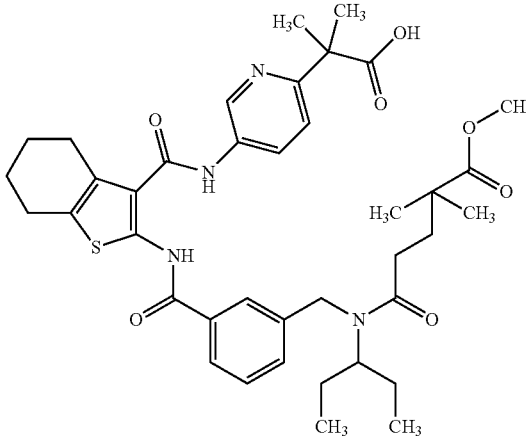 |
| 11 | 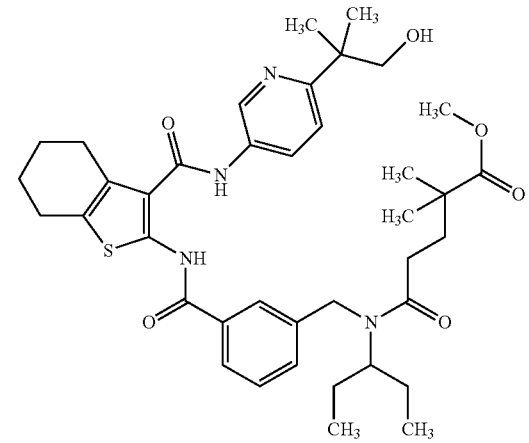 [SMILES: CCC(CC)N(Cc1cccc(C(=O)Nc2sc3c(c2C(=O)Nc2ccc(C(C)(C)CO)nc2)CCCC3)c1)C(=O)CCC(C)(C)C(=O)OC] |
TABLE 52
| Ex | Str |
|---|---|
| 12 | 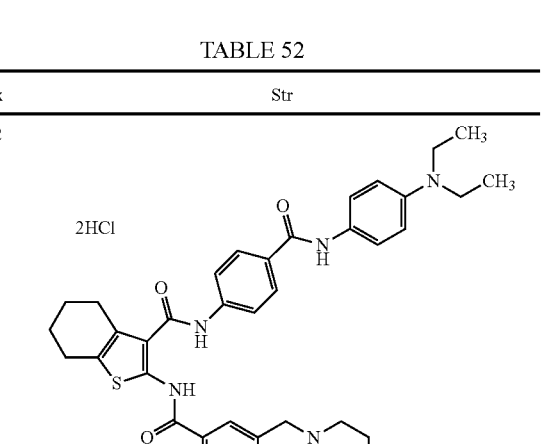 |
| 13 | 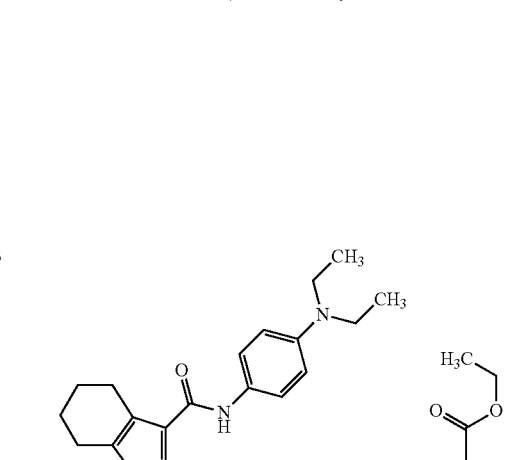 |

TABLE 52-continued
| Ex | Str |
|---|---|
| 14 | 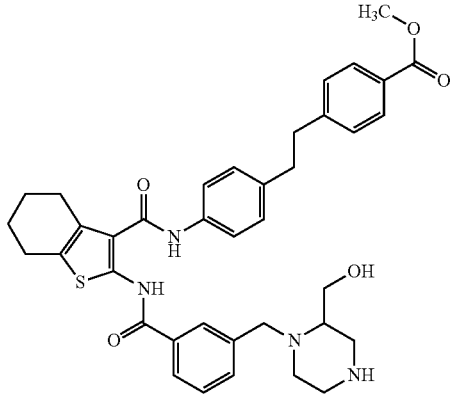 [SMILES: COC(=O)c1ccc(CCc2ccc(NC(=O)c3c(NC(=O)c4cccc(CN5CCNCC5CO)c4)sc4c3CCCC4)cc2)cc1] |
| 15 | 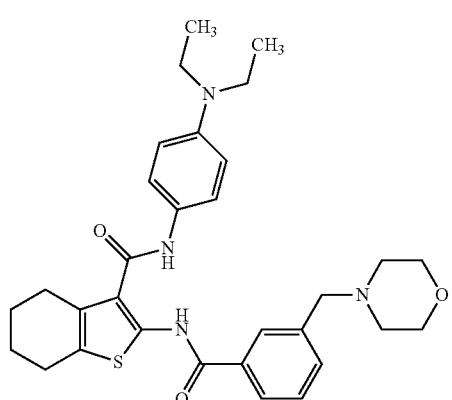 |
| 16 | 2HCl 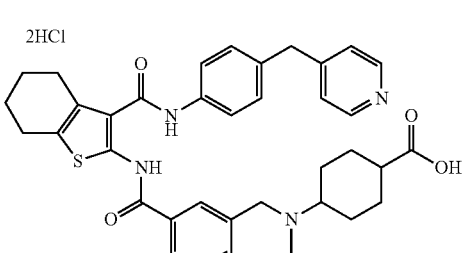 |
| 17 | 2HCl 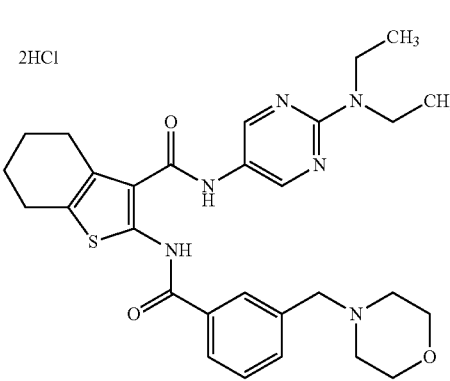 |
| 18 | 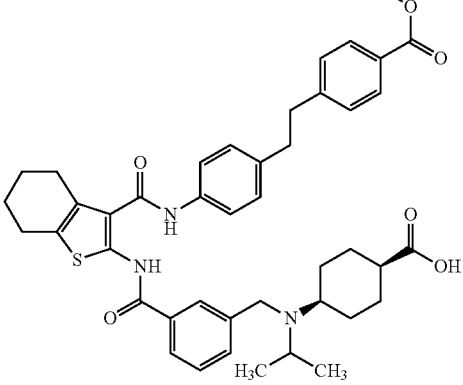 |
| 19 | 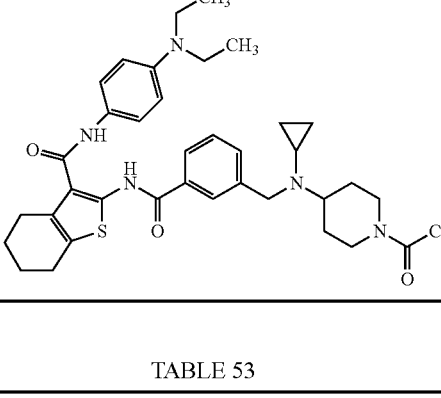 |
TABLE 53
| Ex | Str |
|---|---|
| 20 | 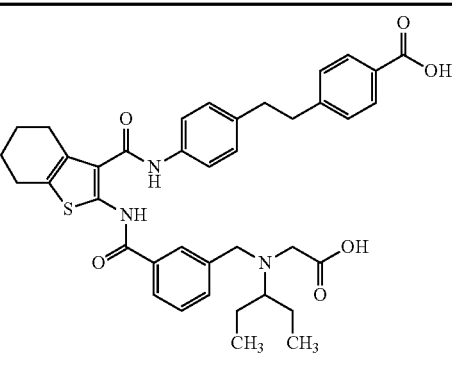 |
| 21 | 2HCl 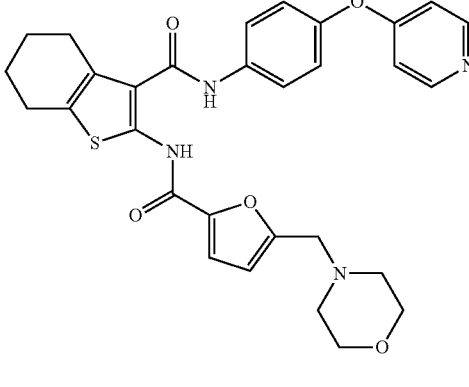 |

TABLE 53-continued
| Ex | Str |
|---|---|
| 22 | 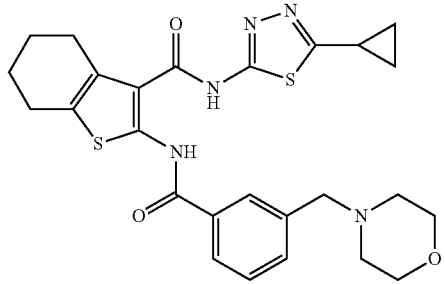 [SMILES: O=C(Nc1sc2c(c1C(=O)Nc1nnc(C3CC3)s1)CCCC2)c1cccc(CN2CCOCC2)c1] |
| 23 | 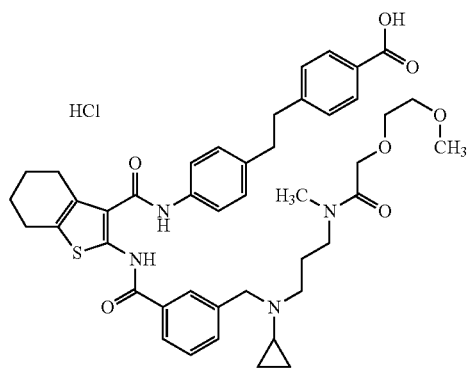 [SMILES: COCCOCC(=O)N(C)CCCN(Cc1cccc(C(=O)Nc2sc3c(c2C(=O)Nc2ccc(CCc4ccc(C(=O)O)cc4)cc2)CCCC3)c1)C1CC1 ; Cl] |
| 24 | 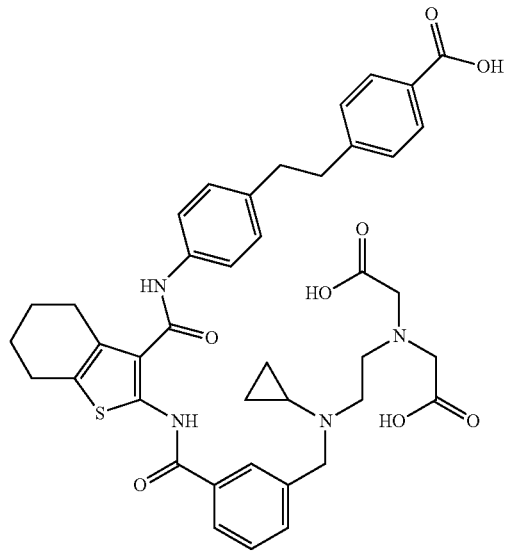 [SMILES: O=C(O)CN(CCN(Cc1cccc(C(=O)Nc2sc3c(c2C(=O)Nc2ccc(CCc4ccc(C(=O)O)cc4)cc2)CCCC3)c1)C1CC1)CC(=O)O] |
| 25 | 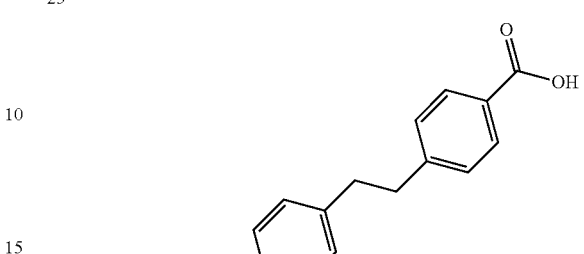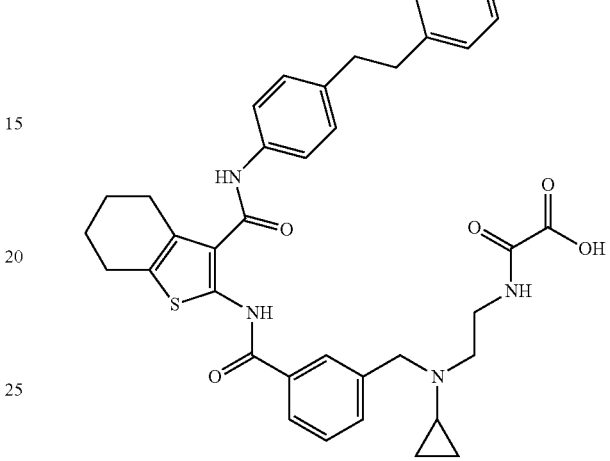 |
| 26 | 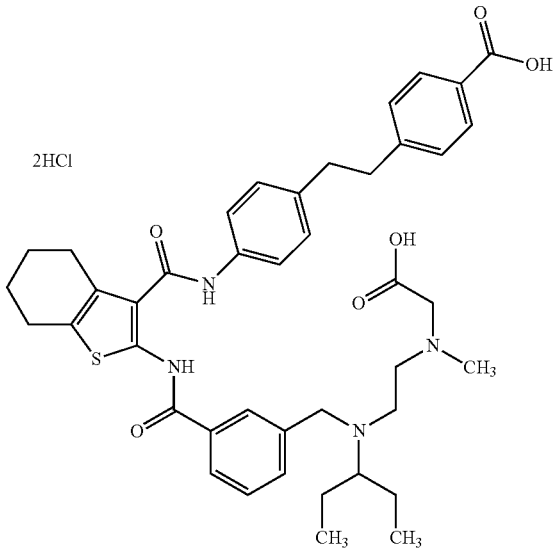 [SMILES: CCC(CC)N(CCN(C)CC(=O)O)Cc1cccc(C(=O)Nc2sc3c(c2C(=O)Nc2ccc(CCc4ccc(C(=O)O)cc4)cc2)CCCC3)c1 ; "2HCl"] |

TABLE 54
| Ex | Str |
|---|---|
| 27 | 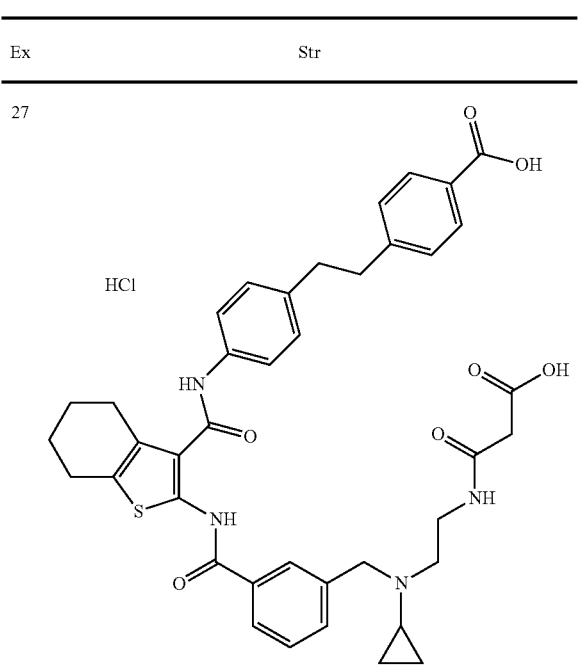 |
| 28 | 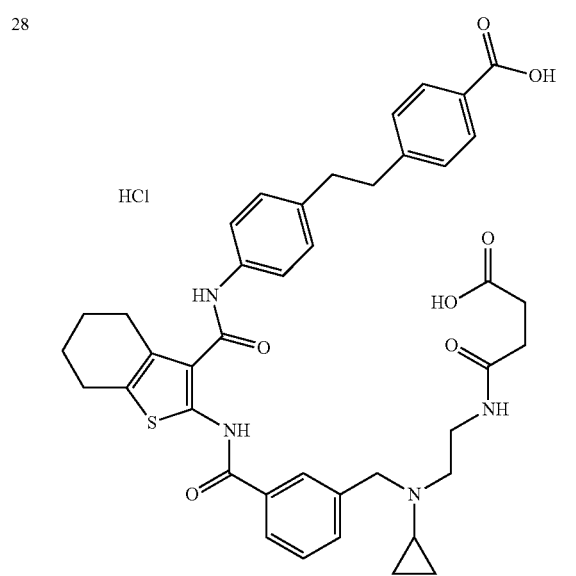 |
TABLE 54-continued
| Ex | Str |
|---|---|
| 29 | 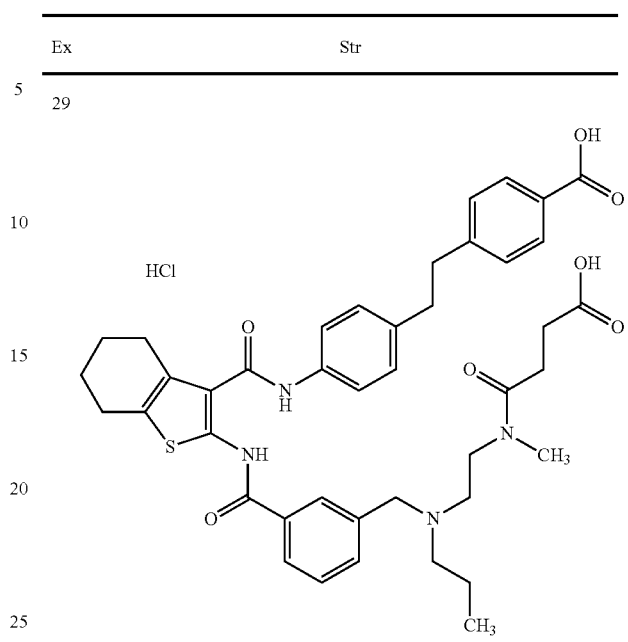 |
| 30 | 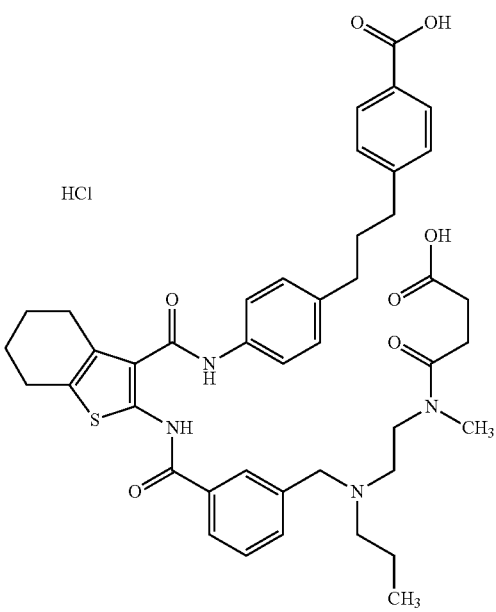 [SMILES: CCCN(CCN(C)C(=O)CCC(=O)O)Cc1cccc(C(=O)Nc2sc3c(c2C(=O)Nc2ccc(CCCc4ccc(C(=O)O)cc4)cc2)CCCC3)c1 ; Cl] |

TABLE 54-continued
| Ex | Str |
|---|---|
| 31 | 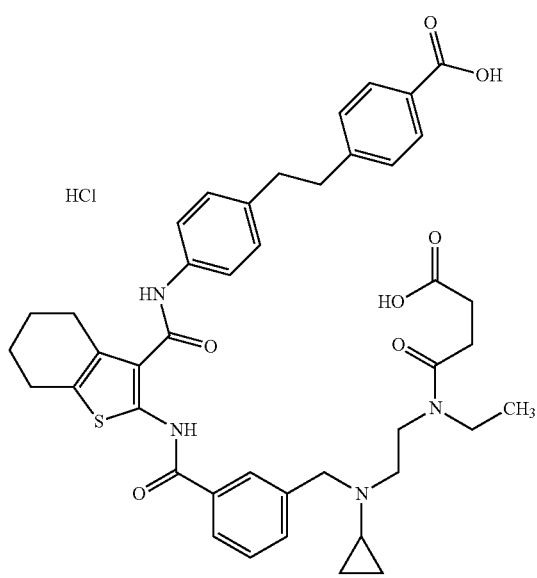 [SMILES: CCN(CCN(Cc1cccc(C(=O)Nc2sc3c(c2C(=O)Nc2ccc(CCc4ccc(C(=O)O)cc4)cc2)CCCC3)c1)C1CC1)C(=O)CCC(=O)O ; Cl] |
| 32 | 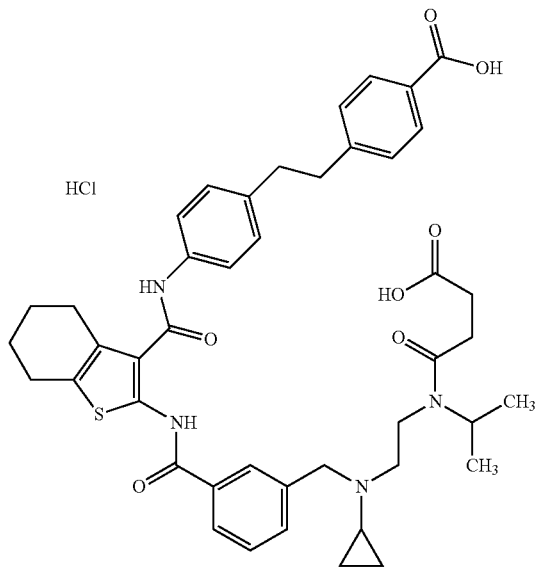 [SMILES: CC(C)N(CCN(Cc1cccc(C(=O)Nc2sc3c(c2C(=O)Nc2ccc(CCc4ccc(C(=O)O)cc4)cc2)CCCC3)c1)C1CC1)C(=O)CCC(=O)O ; Cl] |
TABLE 55
| Ex | Str |
|---|---|
| 33 | 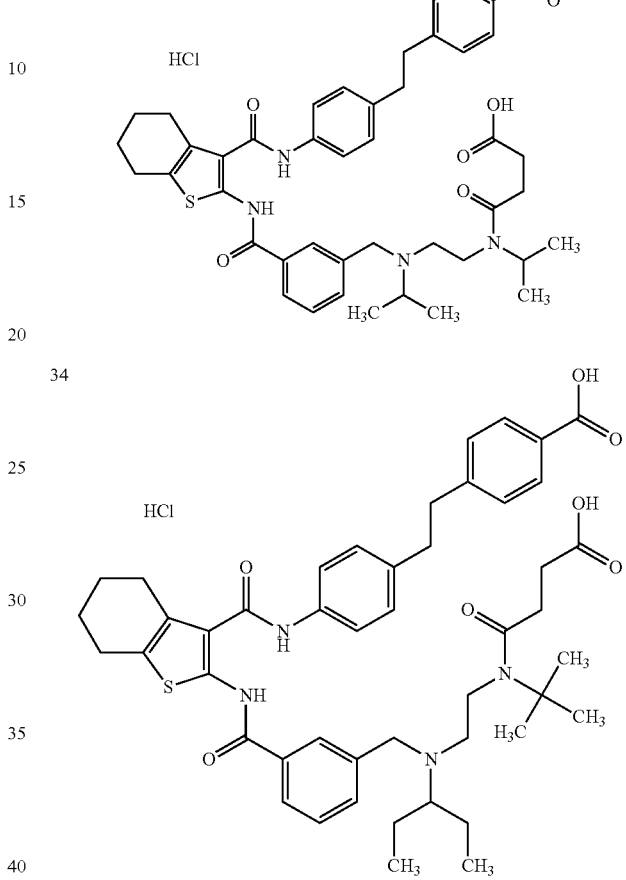 |
| 34 | |
| 35 | 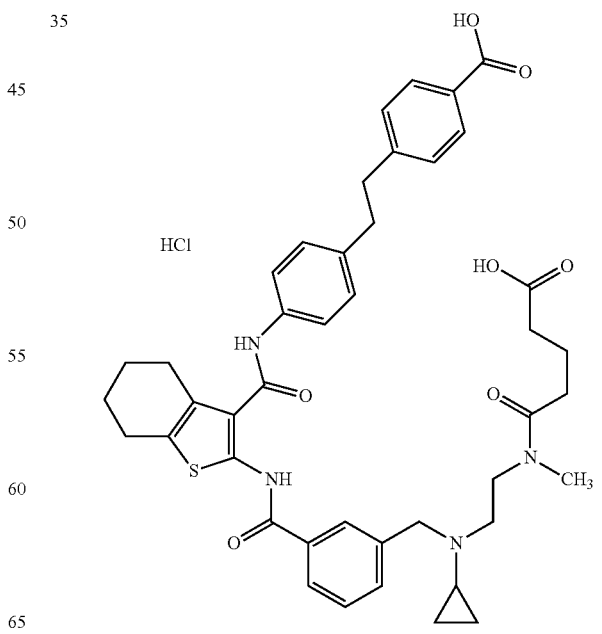 |

TABLE 55-continued
| Ex | Str |
|---|---|
| 36 | 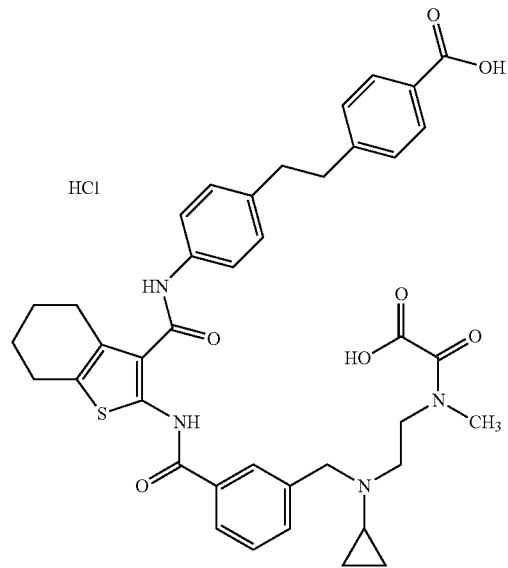 [SMILES: CN(CCN(Cc1cccc(C(=O)Nc2sc3c(c2C(=O)Nc2ccc(CCc4ccc(C(=O)O)cc4)cc2)CCCC3)c1)C1CC1)C(=O)C(=O)O ; Cl] |
| 37 | 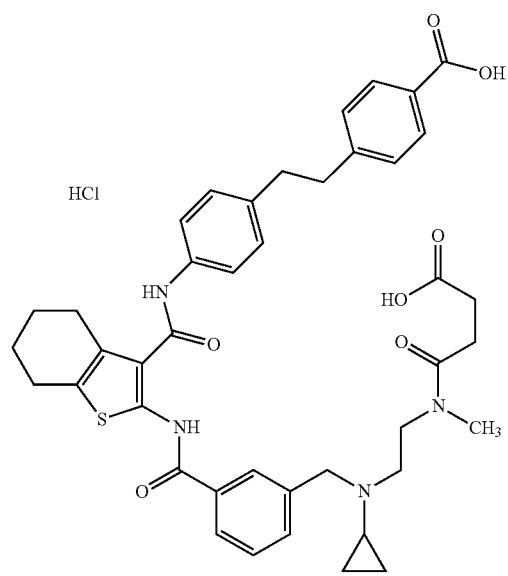 [SMILES: CN(CCN(Cc1cccc(C(=O)Nc2sc3c(c2C(=O)Nc2ccc(CCc4ccc(C(=O)O)cc4)cc2)CCCC3)c1)C1CC1)C(=O)CCC(=O)O ; Cl] |
TABLE 55-continued
| Ex | Str |
|---|---|
| 38 | 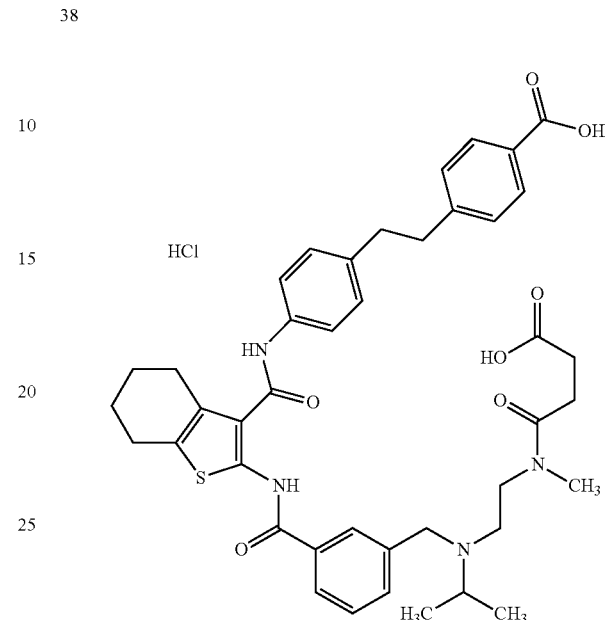 |
TABLE 56
| Ex | Str |
|---|---|
| 39 | 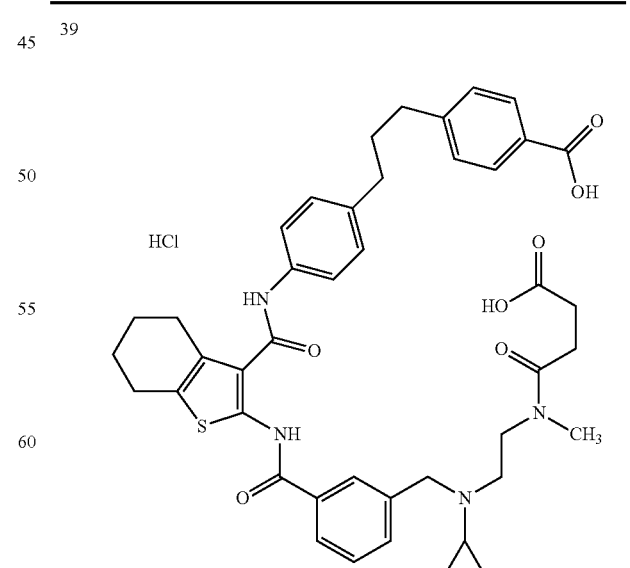 |

TABLE 56-continued
| Ex | Str |
|---|---|
| 40 | 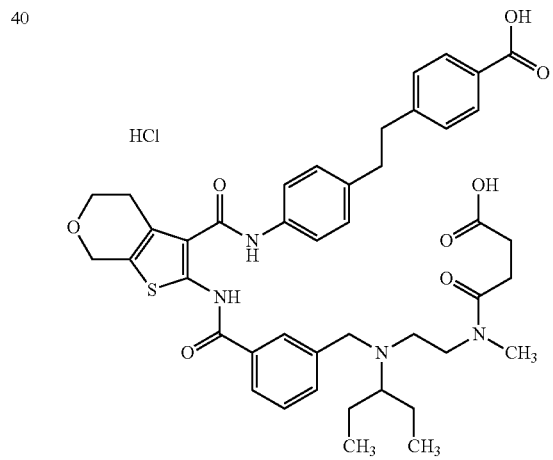 |
| 41 | 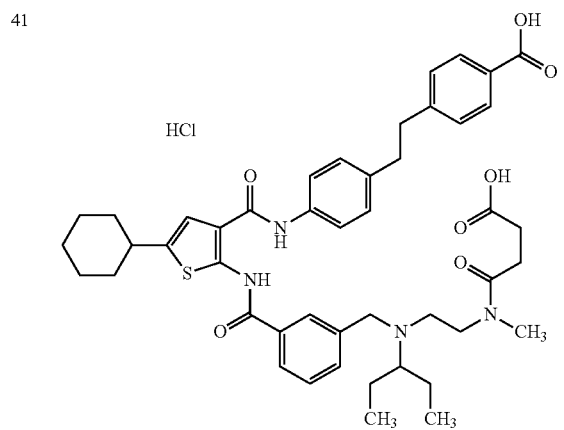 |
| 42 | 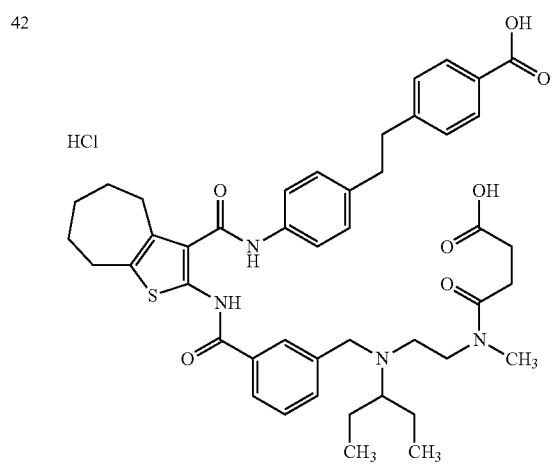 |
TABLE 56-continued
| Ex | Str |
|---|---|
| 43 | 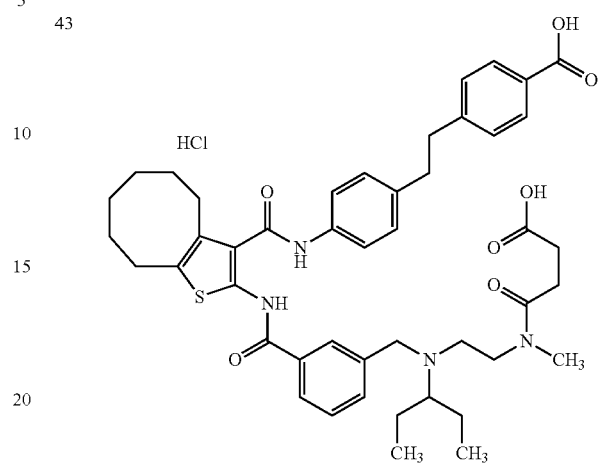 |
| 44 | 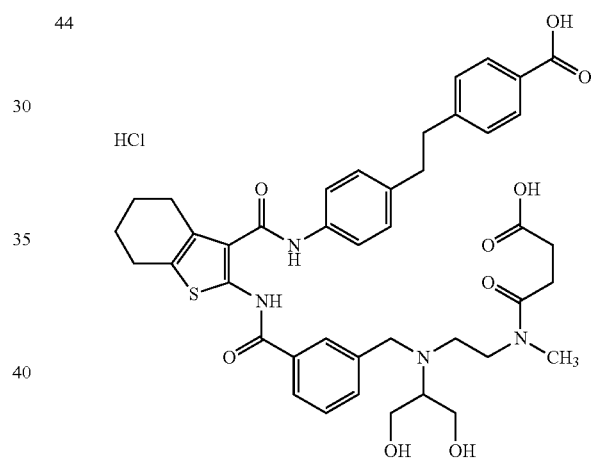 |
TABLE 57
| Ex | Str |
|---|---|
| 45 | 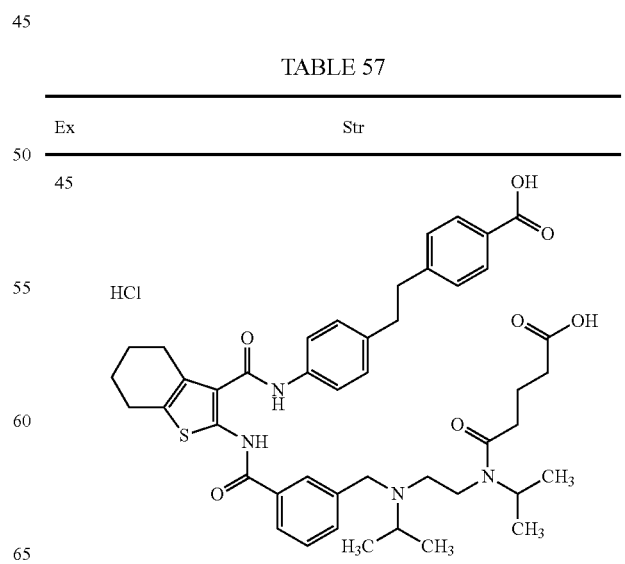 |

TABLE 57-continued
| Ex | Str |
|---|---|
| 46 | 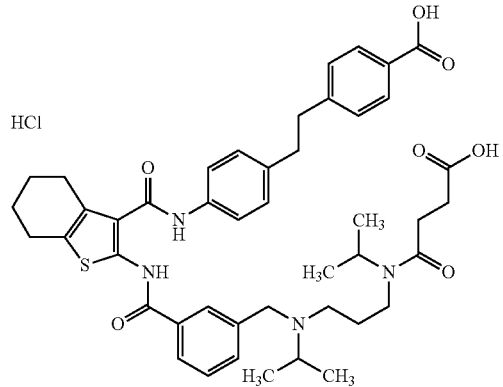 [SMILES: CC(C)N(CCCN(C(=O)CCC(=O)O)C(C)C)Cc1cccc(C(=O)Nc2sc3c(c2C(=O)Nc2ccc(CCc4ccc(C(=O)O)cc4)cc2)CCCC3)c1 ; Cl] |
| 47 | 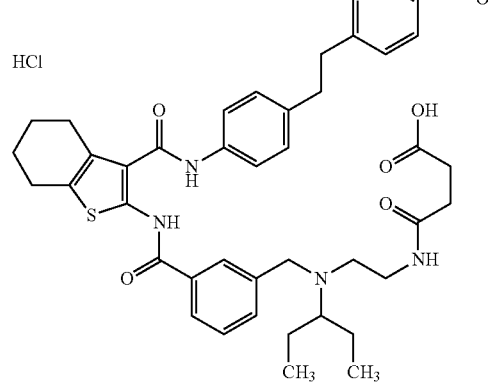 |
| 48 | 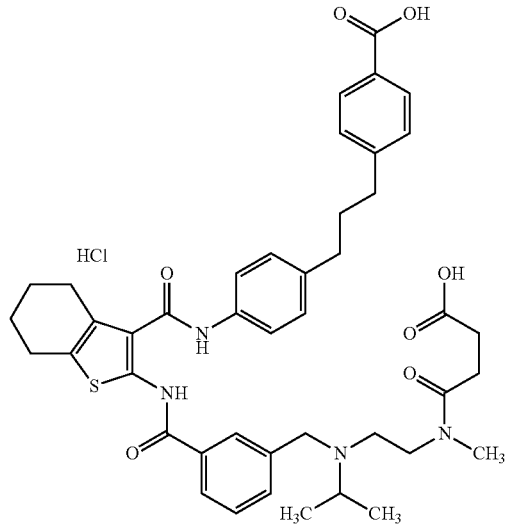 [SMILES: CC(C)N(CCN(C)C(=O)CCC(=O)O)Cc1cccc(C(=O)Nc2sc3c(c2C(=O)Nc2ccc(CCCc4ccc(C(=O)O)cc4)cc2)CCCC3)c1 ; Cl] |
| 49 | 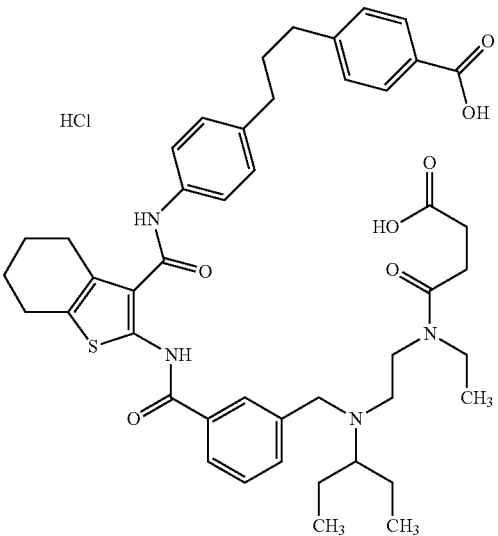 [SMILES: CCC(CC)N(CCN(CC)C(=O)CCC(=O)O)Cc1cccc(C(=O)Nc2sc3c(c2C(=O)Nc2ccc(CCCc4ccc(C(=O)O)cc4)cc2)CCCC3)c1 ; Cl] |
| 50 | 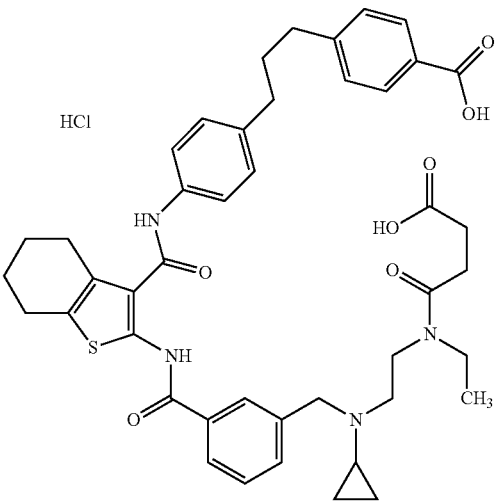 [SMILES: CCN(CCN(Cc1cccc(C(=O)Nc2sc3c(c2C(=O)Nc2ccc(CCCc4ccc(C(=O)O)cc4)cc2)CCCC3)c1)C1CC1)C(=O)CCC(=O)O ; Cl] |

TABLE 58
| Ex | Str |
|---|---|
| 51 | 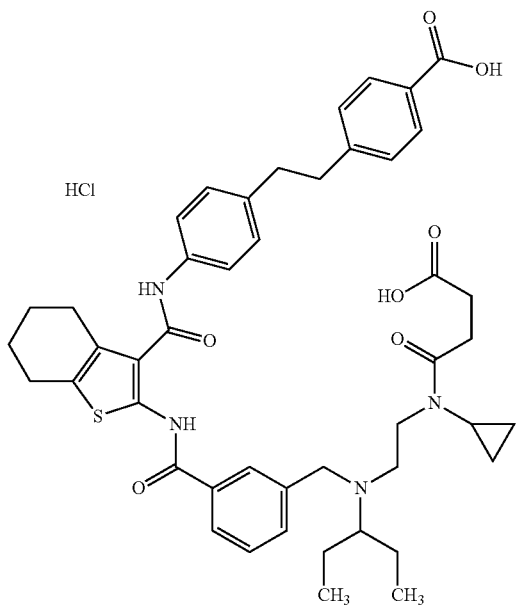 [SMILES: CCC(CC)N(CCN(C(=O)CCC(=O)O)C1CC1)Cc1cccc(C(=O)Nc2sc3c(c2C(=O)Nc2ccc(CCc4ccc(C(=O)O)cc4)cc2)CCCC3)c1 ; Cl] |
| 52 | 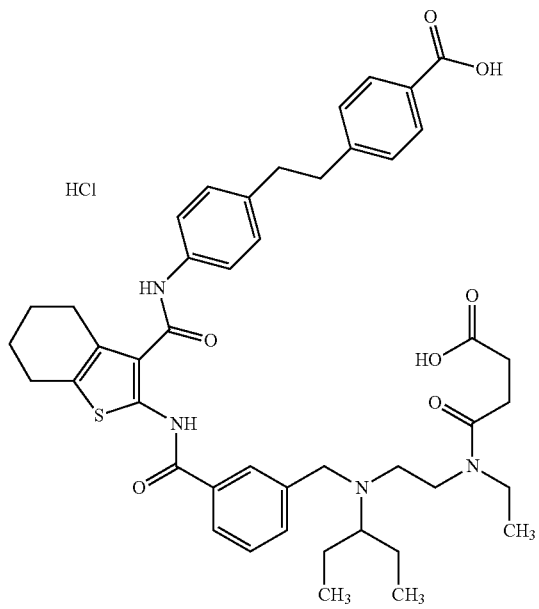 [SMILES: CCC(CC)N(CCN(CC)C(=O)CCC(=O)O)Cc1cccc(C(=O)Nc2sc3c(c2C(=O)Nc2ccc(CCc4ccc(C(=O)O)cc4)cc2)CCCC3)c1 ; Cl] |
TABLE 58-continued
| Ex | Str |
|---|---|
| 53 | 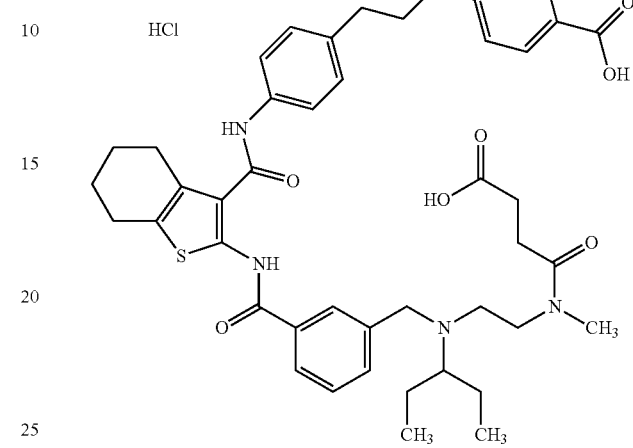 |
| 54 | 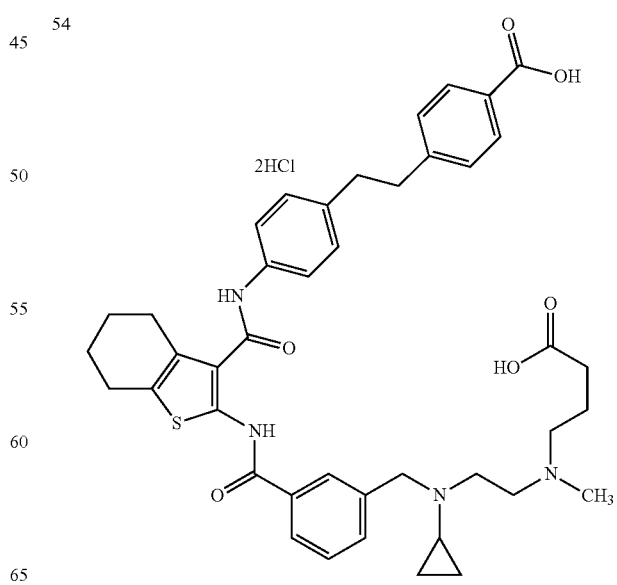 |

TABLE 58-continued
| Ex | Str |
|---|---|
| 55 | 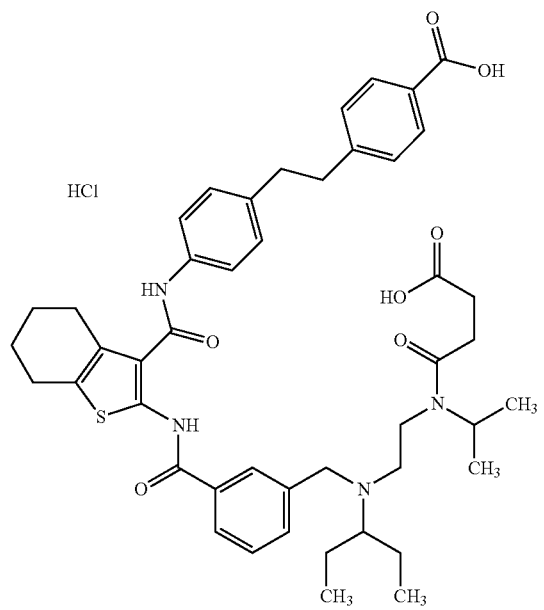 [SMILES: CCC(CC)N(CCN(C(=O)CCC(=O)O)C(C)C)Cc1cccc(C(=O)Nc2sc3c(c2C(=O)Nc2ccc(CCc4ccc(C(=O)O)cc4)cc2)CCCC3)c1 ; Cl] |
| 56 | 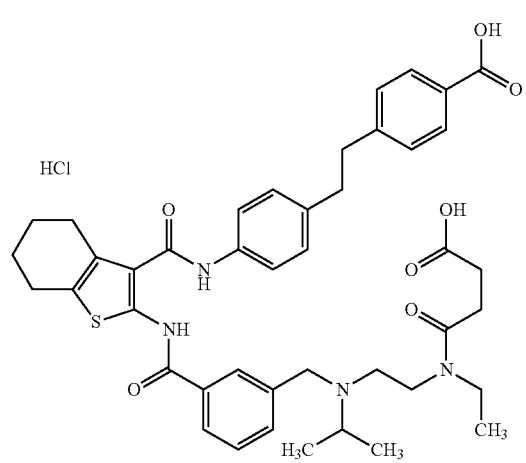 [SMILES: CCN(CCN(Cc1cccc(C(=O)Nc2sc3c(c2C(=O)Nc2ccc(CCc4ccc(C(=O)O)cc4)cc2)CCCC3)c1)C(C)C)C(=O)CCC(=O)O ; Cl] |
TABLE 59
| Ex | Str |
|---|---|
| 57 | 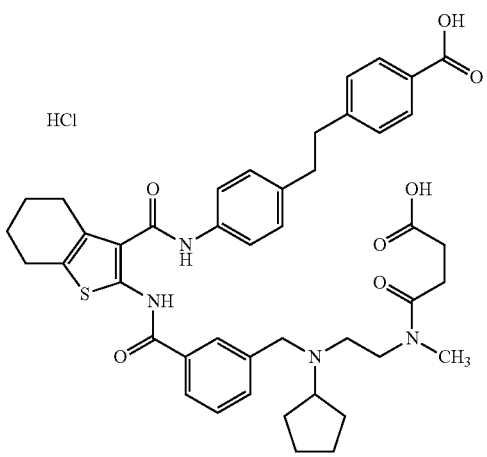 [SMILES: CN(CCN(Cc1cccc(C(=O)Nc2sc3c(c2C(=O)Nc2ccc(CCc4ccc(C(=O)O)cc4)cc2)CCCC3)c1)C1CCCC1)C(=O)CCC(=O)O ; Cl] |
| 58 | 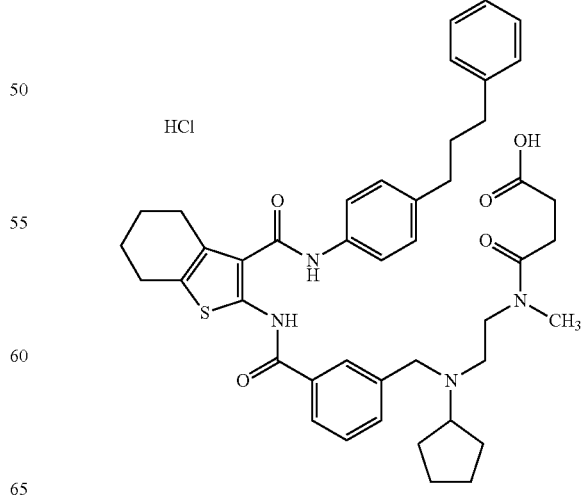 |

TABLE 59-continued
| Ex | Str |
| --- | --- |
| 59 | 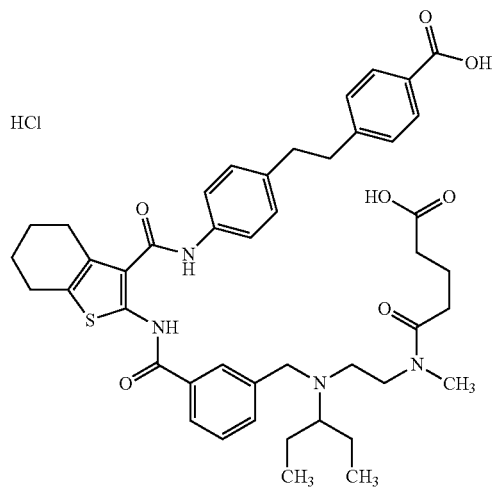 [SMILES: CCC(CC)N(CCN(C)C(=O)CCCC(=O)O)Cc1cccc(C(=O)Nc2sc3c(c2C(=O)Nc2ccc(CCc4ccc(C(=O)O)cc4)cc2)CCCC3)c1 ; Cl] |
| 60 | (structure shown below) |
| 61 | 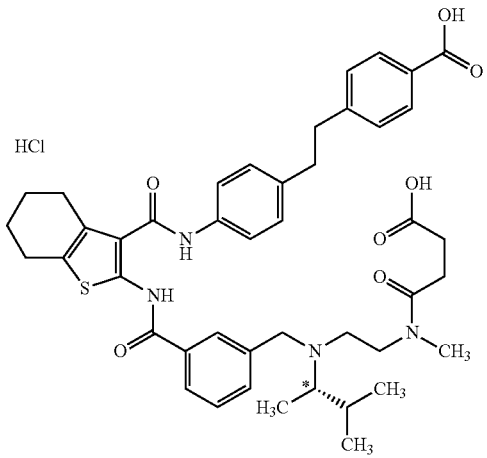 [SMILES: CC(C)[C@H](C)N(CCN(C)C(=O)CCC(=O)O)Cc1cccc(C(=O)Nc2sc3c(c2C(=O)Nc2ccc(CCc4ccc(C(=O)O)cc4)cc2)CCCC3)c1 ; Cl] |
| 62 | 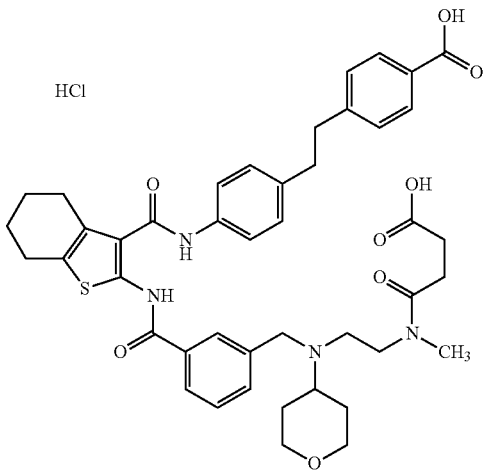 [SMILES: CN(CCN(Cc1cccc(C(=O)Nc2sc3c(c2C(=O)Nc2ccc(CCc4ccc(C(=O)O)cc4)cc2)CCCC3)c1)C1CCOCC1)C(=O)CCC(=O)O ; Cl] |

TABLE 60

| Ex | Str |
|---|---|
| 63 | (structure: HCl salt of tetrahydrobenzothiophene derivative with 4-carboxyphenethyl-phenylamide and N-methyl-(3-methyl)succinamide side chain) |
| 64 | (structure: HCl salt of tetrahydrobenzothiophene derivative with 4-carboxyphenethyl-phenylamide and 3,3-dimethylglutaramide side chain) |
| 65 | (structure: 2HCl salt of tetrahydrobenzothiophene derivative with 4-carboxyphenethyl-phenylamide and diethylaminoethyl-succinamide side chain) |

TABLE 60-continued
| Ex | Str |
|---|---|
| 66 | 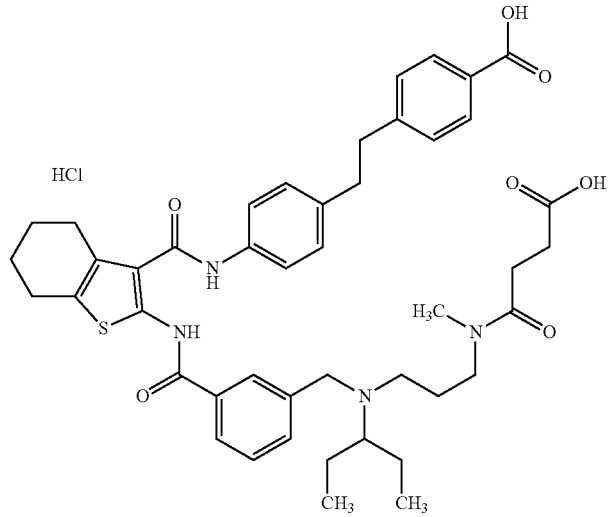 [SMILES: CCC(CC)N(CCCN(C)C(=O)CCC(=O)O)Cc1cccc(C(=O)Nc2sc3c(c2C(=O)Nc2ccc(CCc4ccc(C(=O)O)cc4)cc2)CCCC3)c1 ; Cl] |
| 67 | 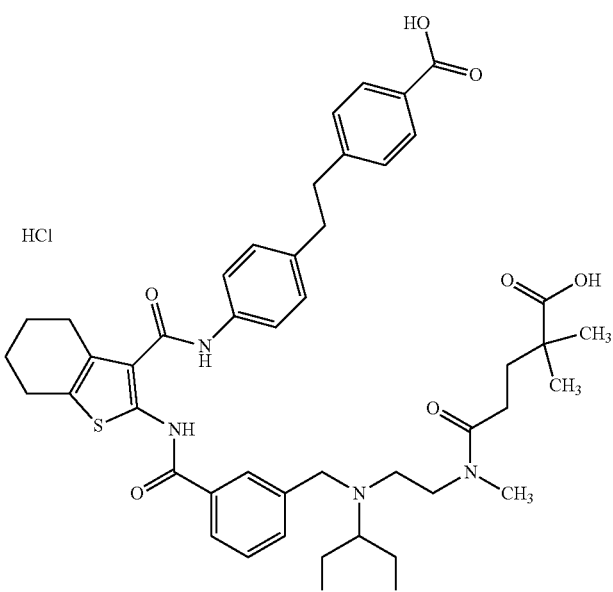 |
| 68 | 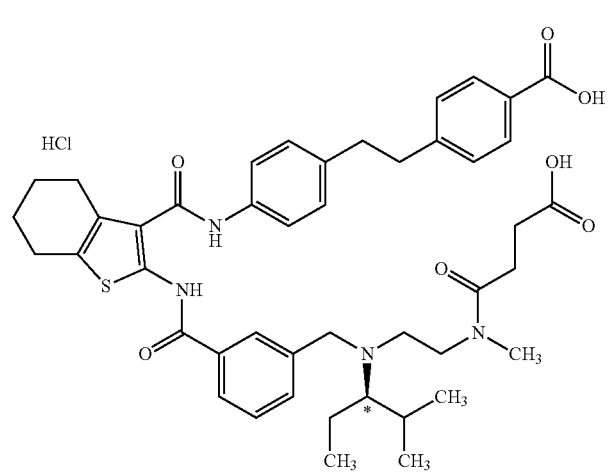 |

TABLE 61
| Ex | Str |
|---|---|
| 69 | 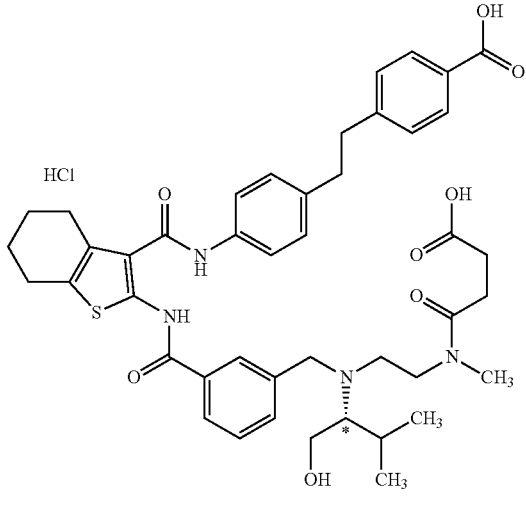 |
| 70 | 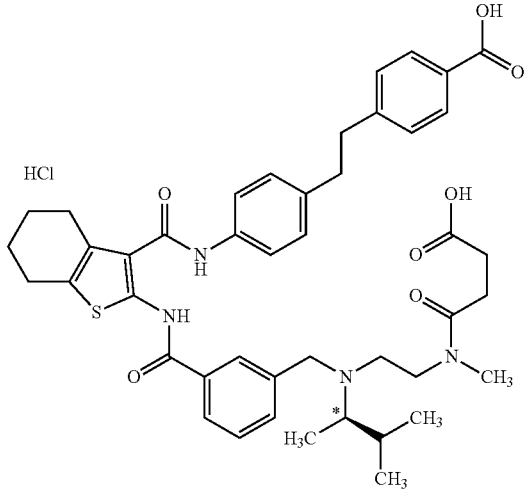 |
| 71 | 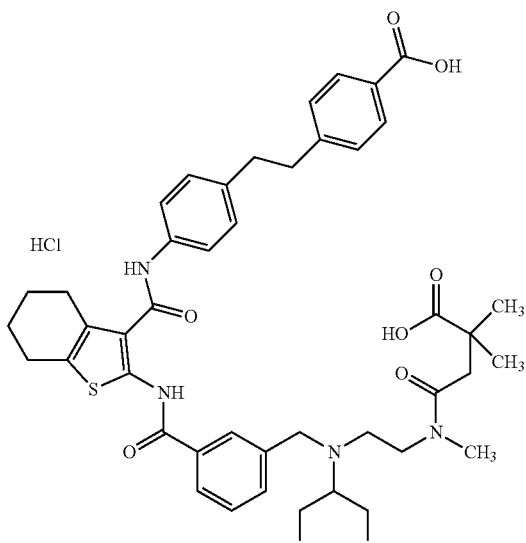 |
TABLE 61-continued
| Ex | Str |
|---|---|
| 72 | 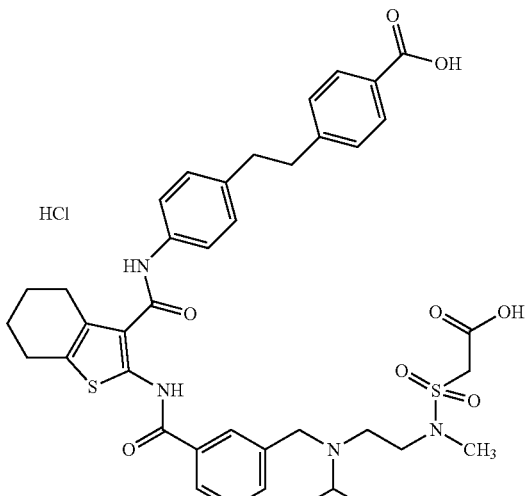 |
| 73 | 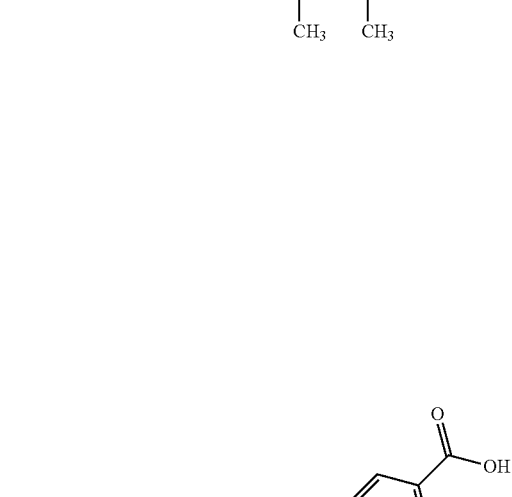 |

TABLE 62
| Ex | Str |
|---|---|
| 74 | 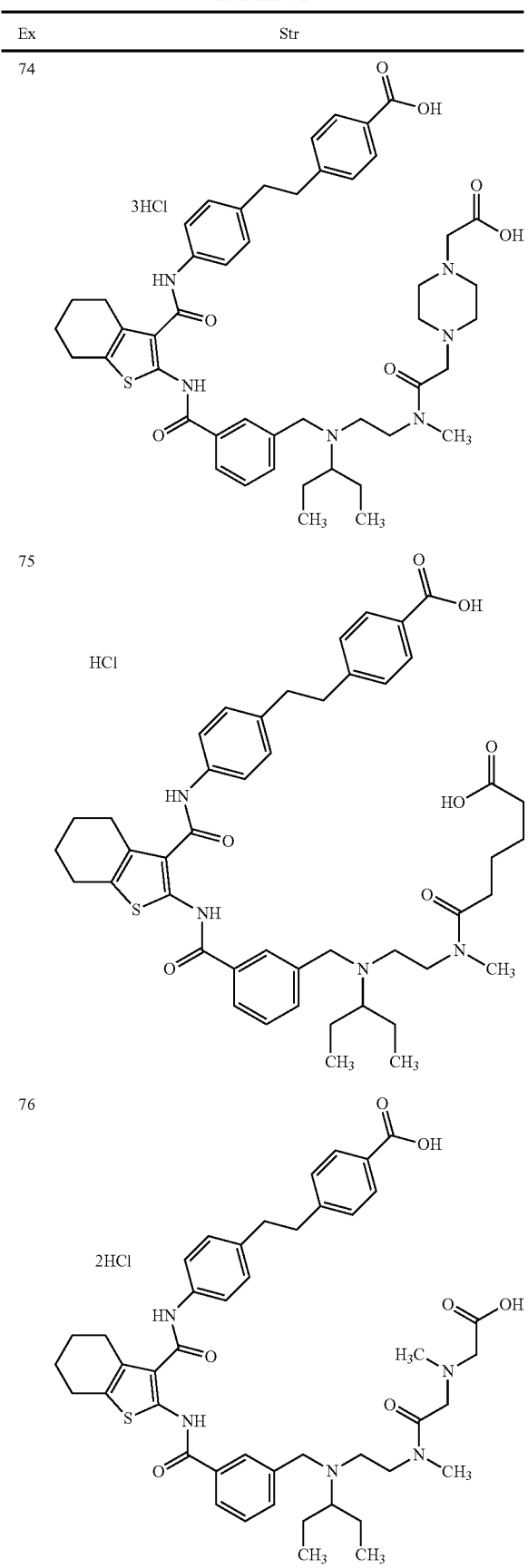 |
| 75 | |
| 76 | |
TABLE 62-continued
| Ex | Str |
|---|---|
| 77 | 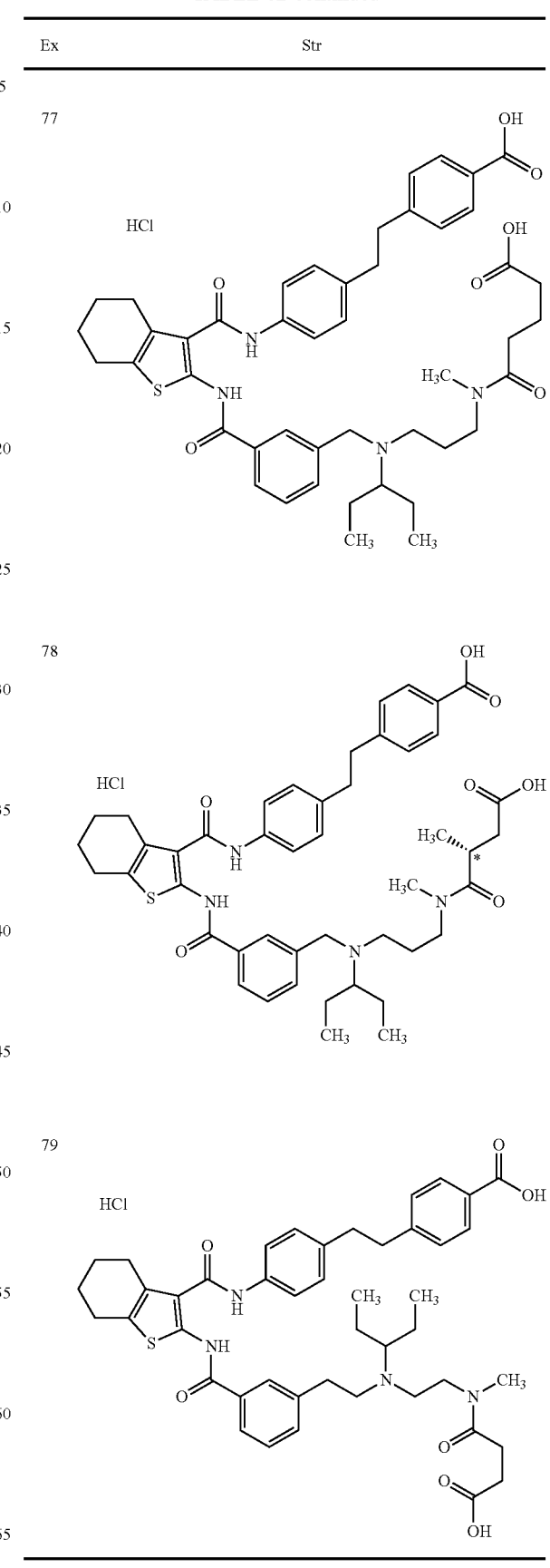 |
| 78 | |
| 79 | |

TABLE 63

| Ex | Str |
|---|---|
| 80 | (structure) |
| 81 | (structure) |
| 82 | (structure) |

TABLE 63-continued

| Ex | Str |
|---|---|
| 83 | (structure) |
| 84 | (structure) |
| 85 | (structure) |

TABLE 64
| Ex | Str |
|---|---|
| 86 | 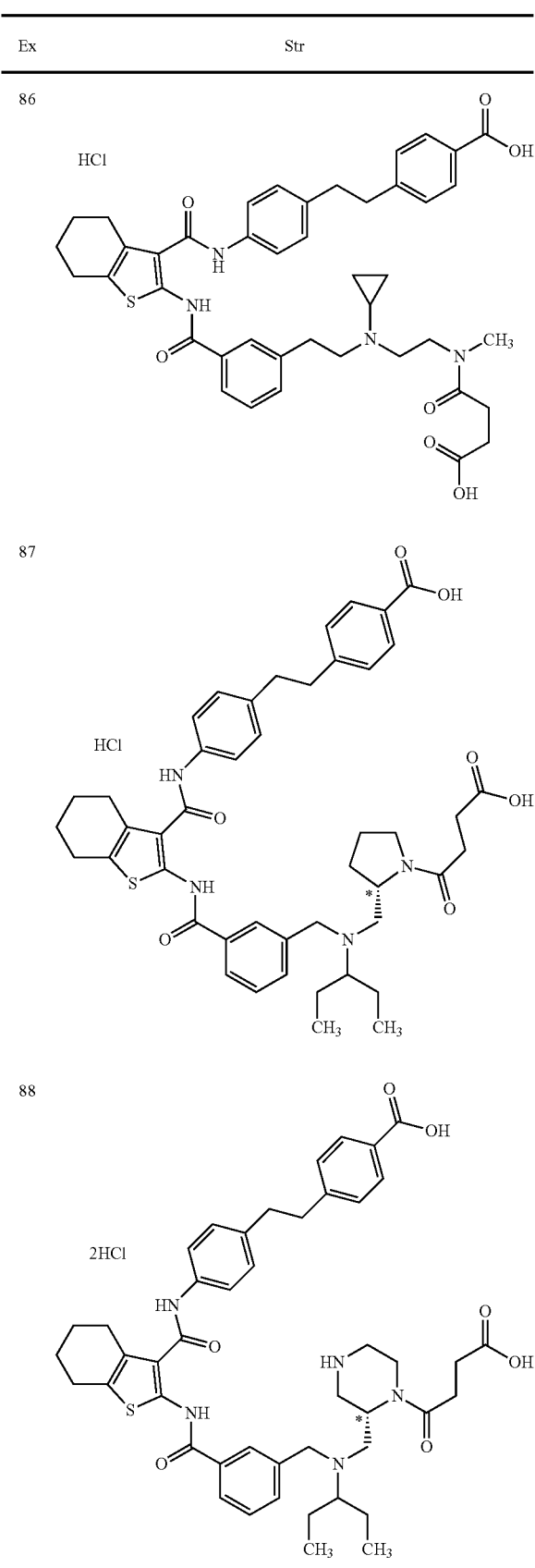 |
| 87 | |
| 88 | |
TABLE 64-continued
| Ex | Str |
|---|---|
| 89 | 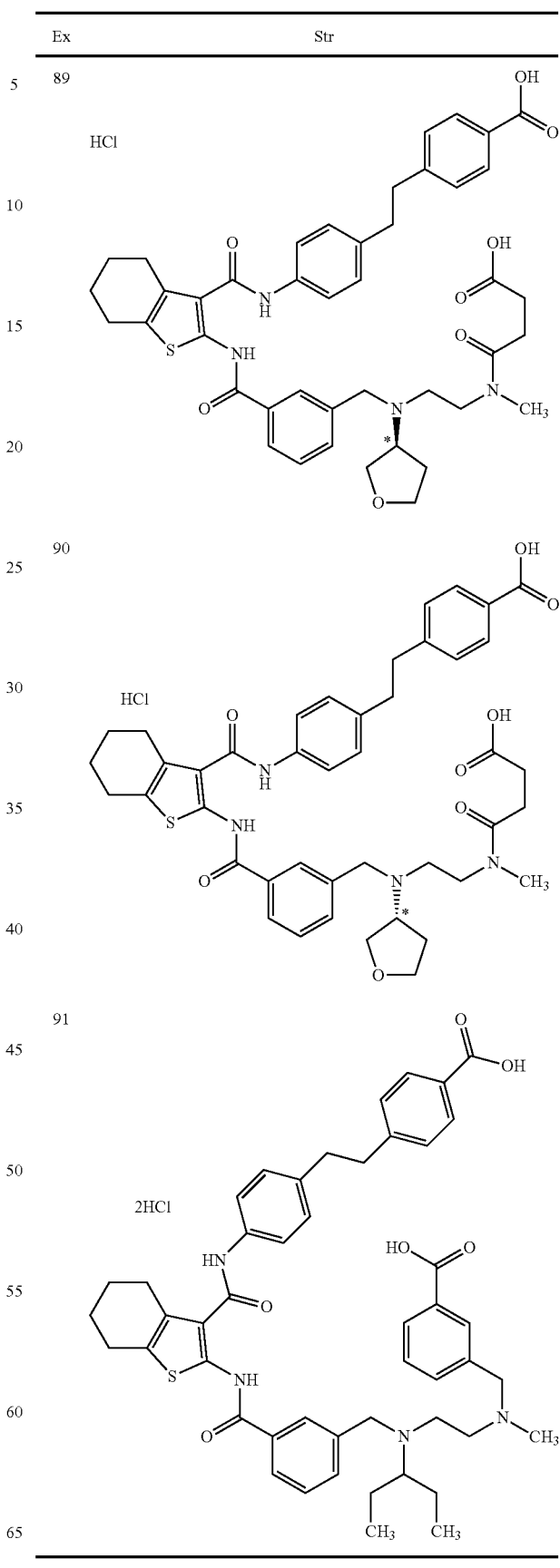 |
| 90 | |
| 91 | |

TABLE 65
| Ex | Str |
|---|---|
| 92 | 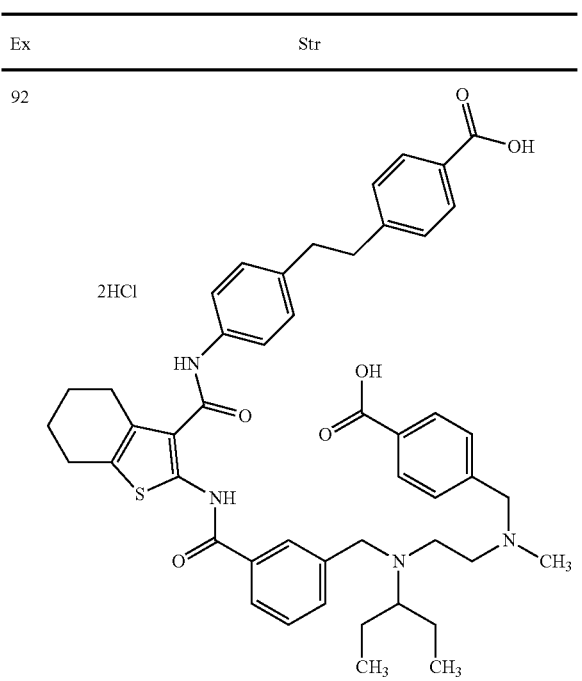 |
| 93 | |
TABLE 65-continued
| Ex | Str |
|---|---|
| 94 | 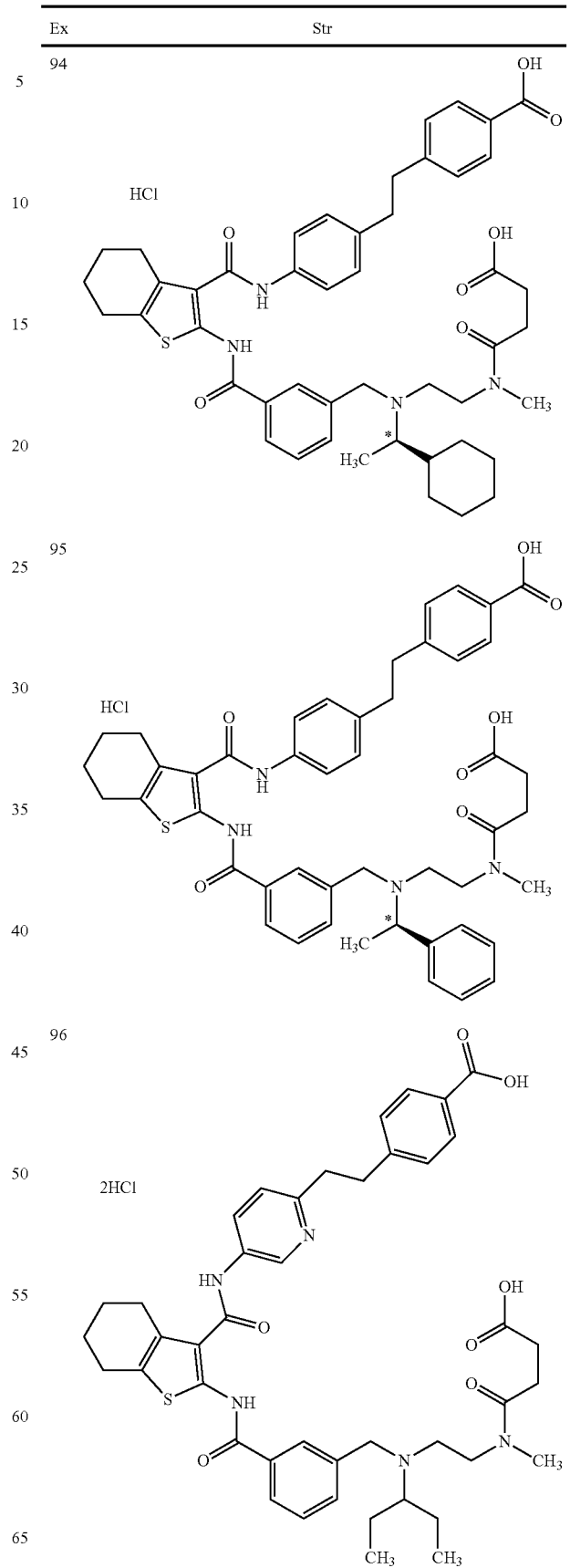 |
| 95 | |
| 96 | |

TABLE 65-continued
| Ex | Str |
|---|---|
| 97 | 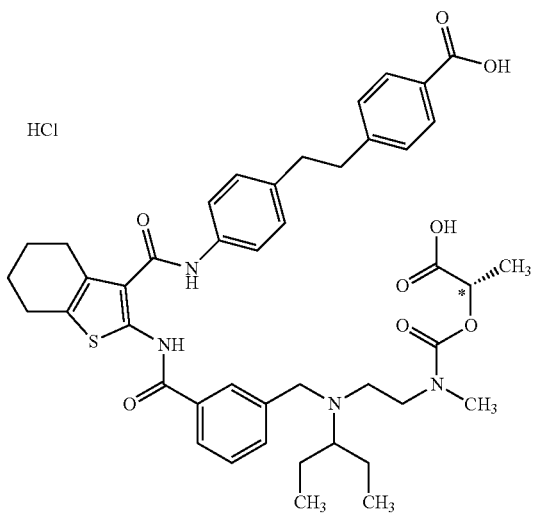 HCl |
TABLE 66
| Ex | Str |
|---|---|
| 98 | 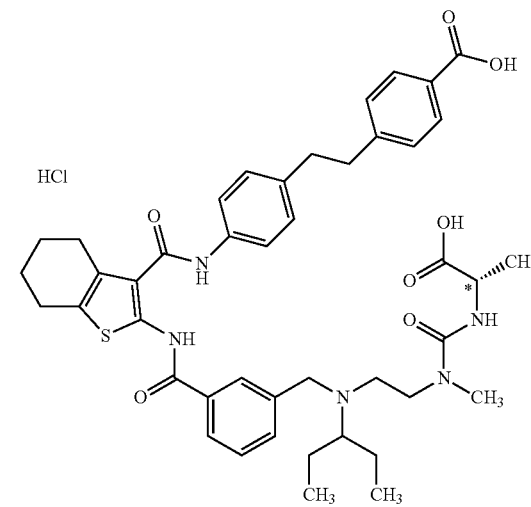 HCl |
TABLE 66-continued
| Ex | Str |
|---|---|
| 99 | 2HCl |
| 100 | |
| 101 | |

TABLE 66-continued
| Ex | Str |
|---|---|
| 102 | 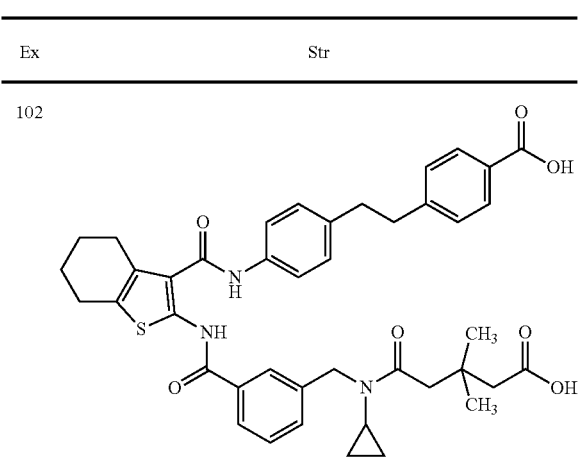 |
| 103 | 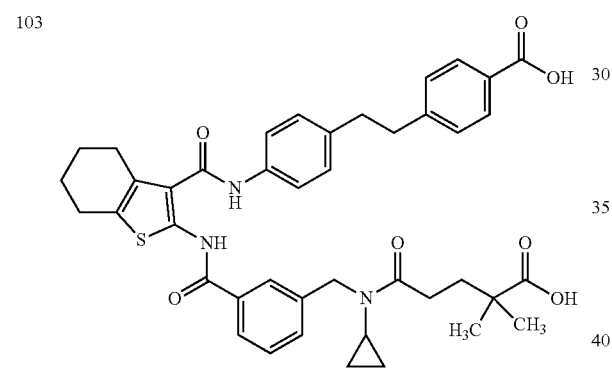 |
TABLE 67
| Ex | Str |
|---|---|
| 104 | 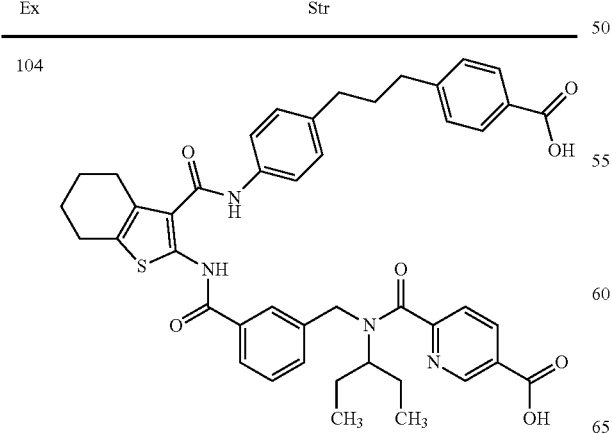 |
TABLE 67-continued
| Ex | Str |
|---|---|
| 105 | 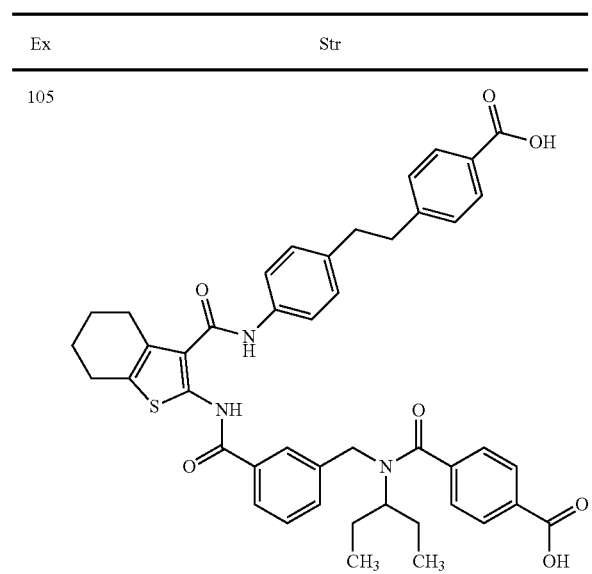 |
| 106 | 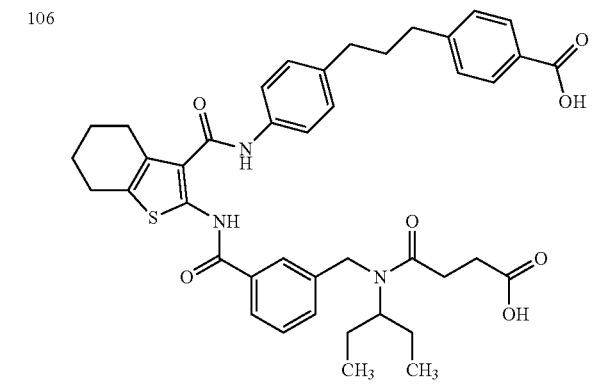 |
| 107 | 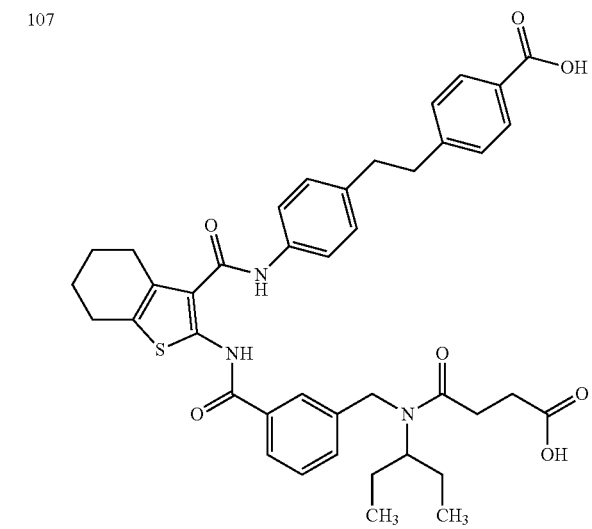 |

TABLE 67-continued

| Ex | Str |
|---|---|
| 108 | (chemical structure) |
| 109 | (chemical structure) |

TABLE 68

| Ex | Str |
|---|---|
| 110 | (chemical structure) |
| 111 | (chemical structure) |

TABLE 68-continued
| Ex | Str |
|---|---|
| 112 | 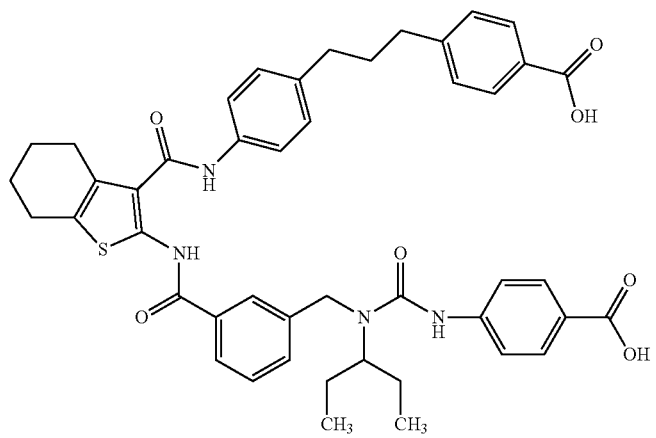 [SMILES: CCC(CC)N(Cc1cccc(C(=O)Nc2sc3c(c2C(=O)Nc2ccc(CCCc4ccc(C(=O)O)cc4)cc2)CCCC3)c1)C(=O)Nc1ccc(C(=O)O)cc1] |
| 113 | 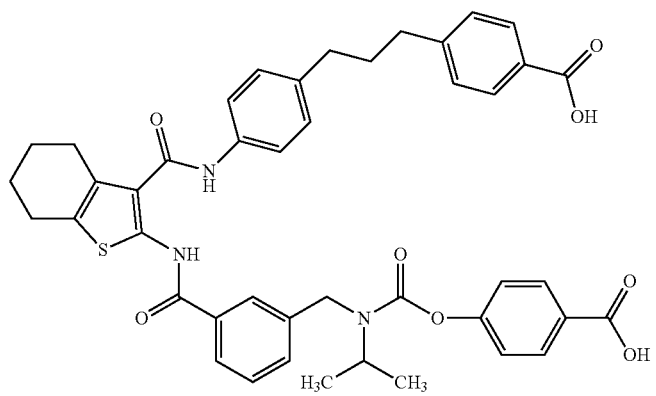 [SMILES: CC(C)N(Cc1cccc(C(=O)Nc2sc3c(c2C(=O)Nc2ccc(CCCc4ccc(C(=O)O)cc4)cc2)CCCC3)c1)C(=O)Oc1ccc(C(=O)O)cc1] |
| 114 | 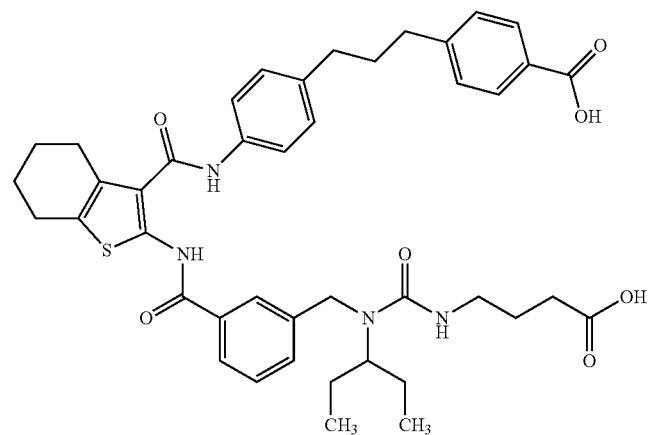 [SMILES: CCC(CC)N(Cc1cccc(C(=O)Nc2sc3c(c2C(=O)Nc2ccc(CCCc4ccc(C(=O)O)cc4)cc2)CCCC3)c1)C(=O)NCCCC(=O)O] |

TABLE 68-continued
| Ex | Str |
|---|---|
| 115 | 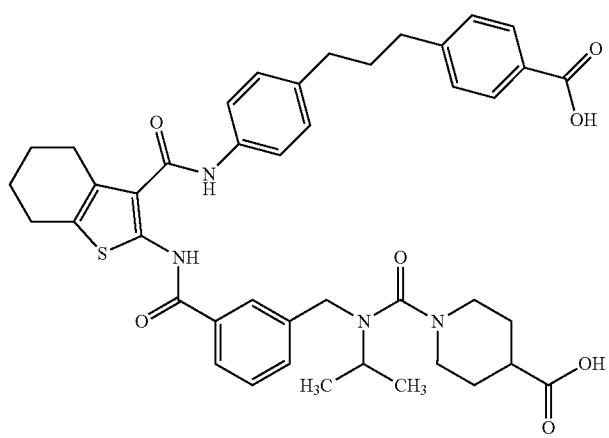 [SMILES: CC(C)N(Cc1cccc(C(=O)Nc2sc3c(c2C(=O)Nc2ccc(CCCc4ccc(C(=O)O)cc4)cc2)CCCC3)c1)C(=O)N1CCC(C(=O)O)CC1] |
| 116 | 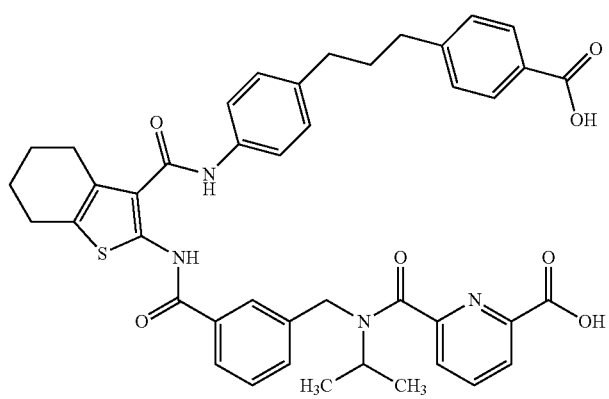 [SMILES: CC(C)N(Cc1cccc(C(=O)Nc2sc3c(c2C(=O)Nc2ccc(CCCc4ccc(C(=O)O)cc4)cc2)CCCC3)c1)C(=O)c1cccc(C(=O)O)n1] |
| 117 | 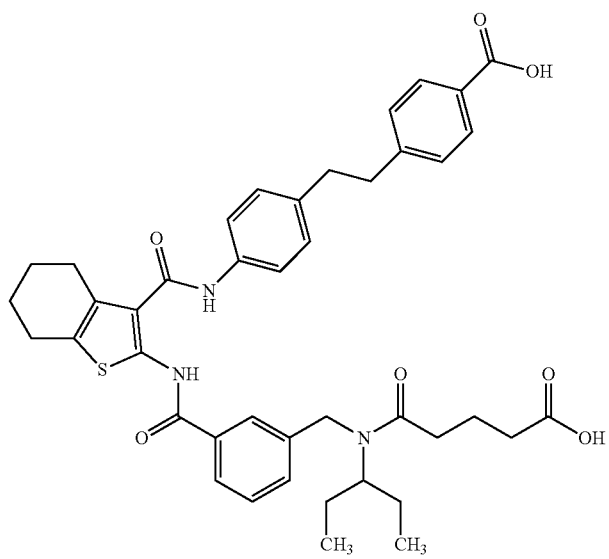 [SMILES: CCC(CC)N(Cc1cccc(C(=O)Nc2sc3c(c2C(=O)Nc2ccc(CCc4ccc(C(=O)O)cc4)cc2)CCCC3)c1)C(=O)CCCC(=O)O] |

TABLE 69
| Ex | Str |
|---|---|
| 118 | 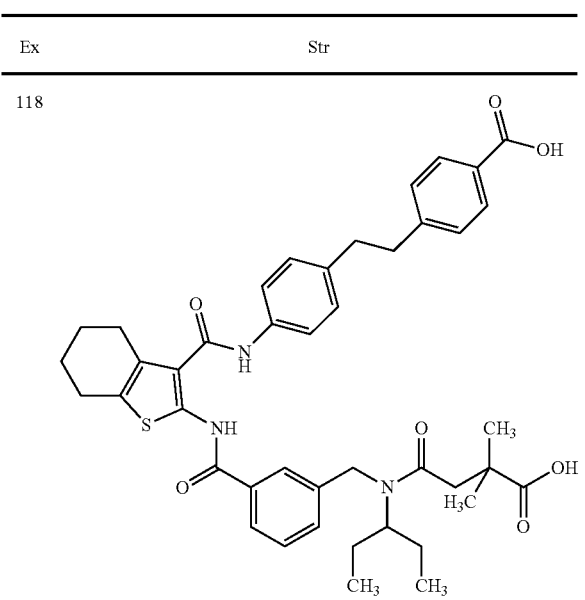 |
| 119 | 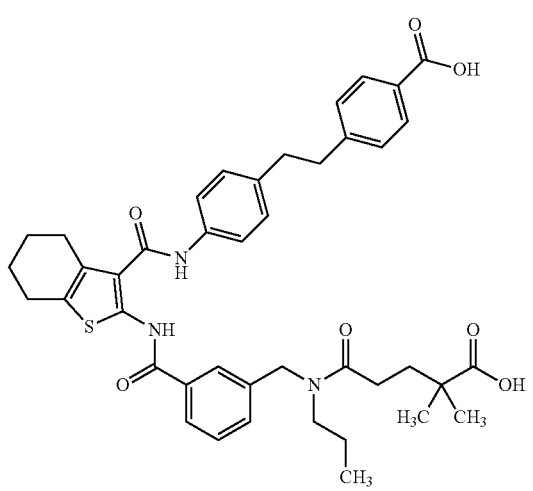 [SMILES: CCCN(Cc1cccc(C(=O)Nc2sc3c(c2C(=O)Nc2ccc(CCc4ccc(C(=O)O)cc4)cc2)CCCC3)c1)C(=O)CCC(C)(C)C(=O)O] |
| 120 | 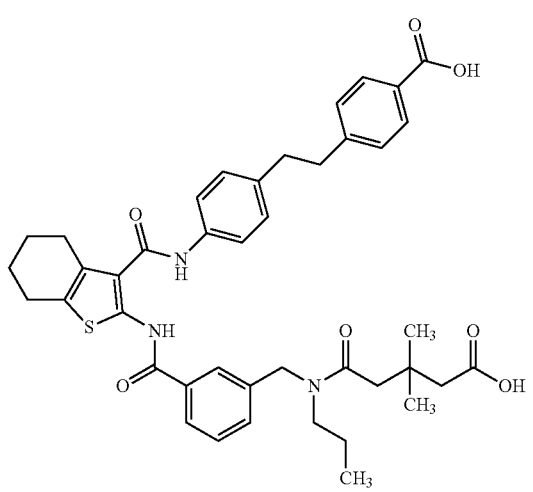 [SMILES: CCCN(Cc1cccc(C(=O)Nc2sc3c(c2C(=O)Nc2ccc(CCc4ccc(C(=O)O)cc4)cc2)CCCC3)c1)C(=O)CC(C)(C)CC(=O)O] |
TABLE 69-continued
| Ex | Str |
|---|---|
| 121 | 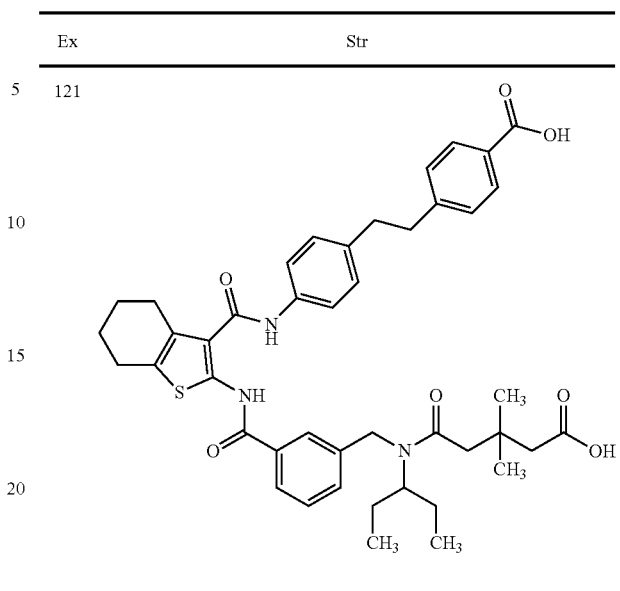 |
| 122 | 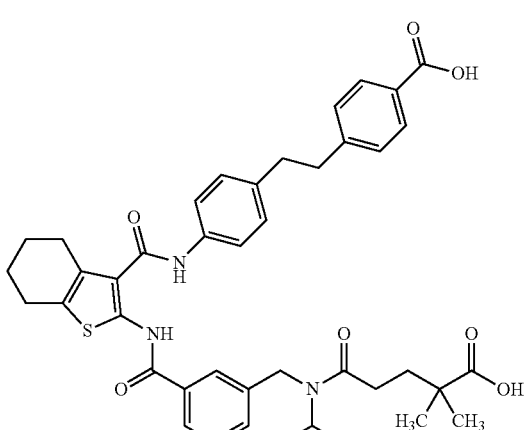 |
| 123 | 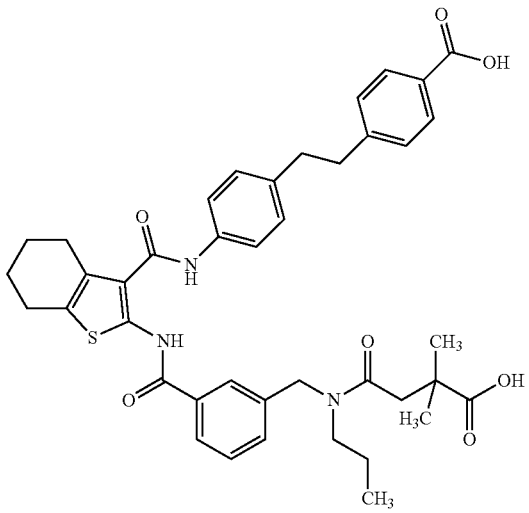 [SMILES: CCCN(Cc1cccc(C(=O)Nc2sc3c(c2C(=O)Nc2ccc(CCc4ccc(C(=O)O)cc4)cc2)CCCC3)c1)C(=O)CC(C)(C)C(=O)O] |

US 9,062,032 B2
TABLE 70
| Ex | Str |
|---|---|
| 124 | 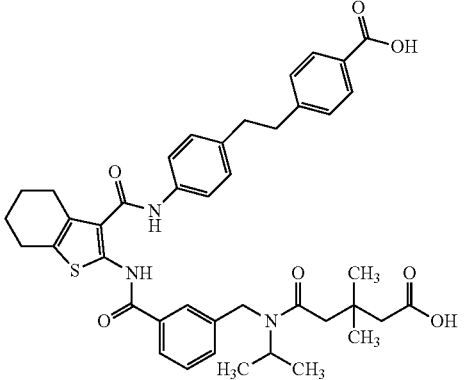 [SMILES: CC(C)N(Cc1cccc(C(=O)Nc2sc3c(c2C(=O)Nc2ccc(CCc4ccc(C(=O)O)cc4)cc2)CCCC3)c1)C(=O)CC(C)(C)CC(=O)O] |
| 125 | 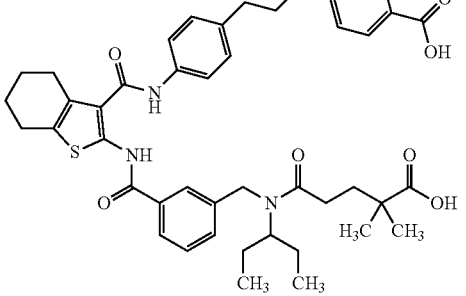 |
| 126 | 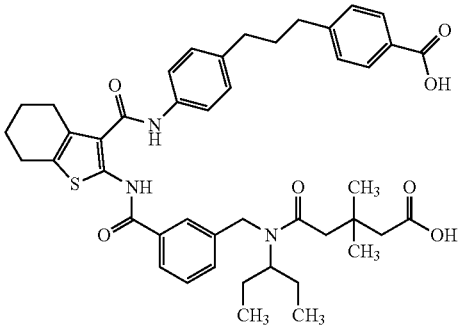 [SMILES: CCC(CC)N(Cc1cccc(C(=O)Nc2sc3c(c2C(=O)Nc2ccc(CCCc4ccc(C(=O)O)cc4)cc2)CCCC3)c1)C(=O)CC(C)(C)CC(=O)O] |
TABLE 70-continued
| Ex | Str |
|---|---|
| 127 | 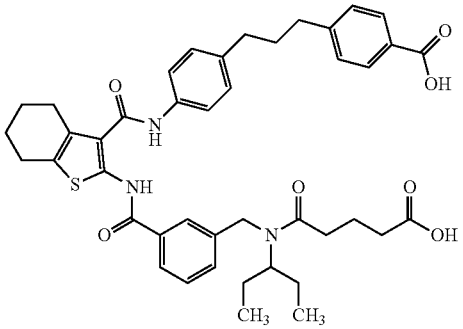 [SMILES: CCC(CC)N(Cc1cccc(C(=O)Nc2sc3c(c2C(=O)Nc2ccc(CCCc4ccc(C(=O)O)cc4)cc2)CCCC3)c1)C(=O)CCCC(=O)O] |
| 128 | 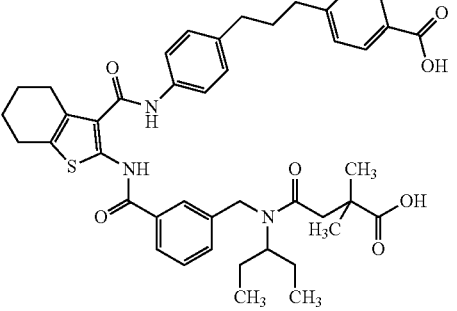 |
| 129 | 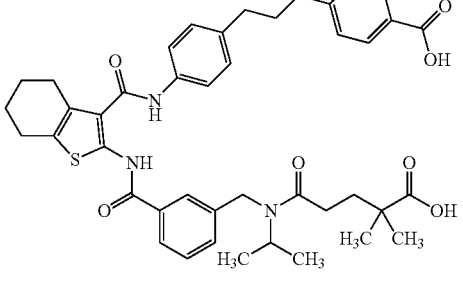 |
| 130 | 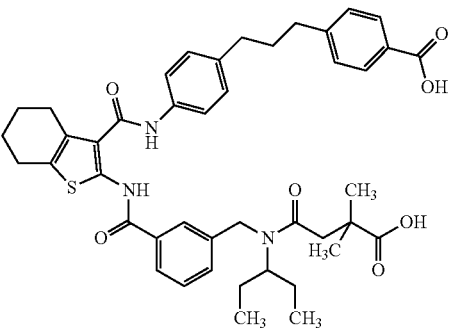 [SMILES: CCC(CC)N(Cc1cccc(C(=O)Nc2sc3c(c2C(=O)Nc2ccc(CCCc4ccc(C(=O)O)cc4)cc2)CCCC3)c1)C(=O)CC(C)(C)C(=O)O] |

TABLE 71
| Ex | Str |
|---|---|
| 131 | 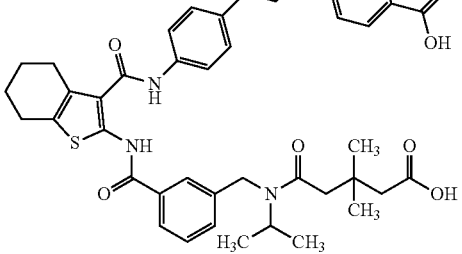 |
| 132 | 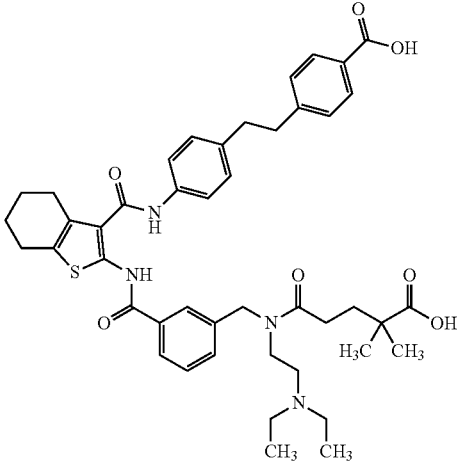 [SMILES: CCN(CC)CCN(Cc1cccc(C(=O)Nc2sc3c(c2C(=O)Nc2ccc(CCc4ccc(C(=O)O)cc4)cc2)CCCC3)c1)C(=O)CCC(C)(C)C(=O)O] |
| 133 | 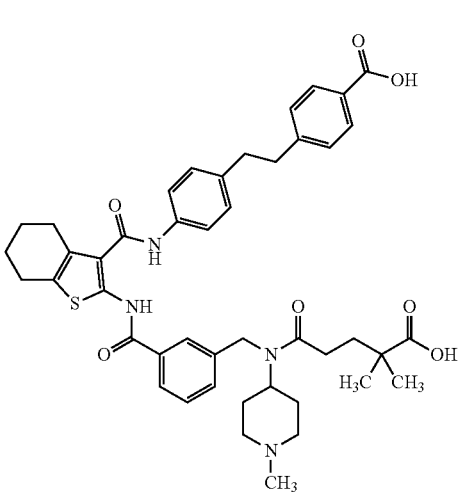 [SMILES: CN1CCC(N(Cc2cccc(C(=O)Nc3sc4c(c3C(=O)Nc3ccc(CCc5ccc(C(=O)O)cc5)cc3)CCCC4)c2)C(=O)CCC(C)(C)C(=O)O)CC1] |
TABLE 71-continued
| Ex | Str |
|---|---|
| 134 | 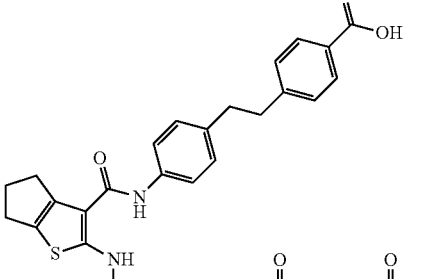 |
| 135 | 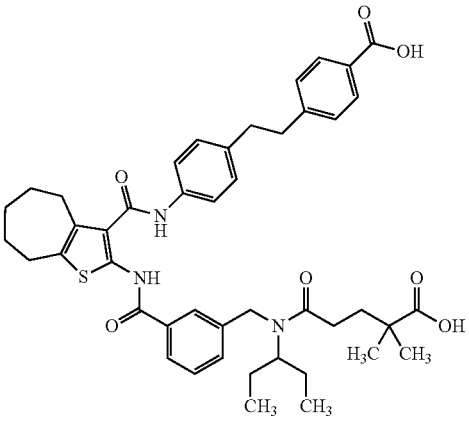 [SMILES: CCC(CC)N(Cc1cccc(C(=O)Nc2sc3c(c2C(=O)Nc2ccc(CCc4ccc(C(=O)O)cc4)cc2)CCCCC3)c1)C(=O)CCC(C)(C)C(=O)O] |
| 136 | 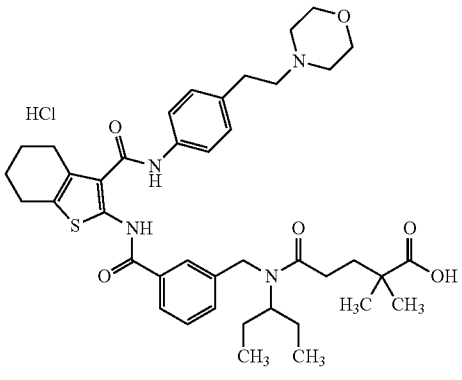 [SMILES: CCC(CC)N(Cc1cccc(C(=O)Nc2sc3c(c2C(=O)Nc2ccc(CCN4CCOCC4)cc2)CCCC3)c1)C(=O)CCC(C)(C)C(=O)O ; Cl] |

TABLE 72
| Ex | Str |
|---|---|
| 137 | 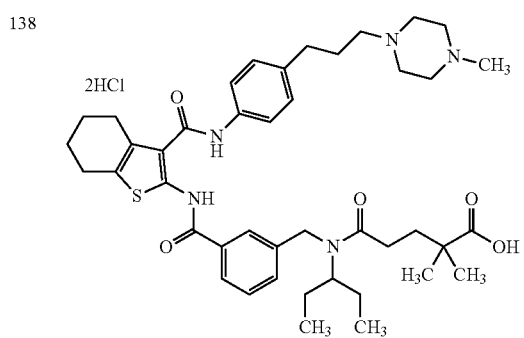 |
| 138 | |
| 139 | 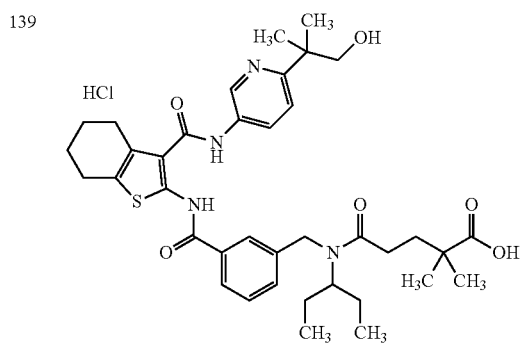 |
TABLE 72-continued
| Ex | Str |
|---|---|
| 140 | |
| 141 | |
| 142 | |

TABLE 73
| Ex | Str |
|---|---|
| 143 | 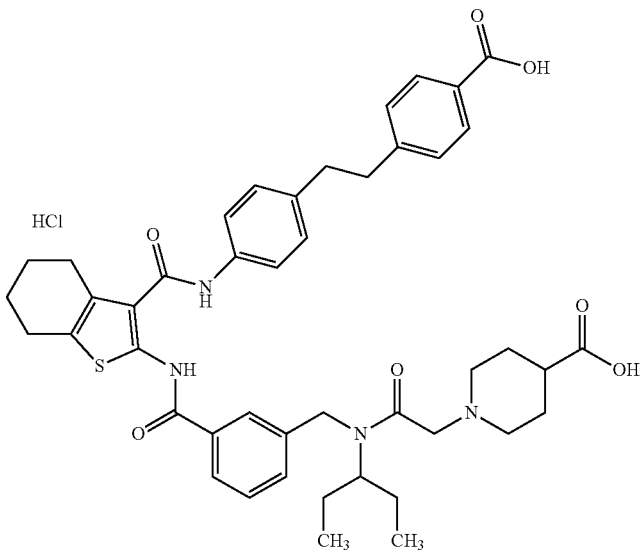 [SMILES: CCC(CC)N(Cc1cccc(C(=O)Nc2sc3c(c2C(=O)Nc2ccc(CCc4ccc(C(=O)O)cc4)cc2)CCCC3)c1)C(=O)CN1CCC(C(=O)O)CC1 ; Cl] |
| 144 | 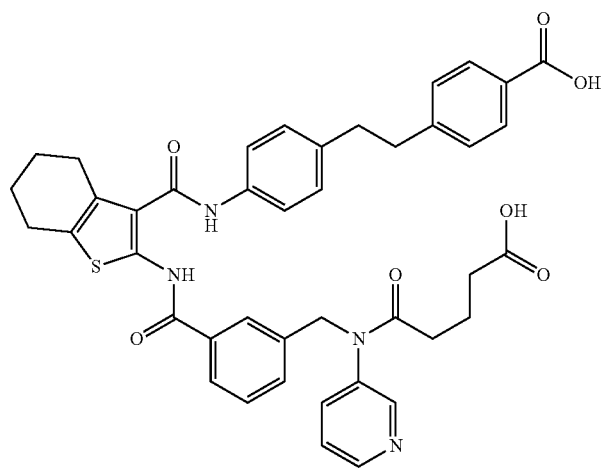 [SMILES: O=C(O)CCCC(=O)N(Cc1cccc(C(=O)Nc2sc3c(c2C(=O)Nc2ccc(CCc4ccc(C(=O)O)cc4)cc2)CCCC3)c1)c1cccnc1] |
| 145 | 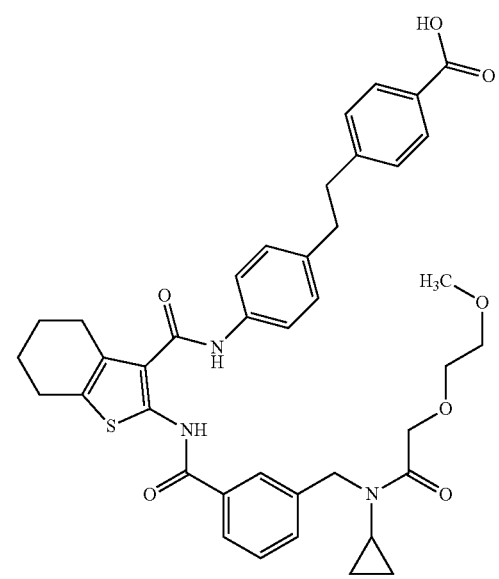 [SMILES: COCCOCC(=O)N(Cc1cccc(C(=O)Nc2sc3c(c2C(=O)Nc2ccc(CCc4ccc(C(=O)O)cc4)cc2)CCCC3)c1)C1CC1] |

TABLE 73-continued
| Ex | Str |
|---|---|
| 146 | 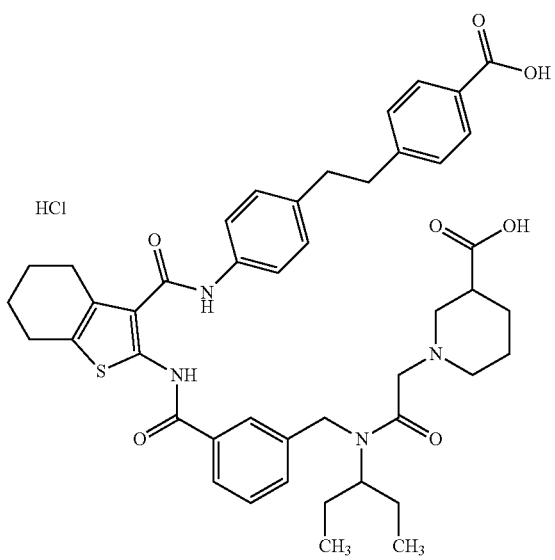 [SMILES: CCC(CC)N(Cc1cccc(C(=O)Nc2sc3c(c2C(=O)Nc2ccc(CCc4ccc(C(=O)O)cc4)cc2)CCCC3)c1)C(=O)CN1CCCC(C(=O)O)C1 ; Cl] |
| 147 | 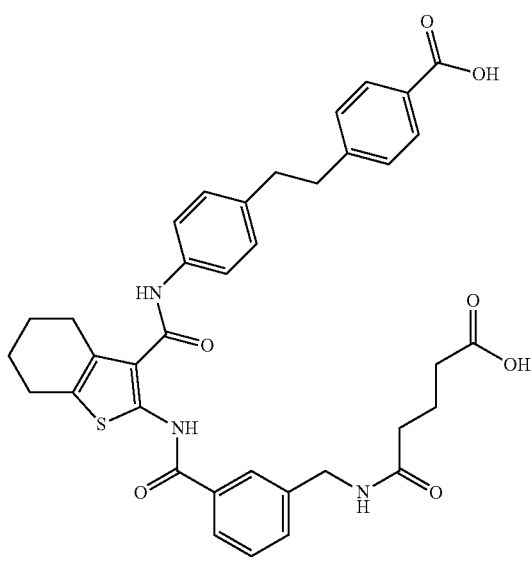 [SMILES: O=C(O)CCCC(=O)NCc1cccc(C(=O)Nc2sc3c(c2C(=O)Nc2ccc(CCc4ccc(C(=O)O)cc4)cc2)CCCC3)c1] |
| 148 | 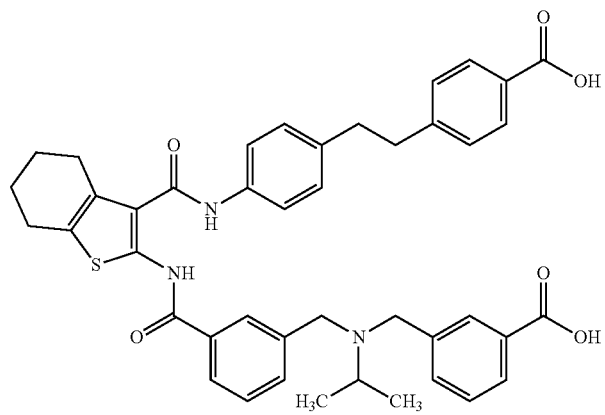 [SMILES: CC(C)N(Cc1cccc(C(=O)O)c1)Cc1cccc(C(=O)Nc2sc3c(c2C(=O)Nc2ccc(CCc4ccc(C(=O)O)cc4)cc2)CCCC3)c1] |

TABLE 74

| Ex | Str |
|---|---|
| 149 | |
| 150 | |
| 151 | HCl |

TABLE 74-continued

| Ex | Str |
|---|---|
| 152 | HCl salt of chemical structure |
| 153 | HCl salt of chemical structure |
| 154 | 2HCl salt of chemical structure |

TABLE 75
| Ex | Str |
|---|---|
| 155 | 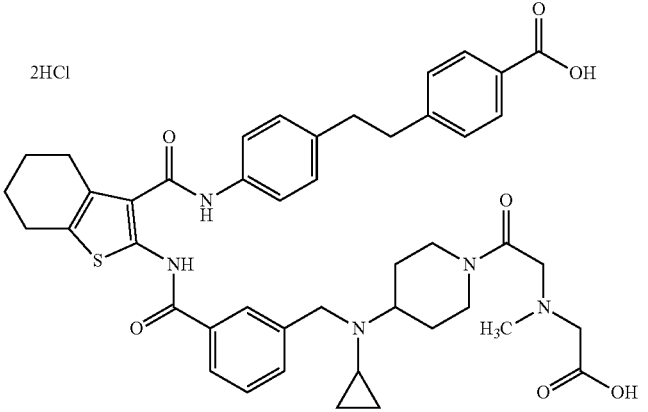 [SMILES: CN(CC(=O)O)CC(=O)N1CCC(N(Cc2cccc(C(=O)Nc3sc4c(c3C(=O)Nc3ccc(CCc5ccc(C(=O)O)cc5)cc3)CCCC4)c2)C2CC2)CC1] |
| 156 | 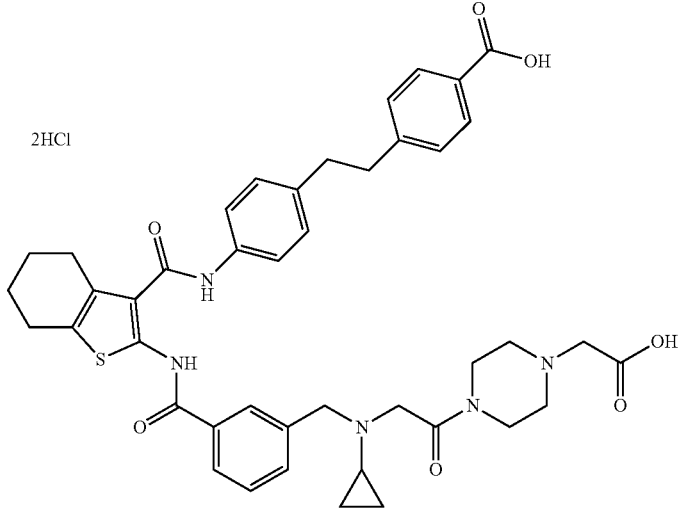 [SMILES: O=C(O)CN1CCN(C(=O)CN(Cc2cccc(C(=O)Nc3sc4c(c3C(=O)Nc3ccc(CCc5ccc(C(=O)O)cc5)cc3)CCCC4)c2)C2CC2)CC1 ; "2HCl"] |
| 157 | 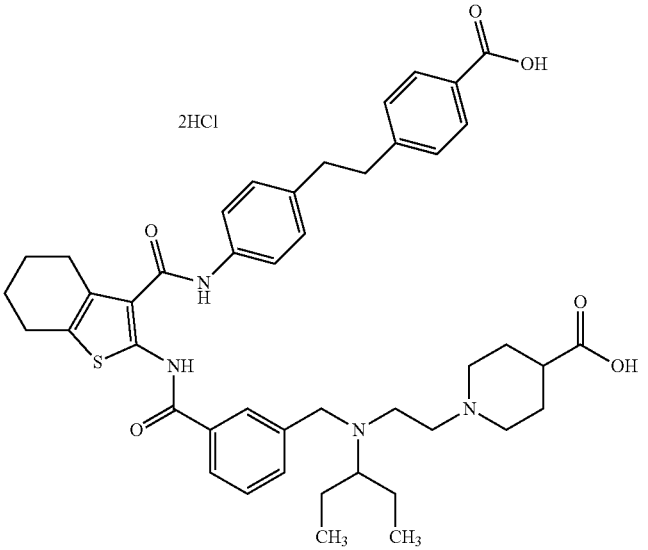 [SMILES: CCC(CC)N(CCN1CCC(C(=O)O)CC1)Cc1cccc(C(=O)Nc2sc3c(c2C(=O)Nc2ccc(CCc4ccc(C(=O)O)cc4)cc2)CCCC3)c1 ; "2HCl"] |

TABLE 75-continued
| Ex | Str |
|---|---|
| 158 | 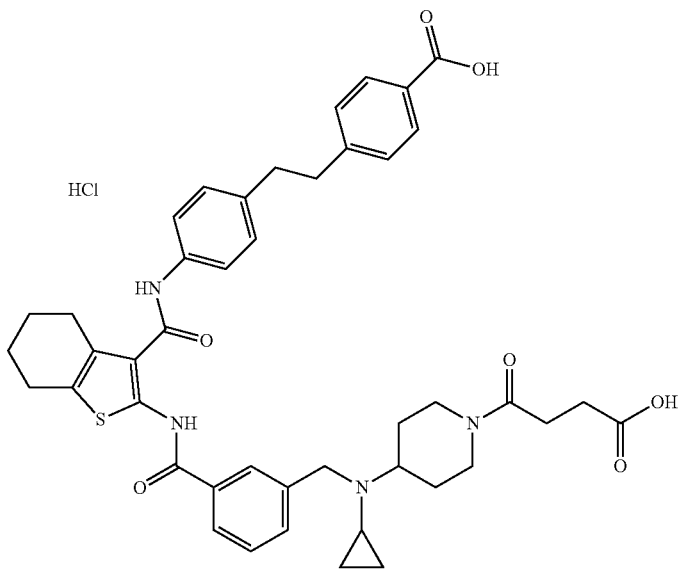 [SMILES: O=C(O)CCC(=O)N1CCC(N(Cc2cccc(C(=O)Nc3sc4c(c3C(=O)Nc3ccc(CCc5ccc(C(=O)O)cc5)cc3)CCCC4)c2)C2CC2)CC1 ; Cl] |
| 159 | 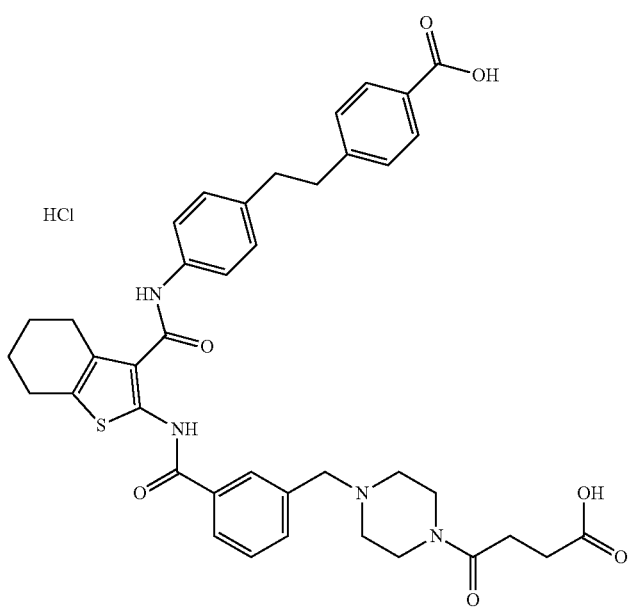 [SMILES: O=C(O)CCC(=O)N1CCN(Cc2cccc(C(=O)Nc3sc4c(c3C(=O)Nc3ccc(CCc5ccc(C(=O)O)cc5)cc3)CCCC4)c2)CC1 ; Cl] |
| 160 | 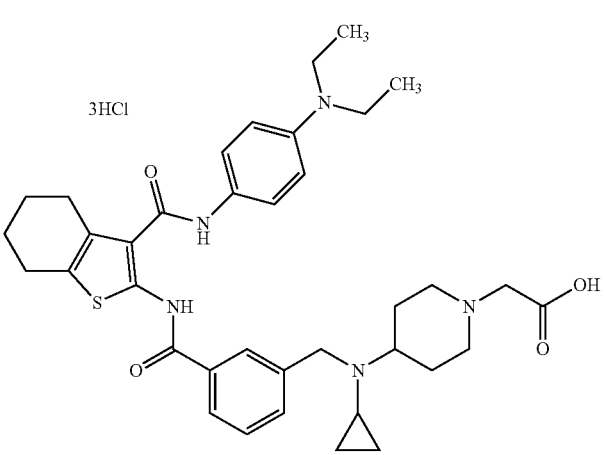 [SMILES: CCN(CC)c1ccc(NC(=O)c2c(NC(=O)c3cccc(CN(C4CC4)C4CCN(CC(=O)O)CC4)c3)sc3c2CCCC3)cc1 ; "3HCl"] |

TABLE 76
| Ex | Str |
|---|---|
| 161 | 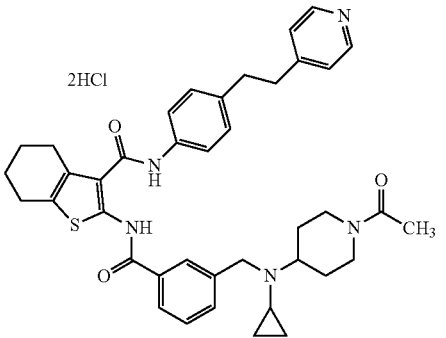 [SMILES: CC(=O)N1CCC(N(Cc2cccc(C(=O)Nc3sc4c(c3C(=O)Nc3ccc(CCc5ccncc5)cc3)CCCC4)c2)C2CC2)CC1 ; "2HCl"] |
| 162 | 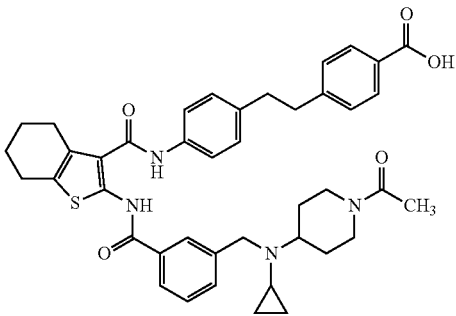 [SMILES: CC(=O)N1CCC(N(Cc2cccc(C(=O)Nc3sc4c(c3C(=O)Nc3ccc(CCc5ccc(C(=O)O)cc5)cc3)CCCC4)c2)C2CC2)CC1] |
| 163 | 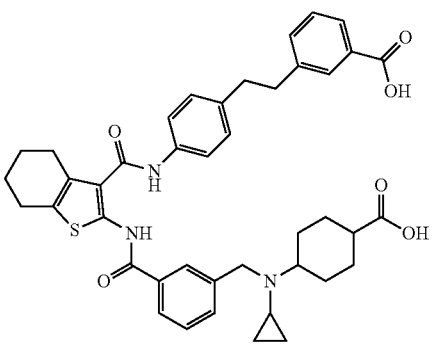 [SMILES: O=C(O)c1cccc(CCc2ccc(NC(=O)c3c(NC(=O)c4cccc(CN(C5CCC(C(=O)O)CC5)C5CC5)c4)sc4c3CCCC4)cc2)c1] |
| 164 | 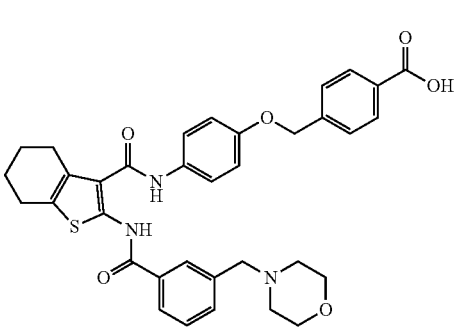 |
TABLE 76-continued
| Ex | Str |
|---|---|
| 165 | 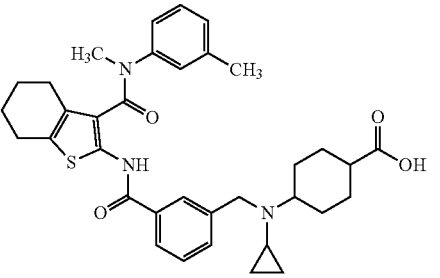 |
| 166 | 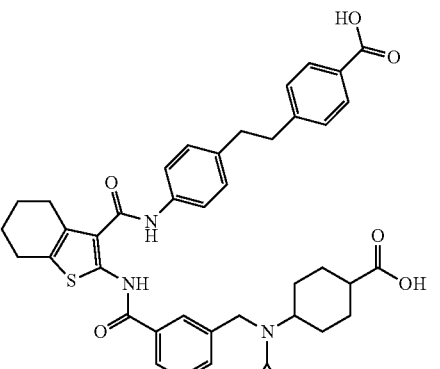 |
| 167 | 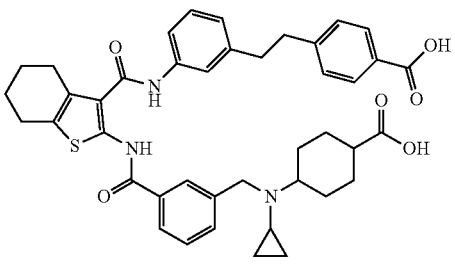 [SMILES: O=C(O)c1ccc(CCc2cccc(NC(=O)c3c(NC(=O)c4cccc(CN(C5CCC(C(=O)O)CC5)C5CC5)c4)sc4c3CCCC4)c2)cc1] |
| 168 | 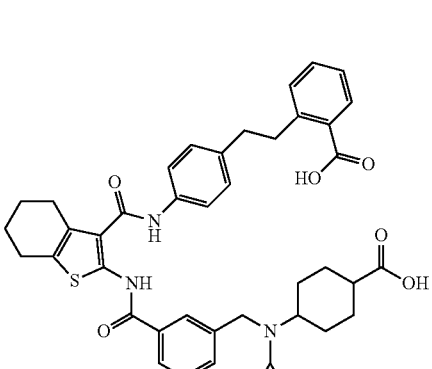 |

TABLE 77

| Ex | Str |
|---|---|
| 169 | (structure shown; HCl salt) |
| 170 | (structure shown) |
| 171 | (structure shown; 2HCl salt) |

TABLE 77-continued
| Ex | Str |
|---|---|
| 172 | 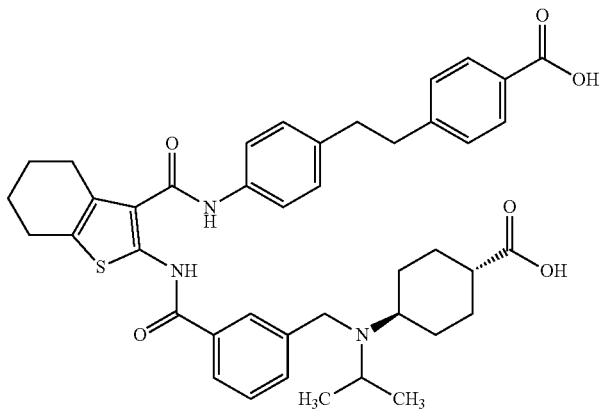 [SMILES: CC(C)N(Cc1cccc(C(=O)Nc2sc3c(c2C(=O)Nc2ccc(CCc4ccc(C(=O)O)cc4)cc2)CCCC3)c1)[C@H]1CC[C@H](C(=O)O)CC1] |
| 173 | 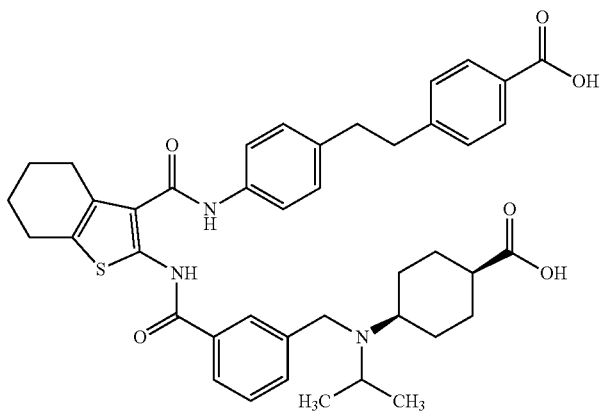 [SMILES: CC(C)N(Cc1cccc(C(=O)Nc2sc3c(c2C(=O)Nc2ccc(CCc4ccc(C(=O)O)cc4)cc2)CCCC3)c1)[C@H]1CC[C@@H](C(=O)O)CC1] |
| 174 | 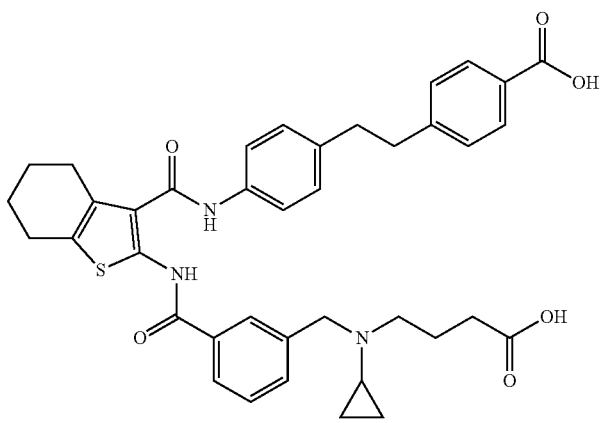 [SMILES: O=C(O)CCCN(Cc1cccc(C(=O)Nc2sc3c(c2C(=O)Nc2ccc(CCc4ccc(C(=O)O)cc4)cc2)CCCC3)c1)C1CC1] |

TABLE 77-continued

| Ex | Str |
|---|---|
| 175 | (structure) |
| 176 | (structure) |

TABLE 78

| Ex | Str |
|---|---|
| 177 | (structure) |

TABLE 78-continued

| Ex | Str |
|---|---|
| 178 | (structure) |

TABLE 78-continued
| Ex | Str |
|---|---|
| 179 | 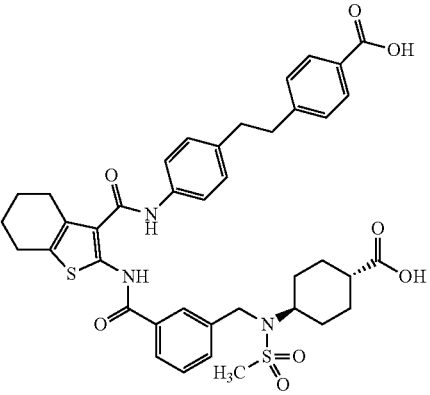 [SMILES: CS(=O)(=O)N(Cc1cccc(C(=O)Nc2sc3c(c2C(=O)Nc2ccc(CCc4ccc(C(=O)O)cc4)cc2)CCCC3)c1)[C@H]1CC[C@H](C(=O)O)CC1] |
| 180 | |
| 181 | |
| 182 | |
TABLE 79
| Ex | Str |
|---|---|
| 183 | 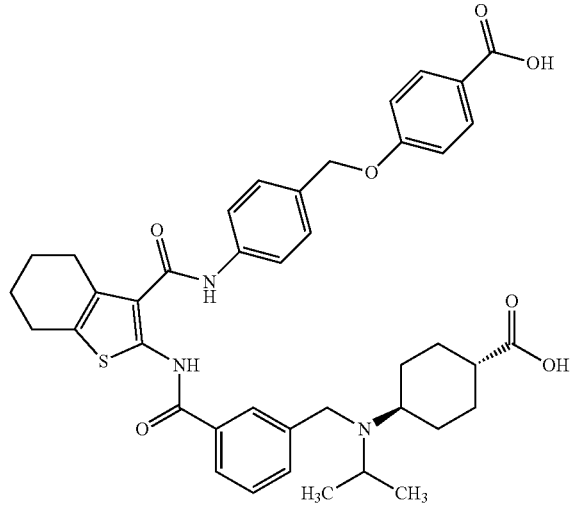 [SMILES: CC(C)N(Cc1cccc(C(=O)Nc2sc3c(c2C(=O)Nc2ccc(COc4ccc(C(=O)O)cc4)cc2)CCCC3)c1)[C@H]1CC[C@H](C(=O)O)CC1] |

TABLE 79-continued

| Ex | Str |
|---|---|
| 184 | |
| 185 | |
| 186 | |

TABLE 79-continued

| Ex | Str |
|---|---|
| 187 | (structure) |
| 188 | (structure) |

TABLE 80

| Ex | Str |
|---|---|
| 189 | (structure) |
| 190 | (structure) |

TABLE 80-continued
| Ex | Str |
|---|---|
| 191 | 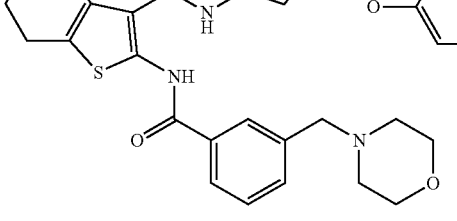 |
| 192 | |
| 193 | |
| 194 | |
TABLE 80-continued
| Ex | Str |
|---|---|
| 195 | 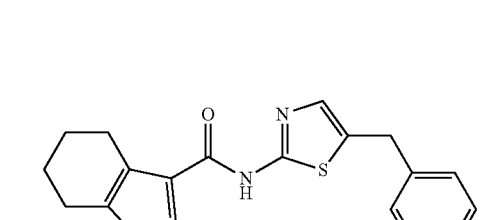 |
| 196 | |
TABLE 81
| Ex | Str |
|---|---|
| 197 | |

TABLE 81-continued
| Ex | Str |
|---|---|
| 198 | 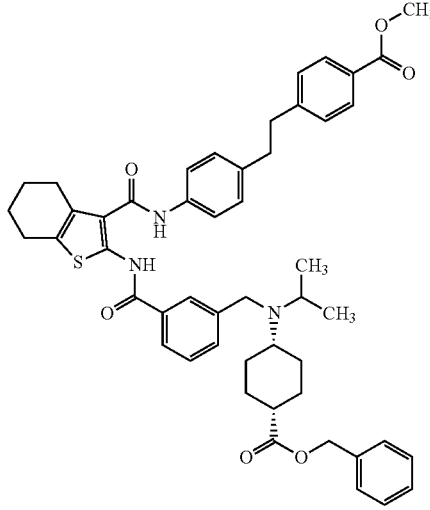 |
| 199 | 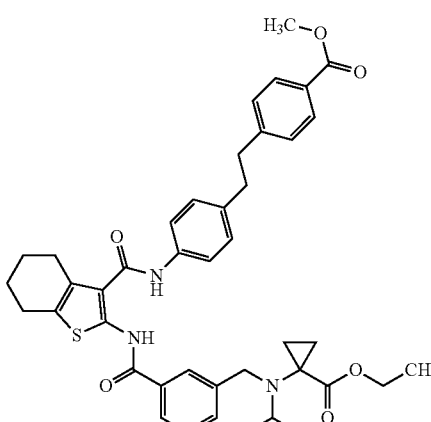 |
| 200 | 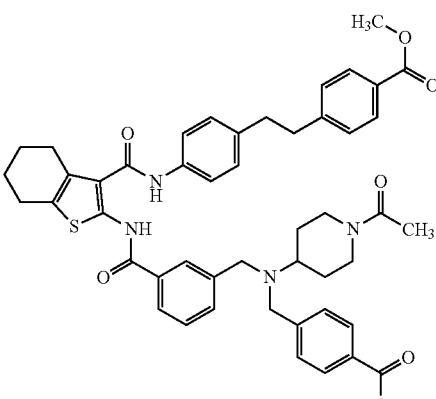 |
TABLE 81-continued
| Ex | Str |
|---|---|
| 201 | 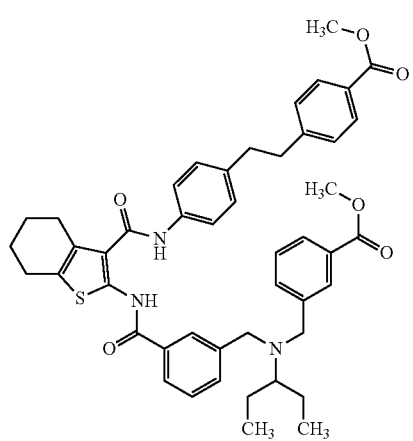 [SMILES: CCC(CC)N(Cc1cccc(C(=O)Nc2sc3c(c2C(=O)Nc2ccc(CCc4ccc(C(=O)OC)cc4)cc2)CCCC3)c1)Cc1cccc(C(=O)OC)c1] |
TABLE 82
| Ex | Str |
|---|---|
| 202 | 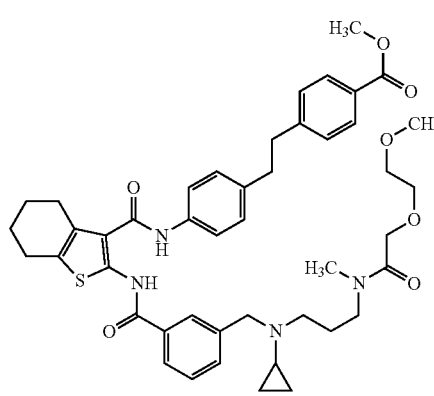 |
| 203 | 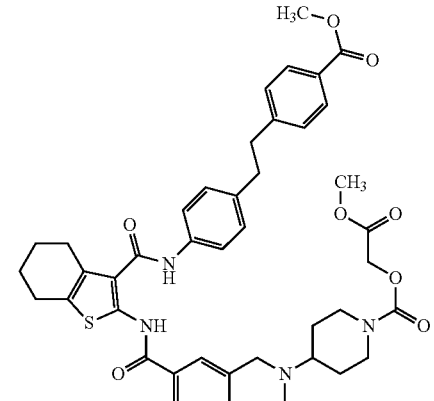 |

TABLE 82-continued
| Ex | Str |
|---|---|
| 204 | 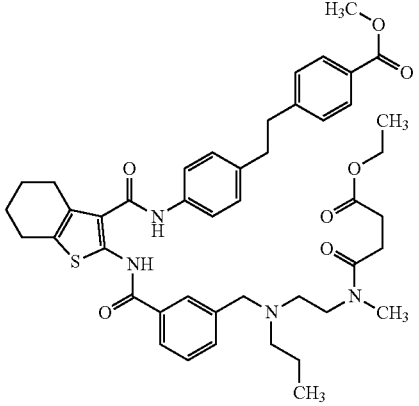 [SMILES: CCCN(CCN(C)C(=O)CCC(=O)OCC)Cc1cccc(C(=O)Nc2sc3c(c2C(=O)Nc2ccc(CCc4ccc(C(=O)OC)cc4)cc2)CCCC3)c1] |
| 205 | 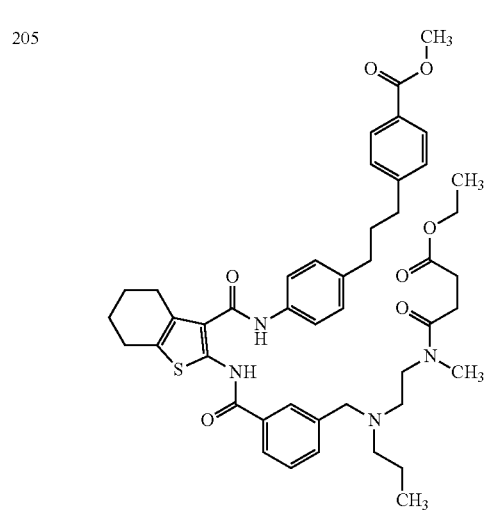 |
| 206 | 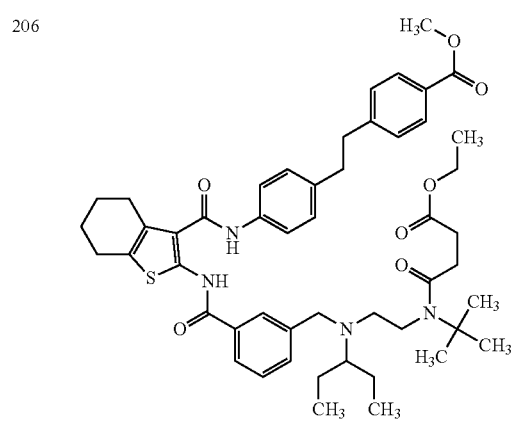 |
TABLE 83
| Ex | Str |
|---|---|
| 207 | 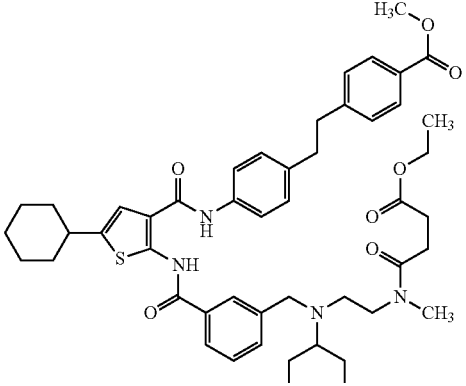 |
| 208 | 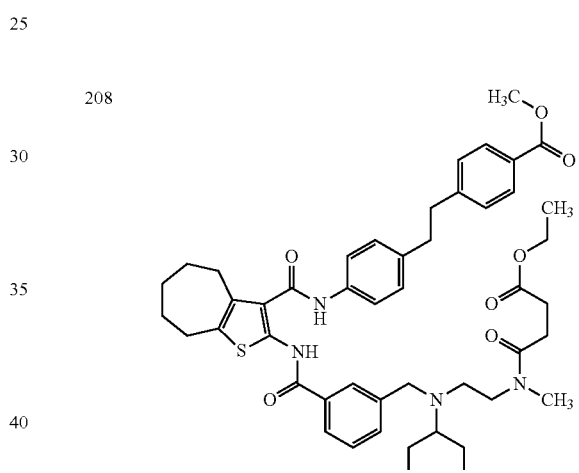 |
| 209 | 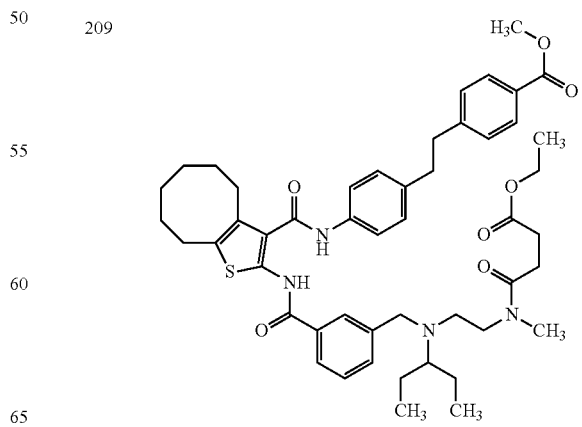 |

TABLE 83-continued

| Ex | Str |
|----|-----|
| 210 | |
| 211 | |
| 212 | |

TABLE 84

| Ex | Str |
|----|-----|
| 213 | |
| 214 | |
| 215 | |

TABLE 84-continued
| Ex | Str |
|---|---|
| 216 | 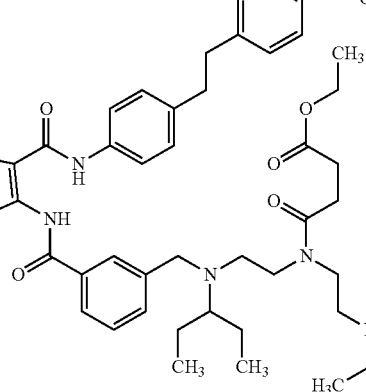 |
| 217 | |
| 218 | |
TABLE 85
| Ex | Str |
|---|---|
| 219 | 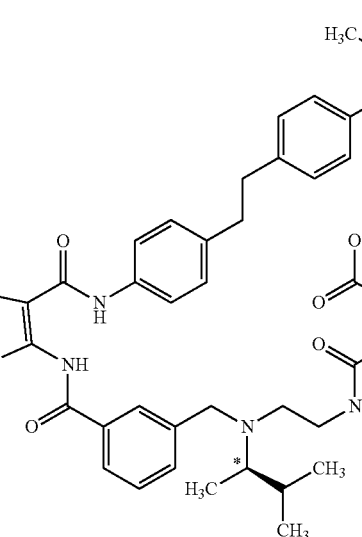 |
| 220 | |
| 221 | 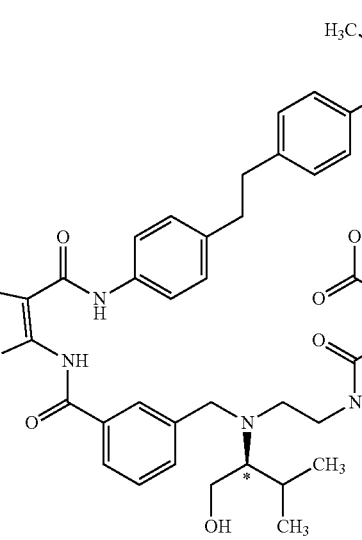 |

TABLE 85-continued

| Ex | Str |
|---|---|
| 222 | |
| 223 | |
| 224 | |

TABLE 86

| Ex | Str |
|---|---|
| 225 | |
| 226 | |
| 227 | |

TABLE 86-continued
| Ex | Str |
|---|---|
| 228 | 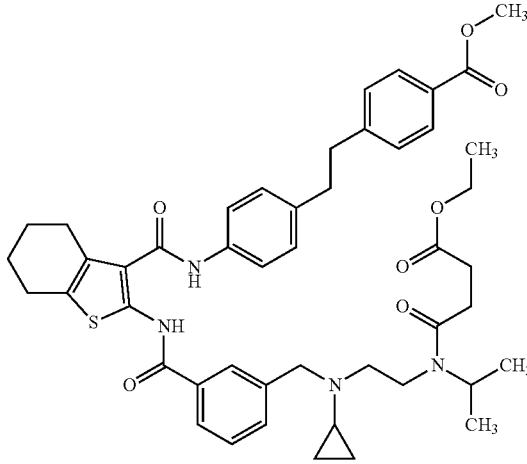 [SMILES: CCOC(=O)CCC(=O)N(CCN(Cc1cccc(C(=O)Nc2sc3c(c2C(=O)Nc2ccc(CCc4ccc(C(=O)OC)cc4)cc2)CCCC3)c1)C1CC1)C(C)C] |
| 229 | 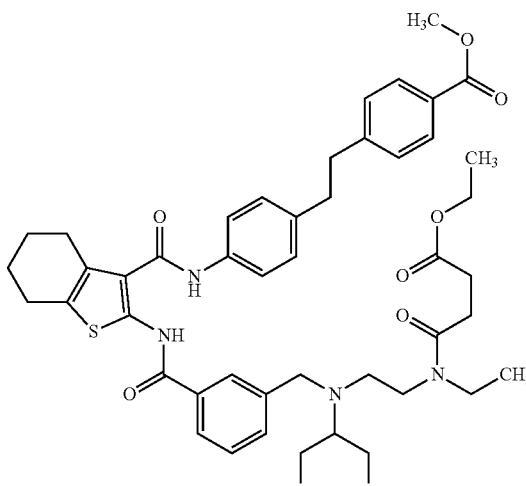 |
| 230 | 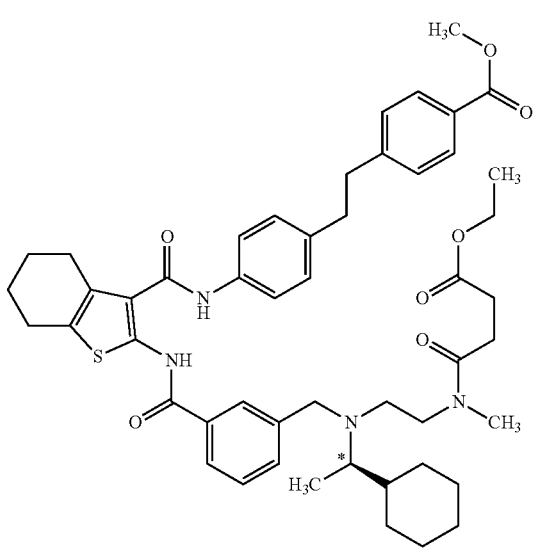 |
TABLE 87
| Ex | Str |
|---|---|
| 231 | 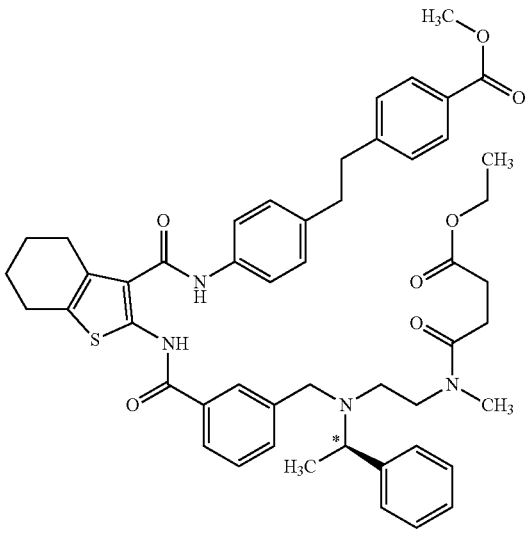 |
| 232 | 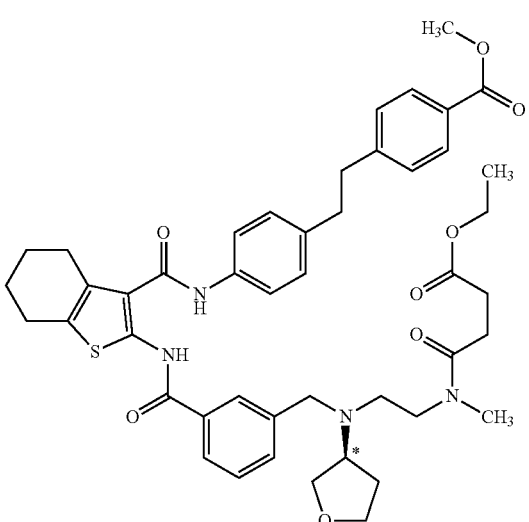 |
| 233 | 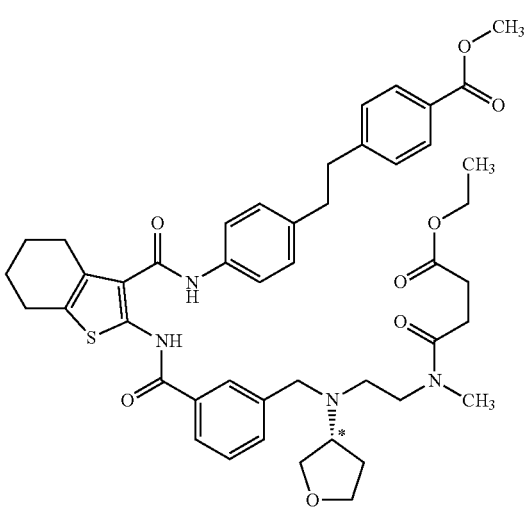 |

TABLE 87-continued

| Ex | Str |
|---|---|
| 234 | (structure) |
| 235 | (structure) |

TABLE 88

| Ex | Str |
|---|---|
| 236 | (structure) |
| 237 | (structure) |

TABLE 88-continued
| Ex | Str |
|---|---|
| 238 | 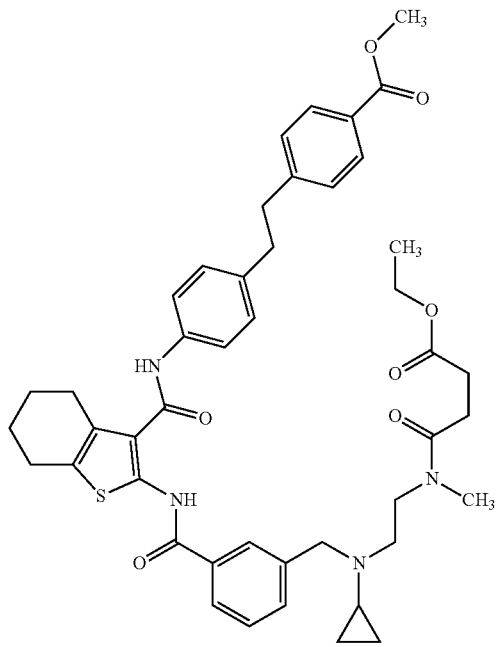 [SMILES: CCOC(=O)CCC(=O)N(C)CCN(Cc1cccc(C(=O)Nc2sc3c(c2C(=O)Nc2ccc(CCc4ccc(C(=O)OC)cc4)cc2)CCCC3)c1)C1CC1] |
| 239 | 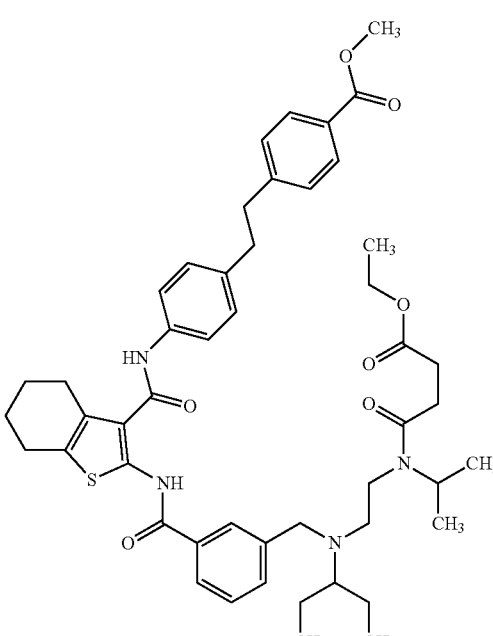 |
TABLE 89
| Ex | Str |
|---|---|
| 240 | 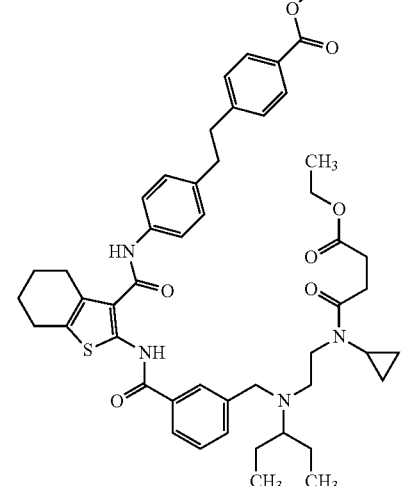 |
| 241 | 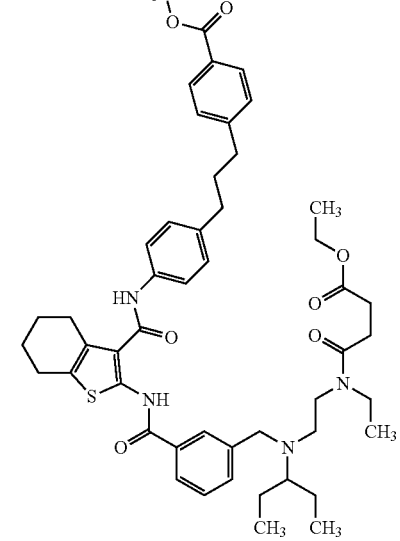 |
| 242 | 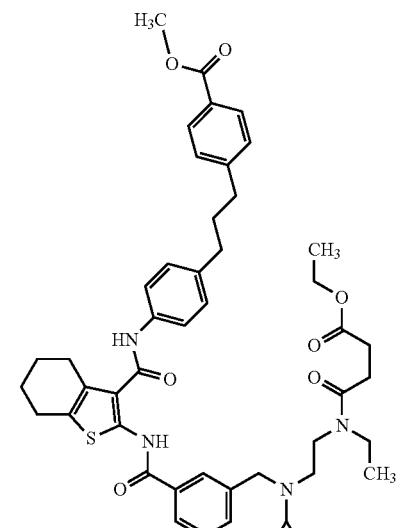 |

TABLE 89-continued
| Ex | Str |
|---|---|
| 243 | 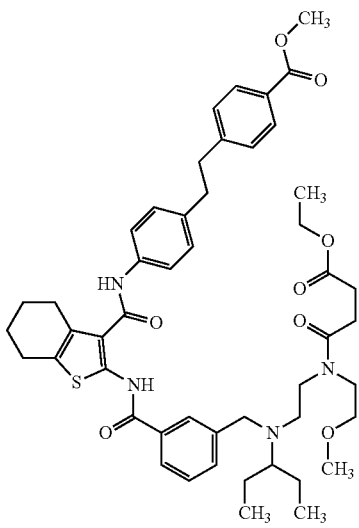 [SMILES: CCOC(=O)CCC(=O)N(CCOC)CCN(Cc1cccc(C(=O)Nc2sc3c(c2C(=O)Nc2ccc(CCc4ccc(C(=O)OC)cc4)cc2)CCCC3)c1)C(CC)CC] |
TABLE 90
| Ex | Str |
|---|---|
| 244 | 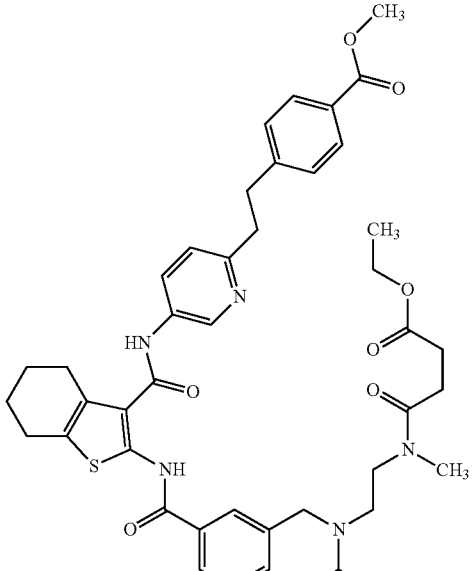 |
TABLE 90-continued
| Ex | Str |
|---|---|
| 245 | 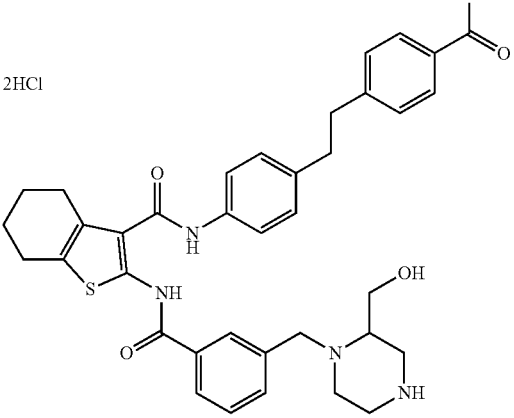 |
| 246 | 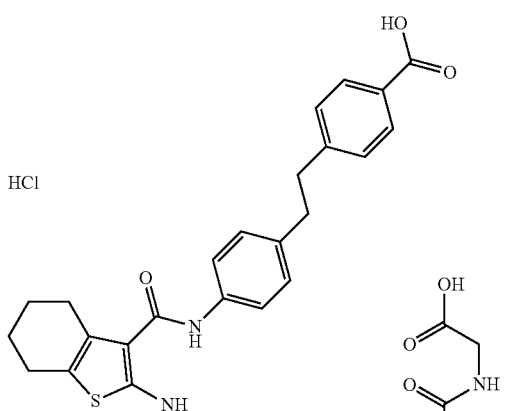 |
TABLE 91
| Pr | PSy | Dat |
|---|---|---|
| 1 | 1 | ESI+: 204 |
| 2 | 2 | CI+: 202 |
| 3 | 3 | ESI+: 230 |
| 4 | 4 | CI+: 287 |
| 5 | 5 | ESI+: 256 |
| 6 | 6 | ESI+: 323 |
| 7 | 7 | ESI+: 435 |
| 8 | 8 | ESI+: 587 |
| 9 | 9 | ESI+: 638 |
| 10 | 10 | ESI+: 695 |
| 11 | 11 | ESI+: 231 |
| 12 | 12 | ESI+: 681 |
| 13 | 13 | ESI+: 809 |
| 14 | 14 | ESI+: 795 |
| 15 | 15 | ESI+: 824 |
| 16 | 16 | ESI+: 823 |
| 17 | 17 | ESI+: 851 |
| 18 | 18 | ESI+: 190 |
| 19 | 19 | ESI+: 439 |
| 20 | 20 | ESI−: 403 |
| 21 | 21 | ESI+: 821 |
| 22 | 22 | ESI+: 583 |

TABLE 91-continued

| Pr | PSy | Dat |
|---|---|---|
| 23 | 23 | ESI+: 652 |
| 24 | 24 | CI+: 256 |
| 25 | 25 | ESI+: 312 |
| 26 | 26 | ESI+: 270 |
| 27 | 27 | ESI+: 781 |
| 28 | 28 | ESI+: 206 |
| 29 | 29 | APCI/ESI+: 751 |
| 30 | 30 | APCI/ESI+: 737 |
| 31 | 31 | APCI/ESI+: 821 |
| 32 | 32 | APCI/ESI+: 823 |
| 33 | 33 | APCI/ESI+: 851 |
| 34 | 34 | APCI/ESI+: 852 |
| 35 | 35 | APCI/ESI+: 231 |
| 36 | 36 | APCI/ESI+: 843 |
| 37 | 37 | APCI/ESI+: 251 |
| 38 | 38 | APCI/ESI+: 436 |
| 39 | 39 | APCI/ESI+: 283 |
| 40 | 40 | ESI+: 679 |
| 41 | 41 | ESI+: 750 |
| 42 | 42 | ESI+: 807 |
| 43 | 43 | ESI+: 787 |
| 44 | 44 | ESI+: 816 |
| 45 | 45 | ESI+: 568 |
| 46 | 46 | ESI+: 835 |
| 47 | 47 | CI+: 251 |
| 48 | 48 | ESI+: 329 |
| 49 | 49 | ESI+: 371 |
| 50 | 50 | ESI+: 383 |
| 51 | 51 | ESI+: 539 |
| 52 | 52 | ESI+: 745 |
| 53 | 53 | ESI+: 350 |
| 54 | 54 | ESI+: 772 |
| 55 | 55 | ESI+: 267 |
| 56 | 56 | ESI+: 492 |
| 57 | 57 | ESI+: 640 |
| 58 | 58 | ESI+: 862 |
| 59 | 59 | ESI+: 758 |
| 60 | 60 | ESI+: 383 |
| 61 | 61 | ESI+: 722 |
| 62 | 62 | EI: 309 |
| 63 | 63 | APCI/ESI+: 494 |
| 64 | 64 | ESI+: 228 |
| 65 | 65 | ESI+: 238 |
| 66 | 66 | APCI/ESI+: 215 |
| 67 | 67 | ESI+: 751 |
| 68 | 68 | APCI/ESI+: 821 |
| 69 | 69 | APCI/ESI+: 262 |
| 70 | 1 | ESI+: 218 |
| 71 | 2 | ESI+: 216 |
| 72 | 1 | ESI+: 246 |
| 73 | 2 | ESI+: 244 |
| 74 | 2 | ESI+: 228 |
| 75 | 4 | ESI+: 246 |
| 76 | 7 | APCI/ESI+: 437 |
| 77 | 8 | APCI/ESI+: 589 |
| 78 | 9 | ESI+: 640 |
| 79 | 7 | APCI/ESI+: 449 |
| 80 | 8 | ESI+: 601 |
| 81 | 9 | ESI+: 652 |
| 82 | 7 | ESI+: 463 |
| 83 | 8 | ESI+: 615 |
| 84 | 9 | ESI+: 666 |
| 85 | 7 | APCI/ESI+: 463 |
| 86 | 8 | APCI/ESI+: 615 |

TABLE 92

| Pr | PSy | Dat |
|---|---|---|
| 87 | 9 | ESI+: 666 |
| 88 | 9 | ESI+: 638 |
| 89 | 9 | ESI+: 638 |
| 90 | 9 | ESI+: 652 |
| 91 | 9 | ESI+: 678 |
| 92 | 9 | ESI+: 672 |

TABLE 92-continued

| Pr | PSy | Dat |
|---|---|---|
| 93 | 13 | ESI+: 823 |
| 94 | 13 | ESI+: 837 |
| 95 | 10 | ESI+: 709 |
| 96 | 13 | ESI+: 837 |
| 97 | 10 | FAB+: 610 |
| 98 | 9 | ESI+: 781 |
| 99 | 12 | ESI+: 695 |
| 100 | 13 | ESI+: 837 |
| 101 | 15 | ESI+: 824 |
| 102 | 17 | ESI+: 851 |
| 103 | 2 | CI+: 188 |
| 104 | 14 | ESI+: 809 |
| 105 | 12 | ESI+: 709 |
| 106 | 13 | ESI+: 837 |
| 107 | 13 | ESI+: 851 |
| 108 | 16 | ESI+: 837 |
| 109 | 17 | ESI+: 865 |
| 110 | 17 | ESI+: 865 |
| 111 | 10 | ESI+: 650 |
| 112 | 24 | ESI+: 270 |
| 113 | 23 | ESI+: 622 |
| 114 | 10 | ESI+: 610 |
| 115 | 10 | ESI+: 642 |
| 116 | 9 | ESI+: 654 |
| 117 | 9 | ESI+: 654 |
| 118 | 10 | ESI+: 636 |
| 119 | 9 | ESI+: 638 |
| 120 | 9 | ESI+: 638 |
| 121 | 9 | ESI+: 624 |
| 122 | 9 | ESI+: 624 |
| 123 | 6 | ESI+: 337 |
| 124 | 7 | ESI+: 449 |
| 125 | 8 | ESI+: 601 |
| 126 | 10 | ESI+: 624 |
| 127 | 10 | ESI+: 624 |
| 128 | 10 | ESI+: 650 |
| 129 | 10 | ESI+: 608 |
| 130 | 14 | ESI+: 765 |
| 131 | 12 | ESI+: 665 |
| 132 | 30 | ESI+: 781 |
| 133 | 2 | CI+: 204 |
| 134 | 11 | APCI/ESI+: 201 |
| 135 | 12 | APCI/ESI+: 651 |
| 136 | 30 | APCI/ESI+: 823 |
| 137 | 13 | APCI/ESI+: 751 |
| 138 | 13 | APCI/ESI+: 751 |
| 139 | 27 | APCI/ESI+: 807 |
| 140 | 13 | ESI+: 765 |
| 141 | 13 | ESI+: 807 |
| 142 | 1 | APCI/ESI+: 232 |
| 143 | 2 | APCI/ESI+: 230 |
| 144 | 12 | APCI/ESI+: 721 |
| 145 | 13 | APCI/ESI+: 849 |
| 146 | 3 | APCI/ESI+: 345 |
| 147 | 31 | APCI/ESI+: 964 |
| 148 | 12 | APCI/ESI+: 864 |
| 149 | 10 | ESI−: 620 |
| 150 | 10 | APCI/ESI+: 652 |
| 151 | 33 | APCI/ESI+: 811 |
| 152 | 13 | APCI/ESI+: 845 |
| 153 | 13 | APCI/ESI+: 771 |
| 154 | 30 | APCI/ESI+: 287 |
| 155 | 33 | APCI/ESI+: 907 |
| 156 | 36 | APCI/ESI+: 857 |
| 157 | 36 | APCI/ESI+: 843 |
| 158 | 36 | ESI+: 779 |
| 159 | 14 | APCI/ESI+: 408 |
| 160 | 12 | APCI/ESI+: 308 |
| 161 | 33 | ESI+: 464 |
| 162 | 21 | APCI/ESI+: 853 |
| 163 | 21 | APCI/ESI+: 852 |
| 164 | 8 | APCI/ESI+: 588 |
| 165 | 10 | APCI/ESI+: 639 |
| 166 | 5 | APCI/ESI+: 257 |

TABLE 92-continued

| Pr | PSy | Dat |
|---|---|---|
| 167 | 6 | APCI/ESI+: 324 |
| 168 | 7 | APCI/ESI+: 436 |
| 169 | 6 | ESI+: 252 |
| 170 | 7 | ESI+: 364 |
| 171 | 8 | ESI+: 516 |

TABLE 93

| Pr | PSy | Dat |
|---|---|---|
| 172 | 10 | ESI+: 537 |
| 173 | 41 | ESI+: 750 |
| 174 | 41 | ESI+: 764 |
| 175 | 41 | ESI+: 764 |
| 176 | 15 | ESI+: 843 |
| 177 | 15 | ESI+: 809 |
| 178 | 13 | ESI+: 802 |
| 179 | 38 | ESI+: 225 |
| 180 | 44 | APCI/ESI−: 722 |
| 181 | 44 | APCI/ESI+: 696 |
| 182 | 40 | ESI+: 714 |
| 183 | 46 | ESI+: 835 |
| 184 | 40 | ESI+: 471 |
| 185 | 21 | ESI+: 787 |
| 186 | 41 | ESI+: 780 |
| 187 | 41 | ESI+: 780 |
| 188 | 41 | ESI+: 752 |
| 189 | 41 | ESI+: 738 |
| 190 | 41 | ESI+: 766 |
| 191 | 44 | ESI+: 800 |
| 192 | 40 | ESI+: 836 |
| 193 | 41 | ESI+: 794 |
| 194 | 41 | ESI+: 794 |
| 195 | 41 | ESI+: 766 |
| 196 | 41 | ESI+: 752 |
| 197 | 41 | ESI+: 780 |
| 198 | 44 | ESI+: 814 |
| 199 | 44 | ESI+: 815 |
| 200 | 41 | ESI+: 766 |
| 201 | 41 | ESI+: 766 |
| 202 | 41 | ESI+: 752 |
| 203 | 41 | ESI+: 752 |
| 204 | 41 | ESI+: 752 |
| 205 | 41 | ESI+: 752 |
| 206 | 41 | FAB+: 738 |
| 207 | 40 | ESI+: 758 |
| 208 | 46 | ESI+: 781 |
| 209 | 10 | ESI+: 667 |
| 210 | 41 | ESI+: 809 |
| 211 | 10 | ESI+: 665 |
| 212 | 41 | ESI+: 807 |
| 213 | 9 | ESI+: 677 |
| 214 | 41 | ESI+: 819 |
| 215 | 9 | ESI+: 677 |
| 216 | 41 | ESI+: 819 |
| 217 | 41 | ESI+: 766 |
| 218 | 41 | ESI+: 794 |
| 219 | 8 | ESI+: 406 |
| 220 | 10 | ESI+: 457 |
| 221 | 41 | ESI+: 525 |
| 222 | 27 | ESI+: 364 |
| 223 | 5 | ESI+: 320 |
| 224 | 52 | ESI+: 858 |
| 225 | 12 | ESI+: 758 |
| 226 | 27 | ESI+: 292 |
| 227 | 53 | ESI+: 278 |
| 228 | 5 | ESI+: 248 |
| 229 | 52 | ESI+: 786 |
| 230 | 5 | ESI+: 237 |
| 231 | 52 | ESI+: 775 |
| 232 | 7 | ESI+: 421 |
| 233 | 8 | FAB−: 571 |
| 234 | 10 | ESI+: 624 |
| 235 | 52 | ESI+: 582 |
| 236 | 8 | ESI+: 497 |

TABLE 93-continued

| Pr | PSy | Dat |
|---|---|---|
| 237 | 10 | ESI+: 548 |
| 238 | 38 | ESI+: 520 |
| 239 | 8 | ESI−: 494 |
| 240 | 29 | ESI+: 700 |
| 241 | 12 | |
| 242 | 13 | ESI+: 791 |
| 243 | 33 | ESI+: 862 |
| 244 | 52 | ESI+: 628 |
| 245 | 29 | ESI+: 791 |
| 246 | 12 | ESI+: 691 |
| 247 | 32 | ESI+: 805 |
| 248 | 29 | ESI+: 693 |
| 249 | 29 | ESI+: 527 |
| 250 | 14 | ESI+: 569 |
| 251 | 50 | ESI+: 495 |
| 252 | 38 | FAB−: 240 |
| 253 | 29 | ESI+: 767 |
| 254 | 6,7 | ESI+: 345 |
| 255 | 16 | ESI+: 232 |
| 256 | 7 | ESI+: 344 |
| 257 | 29 | ESI+: 581 |

TABLE 94

| Pr | PSy | Dat |
|---|---|---|
| 258 | 50 | ESI+: 507 |
| 259 | 8 | ESI+: 378 |
| 260 | 10 | ESI+: 429 |
| 261 | 38 | ESI+: 401 |
| 262 | 10 | APCI/ESI+: 552 |
| 263 | 50 | ESI+: 478 |
| 264 | 52 | ESI+: 748 |
| 265 | 29 | ESI+: 777 |
| 266 | 61 | ESI+: 736 |
| 267 | 61 | ESI+: 750 |
| 268 | 52 | APCI/ESI+: 756 |
| 269 | 10 | FAB+: 257 |
| 270 | 38 | FAB+: 229 |
| 271 | 62 | EI: 235 |
| 272 | 10 | ESI+: 242 |
| 273 | 38 | ESI+: 224 |
| 274 | 39 | EI: 299 |
| 275 | 5 | ESI+: 274 |
| 276 | 52 | ESI+: 768 |
| 277 | 61 | NMR: 0.04 (9H, s), 0.48-0.77 (4H, m), 1.05-1.12 (2H, m), 1.67-1.88 (4H, m), 2.62-3.04 (12H, m), 3.83 (3H, s), 4.37-4.44 (2H, m), 4.48-4.57 (2H, m), 7.15 (2H, d, J = 8.4 Hz), 7.37 (2H, d, J = 8.4 Hz), 7.53-7.64 (3H, m), 7.77-8.12 (6H, m), 8.82-8.88 (1H, m), 9.57 (1H, s), 11.70 (1H, s) |
| 278 | 13 | NMR: 0.36-0.54 (4H, m), 1.25 (3H, t, J = 7.2 Hz), 1.83-2.08 (8H, m), 2.43 (1H, t, J = 14.4 Hz), 2.62 (4H, t, J = 4.4 Hz), 2.68-2.81 (3H, m), 2.84-3.03 (8H, m), 4.13 (2H, q, J = 7.6 Hz ), 4.61-4.69 (1H, m), 7.16 (2H, d, J = 8.4 Hz), 7.39-7.53 (4H, m), 7.65 (1H, s), 7.86-8.01 (4H, m), 13.03 (1H, s) |
| 279 | 13 | APCI/ESI+: 315 |
| 280 | 29 | ESI+: 765 |
| 281 | 52 | ESI+: 776 |
| 282 | 52 | ESI+: 762 |
| 283 | 52 | ESI+: 762 |
| 284 | 52 | ESI+: 776 |
| 285 | 69 | ESI+: 256 |
| 286 | 69 | ESI+: 256 |
| 287 | 63,69 | ESI+: 270 |
| 288 | 10 | ESI+: 527 |

TABLE 94-continued

| Pr | PSy | Dat |
|---|---|---|
| 289 | 50 | ESI+: 453 |
| 290 | 52 | ESI+: 708 |
| 291 | 29 | ESI+: 708 |
| 292 | 29 | ESI+: 784 |
| 293 | 40 | ESI+: 750 |
| 294 | 11 | ESI+: 216 |
| 295 | 29 | ESI+: 766 |
| 296 | 40 | ESI+: 786 |
| 297 | 29 | ESI+: 722 |
| 298 | 29 | ESI+: 680 |
| 299 | 13 | ESI+: 767 |
| 300 | 34 | ESI+: 834 |
| 301 | 61 | ESI+: 722 |
| 302 | 35 | ESI+: 666 |
| 303 | 61 | ESI+: 834 |
| 304 | 12 | ESI+: 734 |
| 305 | 36 | ESI+: 820 |
| 306 | 14 | ESI+: 682 |
| 307 | 54 | ESI+: 287 |
| 308 | 5 | ESI+: 257 |
| 309 | 52 | ESI+: 751 |
| 310 | 54 | ESI+: 301 |
| 311 | 5 | FAB+: 271 |
| 312 | 52 | ESI+: 765 |
| 313 | 57 | EI: 287 |
| 314 | 5 | NMR: 3.88 (3H, s), 4.98 (2H, s), 6.69 (2H, d, J = 8.4 Hz), 6.97 (2H, d, J = 8.9 Hz), 7.21 (2H, d, J = 8.4 Hz), 7.98 (2H, d, J = 8.9 Hz) |
| 315 | 52 | ESI+: 752 |

TABLE 95

| Ex | Syn | Dat |
|---|---|---|
| 1 | 1 | ESI+: 823 |
| 2 | 2 | ESI+: 781 NMR: 0.80-1.00 (6H, m), 1.59-2.04 (7H, m), 2.30-2.47 (2H, m), 2.65-2.81 (4H, m), 2.81-3.05 (7H, m), 3.11-3.22 (1H, m), 3.60-3.80 (1H, m), 4.44-4.56 (2H, m), 7.18 (2H, d, J = 8.5 Hz), 7.35 (2H, d, J = 8.3 Hz), 7.60 (2H, d, J = 8.5 Hz), 7.65-7.71 (1H, m), 7.81-8.00 (4H, m), 8.11-8.19 (1H, m), 9.38 (1H, s), 9.60 (1H, s), 11.67 (1H, s), 12.00-12.80 (2H, m) |
| 3 | 3 | ESI+: 811 |
| 4 | 4 | ESI+: 783 NMR: 0.76-1.01 (6H, m), 1.59-2.04 (8H, m), 2.65-3.06 (12H, m), 3.06-3.30 (1H, m), 3.64-3.80 (1H, m), 4.38-4.60 (4H, m), 7.18 (2H, d, J = 8.5 Hz), 7.35 (2H, d, J = 8.3 Hz), 7.60 (2H, d, J = 8.5 Hz), 7.63-7.70 (1H, m), 7.85 (2H, d, J = 8.3 Hz), 7.88-8.00 (2H, m), 8.13-8.22 (1H, m), 9.50-9.90 (2H, m), 11.67 (1H, s), 12.43-13.27 (2H, m) |
| 5 | 5 | ESI+: 767 |
| 6 | 6 | APCI/ESI+: 695 |
| 7 | 7 | APCI/ESI+: 785 |
| 8 | 8 | ESI+: 783 |
| 9 | 9 | APCI/ESI+: 774 |
| 10 | 10 | ESI+: 719 |
| 11 | 11 | ESI+: 705 |
| 12 | 12 | ESI+: 666 |
| 13 | 13 | ESI+: 686 |
| 14 | 14 | ESI+: 667 |

TABLE 95-continued

| Ex | Syn | Dat |
|---|---|---|
| 15 | 15 | ESI+: 547 |
| 16 | 16 | ESI+: 663 |
| 17 | 17 | FAB+: 549 |
| 18 | 18 | ESI+: 736 |
| 19 | 19 | ESI+: 642 |
| 20 | 20 | ESI+: 682 |
| 21 | 21 | ESI+: 557 |
| 22 | 22 | ESI+: 524 |
| 23 | 5 | ESI+: 781 |
| 24 | 6 | APCI/ESI+: 753 |
| 25 | 6 | APCI/ESI+: 709 |
| 26 | 5 | ESI+: 739 |
| 27 | 5 | APCI/ESI+: 723 |
| 28 | 6 | APCI/ESI+: 737 |
| 29 | 4 | ESI+: 753 |
| 30 | 4 | ESI+: 767 |
| 31 | 2 | ESI+: 765 |
| 32 | 2 | ESI+: 779 |
| 33 | 2 | ESI+: 781 |
| 34 | 2 | ESI+: 823 |
| 35 | 2 | ESI+: 765 |
| 36 | 2 | ESI+: 723 |
| 37 | 2 | ESI+: 751 |
| 38 | 2 | ESI+: 753 |
| 39 | 2 | ESI+: 765 |
| 40 | 2 | ESI+: 783 |
| 41 | 2 | ESI+: 809 |
| 42 | 2 | ESI+: 795 |
| 43 | 2 | ESI+: 809 |
| 44 | 4 | ESI+: 785 |
| 45 | 2 | ESI+: 795 |
| 46 | 2 | ESI+: 795 |

TABLE 96

| Ex | Syn | Dat |
|---|---|---|
| 47 | 2 | ESI+: 767 |
| 48 | 4 | ESI+: 767 |
| 49 | 2 | ESI+: 809 |
| 50 | 2 | ESI+: 779 |
| 51 | 2 | ESI+: 807 |
| 52 | 2 | ESI+: 795 |
| 53 | 2 | ESI+: 795 |
| 54 | 2 | ESI+: 737 |
| 55 | 2 | ESI+: 809 |
| 56 | 2 | ESI+: 767 |
| 57 | 4 | ESI+: 779 |
| 58 | 4 | ESI+: 793 |
| 59 | 2 | ESI+: 795 |
| 60 | 2 | ESI+: 825 NMR: 0.84-1.09 (6H, m), 1.26-2.03 (8H, m), 2.66-2.85 (3H, m), 3.66-3.82 (1H, m), 4.42-4.60 (1H, m), 7.16 (2H, d, J = 8.4 Hz), 7.32 (2H, d, J = 8.0 Hz), 7.43-7.54 (1H, m), 7.57 (2H, d, J = 8.0 Hz), 7.84 (2H, d, J = 8.4 Hz), 7.87-8.22 (1H, m), 9.15-9.37 (1H, m), 11.68 (1H, s) |
| 61 | 2 | ESI+: 781 |
| 62 | 2 | ESI+: 795 |
| 63 | 2 | ESI+: 795 |
| 64 | 2 | ESI+: 823 |
| 65 | 2 | ESI+: 866 |
| 66 | 2 | ESI+: 795 NMR: 0.91-1.00 (6H, m), 1.58-2.10 (10H, m), 2.36-2.48 (4H, m), 2.67-2.81 (4H, m), 2.86-3.14 (8H, m), 3.20-3.30 (1H, m), 4.32-4.53 (2H, m), 7.19 (2H, d, J = 8.5 Hz), 7.35 (2H, d, J = 8.3 Hz), 7.60 (2H, d, J = 8.5 Hz), 7.63-7.69 (1H, |

TABLE 96-continued

| Ex | Syn | Dat |
|---|---|---|
|  |  | m), 7.83-7.96 (4H, m), 8.12-8.19 (1H, m), 9.52 (1H, s), 9.61 (1H, s), 11.67 (1H, s), 12.16-12.66 (2H, m) |
| 67 | 2 | ESI+: 823<br>NMR: 0.88-1.00 (6H, m), 1.07 (6H, s), 1.57-1.88 (9H, m), 1.89-2.03 (1H, m), 2.07-2.25 (2H, m), 2.66-2.81 (4H, m), 2.85-3.08 (8H, m), 3.11-3.23 (1H, m), 3.63-3.76 (1H, m), 4.41-4.57 (2H, m), 7.19 (2H, d, J = 8.5 Hz), 7.35 (2H, d, J = 8.3 Hz), 7.61 (2H, d, J = 8.5 Hz), 7.64-7.71 (1H, m), 7.81-7.98 (4H, m), 8.13-8.20 (1H, m), 9.63 (1H, s), 9.72 (1H, s), 11.68 (1H, s), 12.20-12.80 (2H, m) |
| 68 | 4 | ESI+: 797 |
| 69 | 4 | ESI+: 797 |
| 70 | 2 | ESI+: 781 |
| 71 | 2 | ESI+: 809 |
| 72 | 2 | ESI+: 803 |
| 73 | 2 | APCI/ESI+: 681 |
| 74 | 2 | ESI+: 865 |
| 75 | 2 | ESI+: 809 |
| 76 | 2 | ESI+: 810 |
| 77 | 2 | ESI+: 809 |
| 78 | 2 | ESI+: 809 |
| 79 | 2 | ESI+: 795 |
| 80 | 2 | ESI+: 797 |
| 81 | 2 | ESI+: 837 |
| 82 | 4 | ESI+: 767 |
| 83 | 4 | ESI+: 767 |
| 84 | 2 | ESI+: 837 |
| 85 | 2 | ESI+: 793 |
| 86 | 2 | ESI+: 765 |
| 87 | 2 | ESI+: 807 |
| 88 | 2 | ESI+: 822 |
| 89 | 4 | ESI+: 781 |
| 90 | 4 | ESI+: 781 |
| 91 | 2 | ESI+: 815 |
| 92 | 2 | ESI+: 815 |
| 93 | 2 | APCI/ESI+: 815 |

TABLE 97

| Ex | Syn | Dat |
|---|---|---|
| 94 | 2 | ESI+: 821 |
| 95 | 2 | ESI+: 815 |
| 96 | 2 | ESI+: 782 |
| 97 | 2 | ESI+: 797 |
| 98 | 2 | ESI+: 796 |
| 99 | 8 | ESI+: 782 |
| 100 | 6 | ESI+: 651 |
| 101 | 6 | ESI+: 786 |
| 102 | 6 | ESI+: 736 |
| 103 | 6 | ESI+: 736 |
| 104 | 6 | ESI+: 787 |
| 105 | 6 | ESI+: 772 |
| 106 | 6 | ESI+: 738 |
| 107 | 6 | ESI+: 724 |
| 108 | 6 | ESI+: 808 |
| 109 | 6 | ESI+: 766<br>NMR: 0.69-0.80 (6H, m), 0.93-1.15 (6H, m), 1.34-1.53 (4H, m), 1.67-1.85 (6H, m), 2.13-2.43 (2H, m), 2.65-2.82 (4H, m), 2.85-3.00 (4H, m), 3.64-4.36 (1H, m), 4.39-4.58 (2H, m), 7.19 (2H, d, J = 8.4 Hz), 7.35 (2H, d, J = 8.2 Hz), 7.42-7.90 (8H, m), 9.52 (1H, s), 11.56-11.77 (1H, m), 12.26-12.62 (2H, m) |
| 110 | 6 | ESI+: 750 |
| 111 | 6 | ESI+: 750 |
| 112 | 6 | ESI+: 823 [M + Na]+ |
| 113 | 6 | ESI+: 774 |
| 114 | 6 | ESI+: 767 |
| 115 | 6 | ESI+: 765 |
| 116 | 6 | ESI+: 759 |
| 117 | 6 | ESI+: 738 |
| 118 | 6 | ESI+: 752 |
| 119 | 6 | ESI+: 738 |
| 120 | 6 | ESI+: 738 |
| 121 | 6 | ESI+: 766<br>NMR: 0.68-0.81 (6H, m), 0.97-1.11 (6H, m), 1.32-1.53 (4H, m), 1.68-1.87 (4H, m), 2.33-2.61 (4H, m), 2.66-2.82 (4H, m), 2.85-3.00 (4H, m), 3.73-4.37 (1H, m), 4.40-4.62 (2H, m), 7.19 (2H, d, J = 8.4 Hz), 7.35 (2H, d, J = 8.2 Hz), 7.42-7.81 (6H, m), 7.85 (2H, d, J = 8.2 Hz), 9.46-9.57 (1H, m), 11.68 (1H, s), 12.12-12.55 (2H, m) |
| 122 | 6 | ESI+: 738 |
| 123 | 6 | ESI+: 724 |
| 124 | 6 | ESI+: 738 |
| 125 | 6 | ESI+: 780 |
| 126 | 6 | ESI+: 780 |
| 127 | 6 | ESI+: 752 |
| 128 | 6 | ESI+: 766 |
| 129 | 6 | ESI+: 752 |
| 130 | 6 | ESI+: 753 |
| 131 | 6 | ESI+: 752 |
| 132 | 6 | ESI+: 795 |
| 133 | 6 | ESI+: 793 |
| 134 | 6 | ESI+: 752 |
| 135 | 6 | ESI+: 780 |
| 136 | 5 | ESI+: 731 |
| 137 | 5 | ESI+: 772 |
| 138 | 5 | ESI+: 758 |
| 139 | 5 | ESI+: 691 |
| 140 | 6 | APCI/ESI+: 802 |
| 141 | 5 | ESI+: 805 |
| 142 | 5 | ESI+: 805 |
| 143 | 5 | ESI+: 793 |
| 144 | 6 | ESI+: 745 |
| 145 | 6 | APCI/ESI−: 708 |
| 146 | 5 | ESI+: 793 |
| 147 | 6 | APCI/ESI+: 668 |
| 148 | 148 | ESI+: 730 |
| 149 | 6 | ESI+: 735 |
| 150 | 6 | APCI/ESI+: 716 |

TABLE 98

| Ex | Syn | Dat |
|---|---|---|
| 151 | 5 | ESI+: 848 |
| 152 | 5 | ESI+: 779 |
| 153 | 5 | ESI+: 723 |
| 154 | 5 | APCI/ESI+: 729 |
| 155 | 5 | ESI+: 806 |
| 156 | 5 | ESI+: 778 |
| 157 | 5 | ESI+: 779 |
| 158 | 6 | ESI+: 777 |
| 159 | 2 | ESI+: 723 |
| 160 | 5 | ESI+: 658 |
| 161 | 17 | ESI+: 676 |
| 162 | 6 | ESI+: 600 |
| 163 | 22 | FAB+: 719 |
| 164 | 6 | ESI+: 720 |
| 165 | 6 | ESI+: 720 |

TABLE 98-continued

| Ex | Syn | Dat |
|---|---|---|
| 166 | 6 | ESI+: 720 |
| 167 | 6 | ESI+: 626 |
| 168 | 6 | ESI+: 720 |
| 169 | 5 | ESI+: 706 |
| 170 | 6 | ESI+: 666 |
| 171 | 5 | ESI+: 735 |
| 172 | 6 | ESI+: 722 |
| 173 | 6 | ESI+: 722 |
| 174 | 6 | ESI+: 680 |
| 175 | 6 | ESI+: 694 |
| 176 | 6 | ESI+: 708 |
| 177 | 6 | ESI+: 722 |
| 178 | 6 | ESI+: 738 |
| 179 | 6 | FAB+: 758 |
| 180 | 6 | ESI+: 680 |
| 181 | 6 | ESI+: 728 |
| 182 | 6 | ESI+: 723 |
| 183 | 6 | ESI+: 724 |
| 184 | 6 | ESI+: 737 |
| 185 | 6 | ESI+: 680 |
| 186 | 6 | ESI+: 791 |
| 187 | 6 | ESI+: 740 |
| 188 | 6 | FAB+: 813 |
| 189 | 6 | ESI+: 758 |
| 190 | 22 | ESI+: 556 |
| 191 | 22 | ESI+: 640 |
| 192 | 22 | ESI+: 573 |
| 193 | 22 | ESI+: 558 |
| 194 | 21 | ESI+: 574 |
| 195 | 21 | ESI+: 573 |
| 196 | 21 | ESI+: 569 |
| 197 | 1 | ESI+: 750 |
| 198 | 1 | ESI+: 826 |
| 199 | 1 | ESI+: 722 |
| 200 | 1 | ESI+: 841 |
| 201 | 1 | ESI+: 786 |
| 202 | 1 | ESI+: 795 |
| 203 | 3 | ESI+: 807 |
| 204 | 1 | ESI+: 795 |
| 205 | 1 | ESI+: 809 |
| 206 | 1 | ESI+: 865 |
| 207 | 1 | ESI+: 851 |
| 208 | 1 | ESI+: 837 |
| 209 | 1 | ESI+: 851 |
| 210 | 1 | ESI+: 825 |
| 211 | 1 | ESI+: 827 |
| 212 | 1 | ESI+: 809 |
| 213 | 1 | APCI/ESI+: 807 |
| 214 | 1 | ESI+: 823 |
| 215 | 1 | ESI+: 837 |
| 216 | 1 | ESI+: 809 |
| 217 | 1 | ESI+: 821 |
| 218 | 1 | ESI+: 835 |
| 219 | 1 | ESI+: 908 |
| 220 | 1 | ESI+: 823 |
| 221 | 1 | ESI+: 839 |
| 222 | 1 | ESI+: 839 |
| 223 | 1 | ESI+: 837 |
| 224 | 1 | ESI+: 835 |
| 225 | 1 | ESI+: 809 |
| 226 | 1 | ESI+: 809 |
| 227 | 1 | ESI+: 807 |
| 228 | 1 | APCI/ESI+: 821 |
| 229 | 1 | ESI+: 837 |
| 230 | 1 | ESI+: 863 |
| 231 | 1 | ESI+: 857 |
| 232 | 1 | ESI+: 823 |
| 233 | 1 | ESI+: 823 |
| 234 | 3 | ESI+: 825 |

TABLE 99

| Ex | Syn | Dat |
|---|---|---|
| 235 | 1 | APCI/ESI+: 837 |
| 236 | 1 | APCI/ESI+: 807 |
| 237 | 1 | APCI/ESI+: 795 |
| 238 | 1 | |
| 239 | 1 | APCI/ESI+: 851 |
| 240 | 1 | APCI/ESI+: 849 |
| 241 | 1 | APCI/ESI+: 851 |
| 242 | 1 | APCI/ESI+: 821 |
| 243 | 1 | ESI+: 867 |
| 244 | 1 | APCI/ESI+: 824 |
| 245 | 5 | ESI+: 653 |
| 246 | 2 | ESI+: 782 |

INDUSTRIAL APPLICABILITY

The compound of Formula (I) and a salt thereof has an NPT-IIb inhibitory action, and can be used as an agent for preventing and/or treating hyperphosphatemia, renal insufficiency, or abnormality in bone metabolism caused by renal insufficiency.

The invention claimed is:

1. A compound of formula (I) or a salt thereof, or hydrate thereof,

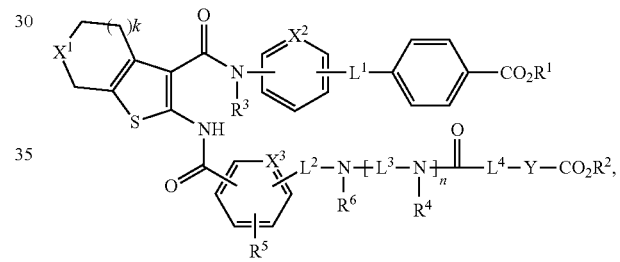

(1)

wherein:
$X^1$ represents $CH_2$ or O;
k represents 1, 2, or 3;
$R^3$ represents H or lower alkyl;
$X^2$ represents CH or N;
$L^1$ represents lower alkylene;
$R^1$ represents H or lower alkyl;
$X^3$ represents CH or N;
$L^2$ represents lower alkylene;
$R^5$ represents H or lower alkyl;
$R^6$ represents H, lower alkyl, lower alkyl substituted with one to two of —$OR^0$, —C(O)-lower alkyl, —$S(O)_m$-lower alkyl, -lower alkylene-N(lower alkyl)$_2$, —$R^{00}$-heterocycle, —$R^{00}$-phenyl, or —$R^{00}$-cycloalkyl, wherein the heterocycle, phenyl and cycloalkyl may be substituted with one to two lower alkyl or C(O)-lower alkyl, and —$R^{00}$ may be substituted with one —$OR^0$, wherein
$R^{00}$ represents a bond or lower alkylene,
$R^0$ represents H or lower alkyl, and
m represents 0, 1, or 2;
$L^3$ represents lower alkylene;
n represents 0 or 1;
$R^4$ represents H, lower alkyl, -lower alkylene-COO—$R^0$, -lower alkylene-$OR^0$, -lower alkylene-$NHR^0$, -lower alkylene-N(lower alkyl)$_2$, or cycloalkyl;
$L^4$ represents a bond, O, or —$NR^0$—;

Y represents —R$^{oo}$-monocyclic heterocycle-R$^{oo}$—, —R$^{oo}$-phenyl-R$^{oo}$—, -lower alkylene-NR$^o$-lower alkylene-, lower alkylene-O-lower alkylene-, or lower alkylene which may be substituted with a hydroxyl group; and, R$^2$ represents H or lower alkyl.

2. The compound or a salt thereof or hydrate thereof according to claim 1, wherein in formula (I), R$^6$ represents lower alkyl or cycloalkyl.

3. The compound or a salt thereof or hydrate thereof according to claim 2, wherein in formula (I), n represents 1, and R$^4$ represents H, lower alkyl, or lower alkylene-OR$^o$.

4. The compound or a salt thereof or hydrate thereof according to claim 3, wherein in formula (I), Y represents lower alkylene which may be substituted with a hydroxyl group.

5. The compound or a salt thereof or hydrate thereof according to claim 4, wherein in formula (I), X$^1$ represents CH$_2$, and k represents 1.

6. The compound or a salt thereof or hydrate thereof according to claim 5, wherein in formula (I), both the X$^2$ and X$^3$ represent CH.

7. The compound of claim 1, wherein said compound is selected from the group consisting of:

4-(2-{4-[({2-[(3-{[{2-[(3-carboxypropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid;

4-(2-{4-[({2-[(3-{[(2-{[(carboxymethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoic acid;

4-(2-{4-[({2-[(3-{[{2-[(4-carboxy-4-methylpentanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid;

4-(2-{4-[({2-[(3-{[{3-[(3-carboxypropanoyl)(methyl)amino]propyl}(pentan-3-yl)amino]methyl}benzoyl)amino]-4,5,6,7-tetrahydro-1-benzothiophen-3-yl}carbonyl)amino]phenyl}ethyl)benzoic acid;

4-(2-{4-[({2-[(3-{[{2-[(3-carboxypropanoyl)(2-methoxyethyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid;

4-(2-{4-[({2-[(3-{[(4-carboxy-4-methylpentanoyl)(pentan-3-yl)amino]methyl}benzoyl)amino]-4,5,6,7-tetrahydro-1-benzothiophen-3-yl}carbonyl)amino]phenyl}ethyl)benzoic acid; and 4-(2-{4-[({2-[(3-{[(4-carboxy-3,3-dimethylbutanoyl)(pentan-3-yl)amino]methyl}benzoyl)amino]-4,5,6,7-tetrahydro-1-benzothiophen-3-yl}carbonyl)amino]phenyl}ethyl)benzoic acid, or a salt thereof, or hydrate thereof.

8. A pharmaceutical composition comprising:
the compound or a salt thereof or hydrate thereof according to claim 7; and
a pharmaceutically acceptable excipient.

9. A method of preventing or treating hyperphosphatemia, the method comprising:
administering an effective amount of the compound or a salt thereof or hydrate thereof according to claim 7 to a subject in need thereof.

10. The compound of claim 7, wherein said compound is 4-(2-{4-[({2-[(3-{[{2-[(3-carboxypropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid, or a salt thereof, or hydrate thereof.

11. The compound of claim 7, wherein said compound is magnesium 4-(2-{4-[({2-[(3-{[{2-[(3-carboxylatopropanoyl)(methyl)amino]ethyl}(pentan-3-yl)amino]methyl}benzoyl)amino]-4,5,6,7-tetrahydro-1-benzothiophen-3-yl}carbonyl)amino]phenyl}ethyl)benzoate, or hydrate thereof.

12. The compound of claim 7, wherein said compound is 4-(2-{4-[({2-[(3-{[(2-{[(carboxymethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoic acid, or a salt thereof, or hydrate thereof.

13. The compound of claim 7, wherein said compound is 4-(2-{4-[({2-[(3-{[{2-[(3-carboxypropanoyl)(2-methoxyethyl)amino]ethyl}(pentan-3-yl)amino]methyl}benzoyl)amino]-4,5,6,7-tetrahydro-1-benzothiophen-3-yl}carbonyl)amino]phenyl}ethyl)benzoic acid, or a salt thereof, or hydrate thereof.

14. The compound of claim 7, wherein said compound is magnesium 4-(2-{4-[({2-[(3-{[(2-{[(carboxylatomethoxy)carbonyl](methyl)amino}ethyl)(pentan-3-yl)amino]methyl}benzoyl)amino]-4,5,6,7-tetrahydro-1-benzothiophen-3-yl}carbonyl)amino]phenyl}ethyl)benzoate, or hydrate thereof.

* * * * *